(12) United States Patent
Motoki et al.

(10) Patent No.: US 8,198,269 B2
(45) Date of Patent: Jun. 12, 2012

(54) FUSED AMINODIHYDROTHIAZINE DERIVATIVE

(75) Inventors: Takafumi Motoki, Tsukuba (JP); Kunitoshi Takeda, Tsukuba (JP); Yoichi Kita, Tsukuba (JP); Mamoru Takaishi, Tsukuba (JP); Yuichi Suzuki, Tsukuba (JP); Tasuku Ishida, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 281 days.

(21) Appl. No.: 12/568,151

(22) Filed: Sep. 28, 2009

(65) Prior Publication Data
US 2010/0093999 A1    Apr. 15, 2010

Related U.S. Application Data

(60) Provisional application No. 61/226,365, filed on Jul. 17, 2009, provisional application No. 61/170,179, filed on Apr. 17, 2009, provisional application No. 61/101,359, filed on Sep. 30, 2008.

(30) Foreign Application Priority Data

Sep. 30, 2008  (JP) ................. 2008-252062
Apr. 17, 2009  (JP) ................. 2009-100457
Jul. 17, 2009  (JP) ................. 2009-168490

(51) Int. Cl.
*C07D 513/04* (2006.01)
*C07D 239/14* (2006.01)
*A61K 31/542* (2006.01)

(52) U.S. Cl. ........................ 514/224.2; 544/48
(58) Field of Classification Search .............. 544/48; 514/224.2
See application file for complete search history.

(56) References Cited

U.S. PATENT DOCUMENTS

| 3,227,713 A | 1/1966 | Behner et al. |
| 3,235,551 A | 2/1966 | Schubert et al. |
| 7,648,983 B2 | 1/2010 | Audia et al. |
| 2004/0110743 A1 | 6/2004 | Miyamato et al. |
| 2006/0052406 A1 | 3/2006 | Fisher et al. |
| 2007/0021454 A1 | 1/2007 | Coburn et al. |
| 2008/0139538 A1 | 6/2008 | McGaughey et al. |
| 2009/0082560 A1 | 3/2009 | Kobayashi et al. |
| 2009/0209755 A1 | 8/2009 | Suzuki et al. |
| 2010/0075957 A1 | 3/2010 | Tamura et al. |
| 2010/0160290 A1 | 6/2010 | Kobayashi et al. |
| 2010/0317850 A1 | 12/2010 | Suzuki et al. |
| 2011/0009395 A1 | 1/2011 | Audia et al. |
| 2011/0152253 A1 | 6/2011 | Motoki et al. |
| 2011/0207723 A1 | 8/2011 | Motoki et al. |

FOREIGN PATENT DOCUMENTS

| EP | 1 942 105 | 7/2008 |
| EP | 2 233 474 | 9/2010 |
| JP | 09-67355 | 3/1997 |
| JP | 2004-149429 | 5/2004 |
| WO | 01/87293 | 11/2001 |
| WO | 02/096897 | 12/2002 |
| WO | 2004/014843 | 2/2004 |
| WO | 2004/043916 | 5/2004 |
| WO | 2005/058311 | 6/2005 |
| WO | 2005/097767 | 10/2005 |
| WO | 2006/041404 | 4/2006 |
| WO | 2006/041405 | 4/2006 |
| WO | WO 2007/011810 | 1/2007 |
| WO | 2007/049532 | 5/2007 |
| WO | 2008/133273 | 11/2008 |
| WO | 2008/133274 | 11/2008 |
| WO | WO 2010/013302 | 2/2010 |
| WO | WO 2010/013794 | 2/2010 |
| WO | WO 2011/009897 | 1/2011 |
| WO | WO 2011/009898 | 1/2011 |

OTHER PUBLICATIONS

Cohen et al., "Synthesis of 2-Amino-5,6-dihydro-4H-1, 3-thiazines and Related Compound by Acid Catalyzed Cyclization of Allylic Isothiuronium Salts", J. of Heterocyclic Chem. 14:717-723 (1977).
Kuo et al., "A Synthesis of Estrone via Novel Intermediates. Mechanism of the Coupling Reaction of a Vinyl Carbinol with a β Diketone", J. of Organic Chem. 33:3126-3132 (1968).
Gong et al., "Alzheimer's disease-affected brain: Presence of oligomeric Aβ ligands (ADDLs) suggests a molecular basis for reversible memory loss", PNAS USA 100(18):10417-10422 (2003).
Hock et al., "Antibodies against β-Amyloid Slow Cognitive Decline in Alzheimer's Disease", Neuron 38:547-554 (2003).
Jarrett et al., "The Carboxy Terminus of the β Amyloid Protein is Critical for the Seeding of Amyloid Formation: Implications for the Pathogenesis of Alzheimer's Disease", Biochemisty 32(18)4693-4697 (1993).

(Continued)

*Primary Examiner* — Kahsay T Habte
(74) *Attorney, Agent, or Firm* — Fish & Richardson P.C.

(57) ABSTRACT

A compound represented by the general formula:

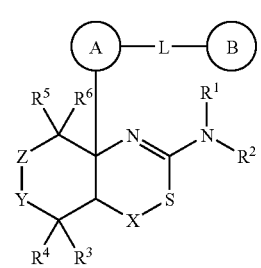

(I)

wherein Ring A is a $C_{6-14}$ aryl group or the like, L is —$NR^L$CO— or the like (wherein $R^L$ is a hydrogen atom or the like), Ring B is a $C_{6-14}$ aryl group or the like, X is a $C_{1-3}$ alkylene group or the like, Y is a $C_{1-3}$ alkylene group or the like, Z is an oxygen atom or the like, $R^1$ and $R^2$ are each independently a hydrogen atom or the like, and $R^3$, $R^4$, $R^5$ and $R^6$ are independently a hydrogen atom, a halogen atom or the like, or a pharmaceutically acceptable salt thereof, or a solvate thereof, has an Aβ production inhibitory effect or a BACE1 inhibitory effect and is useful as a therapeutic agent for a neurodegenerative disease caused by Aβ and typified by Alzheimer-type dementia.

9 Claims, No Drawings

OTHER PUBLICATIONS

Glenner et al., "Alzheimer's Disease: Initial Report of the Purification and Characterization of a Novel Cerebrovascular Amyloid Protein", Biochemical and Biophysical Research Communications 120(3):885-890 (1984).
Masters et al., "Amyloid plague core protein in Alzheimer disease and Down Syndrome", PNAS USA 82(12):4245-4249 (1985).
Gouras et al., "Short Communication Intraneuronal Aβ42 Accumulation in Human Brain", American Journal of Pathology 156(1):15-20 (2000).
Scheuner et al., "Secreted amyloid β-protein similar to that in the senile plagues of Alzheimer's disease is increased in vivo by the presenilin 1 and 2 and APP mutations linked to familial Alzheimer's disease", Nature Medicine 2(8):864-870 (1996).
Forman et al., "Differential Effects of the Swedish Mutant Amyloid Precursor Protein on β-Amyloid Accumulation and Secretion in Neurons and Nonneuronal Cells", J. of Biological Chemistry 272(51):32247-32253 (1997).
Sankaranarayanan, et al., "In Vivo β-Secretase 1 Inhibition Leads to Brain Aβ Lowering and Increased α-Secretase Processing of Amyloid Precursor Protein without Effect on Neureglin-1", 324(3):957-969 (2008).
Meredith, Jr. et al. "P-Glycoprotein Efflux and Other Factors Limit Brain Amyloid β Reduction by β-Site Amyloid Precursor Protein-Cleaving Enzyme 1 Inhibitors in Mice", The Journal of Pharmacology and Experimental Therapeutics 326(2):502-513 (2008).
Khimiya I Khimicheskaya Tekhologiya 33(10):15-18 (1990).
Bobrov et al., "Interaction of Quinone Oxide with Thiourea" Chemistry and Chemical Technology 33(10):15-18 (1990) (original and English language translation).
Office Action from U.S. Appl. No. 12/355,154 (Jun. 3, 2011).
Office Action from Japanese Application No. 2009-550050 and English translation (Feb. 9, 2011).
Acceptance of Complete Specification from South African Application No. 2010/04799 (Aug. 16, 2011).
Amended Claims and Specification Filed with Response to Office Action from Chilean Application No. 96/2009 and English Translation (Nov. 4, 2011).
Amendment and Response to Office Action from Mexican Application No. MX/a/2010/007337 and English Translation (Jan. 3, 2012).
Amendment and Response to Office Action from Singapore Application No. 201102027-8 (Dec. 28, 2011).
Argument and Amendment in Response to Office Action from Japanese Application No. 2009-550050 and English Translation (Apr. 12, 2010).
Argument and Amendment in Response to Office Action from New Zealand Application No. 586796 (Apr. 28, 2011).
Argument and Amendment in Response to Office Action from Pakistan Application No. 43/2009 (May 21, 2010).
Decision of Granting Patent from Japanese Application No. 2009-550050 and English Translation (May 7, 2010).
English Translation of Office Action from Mexican Application No. MX/a/2010/007337 (2011).
European Search Report for App. Ser. No. EP 09 81 7719, dated Feb. 14, 2012.
Examination Report and Notice of Acceptance of Complete Specification from New Zealand Application No. 586796 (Oct. 6, 2011).
Extended Search Report from European Application No. 09701914.5 (Sep. 30, 2011).
International Preliminary Report on Patentability from PCT Application No. PCT/JP2009/050511 (Aug. 31, 2010).
International Search Report from PCT Application No. PCT/JP2009/050511 (Mar. 24, 2009).
Newspaper Publication of Venezuelan Application No. 2009-000078 (2011).
Office Action from Chilean Application No. 96/2009 and English Translation (2011).
Office Action from Chilean Application No. 96/2009 and English Translation (Aug. 1, 2011).
Office Action from Mexican Application No. MX/a/2010/007337 and English Translation (Oct. 19, 2011).
Office Action from New Zealand Application No. 586796 (Feb. 21, 2011).
Office Action from Pakistan Application No. 43/2009 (Mar. 26, 2010).
Official Acceptance Notice for Pakistan Application No. 43/2009 (Jun. 10, 2010).
Response to Office Action from Chilean Application No. 96/2009 and English Translation (Nov. 4, 2011).
Restriction Requirement from U.S. Appl. No. 12/355,154 (Apr. 19, 2011).
Response to Restriction Requirement from U.S. Appl. No. 12/355,154 (May 9, 2011).
Amendment in Reply to Office Action of Jun. 3, 2011 in U.S. Appl. No. 12/355,154 (Sep. 2, 2011).
Supplemental Amendment in Reply to Office Action of Jun. 3, 2011 in U.S. Appl. No. 12/355,154 (Sep. 27, 2011).
Notice of Allowance from U.S. Appl. No. 12/355,154 (Oct. 5, 2011).
Amendment filed with Request for Continued Examination from U.S. Appl. No. 12/355,154 (Jan. 5, 2012).
Notice of Allowance from U.S. Appl. No. 12/355,154 (Jan. 18, 2012).
Notice of Allowance from U.S. Appl. No. 12/355,154 (Feb. 17, 2012).
Written Opinion from Singapore Application No. 201102027-8 (Aug. 24, 2011).

FUSED AMINODIHYDROTHIAZINE DERIVATIVE

RELATED APPLICATIONS

The present application claims priority from U.S. provisional application Ser. No. 61/101,359 filed on Sep. 30, 2008, U.S. provisional application Ser. No. 61/170,179 filed on Apr. 17, 2009, U.S. provisional application Ser. No. 61/226,365 filed on Jul. 17, 2009, Japanese patent application no. 2008-252062 filed on Sep. 30, 2008, Japanese patent application no. 2009-100457 filed on Apr. 17, 2009, and Japanese patent application no. 2009-168490 filed on Jul. 17, 2009, all of the contents of which are incorporated herein by reference.

BACKGROUND OF THE INVENTION

1. Field of the Invention

The present invention relates to a fused aminodihydrothiazine derivative and pharmaceutical use thereof. More particularly, the present invention relates to a fused aminodihydrothiazine derivative which has an amyloid-β (hereinafter referred to as Aβ) protein production inhibitory effect or a beta-site amyloid-β precursor protein cleavage enzyme 1 (hereinafter referred to as BACE1 or beta-secretase) inhibitory effect and is effective for treating a neurodegenerative disease caused by Aβ protein, in particular, Alzheimer-type dementia, Down's syndrome or the like, and to a pharmaceutical composition comprising the fused aminodihydrothiazine derivative as an active ingredient.

2. Description of Related Art

Alzheimer's disease is a disease characterized by degeneration and loss of neurons as well as formation of senile plaques and neurofibrillary tangles. Currently, Alzheimer-type dementia is treated only with symptomatic treatment using a symptom improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer-type dementia.

It is assumed that Aβ-proteins as metabolites of amyloid precursor proteins (hereinafter referred to as APP) are highly involved in degeneration and loss of neurons and onset of symptoms of dementia (see Non-Patent Documents 3 and 4, for example). Aβ-proteins have, as main components, Aβ40 consisting of 40 amino acids and Aβ42 with two amino acids added at the C-terminal. The Aβ40 and Aβ42 are known to have high aggregability (see Non-Patent Document 5, for example) and to be main components of senile plaques (see Non-Patent Documents 5, 6 and 7, for example). Further, it is known that the Aβ40 and Aβ42 are increased by mutation in APP and presenilin genes which is observed in familial Alzheimer's disease (see Non-Patent Documents 8, 9 and 10, for example). Accordingly, a compound that reduces production of Aβ40 and Aβ42 is expected as a progression inhibitor or prophylactic agent for Alzheimer-type dementia.

Aβ is produced by cleaving APP by beta-secretase (BACE1) and subsequently by gamma-secretase. For this reason, attempts have been made to create gamma-secretase and beta-secretase inhibitors in order to inhibit Aβ production. Already known beta-secretase inhibitors are reported in Patent Documents 1 to 15 and Non-Patent Documents 1 and 2 shown below and the like. In particular, Patent Documents 1, 14 and 15 describes an aminodihydrothiazine derivative and a compound having BACE1 inhibitory activity.

[Prior Art Documents]
[Patent Documents]
[Patent Document 1] WO 2007/049532
[Patent Document 2] U.S. Pat. No. 3,235,551
[Patent Document 3] U.S. Pat. No. 3,227,713
[Patent Document 4] JP-A-09-067355
[Patent Document 5] WO 01/087293
[Patent Document 6] WO 04/014843
[Patent Document 7] JP-A-2004-149429
[Patent Document 8] WO 02/96897
[Patent Document 9] WO 04/043916
[Patent Document 10] WO 2005/058311
[Patent Document 11] WO 2005/097767
[Patent Document 12] WO 2006/041404
[Patent Document 13] WO 2006/041405
[Patent Document 14] WO 2008/133273
[Patent Document 15] WO 2008/133274
[Non-Patent Documents]
[Non-Patent Document 1] Journal of Heterocyclic Chemistry, Vol. 14, p. 717-723 (1977)
[Non-Patent Document 2] Journal of Organic Chemistry, Vol. 33, p. 3126-3132 (1968)
[Non-Patent Document 3] Klein W L, and seven others, Alzheimer's disease-affected brain: Presence of oligomeric Aβ ligands (ADDLs) suggests a molecular basis for reversible memory loss, Proceedings of National Academy of Science USA 2003, Sep. 2; 100 (18), p. 10417-10422.
[Non-Patent Document 4] Nitsch R M, and sixteen others, Antibodies against β-amyloid slow cognitive decline in Alzheimer's disease, Neuron, 2003, May 22; 38, p. 547-554.
[Non-Patent Document 5] Jarrett J T, and two others, The carboxy terminus of the β amyloid protein is critical for the seeding of amyloid formation: Implications for the pathogenesis of Alzheimers' disease, Biochemistry, 1993, 32 (18), p. 4693-4697.
[Non-Patent Document 6] Glenner G G, and one other, Alzheimer's disease: initial report of the purification and characterization of a novel cerebrovascular amyloid protein, Biochemical and biophysical research communications, 1984, May 16, 120 (3), p. 885-890.
[Non-Patent Document 7] Masters C L, and five others, Amyloid plaque core protein in Alzheimer disease and Down syndrome, Proceedings of National Academy of Science USA, June 1985, 82 (12), p. 4245-4249.
[Non-Patent Document 8] Gouras G K, and eleven others, Intraneuronal Aβ42 accumulation in human brain, American Journal of Pathology, January 2000, 156 (1), p. 15-20.
[Non-Patent Document 9] Scheuner D, and 20 others, Secreted amyloid β-protein similar to that in the senile plaques of Alzheimer's disease is increased in vivo by the presenilin 1 and 2 and APP mutations linked to familial Alzheimer's disease, Nature Medicine, 1996, Aug. 2 (8), p. 864-870.
[Non-Patent Document 10] Forman M S, and four others, Differential effects of the swedish mutant amyloid precursor protein on β-amyloid accumulation and secretion in neurons and nonneuronal cells, The Journal of Biological Chemistry, 1997, Dec. 19, 272 (51), p. 32247-32253.

BRIEF SUMMARY OF THE INVENTION

An object of the present invention is to provide a fused aminodihydrothiazine compound which differs from an aminodihydrothiazine derivative and a compound having BACE1 inhibitory activity described in Patent Document 1 and which has an Aβ production inhibitory effect or a BACE1 inhibitory effect and is useful as a therapeutic agent for a neurodegenerative disease caused by Aβ and typified by Alzheimer-type dementia, and pharmaceutical use thereof.

The present invention relates to:

[1] A compound represented by the formula (I):

[Formula 1]

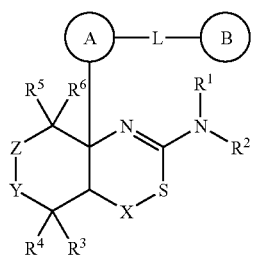

(I)

or a pharmaceutically acceptable salt thereof, or a solvate thereof, wherein

Ring A is a $C_{6-14}$ aryl group which may have 1 to 3 substituents selected from Substituent Group α, a 5- to 6-membered heteroaryl group which may have 1 to 3 substituents selected from Substituent Group α or a 9- to 10-membered benzo-fused heterocyclic group which may have 1 to 3 substituents selected from Substituent Group α, L is a single bond, an oxygen atom, —$NR^L$CO— (wherein $R^L$ is a hydrogen atom or a $C_{1-6}$ alkyl group which may have 1 to 3 substituents selected from Substituent Group α), an —$NR^L$CO—$C_{1-6}$ alkyl group (wherein $R^L$ is a hydrogen atom or a $C_{1-6}$ alkyl group which may have 1 to 3 substituents selected from Substituent Group α), —$NR^L SO_2$— (wherein $R^L$ is a hydrogen atom or a $C_{1-6}$ alkyl group which may have 1 to 3 substituents selected from Substituent Group α), a $C_{1-6}$ alkylene group which may have 1 to 3 substituents selected from Substituent Group α, a $C_{2-6}$ alkenylene group which may have 1 to 3 substituents selected from Substituent Group α or a $C_{2-6}$ alkynylene group which may have 1 to 3 substituents selected from Substituent Group α, Ring B is a $C_{3-8}$ cycloalkyl group which may have 1 to 3 substituents selected from Substituent Group α, a $C_{6-14}$ aryl group which may have 1 to 3 substituents selected from Substituent Group α or a 5- to 10-membered heterocyclic group which may have 1 to 3 substituents selected from Substituent Group α, X is a single bond or a $C_{1-3}$ alkylene group which may have 1 to 3 substituents selected from Substituent Group α, Y is a $C_{1-3}$ alkylene group which may have 1 to 3 substituents selected from Substituent Group α or a $C_{2-3}$ alkenylene group which may have 1 to 3 substituents selected from Substituent Group α, Z is an oxygen atom, a sulfur atom, a sulfoxide, a sulfone or —$NR^M$— (wherein $R^M$ is a hydrogen atom, a $C_{1-6}$ alkyl group which may have 1 to 3 substituents selected from Substituent Group α, a $C_{3-8}$ cycloalkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{6-14}$ aryl group which may have 1 to 3 substituents selected from Substituent Group α or a 5- to 10-membered heterocyclic group which may have 1 to 3 substituents selected from Substituent Group α), $R^1$ and $R^2$ are each independently a hydrogen atom, a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{3-8}$ carbocyclic group which may have 1 to 3 substituents selected from Substituent Group α or a 5- to 10-membered heterocyclic group which may have 1 to 3 substituents selected from Substituent Group α, and $R^3$, $R^4$, $R^5$ and $R^6$ are independently a hydrogen atom, a halogen atom, a hydroxy group, a $C_{1-6}$ alkyl group which may have 1 to 3 substituents selected from Substituent Group α, a $C_{1-6}$ alkoxy group which may have 1 to 3 substituents selected from Substituent Group α, a 3- to 10-membered carbocyclic group which may have 1 to 3 substituents selected from Substituent Group α or a 5- to 10-membered heterocyclic group which may have 1 to 3 substituents selected from Substituent Group α, or $R^4$ and $R^6$ together may form a ring represented by the formula (II):

[Formula 2]

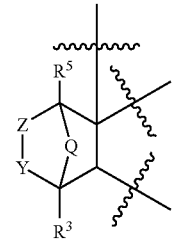

(II)

wherein Y, Z, $R^5$ and $R^3$ are the same as defined above and Q is an oxygen atom, a methylene group or an ethylene group

[Substituent Group α: a hydrogen atom, a halogen atom, a hydroxy group, a nitro group, a $C_{1-6}$ alkylthio group, a $C_{6-14}$ aryl group, a $C_{6-14}$ aryloxycarbonyl group, a $C_{6-14}$ arylcarbonyl group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group may be substituted with 1 to 2 $C_{1-6}$ alkyl groups), a $C_{2-6}$ alkenyl group which may have 1 to 2 substituents selected from Substituent Group β, a $C_{2-6}$ alkynyl group which may have 1 to 2 substituents selected from Substituent Group β, a carbamoyl group which may be substituted with 1 to 2 $C_{1-6}$ alkyl groups, a $C_{1-6}$ alkoxy group which may have 1 to 3 substituents selected from Substituent Group β, a $C_{1-6}$ alkyl group which may have 1 to 3 substituents selected from Substituent Group β and a 5- to 10-membered heterocyclic group which may have 1 to 3 substituents selected from Substituent Group β, Substituent Group β: a halogen atom, a cyano group, a hydroxy group and a $C_{1-6}$ alkoxy group (wherein the alkoxy group may be substituted with a phenyl group which may be substituted with 1 to 3 substituents selected from a hydrogen atom, a halogen atom, a hydroxy group and a nitro group)];

[2] A compound represented by the formula (I):

[Formula 3]

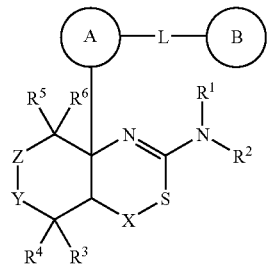

(I)

or a pharmaceutically acceptable salt thereof, or a solvate thereof, wherein

Ring A is a $C_{6-14}$ aryl group which may have 1 to 3 substituents selected from Substituent Group α, a 5- to 6-membered heteroaryl group which may have 1 to 3 substituents selected from Substituent Group α or a 9- to 10-membered benzo-fused heterocyclic group which may have 1 to 3 substituents selected from Substituent Group α, L is a single bond, an oxygen atom, —NR$^L$CO— (wherein R$^L$ is a hydrogen atom or a $C_{1-6}$ alkyl group which may have 1 to 3 substituents selected from Substituent Group α), —NR$^L$SO$_2$— (wherein R$^L$ is a hydrogen atom or a $C_{1-6}$ alkyl group which may have 1 to 3 substituents selected from Substituent Group α), a $C_{1-6}$ alkylene group which may have 1 to 3 substituents selected from Substituent Group α, a $C_{2-6}$ alkenylene group which may have 1 to 3 substituents selected from Substituent Group α or a $C_{2-6}$ alkynylene group which may have 1 to 3 substituents selected from Substituent Group α, Ring B is a $C_{3-8}$ cycloalkyl group which may have 1 to 3 substituents selected from Substituent Group α, a $C_{6-14}$ aryl group which may have 1 to 3 substituents selected from Substituent Group α or a 5- to 10-membered heterocyclic group which may have 1 to 3 substituents selected from Substituent Group α, X is a single bond or a $C_{1-3}$ alkylene group which may have 1 to 3 substituents selected from Substituent Group α, Y is a $C_{1-3}$ alkylene group which may have 1 to 3 substituents selected from Substituent Group α or a $C_{2-3}$ alkenylene group which may have 1 to 3 substituents selected from Substituent Group α, Z is an oxygen atom, a sulfur atom, a sulfoxide, a sulfone or —NR$^M$— (wherein R$^M$ is a hydrogen atom, a $C_{1-6}$ alkyl group which may have 1 to 3 substituents selected from Substituent Group α, a $C_{3-8}$ cycloalkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{6-14}$ aryl group which may have 1 to 3 substituents selected from Substituent Group α or a 5- to 10-membered heterocyclic group which may have 1 to 3 substituents selected from Substituent Group α), R$^1$ and R$^2$ are each independently a hydrogen atom, a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{3-8}$ carbocyclic group which may have 1 to 3 substituents selected from Substituent Group α or a 5- to 10-membered heterocyclic group which may have 1 to 3 substituents selected from Substituent Group α, and R$^3$, R$^4$, R$^5$ and R$^6$ are independently a hydrogen atom, a halogen atom, a hydroxy group, a $C_{1-6}$ alkyl group which may have 1 to 3 substituents selected from Substituent Group α, a $C_{1-6}$ alkoxy group which may have 1 to 3 substituents selected from Substituent Group α, a 3- to 10-membered carbocyclic group which may have 1 to 3 substituents selected from Substituent Group α or a 5- to 10-membered heterocyclic group which may have 1 to 3 substituents selected from Substituent Group α, or R$^4$ and R$^6$ together may form a ring represented by the formula (II):

[Formula 4]

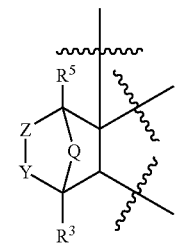

(II)

wherein Y, Z, R$^5$ and R$^3$ are the same as defined above and Q is an oxygen atom, a methylene group or an ethylene group

[Substituent Group α: a hydrogen atom, a halogen atom, a hydroxy group, a nitro group, a $C_{1-6}$ alkylthio group, a $C_{6-14}$ aryl group, a $C_{6-14}$ aryloxycarbonyl group, a $C_{6-14}$ arylcarbonyl group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group may be substituted with 1 to 2 $C_{1-6}$ alkyl groups), a $C_{2-6}$ alkenyl group which may have 1 to 2 substituents selected from Substituent Group β, a $C_{2-6}$ alkynyl group which may have 1 to 2 substituents selected from Substituent Group β, a carbamoyl group which may be substituted with 1 to 2 $C_{1-6}$ alkyl groups, a $C_{1-6}$ alkoxy group which may have 1 to 3 substituents selected from Substituent Group β, a $C_{1-6}$ alkyl group which may have 1 to 3 substituents selected from Substituent Group β and a 5- to 10-membered heterocyclic group which may have 1 to 3 substituents selected from Substituent Group β, Substituent Group β: a halogen atom, a cyano group, a hydroxy group and a $C_{1-6}$ alkoxy group];

[3] A compound represented by the formula (I):

[Formula 5]

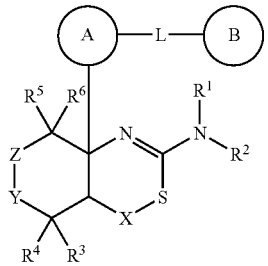

(I)

or a pharmaceutically acceptable salt thereof, or a solvate thereof, wherein

Ring A is a $C_{6-14}$ aryl group which may have 1 to 3 substituents selected from Substituent Group α, a 5- to 6-membered heteroaryl group which may have 1 to 3 substituents selected from Substituent Group α or a 9- to 10-membered benzo-fused heterocyclic group which may have 1 to 3 substituents selected from Substituent Group α, L is a single bond, an oxygen atom, —$NR^L CO$— (wherein $R^L$ is a hydrogen atom or a $C_{1-6}$ alkyl group which may have 1 to 3 substituents selected from Substituent Group α), —$NR^L SO_2$— (wherein $R^L$ is a hydrogen atom or a $C_{1-6}$ alkyl group which may have 1 to 3 substituents selected from Substituent Group α), a $C_{1-6}$ alkylene group which may have 1 to 3 substituents selected from Substituent Group α, a $C_{2-6}$ alkenylene group which may have 1 to 3 substituents selected from Substituent Group α or a $C_{2-6}$ alkynylene group which may have 1 to 3 substituents selected from Substituent Group α, Ring B is a $C_{3-8}$ cycloalkyl group which may have 1 to 3 substituents selected from Substituent Group α, a $C_{6-14}$ aryl group which may have 1 to 3 substituents selected from Substituent Group α or a 5- to 10-membered heterocyclic group which may have 1 to 3 substituents selected from Substituent Group α, X is a single bond or a $C_{1-3}$ alkylene group which may have 1 to 3 substituents selected from Substituent Group α, Y is a $C_{1-3}$ alkylene group which may have 1 to 3 substituents selected from Substituent Group α or a $C_{2-3}$ alkenylene group which may have 1 to 3 substituents selected from Substituent Group α, Z is an oxygen atom, a sulfur atom, a sulfoxide, a sulfone or —$NR^M$— (wherein $R^M$ is a hydrogen atom, a $C_{1-6}$ alkyl group which may have 1 to 3 substituents selected from Substituent Group α, a $C_{3-8}$ cycloalkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{6-14}$ aryl group which may have 1 to 3 substituents selected from Substituent Group α or a 5- to 10-membered heterocyclic group which may have 1 to 3 substituents selected from Substituent Group α), $R^1$ and $R^2$ are each independently a hydrogen atom, a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{3-8}$ carbocyclic group which may have 1 to 3 substituents selected from Substituent Group α or a 5- to 10-membered heterocyclic group which may have 1 to 3 substituents selected from Substituent Group α, and $R^3$, $R^4$, $R^5$ and $R^6$ are independently a hydrogen atom, a halogen atom, a hydroxy group, a $C_{1-6}$ alkyl group which may have 1 to 3 substituents selected from Substituent Group α, a $C_{1-6}$ alkoxy group which may have 1 to 3 substituents selected from Substituent Group α, a 3- to 10-membered carbocyclic group which may have 1 to 3 substituents selected from Substituent Group α or a 5- to 10-membered heterocyclic group which may have 1 to 3 substituents selected from Substituent Group α

[Substituent Group α: a hydrogen atom, a halogen atom, a hydroxy group, a nitro group, a $C_{1-6}$ alkylthio group, a $C_{6-14}$ aryl group, a $C_{6-14}$ aryloxycarbonyl group, a $C_{6-14}$ arylcarbonyl group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group may be substituted with 1 to 2 $C_{1-6}$ alkyl groups), a $C_{2-6}$ alkenyl group which may have 1 to 2 substituents selected from Substituent Group β, a $C_{2-6}$ alkynyl group which may have 1 to 2 substituents selected from Substituent Group β, a carbamoyl group which may be substituted with 1 to 2 $C_{1-6}$ alkyl groups, a $C_{1-6}$ alkoxy group which may have 1 to 3 substituents selected from Substituent Group β, a $C_{1-6}$ alkyl group which may have 1 to 3 substituents selected from Substituent Group β and a 5- to 10-membered heterocyclic group which may have 1 to 3 substituents selected from Substituent Group β, Substituent Group β: a halogen atom, a cyano group, a hydroxy group and a $C_{1-6}$ alkoxy group];

[4] The compound or pharmaceutically acceptable salt thereof, or solvate thereof according to any one of [1] to [3] above, wherein X is a methylene group which may have 1 to 2 substituents selected from Substituent Group α;

[5] The compound or pharmaceutically acceptable salt thereof, or solvate thereof according to any one of [1] to [4] above, wherein Z is an oxygen atom and Y is a $C_{1-3}$ alkylene group which may have 1 to 3 substituents selected from Substituent Group α;

[6] The compound or pharmaceutically acceptable salt thereof, or solvate thereof according to any one of [1] to [4] above, wherein Z is an oxygen atom and Y is a $C_{2-3}$ alkenylene group which may have 1 to 3 substituents selected from Substituent Group α;

[7] The compound or pharmaceutically acceptable salt thereof, or solvate thereof according to any one of [1] to [4] above, wherein Z is a sulfur atom or a sulfone and Y is a $C_{1-3}$ alkylene group which may have 1 to 3 substituents selected from Substituent Group α;

[8] The compound or pharmaceutically acceptable salt thereof, or solvate thereof according to any one of [1] to [4] above, wherein L is —$NR^L CO$— (wherein $R^L$ is a hydrogen atom or a $C_{1-6}$ alkyl group which may have 1 to 3 substituents selected from Substituent Group α);

[9] The compound or pharmaceutically acceptable salt thereof, or solvate thereof according to any one of [1] to [8] above, wherein the substituents selected from Substituent Group α is a hydrogen atom, a halogen atom, a $C_{1-6}$ alkoxy group which may have 1 to 3 substituents selected from Substituent Group β or a $C_{1-6}$ alkyl group which may have 1 to 3 substituents selected from Substituent Group β.

[10] A compound or a pharmaceutically acceptable salt thereof, or a solvate thereof, wherein the compound is selected from the following compounds:

1) N-[3-((4aR*,8aS*)-2-amino-4,4a,5,6,8,8a-hexahydro-7-oxa-3-thia-1-azanaphthalen-8a-yl)-4-fluorophenyl]-5-cyanopyridine-2-carboxamide, 2) N-[3-((8aR*)-2-amino-4,4a,5,6,8,8a-hexahydro-7-oxa-3-thia-1-azanaphthalen-8a-yl) -4-fluorophenyl]-5-fluoromethoxypyrazine-2-carboxamide, 3) N-[3-((4aR*,8aS*)-2-amino-4,4a,5,6,8,8a-hexahydro-7-oxa-3-thia-1-azanaphthalen-8a-yl) -4-fluorophenyl]-5-difluoromethoxypyrazine-2-carboxamide, 4) N-[3-((4aR*,8aS*)-2-amino-4,4a,5,6,8,8a-hexahydro-7-oxa-3-thia-1-azanaphthalen -8a-yl)-4-trifluoromethoxyphenyl]-5-cyanopyridine-2-carboxamide, 5) N-[3-((8aS*)-2-amino-4,4a,5,6,8,8a-hexahydro-7-oxa-3-thia-1-azanaphthalen-8a-yl)-4-trifluoromethoxyphenyl]-5-chloropyridine-2-carboxamide, 6) N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-chloropyridine-2-carboxamide, 7) N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-cyanopyridine-2-carboxamide, 8) N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-trifluoromethylpyridine-2-carboxamide, 9) N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-difluoromethoxypyrazine-2-carboxamide, 10) N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-fluoromethoxypyrazine-2-carboxamide, 11) N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-cyanopyridine-2-carboxamide, 12) N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-difluoromethylpyrazine-2-carboxamide, 13) N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-chloropyridine-2-carboxamide, 14) N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-fluoromethoxypyrazine-2-carboxamide, 15) N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-difluoromethoxypyrazine-2-carboxamide, 16) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-cyanopyridine-2-carboxamide, 17) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-difluoromethylpyrazine-2-carboxamide, 18) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-chloropyridine-2-carboxamide, 19) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-trifluoromethylpyridine-2-carboxamide, 20) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-difluoromethoxypyridine-2-carboxamide, 21) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-fluoromethoxypyrazine-2-carboxamide, 22) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-difluoromethoxypyrazine-2-carboxamide, 23) N-[3-((4aR*,5S*,8aS*)-2-amino-5-methyl-4,4a,5,6,8,8a-hexahydro-7-oxa-3-thia-1-azanaphthalen-8a-yl)-4-fluorophenyl]-5-chloropyridine-2-carboxamide, 24) N-[3-((4aR*,5S*,8aS*)-2-amino-5-methyl-4,4a,5,6,8,8a-hexahydro-7-oxa-3-thia-1-azanaphthalen-8a-yl)-4-fluorophenyl]-5-cyanopyridine-2-carboxamide, 25) N-[3-((4aR*,5S*,8aS*)-2-amino-5-methyl-4,4a,5,6,8,8a-hexahydro-7-oxa-3-thia-1-azanaphthalen-8a-yl)-4-fluorophenyl]-5-difluoromethoxypyrazine-2-carboxamide, 26) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-chloropyridine-2-carboxamide, 27) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-cyanopyridine-2-carboxamide, 28) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-difluoromethoxypyrazine-2-carboxamide, 29) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-difluoromethylpyrazine-2-carboxamide, 30) N-[3-((4aS*,5R*,8aS*)-2-amino-5-methoxy-4,4a,5,6,8,8a-hexahydro-7-oxa-3-thia-1-azanaphthalen-8a-yl)-4-fluorophenyl]-5-cyanopyridine-2-carboxamide, 31) N-[3-((2R*,4aR*,8aS*)-2-amino-4-methyl-4,4a,5,6,8,8a-hexahydro-7-oxa-3-thia-1-azanaphthalen-8a-yl)-4-fluorophenyl]-5-cyanopyridine-2-carboxamide, 32) N-[3-((2R*,4aR*,8aS*)-2-amino-4-methyl-4,4a,5,6,8,8a-hexahydro-7-oxa-3-thia-1-azanaphthalen-8a-yl)-4-fluorophenyl]-5-difluoromethylpyrazine-2-carboxamide, 33) N-[3-((4aR,6R,8aS)-2-amino-6-hydroxymethyl-4,4a,5,6,8,8a-hexahydro-7-oxa-3-thia-1-azanaphthalen-8a-yl)-4-fluorophenyl]-5-chloropyridine-2-carboxamide, 34) N-[3-((4aR,6R,8aS)-2-amino-6-hydroxymethyl-4,4a,5,6,8,8a-hexahydro-7-oxa-3-thia-1-azanaphthalen-8a-yl)-4-fluorophenyl]-5-cyanopyridine-2-carboxamide, 35) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-cyanopyridine-2-carboxamide, 36) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-difluoromethoxypyrazine-2-carboxamide, 37) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-fluoropyridine-2-carboxamide, 38) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-pyridine-2-carboxamide, 39) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-fluoromethoxypyrazine-2-carboxamide, 40) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-pyrimidine-4-carboxamide, 41) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-3,5-difluoropyridine-2-carboxamide, 42) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-difluoromethoxypyridine-2-carboxamide, 43) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-difluoromethylpyrazine-2-carboxamide, 44) N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-cyanopyridine-2-carboxamide, 45) N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-chloropyridine-2-carboxamide, 46) N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-trifluoromethylpyridine-2-carboxamide, 47) N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-fluoromethoxypyrazine-2-carboxamide, 48) N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-difluoromethylpyrazine-2-carboxamide, 49) N-[3-((4aR*,8aS*)-2-amino-4,4a,5,6,8,8a-hexahydro-7-oxa-3-thia-1-azanaphthalen-8a-yl)-4-fluorophenyl]-5-chloropyridine-2-carboxamide, 50) N-[3-((4aR*,8aS*)-2-amino-4,4a,5,6,8,8a-hexahydro-7-oxa-3-thia-1-azanaphthalen-8a-yl)-4-fluorophenyl]-5-bromopyridine-2-carboxamide, 51) N-[3-((4aR*,8aS*)-2-amino-4,4a,5,6,8,8a-hexahydro-7-oxa-3-thia-1-azanaphthalen-8a-yl)-4-fluorophenyl]-3,5-difluoropyridine-2-carboxamide, 52) N-[3-((4aR*,8aS*)-2-amino-4,4a,5,6,8,8a-hexahydro-7-oxa-3-thia-1-azanaphthalen-8a-yl)-4-fluorophenyl]-3,5-dichloropyridine-2-carboxamide, 53) N-[3-((4aR*,8aS*)-2-amino-4,4a,5,6,8,8a-hexahydro-7-oxa-3-thia-1-azanaphthalen-8a-yl)-4-fluorophenyl]-5-fluoropyridine-2-carboxamide, 54) N-[3-((4aR*,8aS*)-2-amino-4,4a,5,6,8,8a-hexahydro-7-oxa-3-thia-1-azanaphthalen-8a-yl)-4-fluorophenyl]-3,5-dibromopyridine-2-carboxamide, 55) N-[3-((4aR*,8aS*)-2-amino-4,4a,5,6,8,8a-hexahydro-7-oxa-3-thia-1-azanaphthalen-8a-yl)-4-fluorophenyl]-5-trifluoromethylpyridine-2-carboxamide, 56) N-[3-((4aR*,8aS*)-2-amino-4,4a,5,6,8,8a-hexahydro-7-oxa-3-thia-1-azanaphthalen-8a-yl)-4-fluorophenyl]-5-difluoromethylpyridine-2-carboxamide, 57) N-[3-((4aR*,8aS*)-2-amino-4,4a,5,6,8,8a-hexahydro-7-oxa-3-thia-1-azanaphthalen-8a-yl)-4-fluorophenyl]-5-difluoromethylpyrazine-2-carboxamide, 58) N-[3-((4aR*,8aS*)-2-amino-4,4a,5,6,8,8a-hexahydro-7-oxa-3-thia-1-azanaphthalen-8a-yl)-4-fluorophenyl]-5-difluoromethoxypyridine-2-carboxamide, 59) (±)-(4aR*,6R*,8aS*)-8a-[2-fluoro-5-(2-fluoropyridin-3-yl)phenyl]-6-trifluoromethyl-4,4a,5,6,8,8a-hexahydro-7-oxa-3-thia-1-azanaphthalen-2-ylamine, 60) (4aR,6R,8aS)-8a-[2-fluoro-5-(2-fluoropyridin-3-yl)phenyl]-6-fluoromethyl-4,4a,5,6,8,8a-hexahydro-7-oxa-3-thia-1-azanaphthalen-2-ylamine, 61) (±)-(4aR*,8aS*)-8a-[2-fluoro-5-(2-fluoropyridin-3-yl)phenyl]-4,4a,5,6,8,8a-hexahydro-7-oxa-3-thia-1-azanaphthalen-2-ylamine, 62) (±)-(4aR*,8aS*)-8a-(2-fluoro-5-pyrimidin-5-ylphenyl)-4,4a,5,6,8,8a-hexahydro-7-oxa-3-thia-1-azanaphthalen-2-ylamine, 63) (±)-(4aR*,8aS*)-8a-[5-(5-chloropyridin-3-yl)-2-fluorophenyl]-4,4a,5,6,8,8a-hexahydro-7-oxa-3-thia-1-azanaphthalen-2-ylamine, 64) N-[5-((4aR*,8aS*)-2-amino-4,4a,5,6,8,8a-hexahydro-7-oxa-3-thia-1-azanaphthalen-8a-yl)thiophen-3-yl]-5-cyanopyridine-2-carboxamide, 65) (±)-(4aR*,8aR*)-8a-[4-(2-fluoropyridin-3-yl)-thiophen-2-yl]-4,4a,5,6,8,8a-hexahydro-7-oxa-3-thia-1-azanaphthalen-2-ylamine, 66) (4aR,6R,8aS)-8a-[2-fluoro-5-(2-fluoropyridin-3-yl)phenyl]-6-benzyloxymethyl-4,4a,5,6,8,8a-hexahydro-7-oxa-3-thia-1-azanaphthalen-2-ylamine, 67) (±)-N-[7-((4aR*,8aS*)-2-amino-4,4a,5,6,8,8a-hexahydro-7-oxa-3-thia-1-azanaphthalen -8a-yl)-2,2-difluorobenzo[1,3]dioxol-5-yl]-5-cyanopyridine-2-carboxamide, 68) N-[3-((4aR*,8aS*)-2-amino-4,4a,5,6,8,8a-hexahydro-7-oxa-3-thia-1-azanaphthalen-8a-yl)-4-fluorophenyl]-5-(2-methoxyethoxy)-pyrazine-2-carboxamide, 69) N-[3-((4aR*,8aS*)-2-amino-4,4a,5,6,8,8a-hexahydro-7-oxa-3-thia-1-azanaphthalen-8a-yl)-4-fluorophenyl]-2-methylthiazole-4-carboxamide, 70) N-[3-((4aR*,5R*,8aS*)-2-amino-5-methyl-4,4a,5,6,8,8a-hexahydro-7-oxa-3-thia-1-azanaphthalen -8a-yl)-4-fluorophenyl]-2,5-dimethylfuran-3-carboxamide, 71) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-4-methyl-[1,2,3]thiadiazole-5-carboxamide, 72) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-3-piperidin-1-ylpropionamide and 73) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-2-methyloxazole-4-carboxamide,
or a pharmaceutically acceptable salt thereof, or a solvate thereof;

[11] A pharmaceutical composition comprising the compound or pharmaceutically acceptable salt thereof, or solvate thereof according to any one of [1] to [10] above as an active ingredient;

[12] The pharmaceutical composition according to [11] above for inhibiting production of amyloid-β protein;

[13] The pharmaceutical composition according to [11] above for inhibiting beta-site amyloid-β precursor protein cleaving enzyme 1 (BACE1);

[14] The pharmaceutical composition according to any one of [11] to [13] above for treating a neurodegenerative disease; and

[15] The pharmaceutical composition according to [14] above, wherein the neurodegenerative disease is Alzheimer-type dementia or Down's syndrome.

The present invention can provide a compound represented by the general formula:

[Formula 6]

(I)

wherein Ring A is a $C_{6-14}$ aryl group or the like, L is —NR$^L$CO— or the like (wherein R$^L$ is a hydrogen atom or the like), Ring B is a $C_{6-14}$ aryl group or the like, X is a $C_{1-3}$ alkylene group or the like, Y is a $C_{1-3}$ alkylene group or the like, Z is an oxygen atom or the like, R$^1$ and R$^2$ are each independently a hydrogen atom or the like, and R$^3$, R$^4$, R$^5$ and R$^6$ are independently a hydrogen atom, a halogen atom or the like, or a pharmaceutically acceptable salt thereof, or a solvate thereof. The compound of the present invention has an Aβ production inhibitory effect or a BACE1 inhibitory effect and is useful as a therapeutic agent for a neurodegenerative disease caused by Aβ and typified by Alzheimer-type dementia.

DETAILED DESCRIPTION OF THE INVENTION

Meanings of symbols, terms and the like used in the present specification will be explained and the present invention will be described in detail below.

In the present specification, a structural formula of a compound may represent a certain isomer for convenience. However, the present invention includes all isomers and isomer mixtures such as geometric isomers which can be generated from the structure of a compound, optical isomers based on asymmetric carbon, stereoisomers and tautomers. The present invention is not limited to the description of a chemical formula for convenience and may include any one of the isomers or mixtures thereof. Accordingly, the compound of the present invention may have an asymmetric carbon atom in the molecule and exist as an optically active compound or racemate, and the present invention includes each of the optically active compound and the racemate without limitations. Although crystal polymorphs of the compound may be present, the compound is similarly not limited thereto and may be present as a single crystal form or a mixture of single crystal forms. The compound may be an anhydride or a hydrate. Any of these forms is included in the claims of the present specification.

The "halogen atom" herein refers to a fluorine atom, a chlorine atom, a bromine atom, an iodine atom or the like and is preferably a fluorine atom or a chlorine atom.

The "$C_{1-6}$ alkyl group" refers to an alkyl group having 1 to 6 carbon atoms. Preferable examples of the group include linear or branched alkyl groups such as a methyl group, an ethyl group, an n-propyl group, an isopropyl group, an n-butyl group, an isobutyl group, a t-butyl group, an n-pentyl group, an isopentyl group, a neopentyl group, an n-hexyl group, a 1-methylpropyl group, an 1,2-dimethylpropyl group, a 1-ethylpropyl group, a 1-methyl-2-ethylpropyl group, a 1-ethyl-2-methylpropyl group, a 1,1,2-trimethylpropyl group, a 1-methylbutyl group, a 2-methylbutyl group, a 1,1-dimethylbutyl group, a 2,2-dimethylbutyl group, a 2-ethylbutyl group, a 1,3-dimethylbutyl group, a 2-methylpentyl group and a 3-methylpentyl group. The group is more preferably a methyl group, an ethyl group or an n-propyl group.

The "$C_{2-6}$ alkenyl group" refers to an alkenyl group having 2 to 6 carbon atoms. Preferable examples of the group include linear or branched alkenyl groups such as a vinyl group, an allyl group, a 1-propenyl group, an isopropenyl group, a 1-buten-1-yl group, a 1-buten-2-yl group, a 1-buten-3-yl group, a 2-buten-1-yl group and a 2-buten-2-yl group.

The "$C_{2-6}$ alkynyl group" refers to an alkynyl group having 2 to 6 carbon atoms. Preferable examples of the group include linear or branched alkynyl groups such as an ethynyl group, a 1-propynyl group, a 2-propynyl group, a butynyl group, a pentynyl group and a hexynyl group.

The "$C_{1-6}$ alkoxy group" refers to an alkyl group having 1 to 6 carbon atoms in which one hydrogen atom is replaced by an oxygen atom. Examples of the group include a methoxy group, an ethoxy group, an n-propoxy group, an isopropoxy group, an n-butoxy group, an isobutoxy group, a sec-butoxy group, a t-butoxy group, an n-pentoxy group, an isopentoxy group, a sec-pentoxy group, a t-pentoxy group, an n-hexoxy group, an isohexoxy group, a 1,2-dimethylpropoxy group, a 2-ethylpropoxy group, a 1-methyl-2-ethylpropoxy group, a 1-ethyl-2-methylpropoxy group, a 1,1,2-trimethylpropoxy group, a 1,1-dimethylbutoxy group, a 2,2-dimethylbutoxy group, a 2-ethylbutoxy group, a 1,3-dimethylbutoxy group, a 2-methylpentoxy group, a 3-methylpentoxy group and a hexyloxy group.

The "$C_{1-6}$ alkylthio group" refers to an alkyl group having 1 to 6 carbon atoms in which one hydrogen atom is replaced by a sulfur atom. Examples of the group include a methylthio group, an ethylthio group, an n-propylthio group, an isopropylthio group, an n-butylthio group, an isobutylthio group, a t-butylthio group, an n-pentylthio group, an isopentylthio group, a neopentylthio group, an n-hexylthio group and a 1-methylpropylthio group.

The "$C_{1-6}$ alkylsulfonyl group" refers to an alkyl group having 1 to 6 carbon atoms in which one hydrogen atom is replaced by a sulfonyl group. Examples of the group include a methylsulfonyl group, an ethylsulfonyl group, an n-propylsulfonyl group, an isopropylsulfonyl group, an n-butylsulfonyl group, an isobutylsulfonyl group, a t-butylsulfonyl group, an n-pentylsulfonyl group, an isopentylsulfonyl group, a neopentylsulfonyl group, an n-hexylsulfonyl group and a 1-methylpropylsulfonyl group.

The "$C_{1-6}$ alkylcarbonyl group" refers to an alkyl group having 1 to 6 carbon atoms in which one hydrogen atom is replaced by a carbonyl group. Preferable examples of the group include an acetyl group, a propionyl group and a butyryl group.

The "$C_{6-14}$ aryl group" refers to an aromatic hydrocarbon ring group having 6 to 14 carbon atoms. Examples of the group include a phenyl group, a naphthyl group and an anthryl group. A phenyl group is particularly preferable.

The "$C_{7-12}$ aralkyl group" refers to a group having 7 to 12 carbon atoms in which an aromatic ring such as a phenyl group or a naphthyl group is substituted with a C1-6 alkyl group. Examples of the group include a benzyl group, a phenethyl group, a phenylpropyl group and a naphthylmethyl group. A benzyl group is particularly preferable.

The "$C_{6-14}$ aryloxycarbonyl group" refers to a group in which carbonyl is bonded to an aromatic ring phenol having 6 to 14 carbon atoms. Preferable examples of the group include a phenyloxycarbonyl group, a naphthyloxycarbonyl group and an anthryloxycarbonyl group. A phenyloxycarbonyl group is more preferable.

The "$C_{6-14}$ arylcarbonyl group" refers to a group in which a carbonyl group is bonded to an aromatic ring having 6 to 14 carbon atoms. Preferable examples of the group include a benzoyl group and a naphthoyl group. A benzoyl group is more preferable.

The "$C_{6-14}$ arylsulfonyl group" refers to a group in which a sulfonyl group is bonded to an aromatic ring having 6 to 14 carbon atoms. Preferable examples of the group include a benzenesulfonyl group and a naphthylsulfonyl group. A benzenesulfonyl group is more preferable.

The "$C_{3-8}$ cycloalkyl group" refers to a cyclic alkyl group having 3 to 8 carbon atoms. Preferable examples of the group include a cyclopropyl group, a cyclobutyl group, a cyclopentyl group, a cyclohexyl group, a cycloheptyl group and a cyclooctyl group.

The "$C_{3-8}$ cycloalkoxy group" refers to a cyclic alkyl group having 3 to 8 carbon atoms in which one hydrogen atom is replaced by an oxygen atom. Examples of the group include a cyclopropoxy group, a cyclobutoxy group, a cyclopentoxy group, a cyclohexoxy group, a cycloheptyloxy group and a cyclooctyloxy group.

The "$C_{3-8}$ cycloalkylthio group" refers to a cyclic alkyl group having 3 to 8 carbon atoms in which one hydrogen atom is replaced by a sulfur atom. Examples of the group include a cyclopropylthio group, a cyclobutylthio group, a cyclopentylthio group, a cyclohexylthio group, a cycloheptylthio group and a cyclooctylthio group.

The "5- to 10-membered heterocyclic group" refers to a heteroatom-containing cyclic group having 5 to 10 members in total. Preferable examples of the group include a piperidinyl group, a pyrrolidinyl group, an azepinyl group, an azocanyl group, a piperazinyl group, a 1,4-diazepanyl group, a morpholinyl group, a thiomorpholinyl group, a pyrrolyl group, an imidazolyl group, a pyrazolyl group, a pyridinyl group, a pyridazinyl group, a pyrimidinyl group, a pyrazinyl group, a triazolyl group, a triazinyl group, a tetrazolyl group, an isoxazolyl group, an oxazolyl group, an oxadiazolyl group, an isothiazolyl group, a triazolyl group, a thiadiazolyl group, a furyl group, a thienyl group, a quinolinyl group, an isoquinolinyl group, a benzofuryl group, a benzopyranyl group, a benzimidazolyl group, a benzotriazolyl group, a benzisothiazolyl group, an indolinyl group, an isoindolinyl group, a chromanyl group, an isochromanyl group, a 1,3-dioxaindanyl group, a 1,4-dioxatetralinyl group, a tetrahydrofuranyl group and a tetrahydropyranyl group.

The "5- to 6-membered heteroaryl group" refers to the "5- to 10-membered heterocyclic group" which is a heteroatom-containing aromatic cyclic group having 5 to 6 members in total. Examples of the group include a pyrrolyl group, an imidazolyl group, a pyrazolyl group, a pyridinyl group, a pyridazinyl group, a pyrimidinyl group, a pyrazinyl group, a triazolyl group, a triazinyl group, a tetrazolyl group, an isoxazolyl group, an oxazolyl group, an oxadiazolyl group, an isothiazolyl group, a triazolyl group, a thiadiazolyl group, a furyl group and a thienyl group.

The "9- to 10-membered benzo-fused heterocyclic group" refers to the "5- to 10-membered heterocyclic group" which is a heteroatom-containing cyclic group having 9 to 10 members in total fused with a benzene ring. Preferable examples of the group include an indolinyl group, an isoindolinyl group, a chromanyl group, an isochromanyl group, a 1,3-dioxaindanyl group and a 1,4-dioxatetralinyl group.

The "3- to 10-membered carbocyclic group" refers to a carbocyclic group having 3 to 10 members in total. Preferable examples of the group include a cyclopropyl group, a cyclobutyl group, a cyclopentyl group, a cyclohexyl group, a cycloheptyl group, a cyclooctyl group, a spiro[3.4]octanyl group, a decanyl group, an indanyl group, a 1-acenaphthenyl group, a cyclopentacyclooctenyl group, a benzocyclooctenyl group, an indenyl group, a tetrahydronaphthyl group, a 6,7,8,9-tetrahydro-5H-benzocycloheptenyl group and a 1,4-dihydronaphthalenyl group.

The "$C_{1-6}$ alkylene group" refers to a divalent group derived by excluding any one hydrogen atom from the "$C_{1-6}$ alkyl group" as defined above. Examples of the group include a methylene group, a 1,2-ethylene group, a 1,1-ethylene group, a 1,3-propylene group, a tetramethylene group, a pentamethylene group and a hexamethylene group.

The "$C_{2-6}$ alkenylene group" refers to a divalent group derived by excluding any one hydrogen atom from the "$C_{2-6}$ alkenyl group" as defined above. Examples of the group include a 1,2-vinylene group (ethenylene group), a propenylene group, a butenylene group, a pentenylene group and a hexenylene group.

The "$C_{2-6}$ alkynylene group" refers to a divalent group derived by excluding any one hydrogen atom from the "$C_{2-6}$ alkynyl group" as defined above. Examples of the group include an ethynylene group, a propynylene group, a butynylene group, a pentynylene group and a hexynylene group.

Examples of the "$C_{1-3}$ alkylene group" include a methylene group, an ethylene group and a propylene group.

Examples of the "$C_{2-3}$ alkynylene group" include an ethynylene group and a propynylene group.

Examples of the sulfonylamino group which may be substituted with a $C_{1-6}$ alkyl group in the "sulfonylamino group (wherein the sulfonylamino group may be substituted with a $C_{1-6}$ alkyl group)" include a methylsulfonylmethylamino group, an ethylsulfonylmethylamino group and an ethylsulfonylethylamino group.

"Substituent Group α" refers to a hydrogen atom, a halogen atom, a hydroxy group, a nitro group, a $C_{1-6}$ alkylthio group, a $C_{6-14}$ aryl group, a $C_{6-14}$ aryloxycarbonyl group, a $C_{6-14}$ arylcarbonyl group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group may be substituted with 1 to 2 $C_{1-6}$ alkyl groups), a $C_{2-6}$ alkenyl group which may have 1 to 2 substituents selected from Substituent Group β, a $C_{2-6}$ alkynyl group which may have 1 to 2 substituents selected from Substituent Group β, a carbamoyl group which may be substituted with 1 to 2 $C_{1-6}$ alkyl groups, a $C_{1-6}$ alkoxy group which may have 1 to 3 substituents selected from Substituent Group β, a $C_{1-6}$ alkyl group which may have 1 to 3 substituents selected from Substituent Group β and a 5- to 10-membered heterocyclic group which may have 1 to 3 substituents selected from Substituent Group β.

"Substituent Group β" refers to a halogen atom, a cyano group, a hydroxy group and a $C_{1-6}$ alkoxy group (wherein the alkoxy group may be substituted with a phenyl group which may be substituted with 1 to 3 substituents selected from a hydrogen atom, a halogen atom, a hydroxy group and a nitro group).

The fused aminodihydrothiazine derivative of the formula (I) according to the present invention may be a pharmaceutically acceptable salt. Specific examples of the pharmaceutically acceptable salt include inorganic acid salts (such as sulfates, nitrates, perchlorates, phosphates, carbonates, bicarbonates, hydrofluorides, hydrochlorides, hydrobromides and hydroiodides), organic carboxylates (such as acetates, oxalates, maleates, tartrates, fumarates and citrates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

The fused aminodihydrothiazine derivative of the formula (I) or pharmaceutically acceptable salt thereof according to the present invention may be a solvate thereof. Examples of the solvate include a hydrate.

The compound (I) is not limited to a specific isomer and includes all possible isomers (such as a keto-enol isomer, an imine-enamine isomer, a diastereoisomer, an optical isomer and a rotamer) and racemates. For example, the compound (I) wherein $R^1$ is hydrogen includes the following tautomers.

[Formula 7]

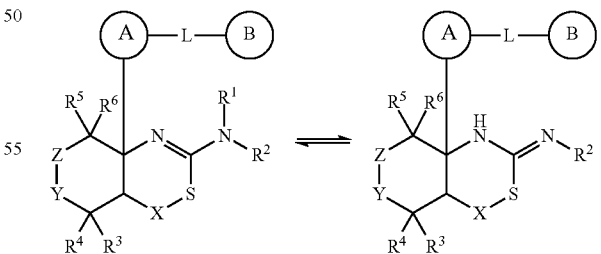

The fused aminodihydrothiazine derivative of the formula (I) according to the present invention is preferably a compound of the formula (I), wherein X is a methylene group which may have 1 to 2 substituents selected from Substituent Group α.

The fused aminodihydrothiazine derivative of the formula (I) according to the present invention is also preferably a compound of the formula (I), wherein Z is an oxygen atom and Y is a $C_{1-3}$ alkylene group which may have 1 to 3 substituents selected from Substituent Group α; or Z is a sulfur atom or a sulfone and Y is a $C_{1-3}$ alkylene group which may have a substituent selected from Substituent Group α.

The fused aminodihydrothiazine derivative of the formula (I) according to the present invention is further preferably a compound of the formula (I), wherein L is —NR$^L$CO— (wherein R$^L$ is a hydrogen atom or a $C_{1-6}$ alkyl group which may have 1 to 3 substituents selected from Substituent Group α).

Preferable compounds in the present invention include the following compounds:

1) N-[3-((4aR*,8aS*)-2-amino-4,4a,5,6,8,8a-hexahydro-7-oxa-3-thia-1-azanaphthalen-8a-yl)-4-fluorophenyl]-5-cyanopyridine-2-carboxamide, 2) N-[3-((8aR*)-2-amino-4,4a,5,6,8,8a-hexahydro-7-oxa-3-thia-1-azanaphthalen-8a-yl)-4-fluorophenyl]-5-fluoromethoxypyrazine-2-carboxamide, 3) N-[3-((4aR*,8aS*)-2-amino-4,4a,5,6,8,8a-hexahydro-7-oxa-3-thia-1-azanaphthalen-8a-yl)-4-fluorophenyl]-5-difluoromethoxypyrazine-2-carboxamide, 4) N-[3-((4aR*,8aS*)-2-amino-4,4a,5,6,8,8a-hexahydro-7-oxa-3-thia-1-azanaphthalen-8a-yl)-4-trifluoromethoxyphenyl]-5-cyanopyridine-2-carboxamide, 5) N-[3-((8aS*)-2-amino-4,4a,5,6,8,8a-hexahydro-7-oxa-3-thia-1-azanaphthalen-8a-yl)-4-trifluoromethoxyphenyl]-5-chloropyridine-2-carboxamide, 6) N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-chloropyridine-2-carboxamide, 7) N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-cyanopyridine-2-carboxamide, 8) N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-trifluoromethylpyridine-2-carboxamide, 9) N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-difluoromethoxypyrazine-2-carboxamide, 10) N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-fluoromethoxypyrazine-2-carboxamide, 11) N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-cyanopyridine-2-carboxamide, 12) N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-difluoromethylpyrazine-2-carboxamide, 13) N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-chloropyridine-2-carboxamide, 14) N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-fluoromethoxypyrazine-2-carboxamide, 15) N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-difluoromethoxypyrazine-2-carboxamide, 16) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-cyanopyridine-2-carboxamide, 17) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-difluoromethylpyrazine-2-carboxamide, 18) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-chloropyridine-2-carboxamide, 19) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-trifluoromethylpyridine-2-carboxamide, 20) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-difluoromethoxypyridine-2-carboxamide, 21) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-fluoromethoxypyrazine-2-carboxamide, 22) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-difluoromethoxypyrazine-2-carboxamide, 23) N-[3-((4aR*,5S*,8aS*)-2-amino-5-methyl-4,4a,5,6,8,8a-hexahydro-7-oxa-3-thia-1-azanaphthalen-8a-yl)-4-fluorophenyl]-5-chloropyridine-2-carboxamide, 24) N-[3-((4aR*,5S*,8aS*)-2-amino-5-methyl-4,4a,5,6,8,8a-hexahydro-7-oxa-3-thia-1-azanaphthalen-8a-yl)-4-fluorophenyl]-5-cyanopyridine-2-carboxamide, 25) N-[3-((4aR*,5S*,8aS*)-2-amino-5-methyl-4,4a,5,6,8,8a-hexahydro-7-oxa-3-thia-1-azanaphthalen-8a-yl)-4-fluorophenyl]-5-difluoromethoxypyrazine-2-carboxamide, 26) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-chloropyridine-2-carboxamide, 27) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-cyanopyridine-2-carboxamide, 28) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-difluoromethoxypyrazine-2-carboxamide, 29) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-difluoromethylpyrazine-2-carboxamide, 30) N-[3-((4aS*,5R*,8aS*)-2-amino-5-methoxy-4,4a,5,6,8,8a-hexahydro-7-oxa-3-thia-1-azanaphthalen-8a-yl)-4-fluorophenyl]-5-cyanopyridine-2-carboxamide, 31) N-[3-((2R*,4aR*,8aS*)-2-amino-4-methyl-4,4a,5,6,8,8a-hexahydro-7-oxa-3-thia-1-azanaphthalen-8a-yl)-4-fluorophenyl]-5-cyanopyridine-2-carboxamide, 32) N-[3-((2R*,4aR*,8aS*)-2-amino-4-methyl-4,4a,5,6,8,8a-hexahydro-7-oxa-3-thia-1-azanaphthalen-8a-yl)-4-fluorophenyl]-5-difluoromethylpyrazine-2-carboxamide, 33) N-[3-((4aR,6R,8aS)-2-amino-6-hydroxymethyl-4,4a,5,6,8,8a-hexahydro-7-oxa-3-thia-1-azanaphthalen-8a-yl)-4-fluorophenyl]-5-chloropyridine-2-carboxamide, 34) N-[3-((4aR,6R,8aS)-2-amino-6-hydroxymethyl-4,4a,5,6,8,8a-hexahydro-7-oxa-3-thia-1-azanaphthalen-8a-yl)-4-fluorophenyl]-5-cyanopyridine-2-carboxamide, 35) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-cyanopyridine-2-carboxamide, 36) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-difluoromethoxypyrazine-2-carboxamide, 37) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-fluoropyridine-2-carboxamide, 38) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-pyridine-2-carboxamide, 39) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-fluoromethoxypyrazine-2-carboxamide, 40) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-pyrimidine-4-carboxamide, 41) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-3,5-difluoropyridine-2-carboxamide, 42) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-difluoromethoxypyridine-2-carboxamide, 43) N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-difluoromethylpyrazine-2-carboxamide, 44) N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-cyanopyridine-2-carboxamide, 45) N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-chloropyridine-2-carboxamide, 46) N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-trifluoromethylpyridine-2-carboxamide, 47) N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-fluoromethoxypyrazine-2-carboxamide, 48) N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-difluoromethylpyrazine-2-carboxamide, 49) N-[3-((4aR*,8aS*)-2-amino-4,4a,5,6,8,8a-hexahydro-7-oxa-3-thia-1-azanaphthalen-8a-yl)-4-fluorophenyl]-5-chloropyridine-2-carboxamide, 50) N-[3-((4aR*,8aS*)-2-amino-4,4a,5,6,8,8a-hexahydro-7-oxa-3-thia-1-azanaphthalen -8a-yl)-4-fluorophenyl]-5-bromopyridine-2-carboxamide, 51) N-[3-((4aR*,8aS*)-2-amino-4,4a,5,6,8,8a-hexahydro-7-oxa-3-thia-1-azanaphthalen-8a-yl)-4-fluorophenyl]-3,5-difluoropyridine-2-carboxamide, 52) N-[3-((4aR*,8aS*)-2-amino-4,4a,5,6,8,8a-hexahydro-7-oxa-3-thia-1-azanaphthalen-8a-yl)-4-fluorophenyl]-3,5-dichloropyridine-2-carboxamide, 53) N-[3-((4aR*,8aS*)-2-amino-4,4a,5,6,8,8a-hexahydro-7-oxa-3-thia-1-azanaphthalen-8a-yl)-4-fluorophenyl]-5-fluoropyridine-2-carboxamide, 54) N-[3-((4aR*,8aS*)-2-amino-4,4a,5,6,8,8a-hexahydro-7-oxa-3-thia-1-azanaphthalen-8a-yl)-4-fluorophenyl]-3,5-dibromopyridine-2-carboxamide, 55) N-[3-((4aR*,8aS*)-2-amino-4,4a,5,6,8,8a-hexahydro-7-oxa-3-thia-1-azanaphthalen-8a-yl)-4-fluorophenyl]-5-trifluoromethylpyridine-2-carboxamide, 56) N-[3-((4aR*,8aS*)-2-amino-4,4a,5,6,8,8a-hexahydro-7-oxa-3-thia-1-azanaphthalen-8a-yl)-4-fluorophenyl]-5-difluoromethylpyridine-2-carboxamide, 57) N-[3-((4aR*,8aS*)-2-amino-4,4a,5,6,8,8a-hexahydro-7-oxa-3-thia-1-azanaphthalen-8a-yl)-4-fluorophenyl]-5-difluoromethylpyrazine-2-carboxamide, 58) N-[3-((4aR*,8aS*)-2-amino-4,4a,5,6,8,8a-hexahydro-7-oxa-3-thia-1-azanaphthalen-8a-yl)-4-fluorophenyl]-5-difluoromethoxypyridine-2-carboxamide, 59) (±)-(4aR*,6R*,8aS*)-8a-[2-fluoro-5-(2-fluoropyridin-3-yl)phenyl]-6-trifluoromethyl-4,4a,5,6,8,8a-hexahydro-7-oxa-3-thia-1-azanaphthalen-2-ylamine, 60) (4aR,6R,8aS)-8a-[2-fluoro-5-(2-fluoropyridin-3-yl)phenyl]-6-fluoromethyl-4,4a,5,6,8,8a-hexahydro-7-oxa-3-thia-1-azanaphthalen-2-ylamine, 61) (±)-(4aR*,8aS*)-8a-[2-fluoro-5-(2-fluoropyridin-3-yl)phenyl]-4,4a,5,6,8,8a-hexahydro-7-oxa-3-thia-1-azanaphthalen-2-ylamine, 62) (±)-(4aR*,8aS*)-8a-(2-fluoro-5-pyrimidin-5-ylphenyl)-4,4a,5,6,8,8a-hexahydro-7-oxa-3-thia-1-azanaphthalen-2-ylamine, 63) (±)-(4aR*,8aS*)-8a-[5-(5-chloropyridin-3-yl)-2-fluorophenyl]-4,4a,5,6,8,8a-hexahydro-7-oxa-3-thia-1-azanaphthalen-2-ylamine, 64) N-[5-((4aR*,8aS*)-2-amino-4,4a,5,6,8,8a-hexahydro-7-oxa-3-thia-1-azanaphthalen-8a-yl)thiophen-3-yl]-5-cyanopyridine-2-carboxamide, 65) (±)-(4aR*,8aR*)-8a-[4-(2-fluoropyridin-3-yl)-thiophen-2-yl]-4,4a,5,6,8,8a-hexahydro-7-oxa-3-thia-1-azanaphthalen-2-ylamine, 66) (4aR,6R,8aS)-8a-[2-fluoro-5-(2-fluoropyridin-3-yl)phenyl]-6-benzyloxymethyl-4,4a,5,6,8,8a-hexahydro-7-oxa-3-thia-1-azanaphthalen-2-ylamine, 67) (±)-N-[7-((4aR*,aS*)-2-amino-4,4a,5,6,8,8a-hexahydro-7-oxa-3-thia-1-azanaphthalen-8a-yl)-2,2-difluorobenzo[1,3]dioxol-5-yl]-5-cyanopyridine-2-carboxamide, 68) N-[3-((4aR*,8aS*)-2-amino-4,4a,5,6,8,8a-hexahydro-7-oxa-3-thia-1-azanaphthalen-8a-yl)-4-fluorophenyl]-5-(2-methoxyethoxy)-pyrazine-2-carboxamide, 69) N-[3-((4aR*,8aS*)-2-amino-4,4a,5,6,8,8a-hexahydro-7-oxa-3-thia-1-azanaphthalen-8a-yl)-4-fluorophenyl]-2-methylthiazole-4-carboxamide, 70) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-2,5-dimethylfuran-3-carboxamide, 71) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-4-methyl-[1,2,3]thiadiazole-5-carboxamide, 72) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-3-piperidin-1-ylpropionamide, and 73) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-2-methyloxazole-4-carboxamide.

Next, methods for preparing the compound of the formula (I) [hereinafter referred to as compound (I); a compound represented by another formula is similarly described] or pharmaceutically acceptable salt thereof according to the present invention will be described.

The "leaving group" in the raw material compound used in preparation of the compound of the formula (I) according to the present invention may be any leaving group used for nucleophilic substitution reaction. Preferable examples of the leaving group include a halogen atom, a $C_{1-6}$ alkylsulfonyloxy group which may be substituted with the above Substituent Group α and an arylsulfonyloxy group which may be substituted with the above Substituent Group α. Specific examples of the leaving group include a chlorine atom, a bromine atom, an iodine atom, a methanesulfonyloxy group, a trifluoromethanesulfonyloxy group and a p-toluenesulfonyloxy group.

1. General Preparation Method 1:

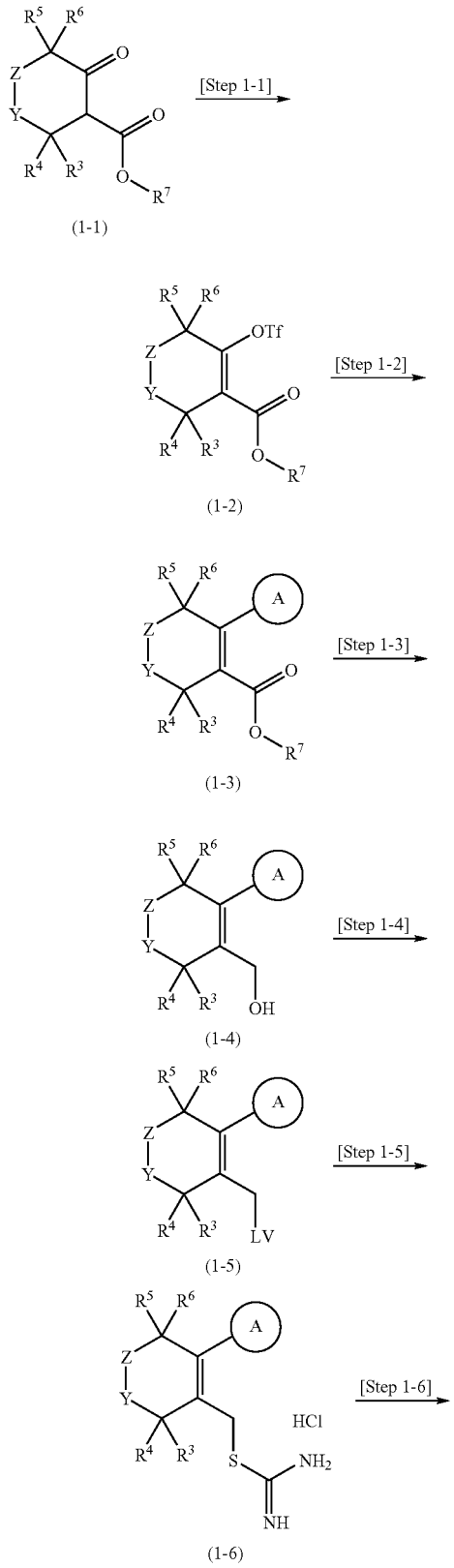

[Formula 8]

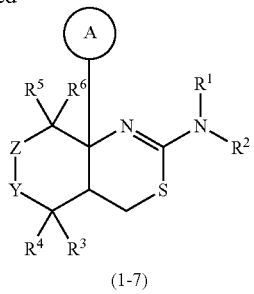

In the formula, $R^7$ represents a $C_{1-6}$ alkyl group such as a methyl group or an ethyl group, a $C_{7-12}$ aralkyl group such as a benzyl group, or the like, LV is a leaving group and represents a halogen atom (such as a chlorine atom, a bromine atom or an iodine atom), for example, or a sulfonyloxy group such as a methanesulfonyloxy group, a p-toluenesulfonyloxy group or a trifluoromethanesulfonyloxy group, for example, and Ring A, $R^1$, $R^2$, $R^3$, $R^4$, $R^5$, $R^6$, Y and Z are as defined above.

General Preparation Method 1 is a method for preparing a compound (1-7) which is a synthetic intermediate of the compound (I) according to the present invention from a compound (1-1) as a raw material through multiple steps of Step 1-1 to Step 1-6.

The compound (1-1) can be a commercially available product used as is, can also be prepared from a commercially available product by a method known to a person skilled in the art, and can further be prepared by a method described in Preparation Examples among Examples.

1-1. Step 1-1:

This step is a step of obtaining a compound (1-2) by trifluoromethanesulfonylation of the compound (1-1).

The reaction in this step can be performed under the same conditions as those usually used in trifluoromethanesulfonylation reaction of a carbonyl compound (such as the conditions described in J. Org. Chem., 57, 6972-6975 (1992), Tetrahedron Letters., 40, 8133-8136 (1999) and Tetrahedron., 61, 4129-4140 (2005)).

Specifically, the compound (1-2) can be obtained by causing a base to act on the compound (1-1), and then reacting the compound with N-phenyltrifluoromethanesulfonimide or trifluoromethanesulfonic anhydride, for example. This reaction can be performed by causing one or more equivalents of a base to act on the compound (1-1) in an organic solvent such as ether, tetrahydrofuran, 1,4-dioxane, 1,2-dimethoxyethane, dichloromethane, 1,2-dichloroethane, benzene or toluene, for example. Examples of the base used include sodium hydride, LDA (lithium diisopropylamide), lithium bis(trimethylsilyl) amide, diisopropylethylamine, pyridine and 2,6-lutidine. The reaction time is not particularly limited and is usually 5 minutes to 24 hours, and preferably 5 minutes to 12 hours. The reaction temperature is usually −100° C. to room temperature, and more preferably −78° C. to room temperature.

1-2. Step 1-2:

This step is a step of obtaining a compound (1-3) by coupling reaction of the compound (1-2) using a transition metal.

This reaction can be performed under the conditions usually used in coupling reaction using a transition metal (such as Suzuki coupling reaction or Stille coupling reaction).

Examples of the reaction using an organoboron reagent as an organometallic compound include reactions in documents such as Tetrahedron: Asymmetry 16 (2005) 2, 529-539 and Org. Lett. 6 (2004) 2, 277-279. Examples of the reaction using an organotin reagent include reaction in a document such as Tetrahedron 61 (2005) 16, 4129-4140. Examples of the reaction using an organozinc reagent as an organometallic compound include reaction in a document such as Tetrahedron 61 (2005) 16, 4129-4140. The organometallic catalyst used in this reaction is not particularly limited. Preferable examples of the organometallic catalyst include tetrakis(triphenylphosphine)palladium (0), dichlorobis(triphenylphosphine)palladium (II), [1,1'-bis(diphenylphosphino)ferrocene]palladium (II) dichloride, bis(tert-butylphosphine) palladium (0), palladium (II) acetate and [1,3-bis(diphenylphosphino)propane]nickel (II). The amount of the organometallic catalyst used is about 0.001 to 0.1 equivalent with respect to the raw material. The organometallic compound is not particularly limited. Preferable examples of the organometallic compound include organotin reagents such as aryltri-n-butyltin, and organoboron reagents such as arylboronic acid. The amount of the organometallic compound used is one to five equivalents with respect to the raw material. The solvent used in this reaction is not particularly limited insofar as it does not inhibit the reaction. Preferable examples of the solvent include benzene, toluene, xylene, N,N-dimethylformamide, 1-methyl-2-pyrrolidone, tetrahydrofuran, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 48 hours, and preferably 0.5 to 24 hours.

A more preferable result such as an improved yield may be achieved by carrying out this reaction in the presence of a base. Such a base is not particularly limited. Preferable examples of the base include bases such as sodium carbonate, potassium carbonate, cesium carbonate, potassium phosphate and solutions thereof, and triethylamine.

1-3. Step 1-3:

This step is a step of obtaining an alcohol compound (1-4) by subjecting the ester compound (1-3) to reduction reaction. The alcohol compound (1-4) can be obtained from the ester compound (1-3) by a method known to a person skilled in the art.

Examples of the reducing agent used in the reaction include lithium aluminum hydride, lithium borohydride and diisobutylaluminum hydride. The reaction temperature is not particularly limited and is usually −78° C. to solvent reflux temperature, and preferably −78° C. to room temperature. The solvent used in the reaction is not particularly limited insofar as it does not inhibit the reaction and allows the starting material to be dissolved therein to a certain extent. Preferable examples of the solvent include tetrahydrofuran, diethyl ether, toluene and dichloromethane.

1-4. Step 1-4:

This step is a step of obtaining a compound (1-5) by converting the hydroxyl group of the compound (1-4) to a leaving group.

Examples of the leaving group include halogen atoms (such as a chlorine atom, a bromine atom and an iodine atom) and sulfonyloxy groups such as a methanesulfonyloxy group, a p-toluenesulfonyloxy group and a trifluoromethanesulfonyloxy group.

The reaction can be performed under the same conditions as those usually used in reaction of converting a hydroxyl group to such a leaving group. When the leaving group is a halogen atom, for example, the compound (1-5) can be prepared by reacting the compound (1-4) with thionyl chloride, thionyl bromide, phosphorus tribromide or tetrahalogenomethane-triphenylphosphine, for example. The solvent used in the reaction is not particularly limited insofar as it does not inhibit the reaction and allows the starting material to be dissolved therein to a certain extent. Preferable examples of the solvent include benzene, toluene, xylene, dichloromethane and chloroform. The reaction temperature is usually −78° C. to solvent reflux temperature, and preferably ice-cold temperature to solvent reflux temperature. The reaction time is not particularly limited and is usually 5 minutes to 48 hours, and preferably 5 minutes to 12 hours.

When the leaving group is a sulfonyloxy group, the compound (1-5) can be prepared by reacting the compound (1-4) with methanesulfonyl chloride, p-toluenesulfonyl chloride or trifluoromethanesulfonic anhydride, for example.

The solvent used in the reaction is not particularly limited insofar as it does not inhibit the reaction and allows the starting material to be dissolved therein to a certain extent. Preferable examples of the solvent include tetrahydrofuran, toluene, xylene, dichloromethane, chloroform and N,N-dimethylformamide. The reaction temperature is usually −78° C. to solvent reflux temperature, and preferably—78° C. to room temperature. A favorable result such as an improved yield may be achieved by addition of a base. The base used is not particularly limited insofar as it does not inhibit the reaction. Preferable examples of the base include sodium carbonate, potassium carbonate, triethylamine, pyridine and diisopropylethylamine.

1-5. Step 1-5:

This step is a step of obtaining a compound (1-6) from the compound (1-5). The thiourea compound (1-6) can be obtained from the compound (1-5) by a method known to a person skilled in the art.

Specifically, the compound (1-6) can be obtained by reacting the compound (1-5) with thiourea in a solvent, for example. This reaction can be performed by causing one or more equivalents of thiourea to act on the compound (1-5) in an organic solvent such as ethanol, 1-propanol, 2-propanol, 1-butanol, tetrahydrofuran, 1,4-dioxane or N,N-dimethylformamide, for example. The reaction time is not particularly limited and is usually 5 minutes to 24 hours, and preferably 5 minutes to 12 hours. The reaction temperature is usually 0° C. to 150° C., and more preferably room temperature to 100° C.

1-6. Step 1-6:

This step is a method of obtaining the compound (1-7) by cyclizing the compound (1-6) with an acid.

This reaction is not particularly limited insofar as it does not inhibit the reaction and allows the starting material to be dissolved therein to a certain extent. For example, the reaction can be performed by causing one equivalent to a large excess of an appropriate acid to act on the compound in the presence or absence of a solvent such as benzene, toluene or dichloromethane. Further, an acid may also be used as a solvent. Examples of the acid used include sulfuric acid, trifluoroacetic acid, methanesulfonic acid, trifluoromethanesulfonic acid and mixtures thereof. The reaction time is not particularly limited and is usually 1 to 72 hours, and preferably 1 to 48 hours. The reaction temperature is usually ice-cold temperature to solvent reflux temperature.

The compound (1-7), wherein both $R^1$ and $R^2$ are hydrogen atoms, can be obtained by the above reaction. The compound (1-7), wherein both $R^1$ and $R^2$ are hydrogen atoms, can be converted to the compound (1-7), wherein at least one of $R^1$ and $R^2$ is substituted with a substituent, by further reaction with a corresponding halide compound or the like such as a $C_{1-6}$ alkyl halide, a $C_{1-6}$ alkylcarbonyl halide, a $C_{6-14}$ arylcarbonyl halide, a $C_{1-6}$ alkylsulfonyl halide, a $C_{6-14}$ arylsulfonyl halide, a 3- to 10-membered carbocyclic halide or a 5- to 10-membered heterocyclic halide.

2. General Preparation Method 2:

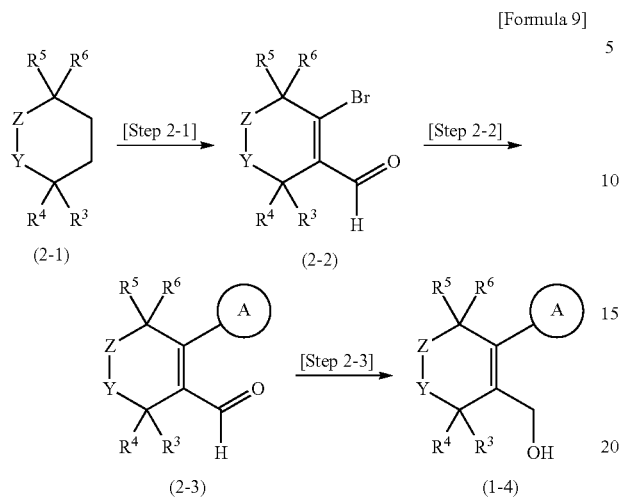

[Formula 9]

In the formula, Ring A, R³, R⁴, R⁵, R⁶, Y and Z are as defined above.

General Preparation Method 2 is a method for preparing a compound of the general formula (1-4) which is a synthetic intermediate of the compound (I) according to the present invention from a compound (2-1) as a raw material through multiple steps of Step 2-1 to Step 2-3.

The compound (2-1) can be a commercially available product used as is, can also be prepared from a commercially available product by a method known to a person skilled in the art, and can further be prepared by a method described in Preparation Examples among Examples.

2-1. Step 2-1:

This step is a step of obtaining a compound (2-2) from the compound (2-1). This reaction can be performed under the same conditions as those usually used in reaction of synthesizing a compound (2-2) from a carbonyl compound (such as the conditions described in J. Org. Chem., 47, 3597-3607 (1982)).

2-2. Step 2-2:

This step is a step of synthesizing a compound (2-3) from the compound (2-2) as a raw material using a method described in the above preparation method (Step 1-2).

2-3. Step 2-3:

This step is a step of obtaining the alcohol compound (1-4) by subjecting the aldehyde compound (2-3) to reduction reaction.

The alcohol compound (1-4) can be obtained from the aldehyde compound (2-3) by a method known to a person skilled in the art. Examples of the reducing agent used in the reaction include sodium borohydride, sodium cyanoborohydride and sodium triacetoxyborohydride. The reaction temperature is not particularly limited and is usually −78° C. to solvent reflux temperature, and preferably −20° C. to room temperature. The solvent used in the reaction is not particularly limited insofar as it does not inhibit the reaction and allows the starting material to be dissolved therein to a certain extent. Preferable examples of the solvent include methanol, ethanol, tetrahydrofuran, ether, toluene and dichloromethane.

3. General Preparation Method 3:

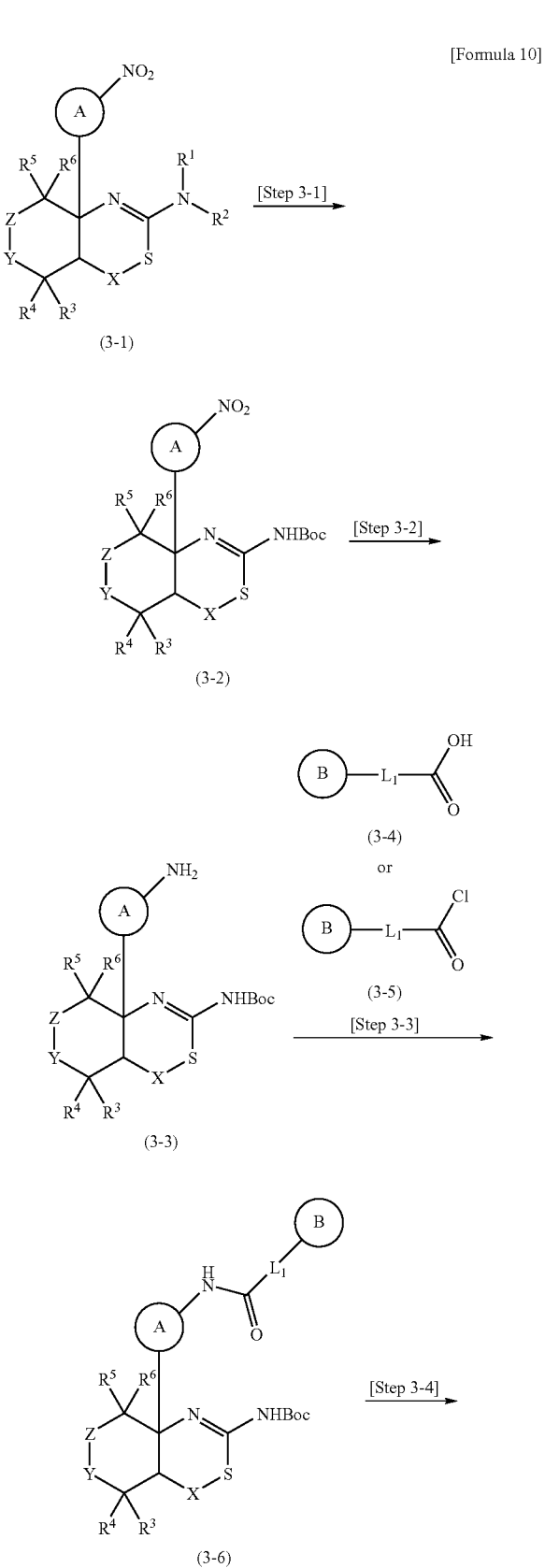

[Formula 10]

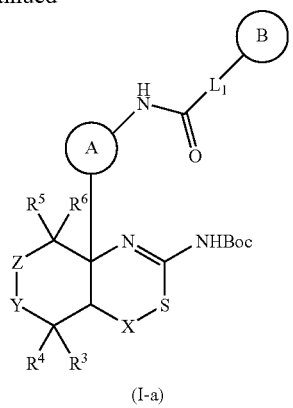

(I-a)

In the formula, $L_1$ represents a single bond or a $C_{1-6}$ alkyl group and Ring A, $R^1$, $R^2$, $R^3$, $R^4$, $R^5$, $R^6$, X, Y, Z and Ring B are as defined above.

General Preparation Method 3 is a method for preparing the compound of the general formula (I) according to the present invention, wherein L is a —NHCO—$C_{1-6}$ alkyl group and $R^1$ and $R^2$ are hydrogen atoms, from a compound (3-1) as a raw material through multiple steps of Step 3-1 to Step 3-4.

The compound (3-1) can be prepared from a commercially available product by General Preparation Method 1, General Preparation Method 2, General Preparation Method 4 or a combination of these three methods, and can also be prepared by a method described in Preparation Examples among Examples. Compounds (3-4) and (3-5) can be commercially available products used directly, can also be prepared from a commercially available product by a method known to a person skilled in the art, and can further be prepared by a method described in Preparation Examples among Examples.

3-1. Step 3-1:

This step is a step of obtaining a compound (3-2) by t-butoxycarbonylation of the amino group of the compound (3-1) when $R^1$ and $R^2$ are both hydrogen.

The reaction can be performed under the same conditions as those generally used in t-butoxycarbonylation of an amino compound such as the conditions described in a document such as T. W. Green and P. G. M. Wuts, "Protective Groups in Organic Chemistry, Second Edition", John Wiley & Sons (1991), p. 327-330. The compound (3-2) can be obtained by reacting the compound (3-1) with di-tert-butyl dicarbonate using triethylamine as a base in a solvent such as tetrahydrofuran, for example.

3-2. Step 3-2:

This step is a step of obtaining a compound (3-3) from the compound (3-2).

The compound (3-3) is synthesized by reducing the nitro compound (3-2) by a synthesis method known to a person skilled in the art. Examples of the method include reduction by catalytic hydrogenation using a noble metal catalyst such as Raney nickel, palladium, ruthenium, rhodium or platinum. In this case, reduction reaction with iron under neutral conditions using ammonium chloride is preferable, for example.

3-3. Step 3-3:

This step is a step of obtaining a compound (3-6) by condensing the compound (3-3) with the compound (3-4) using a condensing agent. Alternatively, this step is a step of obtaining a compound (3-6) by condensing the compound (3-3) with the compound (3-5) by acylation reaction.

The condensation reaction of the compound (3-3) with the compound (3-4) using a condensing agent can be performed under the same conditions as those usually used and described in the following documents. Examples of the known method include those in Rosowsky, A.; Forsch, R. A.; Moran, R. G.; Freisheim, J. H.; J. Med. Chem., 34 (1), 227-234 (1991), Brzostwska, M.; Brossi, A.; Flippen-Anderson, J. L.; Heterocycles, 32 (10), 1969-1972 (1991), and Romero, D. L.; Morge, R. A.; Biles, C.; Berrios-Pena, N.; May, P. D.; Palmer, J. R.; Johnson, P. D.; Smith, H. W.; Busso, M.; Tan, C.-K.; Voorman, R. L.; Reusser, F.; Althaus, I. W.; Downey, K. M.; So, A. G.; Resnick, L.; Tarpley, W. G., Aristoff, P. A.; J. Med. Chem., 37 (7), 999-1014 (1994).

The compound (3-3) may be a free form or a salt.

The solvent in this reaction is not particularly limited insofar as it does not inhibit the reaction. Examples of the solvent include tetrahydrofuran, 1,4-dioxane, ethyl acetate, methyl acetate, dichloromethane, chloroform, N,N-dimethylformamide, toluene and xylene. Examples of the condensing agent include CDI (N,N'-carbonyldiimidazole), Bop (1H-1,2,3-benzotriazol-1-yloxy(tri(dimethylamino))phosphonium hexafluorophosphate), WSC (1-ethyl-3-(3-dimethylaminopropyl)carbodiimide hydrochloride), DCC (N,N-dicyclohexylcarbodiimide), diethylphosphoryl cyanide, PyBOP (benzotriazol-1-yloxytris(pyrrolidino)phosphonium hexafluorophosphate) and EDC.HCl (1-ethyl-3-(3-dimethylaminopropyl)carbodiimide hydrochloride). One equivalent to a large excess of the compound (3-4) is used with respect to the compound (3-3). One equivalent to a large excess of an organic base such as triethylamine may be added where necessary.

The reaction time is not particularly limited and is usually 0.5 to 48 hours, and preferably 0.5 to 24 hours. The reaction temperature varies according to the raw material used, the solvent and the like and is not particularly limited. Ice-cold temperature to solvent reflux temperature is preferable.

3-4. Step 3-4:

This step is a step of obtaining the compound (I-a) by deprotection reaction of the t-butoxycarbonyl group of the compound (3-6).

The reaction can be performed under the same conditions as those generally used in deprotection reaction of a t-butoxycarbonyl group such as the conditions described in a document such as T. W. Green and P. G. M. Wuts, "Protective Groups in Organic Chemistry, Second Edition", John Wiley & Sons (1991), p. 327-330. The compound (I-a) can be obtained by reacting trifluoroacetic acid with the compound (3-6) in a solvent such as dichloromethane, for example.

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{3-8}$ hydrocarbon ring group which may have 1 to 3 substituents selected from Substituent Group α or a 5- to 10-membered heterocyclic group which may have 1 to 3 substituents selected from Substituent Group α, can be obtained by further reacting the compound (I-a) obtained in General Preparation Method 3 with a corresponding halide compound or the like such as a $C_{1-6}$ alkyl halide. Alternatively, the compound of the formula (I) according to the present invention, wherein L is —NR$^L$CO— (wherein R$^L$ is a $C_{1-6}$ alkyl group which may have 1 to 3 substituents selected from Substituent Group α), can be obtained by further reacting the compound (I-a) obtained in General Preparation Method 3 with a corresponding halide compound or the like such as a $C_{1-6}$ alkyl halide.

The compound of the formula (I) according to the present invention, wherein L is —$NR^LSO_2$— (wherein $R^L$ is a hydrogen atom), can be obtained using a corresponding sulfonyl compound or sulfonyl halide compound in place of the compound (3-4) or (3-5) used in General Preparation Method 3. The compound of the formula (I) according to the present invention, wherein L is —$NR^LSO_2$— (wherein $R^L$ is a $C_{1-6}$ alkyl group which may have 1 to 3 substituents selected from Substituent Group α), can be obtained by further reacting this compound with a corresponding halide compound or the like such as a $C_{1-6}$ alkyl halide.

In Step 3-3 of General Preparation Method 3, the compound (3-6) can also be prepared from the compound (3-3) and the compound (3-4) by a method described in the following alternative method (1) or (2).

Alternative Method (1):

The compound (3-6) can be obtained by converting the compound (3-4) to a mixed acid anhydride and then reacting the mixed acid anhydride with the compound (3-3). The mixed acid anhydride can be synthesized by a means known to a person skilled in the art. The synthesis is performed by reacting the compound (3-4) with a chloroformate such as ethyl chloroformate in the presence of a base such as triethylamine, for example. One to two equivalents of the chloroformate and the base are used with respect to the compound (3-4). The reaction temperature is −30° C. to room temperature, and preferably −20° C. to room temperature.

The step of condensing the mixed acid anhydride with the compound (3-3) is performed by reacting the mixed acid anhydride with the compound (3-3) in a solvent such as dichloromethane, tetrahydrofuran or N,N-dimethylformamide, for example. One equivalent to a large excess of the compound (3-3) is used with respect to the mixed acid anhydride.

The reaction time is not particularly limited and is usually 0.5 to 48 hours, and preferably 0.5 to 12 hours. The reaction temperature is −20° C. to 50° C., and preferably −20° C. to room temperature.

Alternative Method (2):

The compound (3-6) can be obtained by converting the compound (3-4) to an active ester and then reacting the active ester with the compound (3-3). The step of obtaining the active ester is performed by reacting the compound (3-4) with an active ester synthesis reagent in a solvent such as 1,4-dioxane, tetrahydrofuran or N,N-dimethylformamide in the presence of a condensing agent such as DCC, for example. Examples of the active ester synthesis reagent include N-hydroxysuccinimide. One to 1.5 equivalents of the active ester synthesis reagent and the condensing agent are used with respect to the compound (3-4). The reaction time is not particularly limited and is usually 0.5 to 48 hours, and preferably 0.5 to 24 hours.

The reaction temperature is −20° C. to 50° C., and preferably −20° C. to room temperature.

The step of condensing the active ester with the compound (3-3) is performed by reacting the active ester with the compound (3-3) in a solvent such as dichloromethane, tetrahydrofuran or N,N-dimethylformamide, for example. One equivalent to a large excess of the compound (3-3) is used with respect to the active ester. The reaction time is not particularly limited and is usually 0.5 to 48 hours, and preferably 0.5 to 24 hours. The reaction temperature is −20° C. to 50° C., and preferably −20° C. to room temperature.

In this acylation reaction, the compound (3-6) can be obtained from the compounds (3-3) and (3-5) by a method known to a person skilled in the art.

Examples of the base used in the reaction include triethylamine, pyridine, potassium carbonate and diisopropylethylamine. The reaction temperature is not particularly limited and is usually −78° C. to solvent reflux temperature, and preferably −20° C. to room temperature. The solvent used in the reaction is not particularly limited insofar as it does not inhibit the reaction and allows the starting material to be dissolved therein to a certain extent. Preferable examples of the solvent include tetrahydrofuran, ether, toluene and dichloromethane.

4. General Preparation Method 4:

[Formula 11]

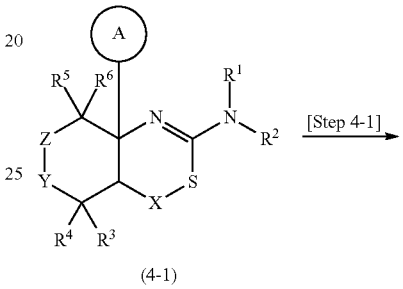

(4-1)

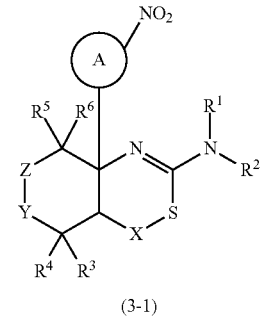

(3-1)

In the formula, Ring A, $R^3$, $R^2$, $R^3$, $R^4$, $R^5$, $R^6$, X, Y and Z are as defined above.

General Preparation Method 4 is a method for preparing a compound of the general formula (3-1) which is a synthetic intermediate of the compound according to the present invention from a compound (4-1) as a raw material through Step 4-1.

The compound (4-1) can be prepared from a commercially available product by General Preparation Method 1, General Preparation Method 2, General Preparation Method 5 or a combination of these methods, and can also be prepared by a method described in Preparation Examples among Examples.

4-1. Step 4-1:

This step is a step of obtaining the compound (3-1) by nitration reaction of the compound (4-1). In this nitration reaction, the compound (3-1) can be obtained from the compound (4-1) by a method known to a person skilled in the art. Examples of the nitrating agent used in the reaction include potassium nitrate/concentrated sulfuric acid and fuming nitric acid/acetic anhydride. The reaction temperature is not particularly limited and is usually −20° C. to room temperature.

5. General Preparation Method 5:

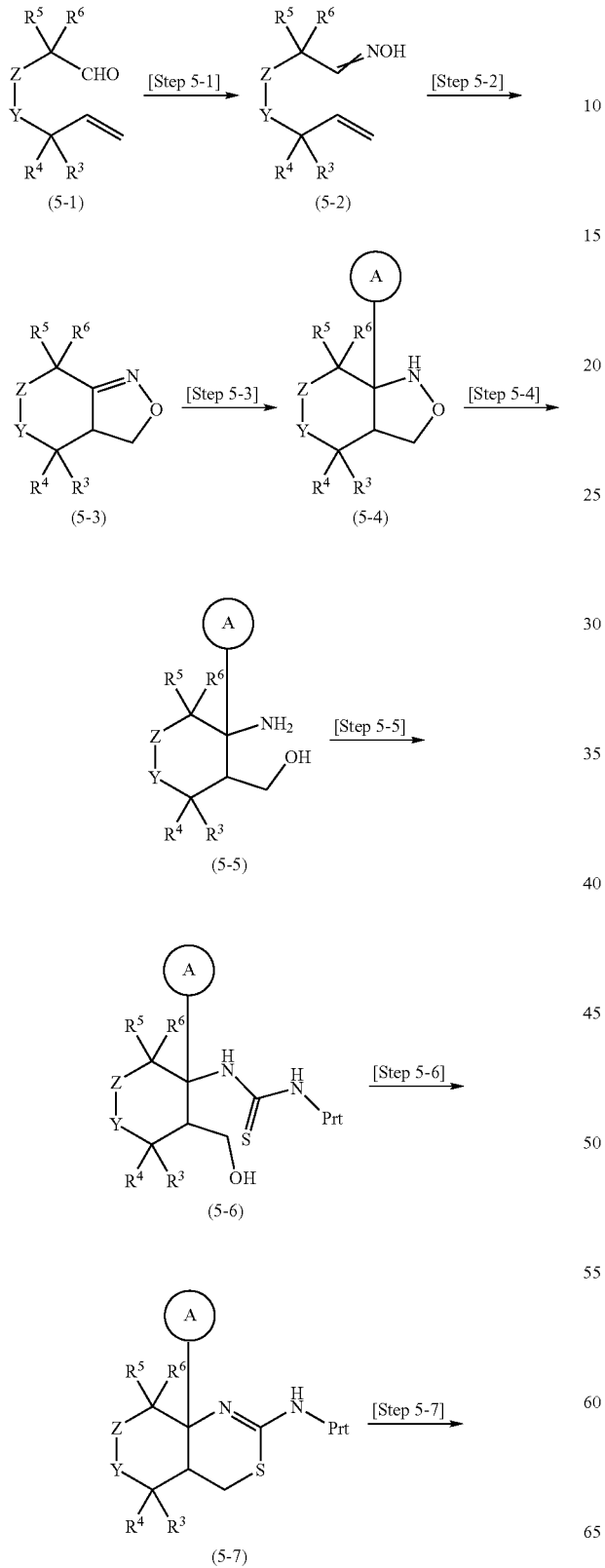

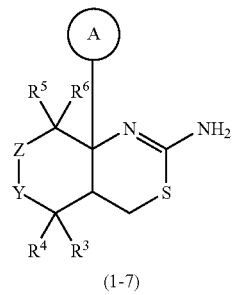

(1-7)

In the formula, Prt represents a protecting group such as a benzoyl group, an acetyl group or a 9-fluorenemethyloxycarbonyl group (Fmoc group), and Ring A, $R^3$, $R^4$, $R^5$, $R^6$, Y and Z are as defined above.

General Preparation Method 5 is a method for preparing a compound (1-7) which is a synthetic intermediate of the compound (I) according to the present invention from a compound (5-1) as a raw material through multiple steps of Step 5-1 to Step 5-7.

The compound (5-1) can be prepared from a commercially available product by a method known to a person skilled in the art, and can further be prepared by a method described in Preparation Examples among Examples.

5-1. Step 5-1:

This step is a step of obtaining a compound (5-2) by oximation of the compound (5-1).

The reaction in this step can be performed under the same conditions as those usually used in oximation reaction of a carbonyl compound such as the conditions described in Org. Lett. 9 (2007) 5, 753-756, Tetrahedron: Asymmetry 5 (1994) 6, 1018-1028 and Tetrahedron 54 (1998) 22, 5869-5882.

Specifically, the compound (5-2) can be obtained by reacting the compound (5-1) with hydroxylamine or a hydroxylamine salt (such as hydroxylamine hydrochloride or hydroxylamine sulfate) in the presence of a base or in the absence of a base, for example.

The solvent used in this reaction is not particularly limited insofar as it does not inhibit the reaction. Preferable examples of the solvent include organic solvents such as ethanol, methanol, tetrahydrofuran, 1,4-dioxane, 1,2-dimethoxyethane and dichloromethane, and mixtures of these solvents and water. Examples of the base used include sodium acetate, pyridine, sodium hydroxide, cesium hydroxide, barium hydroxide and 2,6-lutidine. The reaction time is not particularly limited and is usually 5 minutes to 24 hours, and preferably 5 minutes to 12 hours. The reaction temperature is usually −20° C. to solvent reflux temperature, and more preferably 0° C. to solvent reflux temperature.

5-2. Step 5-2:

This step is a step of obtaining a compound (5-3) by converting the compound (5-2) to a nitrile oxide derivative and performing 1,3-dipolar cycloaddition reaction with the olefin moiety in the same molecule.

The reaction in this step can be performed under the same conditions as those usually used in 1,3-dipolar cycloaddition reaction such as the conditions described in a document such as Org. Lett. 9 (2007) 5, 753-756, Tetrahedron: Asymmetry 5 (1994) 6, 1018-1028 and Tetrahedron 54 (1998) 22, 5869-5882. Examples of the reagent for converting the oxime compound to the nitrile oxide include N-chlorosuccinimide and sodium hypochlorite. The solvent used in this reaction is not particularly limited insofar as it does not inhibit the reaction. Preferable examples of the solvent include dichloromethane, chloroform, benzene, toluene, xylene, N,N-dimethylformamide, tetrahydrofuran and 1,4-dioxane. The reaction temperature is not particularly limited and is usually ice-cold temperature to solvent reflux temperature. The reaction time is not particularly limited and is usually 0.5 to 48 hours, and preferably 0.5 to 24 hours.

A more preferable result such as an improved yield may be achieved by carrying out this reaction in the presence of a base. Such a base is not particularly limited. Examples of the base include bases such as sodium carbonate, potassium carbonate, cesium carbonate, potassium phosphate and solutions thereof, and triethylamine and pyridine.

5-3. Step 5-3:

This step is a step of obtaining a compound (5-4) by addition reaction of an aryllithium reagent (including heterocyclic) or a Grignard reagent (including heterocyclic) with the compound (5-3).

The reaction in this step can be performed under the same conditions as those described in J. Am. Chem. Soc. 2005, 127, 5376-5383, Bull. Chem. Soc. Jpn., 66, 2730-2737 (1993) and SYNLETT. 2004, No. 8, pp 1409-1413, for example.

The aryllithium reagent (including heterocyclic) or the Grignard reagent (including heterocyclic) can be prepared by a method known to a person skilled in the art. Specifically, a corresponding aryl (including heterocyclic) lithium reagent or aryl (including heterocyclic) magnesium reagent can be prepared by halogen-metal exchange between an aryl halide compound and a commercially available organometallic reagent such as an alkyllithium reagent such as n-, sec- or tert-butyllithium or a Grignard reagent such as isopropylmagnesium bromide, or metallic magnesium, for example.

The solvent used in this step varies according to the starting material and the reagent used, and is not particularly limited insofar as it does not inhibit the reaction, allows the starting material to be dissolved therein to a certain extent, and is always inert during the reaction. Preferable examples of the solvent include organic solvents such as diethyl ether, tetrahydrofuran, 1,4-dioxane, 1,2-dimethoxyethane, benzene and toluene, and mixed solvents thereof. The reaction time is not particularly limited and is usually 0.1 to 48 hours, and preferably 0.1 to 12 hours. The reaction temperature varies according to the starting material, the reagent used and the like, and is preferably maintained to be low, for example, at −78° C. to minimize formation of a by-product.

Favorable results such as an improved yield and a reduced reaction time may be achieved by addition of TMEDA (tetramethylethylenediamine), HMPA (hexamethylphosphoramide) or a Lewis acid such as a boron trifluoride-diethyl ether complex (BF3.OEt2) as an additive, for example.

5-4. Step 5-4:

This step is a step of obtaining a compound (5-5) by subjecting the compound (5-4) to reductive cleavage reaction of the N—O bond.

The reductive cleavage reaction of the N—O bond can be performed under the conditions using zinc-acetic acid, a metal catalyst such as hydrogen-platinum oxide, or lithium aluminum hydride, for example.

The reaction using zinc such as zinc-acetic acid can be performed under the same conditions as those described in J. Org. Chem. 2003, 68, 1207-1215 and Org. Lett. 7 (2005) 25, 5741-5742, for example. Examples of the acid used include acetic acid, formic acid and hydrochloric acid. The solvent used in the reaction is not particularly limited insofar as it does not inhibit the reaction and allows the starting material to be dissolved therein to a certain extent. Examples of the solvent include methanol, ethanol, 1,4-dioxane, THF and water. The above acid may also be used as a solvent. The reaction temperature is usually −20° C. to solvent reflux temperature, and preferably ice-cold temperature to solvent reflux temperature. The reaction time is not particularly limited and is usually 5 minutes to 48 hours, and preferably 5 minutes to 24 hours.

The reaction using a metal catalyst such as hydrogen-platinum oxide can be performed under the same conditions as those described in Tetrahedron: Asymmetry 5 (1994) 6, 1019-1028 and Tetrahedron, Vol. 53, No. 16, pp 5752-5746, 1997, for example. The compound (5-5) can be obtained by hydrogenating the compound (5-4) using platinum oxide as a catalyst in a solvent such as methanol, for example.

The reaction using lithium aluminum hydride can be performed under the same conditions as those described in Bull. Chem. Soc. Jpn., 66, 2730-2737 (1993), for example. The compound (5-5) can be obtained by reducing the compound (5-4) using lithium aluminum hydride in a solvent such as ether, for example.

5-5. Step 5-5:

This step is a step of obtaining a compound (5-6) from the compound (5-5). The thiourea derivative (5-6) can be obtained from the compound (5-5) by a method known to a person skilled in the art.

When the protecting group is a benzoyl group, the compound (5-6) can be obtained in this step by reacting the compound (5-5) with benzoyl isothiocyanate in a solvent such as dichloromethane or toluene. This reaction can be performed under the same conditions as those described in J. Org. Chem. 1994, 59, 1912-1917, for example. The solvent used in the reaction is not particularly limited insofar as it does not inhibit the reaction and allows the starting material to be dissolved therein to a certain extent. Examples of the solvent include dichloromethane, chloroform, toluene, methanol, ethanol, 1,4-dioxane and THF. The reaction temperature is usually −20° C. to solvent reflux temperature, and preferably ice-cold temperature to solvent reflux temperature. The reaction time is not particularly limited and is usually 5 minutes to 48 hours, and preferably 5 minutes to 24 hours.

When the protecting group is a 9-fluorenemethyloxycarbonyl group (Fmoc group), the compound (5-6) can be obtained in this step by reacting the compound (5-5) with fluorenemethyloxycarbonyl isothiocyanate in a solvent such as dichloromethane or toluene. This reaction can be performed under the same conditions as those described in J. Org. Chem. 1998, 63, 196-200, for example. The solvent used in the reaction is not particularly limited insofar as it does not inhibit the reaction and allows the starting material to be dissolved therein to a certain extent. Examples of the solvent include dichloromethane, chloroform, toluene, methanol, ethanol, 1,4-dioxane and THF. The reaction temperature is usually −20° C. to solvent reflux temperature, and preferably ice-cold temperature to solvent reflux temperature. The reaction time is not particularly limited and is usually 5 minutes to 48 hours, and preferably 5 minutes to 24 hours.

5-6. Step 5-6:

This step is a method of obtaining a compound (5-7) by cyclizing the compound (5-6).

In this reaction, the compound (5-6) can be cyclized under various conditions to obtain the compound (5-7) by selecting a protecting group of the compound (5-6).

When the protecting group is an Fmoc group or a benzoyl group, for example, the compound (5-7) can be obtained in this reaction by heating the compound (5-6) in a solvent such as methanol in the presence of an acid such as concentrated hydrochloric acid, for example. The solvent used in the reaction is not particularly limited insofar as it does not inhibit the reaction and allows the starting material to be dissolved therein to a certain extent. Examples of the solvent include solvents such as methanol, ethanol, 1-propanol and water, mixed solvents thereof, and acids used as a solvent. The reaction can be performed by causing one equivalent to a large excess of an appropriate acid to act in the presence or absence of such a solvent. Examples of the acid used include concentrated hydrochloric acid, hydrobromic acid, sulfuric acid, trifluoroacetic acid, methanesulfonic acid, trifluoromethanesulfonic acid and mixtures thereof. The reaction time is not particularly limited and is usually 0.5 to 72 hours, and preferably 0.5 to 24 hours. The reaction temperature is usually ice-cold temperature to solvent reflux temperature.

When the protecting group is an Fmoc group or a benzoyl group, the compound (5-7) can be obtained by an alternative method 1 of reacting the compound (5-6) with trifluoromethanesulfonic anhydride in a solvent such as dichloromethane in the presence of a base such as pyridine. This reaction can be performed under the same conditions as those described in Chem Bio Chem. 2005, 6, 186-191, for example. The solvent used in the reaction is not particularly limited insofar as it does not inhibit the reaction and allows the starting material to be dissolved therein to a certain extent. Examples of the solvent include solvents such as dichloromethane, 1,2-dichloroethane, THF, 1,2-dimethoxyethane and toluene, and mixed solvents thereof. The reaction can be performed using 1 to 20 equivalents of an appropriate base in such a solvent. Examples of the base used include pyridine, 2,6-lutidine, sodium carbonate, potassium carbonate and mixtures thereof. The reaction time is not particularly limited and is usually 0.5 to 24 hours, and preferably 0.5 to 12 hours. The reaction temperature is usually −78° C. to room temperature. When the protecting group is a benzoyl group, the compound (5-7) can be obtained by an alternative method 2 of reacting the compound (5-6) with triphenylphosphine and carbon tetrabromide (or bromine) in a solvent such as dichloromethane. The reaction conditions are the same as those of bromination of a primary alcohol which are known to a person skilled in the art.

5-7. Step 5-7:

This step is a method of obtaining the compound (1-7) by deprotecting the protecting group of the compound (5-7). The compound (1-7) can be obtained under deprotection conditions known to a person skilled in the art.

When the protecting group is an Fmoc group, for example, the compound (1-7) can be obtained under the same conditions as those generally used in deprotection of a protecting group of an amine compound (such as the conditions described in a document such as T. W. Green and P. G. M. Wuts, "Protective Groups in Organic Chemistry, Third Edition", John Wiley & Sons, p. 506-507 and J. Org. Chem. 1998, 63, 196-200). In this reaction, the compound (1-7) can be obtained by reacting the compound (5-7) with an excess of an amine such as pyrrolidine in a solvent such as acetonitrile, for example. The solvent used in the reaction is not particularly limited insofar as it does not inhibit the reaction and allows the starting material to be dissolved therein to a certain extent. Examples of the solvent include dichloromethane, THF and acetonitrile. The reaction can be performed by causing one equivalent to a large excess of an appropriate base to act in the presence of such a solvent. Examples of the base used include piperidine, morpholine, pyrrolidine, TBAF and DBU. The reaction time is not particularly limited and is usually 0.5 to 72 hours, and preferably 0.5 to 24 hours. The reaction temperature is usually ice-cold temperature to solvent reflux temperature.

Favorable results such as an improved yield and a reduced reaction time may be achieved by addition of a thiol compound such as 1-octanethiol as an additive, for example.

When the protecting group is a benzoyl group, the compound (1-7) can be obtained in this reaction by heating the compound (5-7) in a solvent such as methanol in the presence of a base such as DBU, for example. This reaction can be performed under the same conditions as those described in Synth. Commun. 32 (2), 265-272 (2002), for example. The solvent used in the reaction is not particularly limited insofar as it does not inhibit the reaction and allows the starting material to be dissolved therein to a certain extent. Examples of the solvent include solvents such as methanol, ethanol and 1-propanol. The reaction can be performed using 1 to 20 equivalents of an appropriate base in such a solvent. Examples of the base used include DBU. The reaction time is not particularly limited and is usually 0.5 to 24 hours, and preferably 0.5 to 12 hours. The reaction temperature is usually room temperature to solvent reflux temperature.

The compound of the formula (1-7), wherein at least one hydrogen atom of the amino group is a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{3-8}$ hydrocarbon ring group which may have 1 to 3 substituents selected from Substituent Group α or a 5- to 10-membered heterocyclic group which may have 1 to 3 substituents selected from Substituent Group α, can be obtained by further reacting the compound (1-7) obtained in General Preparation Method 5 with a corresponding halide compound or the like such as a $C_{1-6}$ alkyl halide.

6. General Preparation Method 6:

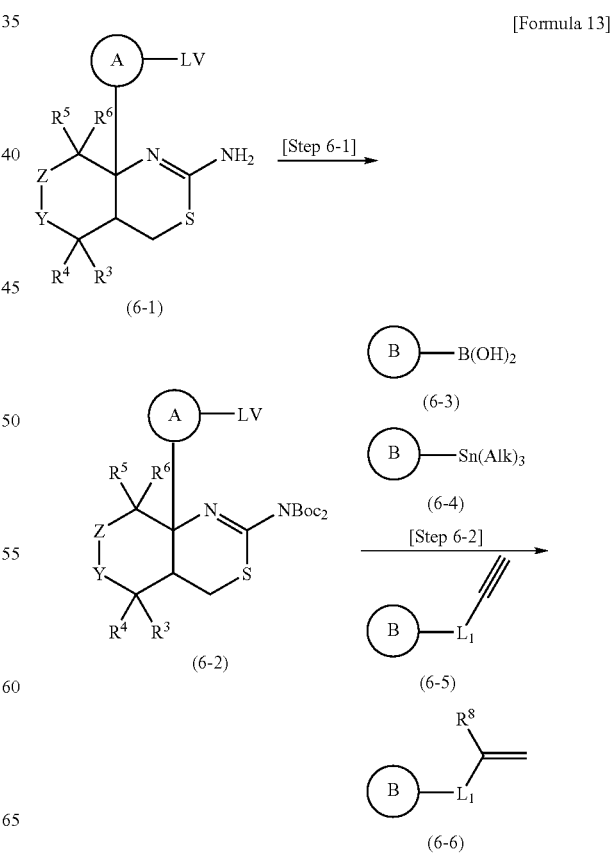

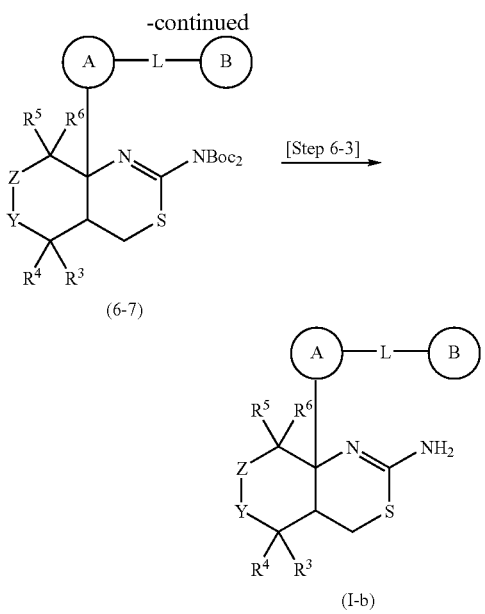

In the formula, Ring A, $R^3$, $R^4$, $R^5$, $R^6$, Y, Z, L, LV and Ring B are as defined above, Alk represents a C1-6 alkyl group, $R^8$ represents a hydrogen atom or a C1-4 alkyl group, and $L_1$ represents a single bond or a C1-4 alkyl group, provided that $R^8$ and $L_1$ in the compound (6-6) have up to four carbon atoms in total.

General Preparation Method 6 is a method for preparing the compound (I-b) of the general formula (I) according to the present invention, wherein L is a single bond, a C2-6 alkenylene group or a C2-6 alkynylene group and $R^1$ and $R^2$ are hydrogen atoms, from a compound (6-1) as a raw material through multiple steps of Step 6-1 to Step 6-3.

The compound (6-1) can be prepared from a commercially available product by General Preparation Method 1, General Preparation Method 5 or a combination of General Preparation Method 1 and General Preparation Method 11, and can also be prepared by a method described in Preparation Examples among Examples. The compounds (6-3), (6-4), (6-5) and (6-6) can be commercially available products used directly, can also be prepared from a commercially available product by a method known to a person skilled in the art, and can further be prepared by a method described in Preparation Examples among Examples.

6-1. Step 6-1:

This step is a step of obtaining a compound (6-2) by di-t-butoxycarbonylating the compound (6-1). This reaction can be performed under the same conditions as those generally used in t-butoxycarbonylation of an amide compound such as the conditions described in T. W. Green and P. G. M. Wuts, "Protective Groups in Organic Chemistry, Third Edition", John Wiley & Sons, P. 642-643 and J. Org. Chem. 2005, 70, 2445-2454. The compound (6-2) can be obtained by reacting the compound (6-1) with di-tert-butyl dicarbonate using 4-dimethylaminopyridine as a base in a solvent such as THF, for example.

The solvent used in this reaction is not particularly limited insofar as it does not inhibit the reaction. Preferable examples of the solvent include organic solvents such as tetrahydrofuran, 1,4-dioxane, 1,2-dimethoxyethane, dichloromethane, DMF and acetonitrile, and mixed solvents thereof. Examples of the base used include triethylamine, 4-dimethylaminopyridine, DBU and mixtures thereof. A catalytic amount to an excess of, and more preferably 0.1 to 5 equivalents of the base is used with respect to the compound (6-1). Two equivalents to an excess of, and more preferably 2 to 10 equivalents of di-tert-butyl dicarbonate is used with respect to the compound (6-1). The reaction time is not particularly limited and is usually 5 minutes to 24 hours, and preferably 5 minutes to 12 hours. The reaction temperature is usually –20° C. to solvent reflux temperature, and more preferably 0° C. to solvent reflux temperature.

6-2. Step 6-2:

This step is a step of obtaining a compound (6-7) by coupling reaction of the compound (6-2) with the compound (6-3), (6-4), (6-5) or (6-6) using a transition metal. This reaction can be performed under the conditions usually used in coupling reaction using a transition metal (such as Suzuki coupling reaction, Stille coupling reaction, Sonogashira reaction or Heck reaction).

Examples of the Suzuki coupling reaction include reactions in documents such as J. Org. Chem. 2007, 72, 7207-7213, J. Am. Chem. Soc. 2000, 122, 4020-4028 and J. Org. Chem. 2007, 72, 5960-5967. Examples of the Stille coupling reaction include reaction in a document such as J. Am. Chem. Soc. 1990, 112, 3093-3100. Examples of the Sonogashira reaction include reactions in documents such as J. Org. Chem. 2007, 72, 8547-8550 and J. Org. Chem. 2008, 73, 234-240. Examples of the Heck reaction include reaction in a document such as J. Am. Chem. Soc. 2005, 127, 16900-16911. The organometallic catalyst used in this reaction is not particularly limited. Preferable examples of the organometallic catalyst include metal catalysts such as tetrakis(triphenylphosphine)palladium (0), dichlorobis(triphenylphosphine)palladium (II), [1,1'-bis(diphenylphosphino)ferrocene]palladium (II) dichloride, bis(tert-butylphosphine)palladium (0), palladium (II) acetate and [1,3-bis(diphenylphosphino)propane]nickel (II), and mixtures of these metal catalysts. The amount of the organometallic catalyst used is about 0.001 to 0.5 equivalent with respect to the raw material. The amount of the compound (6-3), (6-4), (6-5) or (6-6) used is not particularly limited and is usually 1 to 5 equivalents with respect to the compound (6-2). The solvent used in this reaction is not particularly limited insofar as it does not inhibit the reaction. Preferable examples of the solvent include benzene, toluene, xylene, N,N-dimethylformamide, 1-methyl-2-pyrrolidone, tetrahydrofuran, 1,2-dimethoxyethane, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 48 hours, and preferably 0.5 to 24 hours.

A more preferable result such as an improved yield may be achieved by carrying out this reaction in the presence of a base or a salt. Such a base or salt is not particularly limited. Preferable examples of the base or salt include bases or salts such as sodium carbonate, potassium carbonate, barium hydroxide, cesium carbonate, potassium phosphate, potassium fluoride and solutions thereof, and triethylamine, N,N-diisopropylethylamine, lithium chloride and copper (I) iodide.

6-3. Step 6-3:

This step is a step of synthesizing the compound (I-b) from the compound (6-7) as a raw material using a method described in the above preparation method (Step 3-4).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{3-8}$ hydrocarbon ring group which may have 1 to 3 substituents selected from Substituent Group α or a 5- to 10-membered heterocyclic group which may have 1 to 3 substituents selected from Substituent Group α, can be obtained by further reacting the compound (I-b) obtained in General Preparation Method 6 with a corresponding halide compound or the like such as a $C_{1-6}$ alkyl halide.

7. General Preparation Method 7:

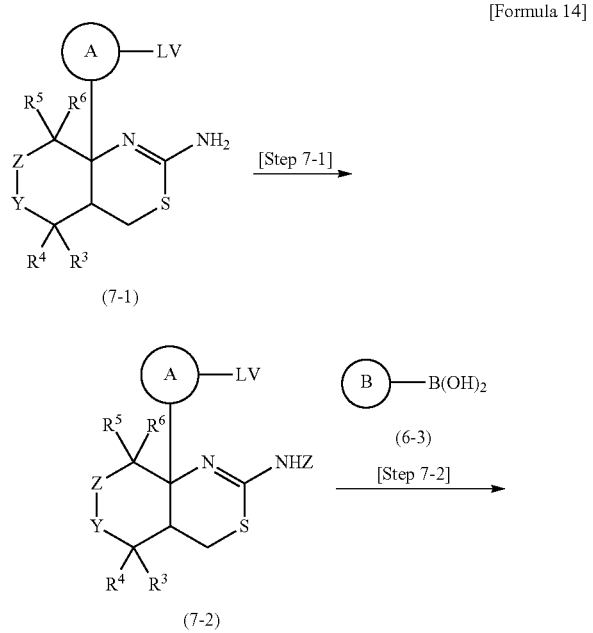

In the formula, Ring A, Ring B, $R^3$, $R^4$, $R^5$, $R^6$, Z, Y, L and LV are as defined above.

General Preparation Method 7 is a method for preparing the compound (I-b) of the general formula (I) according to the present invention, wherein L is a single bond and $R^1$ and $R^2$ are hydrogen atoms, from a compound (7-1) as a raw material through Step 7-1 to Step 7-2.

The compound (7-1) can be prepared from a commercially available product by General Preparation Method 1, General Preparation Method 5 or a combination of General Preparation Method 1 and General Preparation Method 11, and can also be prepared by a method described in Preparation Examples among Examples.

7-1. Step 7-1:

This step is a step of obtaining a compound (7-2) by benzyloxycarbonylation of the compound (7-1).

The reaction can be performed under the same conditions as those generally used in benzyloxycarbonylation (modification with Z group) of an amino compound such as the conditions described in a document such as T. W. Green and P. G. M. Wuts, "Protective Groups in Organic Chemistry, Third Edition", John Wiley & Sons, P. 531-537. The compound (7-2) can be obtained by reacting the compound (7-1) with benzyl chloroformate in a mixed solvent of 1,4-dioxane and a saturated sodium bicarbonate solution, for example.

7-2. Step 7-2:

This step is a step of synthesizing the compound (I-b) from the compound (7-2) as a raw material using a method described in the above preparation method (Step 6-2).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{3-8}$ hydrocarbon ring group which may have 1 to 3 substituents selected from Substituent Group α or a 5- to 10-membered heterocyclic group which may have 1 to 3 substituents selected from Substituent Group α, can be obtained by further reacting the compound (I-b) obtained in General Preparation Method 7 with a corresponding halide compound or the like such as a $C_{1-6}$ alkyl halide.

8. General Preparation Method 8:

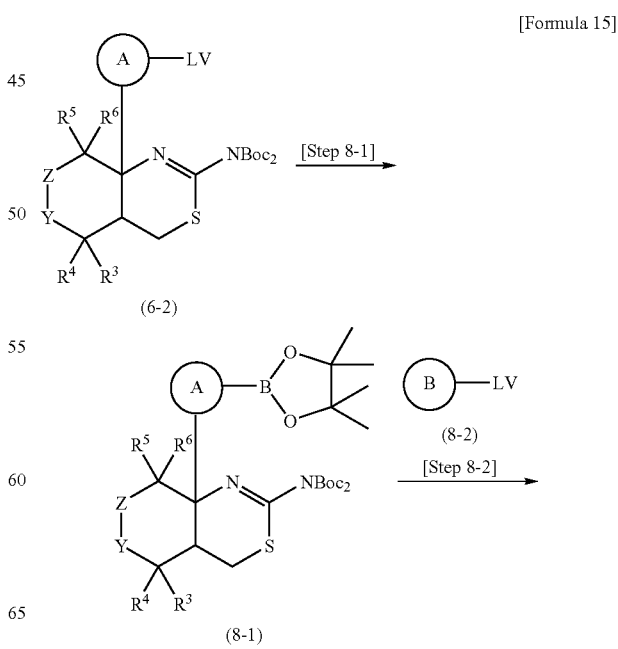

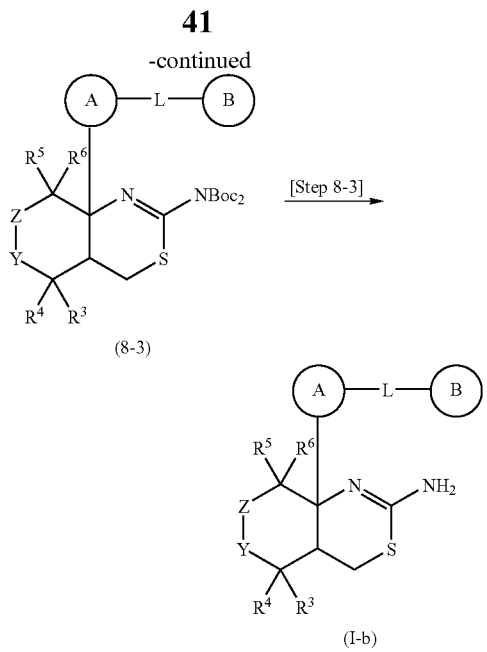

In the formula, Ring A, Ring B, $R^3$, $R^4$, $R^5$, $R^6$, Y, Z, L and LV are as defined above.

General Preparation Method 8 is a method for preparing the compound (I-b) of the general formula (I) according to the present invention, wherein L is a single bond and $R^4$ and $R^2$ are hydrogen atoms, from a compound (6-2) as a raw material through multiple steps of Step 8-1 to Step 8-3.

The compound (6-2) can be prepared from a commercially available product by General Preparation Method 6, and can also be prepared by a method described in Preparation Examples among Examples. A compound (8-2) can be a commercially available product used as is, can also be prepared from a commercially available product by a method known to a person skilled in the art, and can further be prepared by a method described in Preparation Examples among Examples.

8-1. Step 8-1:

This step is a step of obtaining a compound (8-1) by coupling reaction of the compound (6-2) using a transition metal.

The reaction in this step can be performed under the same conditions as those usually used in coupling reaction using a transition metal such as the conditions described in Org. Lett. 2007, Vol. 9, No. 4, 559-562 and Bioorg. Med. Chem, 14 (2006) 4944-4957. Specifically, the compound (8-1) can be obtained by reacting the compound (6-2) with bis(pinacolato) diborane under heating conditions in a solvent such as DMF in the presence of a catalyst such as potassium acetate or [1,1'-bis(diphenylphosphino)ferrocene]palladium (II) dichloride, for example.

The organometallic catalyst used in this reaction is not particularly limited. Preferable examples of the organometallic catalyst include metal catalysts such as dichlorobis(triphenylphosphine)palladium (II), [1,1'-bis(diphenylphosphino)ferrocene]palladium (II) dichloride, bis(tert-butylphosphine)palladium (0), palladium (II) acetate and [1,3-bis(diphenylphosphino)propane]nickel (II). The amount of the organometallic catalyst used is about 0.001 to 0.5 equivalent with respect to the raw material. The solvent used in this reaction is not particularly limited insofar as it does not inhibit the reaction. Preferable examples of the solvent include benzene, toluene, xylene, N,N-dimethylformamide, 1-methyl-2-pyrrolidone, dimethyl sulfoxide, tetrahydrofuran, 1,2-dimethoxyethane, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 72 hours, and preferably 0.5 to 24 hours.

A more preferable result such as an improved yield may be achieved by carrying out this reaction in the presence of a base. Such a base is not particularly limited. Preferable examples of the base include bases such as potassium acetate, sodium acetate, sodium carbonate, potassium carbonate, cesium carbonate, potassium phosphate, potassium fluoride, triethylamine and N,N-diisopropylethylamine.

8-2. Step 8-2:

This step is a step of synthesizing a compound (8-3) from the compound (8-1) as a raw material using a method described in the above preparation method (Step 6-2).

8-3. Step 8-3:

This step is a step of synthesizing the compound (I-b) from the compound (8-3) as a raw material using a method described in the above preparation method (Step 3-4).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{3-8}$ hydrocarbon ring group which may have 1 to 3 substituents selected from Substituent Group α or a 5- to 10-membered heterocyclic group which may have 1 to 3 substituents selected from Substituent Group α, can be obtained by further reacting the compound (I-b) obtained in General Preparation Method 8 with a corresponding halide compound or the like such as a $C_{1-6}$ alkyl halide.

9. General Preparation Method 9:

[Formula 16]

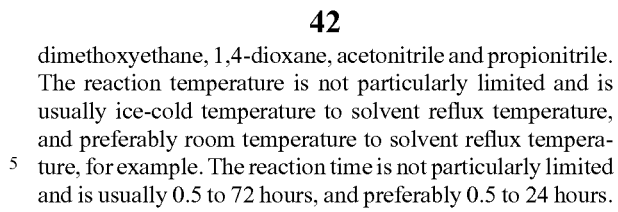

-continued

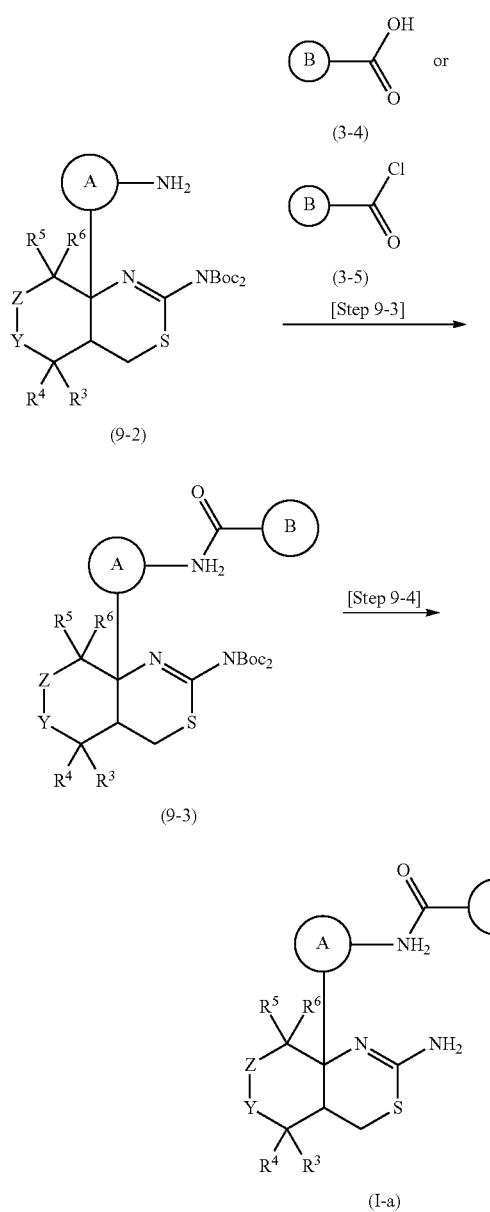

In the formula, Ring A, Ring B, $R^3$, $R^4$, $R^5$, $R^6$, Y and Z are as defined above.

General Preparation Method 9 is a method for preparing the compound (I-a) of the general formula (I) according to the present invention, wherein L is —NHCO— and $R^1$ and $R^2$ are hydrogen atoms, from a compound (8-1) as a raw material through multiple steps of Step 9-1 to Step 9-4.

The compound (8-1) can be prepared from a commercially available product by General Preparation Method 8, and can also be prepared by a method described in Preparation Examples among Examples.

9-1. Step 9-1:

This step is a step of obtaining a compound (9-1) by reaction of the compound (8-1) with sodium azide in the presence of a copper catalyst.

The reaction in this step can be performed under the same conditions as those described in Org. Lett. 2007, Vol. 9, No. 5, 761-764 and Tetrahedron Lett. 2007, 48, 3525-3529, for example. Specifically, the compound (9-1) can be obtained by reacting the compound (8-1) with sodium azide at room temperature using a solvent such as methanol in the presence of a catalyst such as copper (II) acetate, for example.

The catalyst used in this reaction is not particularly limited. Preferable examples of the catalyst include metal catalysts such as copper (II) acetate, copper (II) sulfate, copper (I) iodide and copper (I) chloride. The amount of the catalyst used is not particularly limited and is usually about 0.1 to 0.5 equivalent with respect to the raw material. The solvent used in this reaction is not particularly limited insofar as it does not inhibit the reaction and allows the starting material to be dissolved therein to a certain extent. Preferable examples of the solvent include methanol, N,N-dimethylformamide, 1-methyl-2-pyrrolidone, tetrahydrofuran, 1,2-dimethoxyethane, 1,4-dioxane, acetonitrile, propionitrile and dichloromethane. The reaction temperature is not particularly limited and is usually ice-cold temperature to solvent reflux temperature, and preferably room temperature to solvent reflux temperature, for example. The reaction time is not particularly limited and is usually 0.5 to 100 hours, and preferably 1 to 72 hours.

A more preferable result such as an improved yield may be achieved by carrying out this reaction in an oxygen atmosphere.

9-2. Step 9-2:

This step is a step of obtaining a compound (9-2) by reduction reaction of the azide of the compound (9-1). The reaction in this step can be performed under the same conditions as those described in J. Org. Chem. 2003, 68, 4693-4699, for example. Specifically, the compound (9-2) can be obtained by dissolving the compound (9-1) in a solvent such as methanol, and reacting the solution with sodium borohydride, for example.

9-3. Step 9-3:

This step is a step of synthesizing a compound (9-3) from the compound (9-2) as a raw material using a method described in the above preparation method (Step 3-3).

9-4. Step 9-4:

This step is a step of synthesizing the compound (I-a) from the compound (9-3) as a raw material using a method described in the above preparation method (Step 3-4).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{3-8}$ hydrocarbon ring group which may have 1 to 3 substituents selected from Substituent Group α or a 5- to 10-membered heterocyclic group which may have 1 to 3 substituents selected from Substituent Group α, can be obtained by further reacting the compound (I-a) obtained in General Preparation Method 9 with a corresponding halide compound or the like such as a $C_{1-6}$ alkyl halide. Alternatively, the compound of the formula (I) according to the present invention, wherein L is —NR$^L$CO— (wherein R$^L$ is a $C_{1-6}$ alkyl group which may have 1 to 3 substituents selected from Substituent Group α), can be obtained by further reacting the compound (I-a) obtained in General Preparation Method 9 with a corresponding halide compound or the like such as a $C_{1-6}$ alkyl halide.

The compound of the formula (I) according to the present invention, wherein L is —NR$^L$SO$_2$— (wherein R$^L$ is a hydrogen atom), can be obtained using a corresponding sulfonyl compound or sulfonyl halide compound in place of the compound (3-4) or (3-5) used in General Preparation Method 9. The compound of the formula (I) according to the present invention, wherein L is —NR$^L$SO$_2$— (wherein R$^L$ is a C$_{1-6}$ alkyl group which may have 1 to 3 substituents selected from Substituent Group α), can be obtained by further reacting this compound with a corresponding halide compound or the like such as a C$_{1-6}$ alkyl halide.

10. General Preparation Method 10:

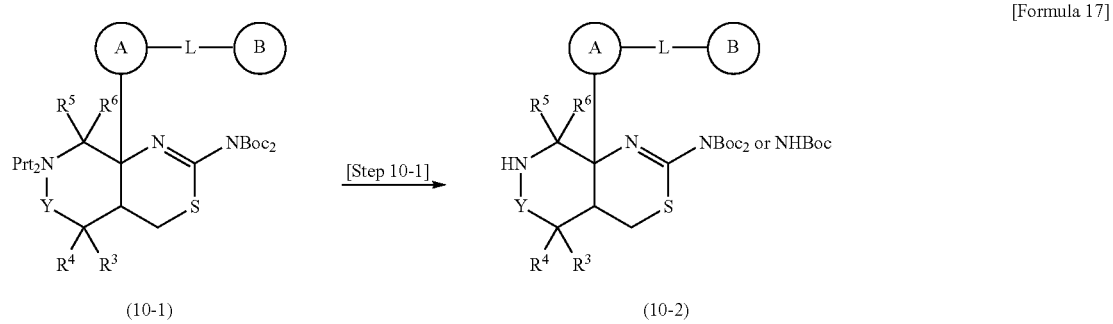

[Formula 17]

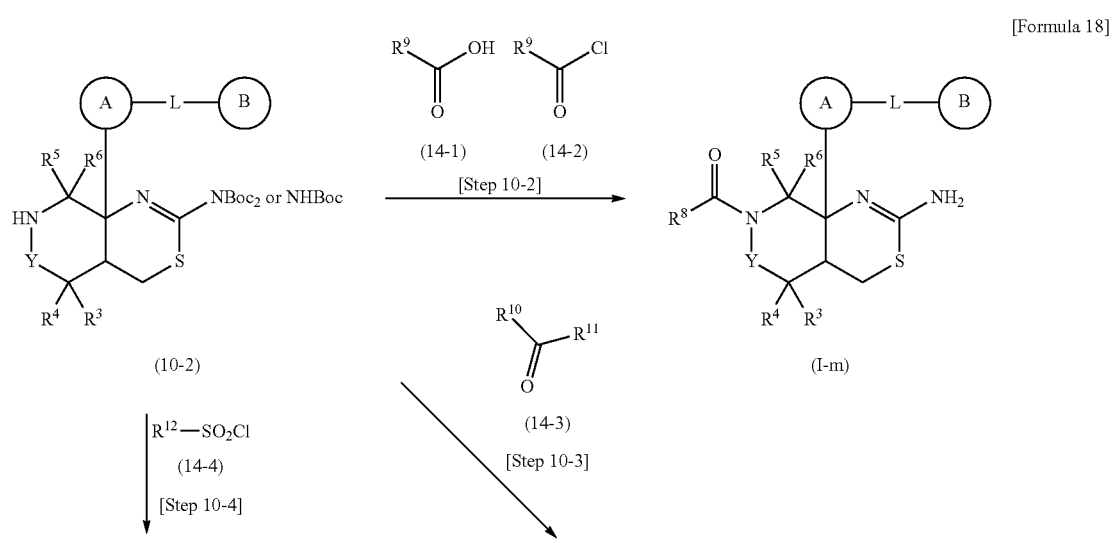

[Formula 18]

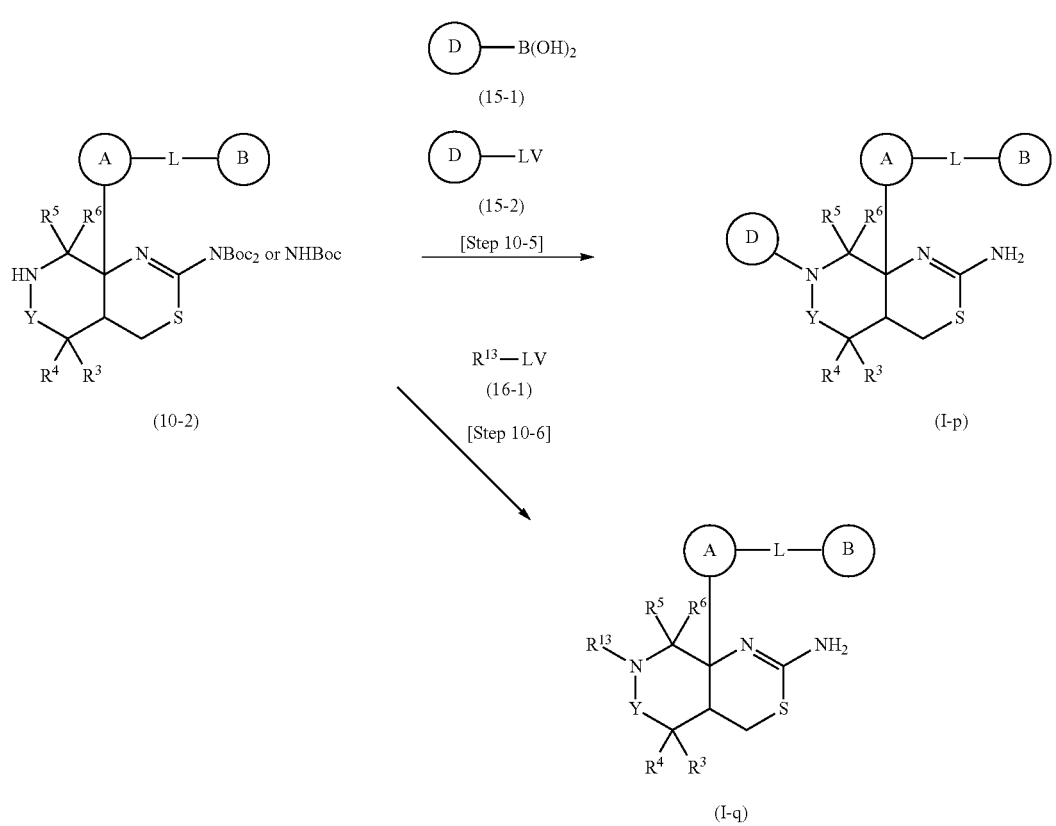

[Formula 19]

In the formula, Ring A, Ring B, $R^3$, $R^4$, $R^5$, $R^6$, L and LV are as defined above; Ring D represents a $C_{6-14}$ aryl group which may have 1 to 3 substituents selected from Substituent Group α or a 5- to 6-membered heteroaryl group which may have 1 to 3 substituents selected from Substituent Group α; $R^9$ represents a $C_{6-14}$ aryl group which may have 1 to 3 substituents selected from Substituent Group α, a 5- to 10-membered heterocyclic group which may have 1 to 3 substituents selected from Substituent Group α, a $C_{3-8}$ cycloalkyl group which may have 1 to 3 substituents selected from Substituent Group α, a $C_{1-6}$ alkyl group which may have 1 to 3 substituents selected from Substituent Group α or a 3- to 10-membered carbocyclic group which may have 1 to 3 substituents selected from Substituent Group α; R10 and $R^{11}$ are each independently a hydrogen atom, a $C_{6-14}$ aryl group which may have 1 to 3 substituents selected from Substituent Group α, a 5- to 10-membered heterocyclic group which may have 1 to 3 substituents selected from Substituent Group α, a $C_{3-8}$ cycloalkyl group which may have 1 to 3 substituents selected from Substituent Group α, a $C_{1-6}$ alkyl group which may have 1 to 3 substituents selected from Substituent Group α or a 3- to 10-membered carbocyclic group which may have 1 to 3 substituents selected from Substituent Group α; or $R^{10}$ and $R^{11}$ together may form a C3-8 cycloalkyl group which may be substituted at the carbon atom(s) with 1 to 2 substituents selected from an oxygen atom, a sulfur atom, a sulfone and —N($R^M$)— (wherein $R^M$ is as defined above); $R^{12}$ represents a $C_{6-14}$ aryl group which may have 1 to 3 substituents selected from Substituent Group α, a 5- to 10-membered heterocyclic group which may have 1 to 3 substituents selected from Substituent Group α, a $C_{3-8}$ cycloalkyl group which may have 1 to 3 substituents selected from Substituent Group α, a $C_{1-6}$ alkyl group which may have 1 to 3 substituents selected from Substituent Group α or a 3- to 10-membered carbocyclic group which may have 1 to 3 substituents selected from Substituent Group α; $R^{13}$ represents a $C_{7-12}$ aralkyl group which may have 1 to 3 substituents selected from Substituent Group α; and Prt2 represents an amine protecting group such as a 2,4-dimethoxybenzyl group or a benzyloxycarbonyl group.

General Preparation Method 10 is a method for preparing the compounds (I-m) to (I-q) of the general formula (I) according to the present invention, wherein Z is —$NR^M$— (wherein $R^M$ is a hydrogen atom, a $C_{1-6}$ alkyl group which may have 1 to 3 substituents selected from Substituent Group α, a $C_{3-8}$ cycloalkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{6-14}$ aryl group which may have 1 to 3 substituents selected from Substituent Group α or a 5- to 10-membered heterocyclic group which may have 1 to 3 substituents selected from Substituent Group α) and $R^1$ and $R^2$ are hydrogen atoms, from a compound (10-1) as a raw material through various steps of Step 10-1 to Step 10-6.

The compound (10-1) can be prepared from a commercially available product by General Preparation Method 5, General Preparation Method 6, General Preparation Method 8, General Preparation Method 9 or a combination of these methods, and can also be prepared by a method described in Preparation Examples among Examples.

10-1. Step 10-1:

This step is a step of obtaining a compound (10-2) by deprotecting the amino group of the compound (10-1).

The reaction can be performed under the same conditions as those generally used in deprotection of a protecting group of an amino compound such as the conditions described in a document such as T. W. Green and P. G. M. Wuts, "Protective Groups in Organic Chemistry, Third Edition", John Wiley & Sons, P. 494-572.

The amino protecting group used in this step is not particularly limited. When Prt2 is a 2,4-dimethoxybenzyl group, for example, the compound (10-2) can be obtained in this step under the same conditions as those generally used (such as the conditions described in a document such as Tetrahedron Vol. 47, No. 26, pp 4591-4602, 1991). In this step, when Prt2 is a 2,4-dimethoxybenzyl group, one Boc group can be deprotected simultaneously with deprotection of the 2,4-dimethoxybenzyl group. When Prt2 is a 2,4-dimethoxybenzyl group in this step, the solvent used in this step is not particularly limited insofar as it does not inhibit the reaction and allows the starting material to be dissolved therein to a certain extent. For example, the first-step reaction solvent may be methylene chloride or chloroform, and the second-step reaction solvent may be methanol. The reaction temperature in this step is usually 0° C. to room temperature. The reaction time in this step is not particularly limited and is usually 0.5 to 24 hours, and preferably 0.5 to 12 hours. When Prt2 is a benzyloxycarbonyl group, the compound (10-2) can be obtained by deprotecting the compound (10-1) by hydrogenation using palladium-carbon as a catalyst in a solvent such as an alcohol, for example.

10-2. Step 10-2:

This step is a step of synthesizing the compound (I-m) from the compound (10-2) as a raw material using a method described in the above preparation method ((Step 3-3) and (Step 3-4)).

10-3. Step 10-3:

This step is a step of synthesizing the compound (I-n) from the compound (10-2) as a raw material using a method described in Step 3-4 after reductive amination reaction with a reducing agent such as borane or a boron hydride complex compound, for example. Examples of the reductive amination reaction using a boron hydride complex compound include a method described in a document such as J. Org. Chem. 1996, 61, 3849. Examples of the boron hydride complex compound that can be used include sodium borohydride, sodium cyanoborohydride and sodium triacetoxyborohydride.

10-4. Step 10-4:

This step is a step of synthesizing the compound (I-o) from the compound (10-2) as a raw material using a method described in Step 3-4 after sulfonylating the amino group using a sulfonyl chloride derivative known to a person skilled in the art.

10-5. Step 10-5:

This step is a step of synthesizing the compound (I-p) from the compound (10-2) as a raw material using a method described in Step 3-4 after coupling reaction with a compound (15-1) or (15-2). Reaction such as coupling using a transition metal complex or the like or nucleophilic aromatic substitution (SNAr reaction) is used in the first step of this step.

The reaction in the first step of this step can be performed under the same conditions as those described in Org. Lett. 2007, Vol. 9, No. 5, 761-764 and Org. Lett. 2003, Vol. 5, No. 23, 4397-4400, for example. Specifically, the compound (10-2) can be reacted with the compound (15-1) at room temperature to 50° C. using a solvent such as dichloromethane in the presence of molecular sieve 4A and a catalyst such as copper (II) acetate, for example.

The catalyst used in this reaction is not particularly limited. Preferable examples of the catalyst include metal catalysts such as copper(II) acetate, copper(II) sulfate, copper(I) iodide and copper(I) chloride. The amount of the catalyst used is not particularly limited and is usually about 0.1 to 0.5 equivalent with respect to the raw material. The solvent used in this reaction is not particularly limited insofar as it does not inhibit the reaction and allows the starting material to be dissolved therein to a certain extent. Preferable examples of the solvent include N,N-dimethylformamide, 1-methyl-2-pyrrolidone, tetrahydrofuran, 1,2-dimethoxyethane, 1,4-dioxane, acetonitrile, propionitrile and dichloromethane. The reaction temperature is not particularly limited and is usually ice-cold temperature to solvent reflux temperature, and preferably room temperature to solvent reflux temperature, for example. The reaction time is not particularly limited and is usually 0.5 to 100 hours, and preferably 1 to 72 hours.

A more preferable result such as an improved yield may be achieved by carrying out this reaction in an oxygen atmosphere.

When the first step in this step is coupling using a transition metal complex or the like as a catalyst, the reaction can be performed using the compound (10-2) and the compound (15-2) which is an aryl halide derivative, a heteroaryl halide derivative, an aryloxy trifluoromethanesulfonate derivative or a heteroaryloxy trifluoromethanesulfonate derivative under the same conditions as those usually used (such as the conditions described in a document such as Org. Lett. 2002, Vol. 4, No. 4, 581). The aryl halide derivative, the heteroaryl halide derivative, the aryloxy trifluoromethanesulfonate derivative or the heteroaryloxy trifluoromethanesulfonate derivative used in this step can be a commercially available product used as is, and can also be prepared from a commercially available product by a method known to a person skilled in the art. Examples of the transition metal complex used in this step include dichlorobis(triphenylphosphine)palladium(II), tetrakis(triphenylphosphine)palladium(0), tris(dibenzylideneacetone)palladium(0) and a copper-diol ligand complex. In this reaction, a phosphorus ligand (such as preferably triphenylphosphine, tri-o-tolylphosphine, tri-tert-butylphosphine, 2,2'-bis(diphenylphosphino)-1,1'-binaphthyl or 1,1'-bis(diphenylphosphino)ferrocene) may be further added in order to obtain favorable results (such as a reduced reaction temperature, a reduced reaction time and an improved yield). When the transition metal complex used is a palladium complex, the reaction in this step is preferably performed in a nitrogen or argon atmosphere.

The solvent used in this step is not particularly limited insofar as it does not inhibit the reaction and allows the starting material to be dissolved therein to a certain extent. For example, when the transition metal complex used is a palladium complex, N,N-dimethylformamide, N-methyl-2-pyrrolidone, 1,4-dioxane, toluene, xylene or the like can be used. When the transition metal complex used is a copper-diol complex, 2-propanol or the like can be used. The reaction temperature in this step is usually room temperature to solvent reflux temperature. The reaction time in this step is not particularly limited and is usually 0.5 to 72 hours, and preferably 0.5 to 24 hours.

When the first step in this step is nucleophilic aromatic substitution (SNAr reaction), the reaction can be performed using the compound (10-2) and the compound (15-2) which is an aryl halide derivative, a heteroaryl halide derivative, an aryloxy trifluoromethanesulfonate derivative or a heteroaryloxy trifluoromethanesulfonate derivative in the presence of a base under the same conditions as those usually used. The aryl halide derivative, the heteroaryl halide derivative, the aryloxy trifluoromethanesulfonate derivative or the heteroaryloxy trifluoromethanesulfonate derivative used in this step can be a commercially available product used as is, and can also be prepared from a commercially available product by a method known to a person skilled in the art. The nucleophilic aromatic substitution (SNAr reaction) used in this step can be performed under the same conditions as those generally used (such as the conditions according to methods described in documents such as Org. Prep. Proced. int. 39 (2007) 4, 399-402, Bioorg. Med. Chem. Lett. 15 (2005) 9, 2409-2413 and Bioorg. Med. Chem. Lett. 15 (2005) 3, 719-723). The solvent used in this step is not particularly limited insofar as it does not inhibit the reaction and allows the starting material to be dissolved therein to a certain extent. Examples of the solvent that can be used include N,N-dimethylformamide, N-methyl-2-pyrrolidone, dimethyl sulfoxide and acetonitrile. The base used in this step is not particularly limited. Examples of the base include potassium carbonate, sodium carbonate, sodium hydride and tetrabutylammonium fluoride. Potassium carbonate, sodium carbonate and tetrabutylammonium fluoride are preferably used. The reaction temperature in this step is usually room temperature to solvent reflux temperature. The reaction time in this step is not particularly limited and is usually 0.5 to 24 hours, and preferably 0.5 to 12 hours.

10-6. Step 10-6:

This step is a step of synthesizing the compound (I-q) from the compound (10-2) as a raw material using a method described in Step 3-4 after N-alkylation reaction of the amino compound.

The first step in this reaction can be performed under the same conditions as those usually used in N-alkylation reaction of an amino compound (such as the conditions described in J. Med. Chem. 2002, 45, 3794-3804 and J. Med. Chem. 2000, 43, 3809-3812).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which may have 1 to 3 substituents selected from Substituent Group α, a $C_{6-14}$ arylcarbonyl group which may have 1 to 3 substituents selected from Substituent Group α, a $C_{1-6}$ alkylsulfonyl group which may have 1 to 3 substituents selected from Substituent Group α, a $C_{6-14}$ arylsulfonyl group which may have 1 to 3 substituents selected from Substituent Group α, a $C_{3-8}$ hydrocarbon ring group which may have 1 to 3 substituents selected from Substituent Group α or a 5- to 10-membered heterocyclic group which may have 1 to 3 substituents selected from Substituent Group α, can be obtained by further reacting the thus-obtained compounds (I-m) to (I-q) of the general formula (I), wherein $R^1$ and $R^2$ are hydrogen atoms, with a corresponding halide compound or the like such as a $C_{1-6}$ alkyl halide.

11. General Preparation Method 11:

[Formula 20]

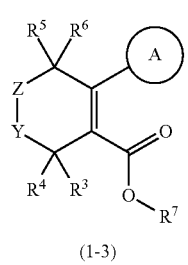

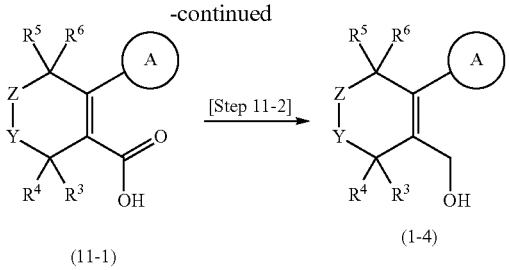

In the formula, Ring A, $R^3$, $R^4$, $R^5$, $R^6$, $R^7$, Y and Z are as defined above.

General Preparation Method 11 is a method for preparing a compound (1-4) which is a synthetic intermediate of the compound (I) according to the present invention from a compound (1-3) as a raw material through Step 11-1 to Step 11-2.

The compound (1-3) can be prepared from a commercially available product by General Preparation Method 1, and can also be prepared by a method described in Preparation Examples among Examples.

11-1. Step 11-1:

This step is a step of obtaining a compound (11-1) by alkaline hydrolysis of the compound (1-3).

The reaction can be performed under the same reaction conditions as those described in J. Med. Chem., 33 (9), 2621-2629 (1990), for example.

Specifically, the compound (11-1) can be obtained by adding a base such as sodium hydroxide to a solution of the compound (1-3), stirring the mixture for several hours to one day, and then treating the solution with an acid such as a citric acid solution, for example.

The solvent used in the reaction is not particularly limited insofar as it does not inhibit the reaction and allows the starting material to be dissolved therein to a certain extent. Examples of the solvent include methanol, ethanol, 2-propanol, tetrahydrofuran and 1,4-dioxane. The base used is not particularly limited and is preferably sodium hydroxide, potassium hydroxide or lithium hydroxide, for example. The amount of the base used is one equivalent to a large excess, and preferably 1 to 20 equivalents with respect to the compound (1-3). The reaction time is not particularly limited and is usually 1 to 24 hours, and preferably 1 to 6 hours. The reaction temperature is not particularly limited and is usually room temperature to solvent reflux temperature.

11-2. Step 11-2:

This step is a step of obtaining the compound (1-4) by subjecting the compound (11-1) to reduction reaction.

The compound (1-4) can be obtained by converting the compound (11-1) to a mixed acid anhydride and then reacting the mixed acid anhydride with sodium borohydride. The mixed acid anhydride can be synthesized by a method known to a person skilled in the art. The synthesis is performed by reacting the compound (11-1) with a chloroformate such as ethyl chloroformate in the presence of a base such as triethylamine, for example. One to two equivalents of the chloroformate and the base are used with respect to the compound (11-1). The reaction temperature is −30° C. to room temperature, and preferably −20° C. to room temperature.

The step of reacting the mixed acid anhydride with a reducing agent such as sodium borohydride is performed by reaction in a solvent such as tetrahydrofuran or 1,2-dimethoxyethane or in a mixed solution of the solvent and water, for example. One equivalent to a large excess of the reducing agent such as sodium borohydride is used with respect to the mixed acid anhydride.

The reaction time is not particularly limited and is usually 0.5 to 48 hours, and preferably 0.5 to 24 hours. The reaction temperature is not particularly limited and is usually −78° C. to solvent reflux temperature, and preferably −20° C. to room temperature. The solvent used in the reaction is not particularly limited insofar as it does not inhibit the reaction and allows the starting material to be dissolved therein to a certain extent. Preferable examples of the solvent include tetrahydrofuran and ether.

12. General Preparation Method 12:

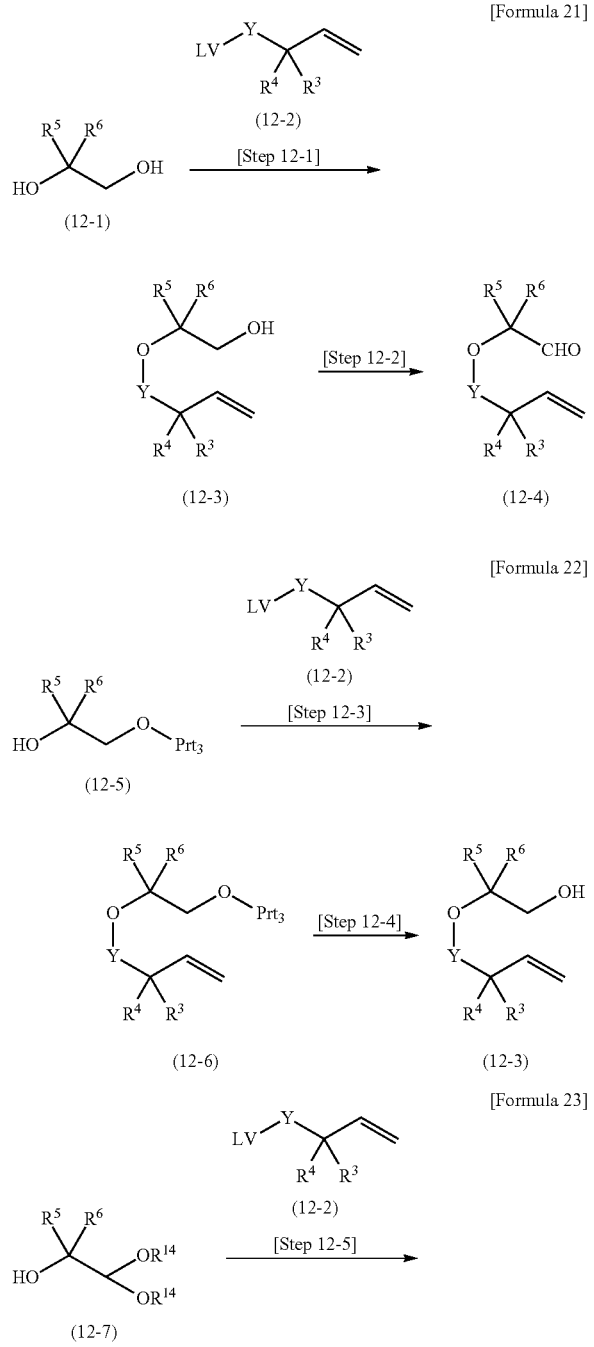

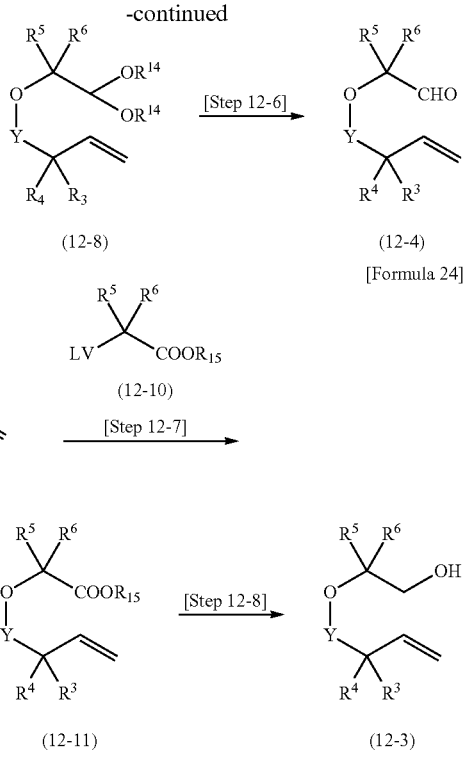

In the formula, $Prt_3$ represents a primary hydroxyl protecting group, $R^{14}$ represents a C1-6 alkyl group, or two $R^{14}$ together may form a ring, $R^{15}$ represents a C1-6 alkyl group, and Y, $R^3$, $R^4$, $R^5$, $R^6$ and LV are as defined above.

General Preparation Method 12 is a method for preparing a compound (12-4) which is a synthetic intermediate of the compound (I) according to the present invention from compounds (12-1), (12-5), (12-7) and (12-9) as raw materials through various steps of Step 12-1 to Step 12-8.

Compounds (12-1), (12-2), (12-5), (12-7), (12-9) and (12-10) can be commercially available products used directly, can also be prepared from a commercially available product by a method known to a person skilled in the art, and can further be prepared by a method described in Preparation Examples among Examples.

12-1. Step 12-1:

This step is a step of obtaining a compound (12-3) by reaction of the compound (12-1) with the compound (12-2).

This reaction can be performed under the same conditions as those usually used in O-alkylation reaction of an alcohol compound (such as the conditions described in Tetrahedron Lett. 46 (2005) 45, 7751-7755). In this reaction, the compound (12-3) can be obtained by adding a base such as sodium hydride to a solution of the compound (12-1) in THF to prepare an alkoxide, and then reacting the alkoxide with the compound (12-2), for example. The solvent used in the reaction is not particularly limited insofar as it does not inhibit the reaction and allows the starting material to be dissolved therein to a certain extent. Examples of the solvent include solvents such as THF, DMF and dimethyl sulfoxide. The reaction can be performed by causing 1 to 3 equivalents of an appropriate base to act in the presence of such a solvent. Examples of the base used include sodium hydride, potassium hydride and t-butoxypotassium. The reaction time is not particularly limited and is usually 0.5 to 72 hours, and preferably 0.5 to 12 hours. The reaction temperature is usually −20° C. to 100° C.

A more preferable result such as an improved yield may be achieved by adding a salt such as tetrabutylammonium iodide in this reaction.

12-2. Step 12-2:

This step is a step of obtaining an aldehyde compound (12-4) by subjecting the alcohol compound (12-3) to oxidation reaction. The aldehyde compound can be obtained from the alcohol compound by a method known to a person skilled in the art.

Examples of the known oxidation method used in the reaction include Swern oxidation, Corey-Kim oxidation, Moffatt oxidation, PCC oxidation, PDC oxidation, Dess-Martin oxidation, $SO_3$-pyridine oxidation and TEMPO oxidation.

The solvent used in the reaction is not particularly limited insofar as it does not inhibit the reaction and allows the starting material to be dissolved therein to a certain extent. Examples of the solvent include dimethyl sulfoxide, tetrahydrofuran, toluene, dichloromethane and chloroform.

The reaction temperature is not particularly limited and is usually −78° C. to solvent reflux temperature, and preferably −78° C. to room temperature. The reaction time is not particularly limited and is usually 0.5 to 48 hours, and preferably 0.5 to 24 hours.

12-3. Step 12-3:

This step is a step of synthesizing a compound (12-6) from the compound (12-5) as a raw material using a method described in the above preparation method (Step 12-1).

12-4. Step 12-4:

This step is a step of obtaining the compound (12-3) by deprotecting the hydroxyl protecting group of the compound (12-6). The hydroxyl protecting group used in this step is not particularly limited.

This reaction can be performed under the same conditions as those generally used in deprotection of an alcohol protecting group such as the conditions described in a document such as T. W. Green and P. G. M. Wuts, "Protective Groups in Organic Chemistry, Third Edition", John Wiley & Sons, P. 17-245.

12-5. Step 12-5:

This step is a step of synthesizing a compound (12-8) from the compound (12-7) as a raw material using a method described in the above preparation method (Step 12-1).

12-6. Step 12-6:

This step is a step of obtaining the compound (12-4) by deprotecting the acetal group of the compound (12-8).

This reaction can be performed under the same conditions as those generally used in deprotection of an aldehyde group such as the conditions described in a document such as T. W. Green and P. G. M. Wuts, "Protective Groups in Organic Chemistry, Third Edition", John Wiley & Sons, P. 293-329.

12-7. Step 12-7:

This step is a step of obtaining a compound (12-11) by reaction of the compound (12-9) with the compound (12-10).

This reaction can be performed under the same conditions as those usually used in O-alkylation reaction of an alcohol compound (such as the conditions described in J. Chem. Soc., Perkin Trans. 1, 1999, 3143-3155). In this reaction, the compound (12-11) can be obtained by adding a base such as sodium hydride to a solution of the compound (12-9) in THF to prepare an alkoxide, and then reacting the alkoxide with the compound (12-10), for example. The solvent used in the reaction is not particularly limited insofar as it does not inhibit the reaction and allows the starting material to be dissolved therein to a certain extent. Examples of the solvent include solvents such as THF, DMF and dimethyl sulfoxide. The reaction can be performed by causing 1 to 3 equivalents of an appropriate base to act in the presence of such a solvent.

Examples of the base used include sodium hydride, potassium hydride and t-butoxypotassium. The reaction time is not particularly limited and is usually 0.5 to 72 hours, and preferably 0.5 to 12 hours. The reaction temperature is usually −20° C. to 100° C.

A more preferable result such as an improved yield may be achieved by adding a salt such as tetrabutylammonium iodide in this reaction.

12-8. Step 12-8:

This step is a step of synthesizing the compound (12-3) from the compound (12-11) as a raw material using a method described in the above preparation method ((Step 1-3) or (Steps 11-1 and 2)).

13. General Preparation Method 13:

[Formula 25]

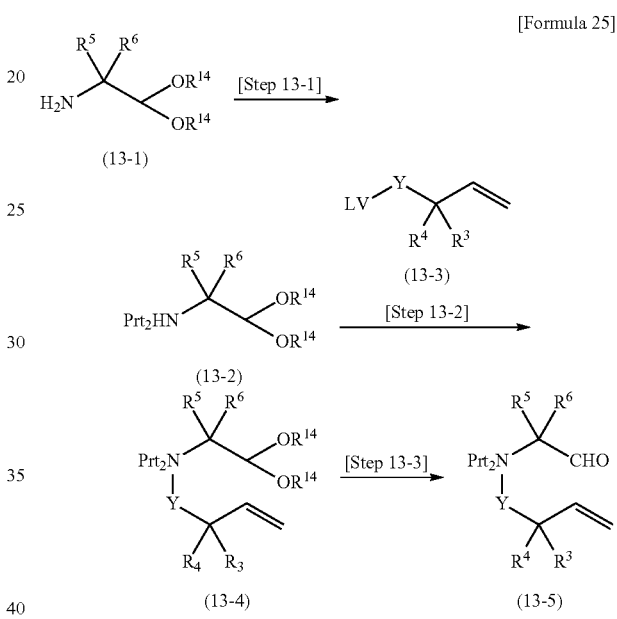

In the formula, $R^{14}$ represents a C1-6 alkyl group, or two $R^{14}$s together may form a ring such as 1,3-dioxolane or 1,3-dioxane, $Prt_2$ represents a protecting group such as a 2,4-dimethoxybenzyl group, and $R^3$, $R^4$, $R^5$, $R^6$, Y and LV are as defined above.

General Preparation Method 13 is a method for preparing a compound (13-5) which is a synthetic intermediate of the compound (I) according to the present invention from a compound (13-1) as a raw material through Step 13-1 to Step 13-3.

Compounds (13-1) and (13-3) can be commercially available products used directly, can also be prepared from a commercially available product by a method known to a person skilled in the art, and can further be prepared by a method described in Preparation Examples among Examples.

13-1. Step 13-1:

This step is a step of obtaining a compound (13-2) by protecting the amino group of the compound (13-1).

This reaction can be performed under the same conditions as those generally used in protection of an amino group such as the conditions described in a document such as T. W. Green and P. G. M. Wuts, "Protective Groups in Organic Chemistry, Third Edition", John Wiley & Sons, P. 494-572 and J. Med. Chem. 2007, 50, 5493-5508.

13-2. Step 13-2:

This step is a step of obtaining a compound (13-4) by N-alkylation reaction of the compound (13-2) with the compound (13-3).

This reaction can be performed under the same conditions as those usually used in N-alkylation reaction of a compound (13-2) (such as the conditions described in J. Med. Chem. 2007, 50, 5493-5508). In this reaction, the compound (13-4) can be obtained by adding a base such as powdery sodium hydroxide to a solution of the compound (13-2) in toluene, and then reacting the mixture with the compound (13-3), for example. The solvent used in the reaction is not particularly limited insofar as it does not inhibit the reaction and allows the starting material to be dissolved therein to a certain extent. Examples of the solvent include solvents such as toluene, THF, DMF and dimethyl sulfoxide. The reaction can be performed by causing 1 to 5 equivalents of an appropriate base to act in such a solvent. Examples of the base used include sodium hydroxide, potassium hydroxide, sodium hydride, potassium hydride and t-butoxypotassium. The reaction time is not particularly limited and is usually 0.5 to 72 hours, and preferably 0.5 to 24 hours. The reaction temperature is usually −20° C. to 100° C.

A more preferable result such as an improved yield may be achieved by adding a salt such as tetrabutylammonium iodide in this reaction.

13-3. Step 13-3:

This step is a step of obtaining the compound (13-5) by deprotecting the acetal group of the compound (13-4).

This reaction can be performed under the same conditions as those generally used in deprotection of an aldehyde group such as the conditions described in a document such as T. W. Green and P. G. M. Wuts, "Protective Groups in Organic Chemistry, Third Edition", John Wiley & Sons, P. 293-329.

The compound of the formula (I) according to the present invention obtained in this manner can be converted to a pharmaceutically acceptable salt by a conventional method where necessary. The salt can be prepared by a method in which methods typically used in the field of organic synthetic chemistry and the like are appropriately combined. Specific examples of the method include neutralization titration of a free solution of the compound of the present invention with an acid solution. The compound of the formula (I) according to the present invention can be converted to a solvate by subjecting the compound to solvate forming reaction known per se where necessary.

The fused aminodihydrothiazine derivative or pharmaceutically acceptable salt thereof, or solvate thereof according to the present invention has an extremely excellent Aβ production inhibitory effect or BACE1 inhibitory effect and is extremely useful as a therapeutic agent for a neurodegenerative disease caused by Aβ and typified by Alzheimer-type dementia.

The fused aminodihydrothiazine derivative or pharmaceutically acceptable salt thereof, or solvate thereof according to the present invention can be formulated by a conventional method. Preferable examples of the dosage form include tablets, coated tablets such as film tablets and sugar-coated tablets, fine granules, granules, powders, capsules, syrups, troches, inhalants, suppositories, injections, ointments, eye drops, nasal drops, ear drops, cataplasms and lotions.

These solid preparations such as tablets, capsules, granules and powders can contain generally 0.01 to 100 wt %, and preferably 0.1 to 100 wt % of the fused aminodihydrothiazine derivative or pharmaceutically acceptable salt thereof, or solvate thereof according to the present invention as an active ingredient.

The active ingredient is formulated by blending ingredients generally used as materials for a pharmaceutical preparation and adding an excipient, a disintegrant, a binder, a lubricant, a colorant and a corrective typically used, and adding a stabilizer, an emulsifier, an absorbefacient, a surfactant, a pH adjuster, a preservative and an antioxidant where necessary, for example, using a conventional method. Examples of such ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminum silicate and aluminum silicate; and purified water. Examples of the excipient used include lactose, corn starch, saccharose, glucose, mannitol, sorbitol, crystalline cellulose and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer and meglumine. Examples of the disintegrant used include starch, agar, gelatin powder, crystalline cellulose, calcium carbonate, sodium bicarbonate, calcium citrate, dextrin, pectin and carboxymethylcellulose calcium. Examples of the lubricant used include magnesium stearate, talc, polyethylene glycol, silica and hydrogenated vegetable oil. Examples of the colorant used include those permitted to be added to pharmaceuticals. Examples of the corrective used include cocoa powder, menthol, empasm, mentha oil, borneol and cinnamon powder. Obviously, the ingredients are not limited to the above additive ingredients.

For example, an oral preparation is prepared by adding the fused aminodihydrothiazine derivative or pharmaceutically acceptable salt thereof, or solvate thereof according to the present invention as an active ingredient, an excipient and, where necessary, a binder, a disintegrant, a lubricant, a colorant, a corrective and the like, and then forming the mixture into powder, fine granules, granules, tablets, coated tablets, capsules or the like by a conventional method. Obviously, tablets or granules may be appropriately coated, for example, sugar coated, where necessary.

For example, a syrup or an injection preparation is prepared by adding a pH adjuster, a solubilizer, an isotonizing agent and the like, and a solubilizing agent, a stabilizer and the like where necessary by a conventional method. The injection may be a previously prepared solution, or may be powder itself or powder containing a suitable additive, which is dissolved before use. The injection can contain usually 0.01 to 100 wt %, and preferably 0.1 to 100 wt % of the active ingredient. Further, a liquid preparation for oral administration such as a suspension or a syrup can contain usually 0.01 to 100 wt %, and preferably 0.1 to 100 wt % of the active ingredient.

For example, an external preparation can be prepared by any conventional method without specific limitations. As a base material, any of various materials usually used for a pharmaceutical, a quasi drug, a cosmetic or the like can be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water. A pH adjuster, an antioxidant, a chelator, a preservative and fungicide, a colorant, a flavor or the like can be added where necessary. Further, ingredients such as an ingredient having a differentiation inducing effect, a blood flow enhancer, a bactericide, an antiphlogistic, a cell activator, vitamin, amino acid, a humectant and a keratolytic agent can be blended where necessary.

The dose of the fused aminodihydrothiazine derivative or pharmaceutically acceptable salt thereof, or solvate thereof according to the present invention varies according to the degree of symptoms, age, sex, body weight, mode of administration, type of salt and specific type of disease, for example. Typically, the active ingredient is orally administered to an adult at about 30 μg to 10 g, preferably 100 μg to 5 g, and more preferably 100 μg to 1 g per day, or is administered to an adult by injection at about 30 μg to 1 g, preferably 100 μg to 500 mg, and more preferably 100 μg to 300 mg per day, in one or several doses, respectively.

The compound of the present invention can be converted to a chemical probe for capturing a target protein in a bioactive low-molecular compound. Specifically, the compound of the present invention can be converted to an affinity chromatography probe, a photoaffinity probe or the like by introducing a labeling group, a linker or the like into a moiety differing from a structural moiety essential for expression of activity of the compound by a technique described in J. Mass Spectrum. Soc. Jpn. Vol. 51, No. 5, 2003, p. 492-498 or WO 2007/139149, for example.

Examples of the labeling group, the linker or the like used for the chemical probe include groups shown in the following group consisting of (1) to (5):

(1) protein labeling groups such as photoaffinity labeling groups (such as a benzoyl group, a benzophenone group, an azido group, a carbonylazido group, a diaziridine group, an enone group, a diazo group and a nitro group) and chemical affinity groups (such as a ketone group substituted at the α-carbon atom with a halogen atom, a carbamoyl group, an ester group, an alkylthio group, Michael acceptors such as α,β-unsaturated ketones and esters, and an oxirane group), (2) cleavable linkers such as —S—S—, —O—Si—O—, monosaccharides (such as a glucose group and a galactose group) and disaccharides (such as lactose), and enzymatically cleavable oligopeptide linkers, (3) fishing tag groups such as biotin and 3-(4,4-difluoro-5,7-dimethyl-4H-3a,4a-diaza-4-bora-s-indacen-3-yl)propionyl, (4) detectable markers such as radioactive labeling groups such as $^{125}I$, $^{32}P$, $^{3}H$ and $^{14}C$; fluorescence labeling groups such as fluorescein, rhodamine, dansyl, umbelliferone, 7-nitrofurazanyl and 3-(4,4-difluoro-5,7-dimethyl-4H-3a,4a-diaza-4-bora-s-indacen-3-yl)propionyl; chemiluminescent groups such as luciferin and luminol; and heavy metal ions such as lanthanoid metal ions and radium ions, and (5) groups bound to solid-phase carriers such as glass beads, glass beds, microtiter plates, agarose beads, agarose beds, polystyrene beads, polystyrene beds, nylon beads and nylon beds.

When a probe is prepared by introducing a labeling group or the like selected from the group consisting of (1) to (5) above into the compound of the present invention in accordance with a method described in the above documents or the like, the probe can be used as a chemical probe for identification of labeled proteins useful for searching for novel drug targets, for example.

The present invention will be described more specifically below with reference to Examples, Preparation Examples and Test Example. However, the present invention is not limited thereto. The abbreviations used in Examples are conventional abbreviations known to a person skilled in the art.

Some abbreviations are shown below.

THF: Tetrahydrofuran

DMF: N,N-Dimethylformamide

TFA: Trifluoroacetic acid

EDC.HCl: 1-Ethyl-3-(3-dimethylaminopropyl)carbodiimide hydrochloride pTLC: Preparative thin-layer chromatography LC-MS: Liquid chromatography-mass spectrometry PyBOP: Benzotriazol-1-yloxytris(pyrrolidino)phosphonium hexafluorophosphate Pd2DBA3: Tris(dibenzylideneacetone)dipalladium Pd(t-Bu3P)2: Bis(tri-t-butylphosphine)palladium Chemical shifts in proton nuclear magnetic resonance spectra are recorded in δ units (ppm) relative to tetramethylsilane and coupling constants are recorded in Hertz (Hz). Patterns are designated as s: singlet, d: doublet, t: triplet, q: quartet, br: broad.

The preparative columns (2 cm×25 cm) used for preparative separation of chiral compounds, CHIRALPAK™ AD-H, CHIRALPAK™ IA, CHIRALPAK™ IB and CHIRALCEL™ OJ-H, were all manufactured by Daicel Chemical Industries, Ltd.

The "room temperature" in the following

Examples and Preparation Examples typically refers to about 10° C. to about 35° C. "%" indicates wt % unless otherwise specified.

PREPARATION EXAMPLE 1

Synthesis of tert-butyl (−)-[(4aR*,8aS*)-8a-(5-amino-2-fluorophenyl)-4,4a,5,6,8,8a-hexahydro-7-oxa-3-thia-1-azanaphthalen-2-yl]carbamate

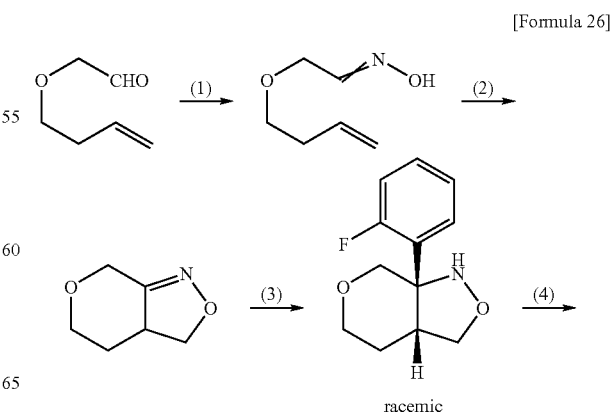

[Formula 26]

racemic

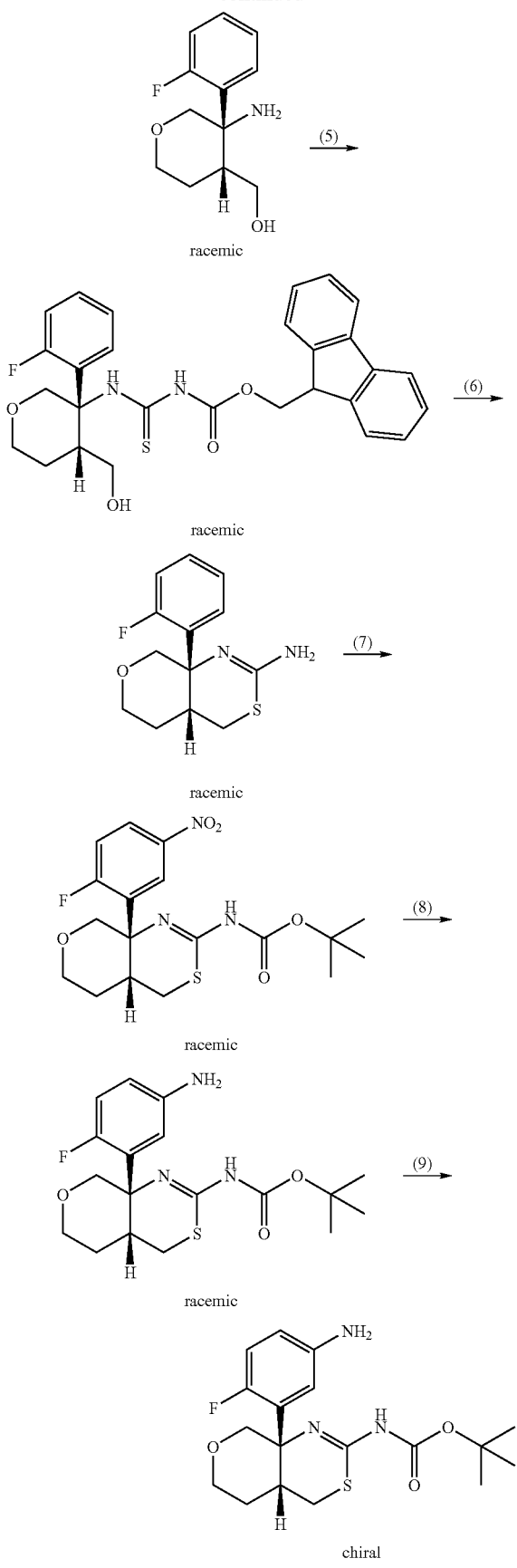

(1) Synthesis of 3-butenyloxyacetaldehyde oxime

Hydroxylamine sulfate (20.5 g), sodium acetate (12.8 g) and water (20 ml) were added to a solution of 3-butenyloxy-acetaldehyde (17.8 g; J. Chem. Soc., Perkin Trans. 1, 1999, 3143-3155) in ethanol (200 ml). The mixture was stirred at room temperature overnight and then water was added. The excess of ethanol was evaporated under reduced pressure and the resulting residue was extracted with ethyl acetate. The organic layer was washed with brine and dried over anhydrous magnesium sulfate. The solvent was evaporated under reduced pressure and the residue was purified by silica gel column chromatography to obtain the title compound (6.20 g).

$^1$H-NMR (400 MHz, CDCl$_3$) δ (ppm): 2.36 (m, 2H), 3.53 (dt, J=6.6, 8.4 Hz, 2H), 4.10 (d, J=5.6 Hz, 1H), 4.35 (d, J=4.0 Hz, 1H), 5.10 (m, 2H), 5.82 (m, 1H), 6.91 (t, J=3.6 Hz, 0.5H), 7.50 (t, J=5.6 Hz, 0.5H).

(2) Synthesis of 3,3a,4,5-tetrahydro-7H-pyrano[3,4-c]isoxazole

A 5% sodium hypochlorite solution (122 ml) was added dropwise to a solution of 3-butenyloxyacetaldehyde oxime (5.30 g) in dichloromethane (530 ml) under ice-cooling. After stirring at the same temperature for two hours, sodium thiosulfate was added. The aqueous layer was extracted with dichloromethane. The organic layers were combined and dried over anhydrous magnesium sulfate. The solvent was evaporated under reduced pressure and the residue was purified by silica gel column chromatography to obtain the title compound (4.15 g).

$^1$H-NMR (400 MHz, CDCl$_3$) δ (ppm): 1.79 (ddd, J=4.4, 12.4, 24.4 Hz, 1H), 2.17 (dd, J=6.4, 13.2 Hz, 1H), 3.40 (ddd, J=6.4, 11.2, 22.0 Hz, 1H), 3.50 (dt, J=2.0, 12.4 Hz, 1H), 3.80 (dd, J=8.0, 11.6 Hz, 1H), 4.06 (dd, 4.4, 12.8 Hz, 1H), 4.12 (dd, J=1.2, 13.6 Hz, 1H), 4.63 (dd, J=8.4, 10.4 Hz, 1H), 4.70 (d, J=13.6 Hz, 1H).

(3) Synthesis of (±)-(3aR*,7aS*)-7a-(2-fluorophenyl)hexahydropyrano[3,4-c]isoxazole 2-Bromofluorobenzene (1.85 g) was dissolved in toluene (30 ml), and tetrahydrofuran (10 ml) was added. n-Butyllithium (2.73 M; 3.68 ml) was added dropwise at −78° C. 2-Fluorophenyllithium was prepared by stirring at the same temperature for one hour. A boron trifluoride-ether complex (1.26 ml) was added to a solution of 3,3a,4,5-tetrahydro-7H-pyrano[3,4-c]isoxazole (630 mg) in toluene (70 ml) at −78° C. After stirring at the same temperature for 10 minutes, 2-fluorophenyllithium prepared above was added to the reaction mixture through a cannula. After stirring at the same temperature for one hour, an ammonium chloride solution was added. The reaction mixture was returned to room temperature, and the aqueous layer was extracted with ethyl acetate. The organic layer was washed with brine and dried over anhydrous magnesium sulfate. The solvent was evaporated under reduced pressure and the residue was purified by silica gel column chromatography to obtain the title compound (1.26 g).

ESI-MS; m/z 224 [M$^+$+H].

$^1$H-NMR (400 MHz, CDCl$_3$) δ (ppm): 1.83 (m, 2H), 3.09 (m, 1H), 3.64 (m, 1H), 3.68 (ddt, J=1.2, 3.2, 11.6 Hz, 1H), 3.73 (d, J=6.8 Hz, 1H), 3.78 (d, J=12.8 Hz, 1H) 4.04 (m, 1H), 4.10 (dd, J=1.6, 12.4 Hz, 1H), 6.32 (s, 1H), 7.04 (ddd, J=1.2, 8.0, 12.4 Hz, 1H), 7.16 (dt, J=1.6, 7.6 Hz, 1H), 7.28 (m, 1H), 7.93 (dt, J=1.6, 8.4 Hz, 1H).

(4) Synthesis of (±)-[(3S*,4R*)-3-amino-3-(2-fluorophenyl)tetrahydropyran-4-yl]methanol Zinc (11.6 g) was added to a solution of (±)-(3aR*,7aS*)-7a-(2-fluorophenyl)hexahydropyrano[3,4-c]isoxazole (3.95 g) in acetic acid (78.4 ml), and the mixture was stirred at room temperature overnight. The insoluble matter was removed by filtration through celite, and the solvent was evaporated under reduced pressure. An ice-cooled 0.5 N sodium hydroxide solution was added to the residue. The aqueous layer was extracted with ethyl acetate and a mixed solution of ethyl acetate and tetrahydrofuran. The organic layers were combined and washed with brine and then dried over anhydrous magnesium sulfate. The solvent was evaporated under reduced pressure and the residue was purified by silica gel column chromatography to obtain the title compound (3.45 g).

$^1$H-NMR (400 MHz, CDCl$_3$) δ (ppm): 1.61 (m, 1H), 2.28 (m, 2H), 3.35 (dd, J=2.8, 11.6 Hz, 2H), 3.55 (dd, J=1.6, 11.6 Hz, 1H), 3.63 (m, 1H), 4.16 (m, 2H), 7.06 (ddd, J=1.2, 8.0, 12.8 Hz, 1H), 7.20 (dt, J=1.6, 8.0 Hz, 1H), 7.31 (m, 1H), 7.64 (dt, J=2.0, 8.0 Hz, 1H).

(5) Synthesis of (±)-9H-fluoren-9-ylmethyl({[(3S*,4R*)-3-(2-fluorophenyl)-4-(hydroxymethyl)tetrahydro-2H-pyran-3-yl]amino}carbonothioyl)carbamic acid Fluorenylmethyloxycarbonyl isothiocyanate (938 mg) was added to a solution of (±)-[(3S*,4R*)-3-amino-3-(2-fluorophenyl)tetrahydropyran-4-yl]methanol (683 mg) in dichloromethane (20 ml). The mixture was stirred at room temperature overnight, and then the solvent was evaporated under reduced pressure at room temperature or lower. The residue was purified by silica gel column chromatography to obtain the title compound (1.57 g).

ESI-MS; m/z 529 [M$^+$+Na].

$^1$H-NMR (400 MHz, CDCl$_3$) δ (ppm): 1.67 (m, 1H), 1.93 (m, 2H), 3.65 (m, 4H), 4.13 (m, 2H), 4.27 (t, J=6.4 Hz, 1H), 4.55 (m, 2H), 7.02 (dd, J=4.4, 12.8 Hz, 1H), 7.16 (t, J=8.0 Hz, 1H), 7.28 (m, 1H), 7.35 (t, J=7.2 Hz, 2H), 7.44 (t, J=7.2 Hz, 2H), 7.58 (d, J=7.6 Hz, 2H), 7.59 (m, 1H), 7.79 (d, J=8.0 Hz, 2H), 7.93 (s, 1H), 10.67 (s, 1H).

(6) Synthesis of (±)-(4R*,4aS*)-8a-(2-fluorophenyl)-4,4a,5,6,8,8a-hexahydro-7-oxa-3-thia-1-azanaphthalen-2-ylamine Concentrated hydrochloric acid (3.00 ml) was added to a solution of (±)-9H-fluoren-9-ylmethyl({[(3S*,4R*)-3-(2-fluorophenyl)-4-(hydroxymethyl)tetrahydro-2H-pyran-3-yl]amino}carbonothioyl)carbamic acid (8.00 g) in methanol (200 ml), and the mixture was heated under reflux for three hours. The reaction solution was cooled to room temperature and the solvent was evaporated under reduced pressure. Acetonitrile (200 ml) was added to the residue, and piperidine (40 ml) was added dropwise in an water bath. The mixture was stirred at room temperature for two hours, and then the solvent was evaporated under reduced pressure. The residue was purified by NH-silica gel column chromatography to obtain a crude product. The resulting crude product was further purified by silica gel column chromatography to obtain the title compound (3.96 g).

ESI-MS; m/z 267 [M$^+$+H].

$^1$H-NMR (400 MHz, CDCl$_3$) δ (ppm): 1.43 (d, J=17.0 Hz, 1H), 2.12 (m, 1H), 2.61 (d, J=15.0 Hz, 1H), 2.91 (m, 1H), 2.96 (dd, J=4.5, 15.5 Hz, 1H), 3.68 (t, J=15.5 Hz, 1H), 3.76 (d, J=14.0 Hz, 1H), 4.09 (m, 2H), 4.58 (brs, 2H), 7.03 (dd, J=10.0, 16.0 Hz, 1H), 7.12 (t, J=10.0 Hz, 1H), 7.25 (m, 1H), 7.36 (dt, J=2.5, 10.0 Hz, 1H).

(7) Synthesis of tert-butyl (±)-[(4R*,4aS*)-8a-(2-fluoro-5-nitrophenyl)-4,4a,5,6,8,8a-hexahydro-7-oxa-3-thia-1-azanaphthalen-2-yl]carbamate (±)-(4R*,4aS*)-8a-(2-Fluorophenyl)-4,4a,5,6,8,8a-hexahydro-7-oxa-3-thia-1-azanaphthalen-2-ylamine obtained in Preparation Example 1-(6) (3.96 g) was dissolved in concentrated sulfuric acid (20 ml), and fuming nitric acid (specific gravity: 1.53; 731 µl) was added dropwise in an ice bath. After stirring at the same temperature for two hours, the reaction mixture was carefully poured into ice. The aqueous layer was neutralized with a sodium bicarbonate solution and a sodium hydroxide solution, followed by extraction with ethyl acetate. The organic layer was washed with brine and dried over anhydrous magnesium sulfate. The drying agent was removed by filtration and the filtrate was concentrated under reduced pressure to obtain a residue. Tetrahydrofuran (200 ml) was added to the residue and then triethylamine (10.3 ml) and di-tert-butyl dicarbonate (4.85 g) were sequentially added, followed by stirring at room temperature overnight. The solvent was evaporated under reduced pressure and the residue was purified by silica gel column chromatography to obtain the title compound (5.30 g).

ESI-MS; m/z 412 [M$^+$+H].

$^1$H-NMR (400 MHz, CDCl$_3$) δ (ppm): 1.53 (s, 9H), 1.55 (m, 1H), 2.21 (m, 1H), 2.62 (dd, J=3.2, 12.8 Hz, 1H), 2.85 (dd, J=2.8, 13.2 Hz, 1H), 3.00 (m, 1H), 3.67 (dt, J=2.4, 12.0 Hz, 1H), 3.74 (d, J=11.2 Hz, 1H), 3.97 (dd, J=2.4, 11.6 Hz, 1H), 4.12 (m, 1H), 7.25 (m, 1H), 8.22 (m, 2H).

(8) Synthesis of tert-butyl (±)-[(4R*,4aS*)-8a-(5-amino-2-fluorophenyl)-4,4a,5,6,8,8a-hexahydro-7-oxa-3-thia-1-azanaphthalen-2-yl]carbamate A saturated ammonium chloride solution (13.2 ml) was added to a solution of tert-butyl (±)-[(4R*,4aS*)-8a-(2-fluoro-5-nitrophenyl)-4,4a,5,6,8,8a-hexahydro-7-oxa-3-thia-1-azanaphthalen-2-yl]carbamate obtained in Preparation Example 1-(7) (5.30 g) in ethanol (132 ml). Iron powder (5.76 g) was added to the reaction mixture, followed by heating under reflux for 30 minutes. The reaction mixture was cooled to room temperature, and the insoluble matter was filtered through celite. The filtrate was evaporated under reduced pressure. The residue was purified by NH-silica gel column chromatography to obtain the title compound (4.56 g).

$^1$H-NMR (400 MHz, CDCl$_3$) δ (ppm): 1.53 (s, 9H), 1.53 (m, 1H), 2.23 (m, 1H), 2.54 (dd, J=2.4, 12.4 Hz, 1H), 2.98 (dd, J=4.0, 12.4 Hz, 1H), 3.03 (m, 1H), 3.66 (m, 2H), 4.07 (dd, J=1.6, 12.4 Hz, 1H), 4.12 (m, 1H), 6.57 (m, 2H), 6.86 (dd, J=8.8, 12.4 Hz, 1H).

(9) Synthesis of tert-butyl (−)-[(4R*,4aS*)-8a-(5-amino-2-fluorophenyl)-4,4a,5,6,8,8a-hexahydro-7-oxa-3-thia-1-azanaphthalen-2-yl]carbamate tert-Butyl (±)-[(4R*,4aS*)-8a-(5-amino-2-fluorophenyl)-4,4a,5,6,8,8a-hexahydro-7-oxa-3-thia-1-azanaphthalen-2-yl]carbamate obtained in Preparation Example 1-(8) (100 mg) was purified by CHIRALPAK™ AD-H (mobile phase: hexane:ethanol=8.5:1.5, flow rate: 20 ml/min), and the fraction with a retention time of 20.9 to 27.8 minutes was collected to obtain the title compound. The same operation was repeated to obtain the title compound (405 mg; >99% ee) from the raw material (1.00 g).

PREPARATION EXAMPLE 2

Synthesis of 5-fluoromethoxypyrazine-2-carboxylic acid

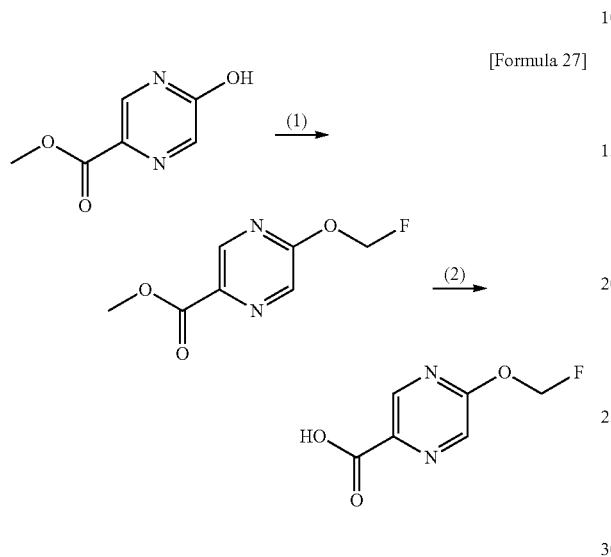

[Formula 27]

(1) Synthesis of methyl 5-fluoromethoxypyrazine-2-carboxylate

Fluoromethyl toluene-4-sulfonate (Journal of Labelled Compounds & Radiopharmaceuticals, 46 (6), 555-566; 2003) (344 mg) and cesium carbonate (824 mg) were added to a solution of methyl 5-hydroxypyrazine-2-carboxylate (130 mg) in N,N-dimethylformamide (2.0 mL). The reaction solution was stirred at 70° C. for five hours and 30 minutes and then cooled to room temperature. Water was added to the reaction solution, followed by extraction with ethyl acetate. The organic layer was concentrated under reduced pressure. The residue was purified by NH-silica gel column chromatography to obtain the title compound (18.0 mg).

$^1$H-NMR (400 MHz, CDCl$_3$) δ (ppm): 4.03 (s, 3H), 6.14 (d, J=51.2 Hz, 2H), 8.42 (d, J=1.2 Hz, 1H), 8.94 (d, J=1.2 Hz, 1H).

(2) Synthesis of 5-fluoromethoxypyrazine-2-carboxylic acid

Potassium trimethylsilanolate (18.6 mg) was added to a solution of methyl 5-fluoromethoxypyrazine-2-carboxylate obtained in Preparation Example 15-(1) (18.0 mg) in tetrahydrofuran (1.0 mL). The reaction solution was stirred at room temperature for one hour.

Water and ethyl acetate were added to the reaction solution, and the organic layer was separated. The aqueous layer was made acidic with 1 M hydrochloric acid, followed by extraction with ethyl acetate. The organic layer was dried over anhydrous magnesium sulfate. The drying agent was removed by filtration and the filtrate was concentrated under reduced pressure to obtain a crude product of the title compound (10.2 mg). The compound was used for the next reaction without further purification.

$^1$H-NMR (400 MHz, CDCl$_3$) δ (ppm): 6.16 (d, J=50.8 Hz, 2H), 8.34 (d, J=1.4 Hz, 1H), 9.05 (d, J=1.4 Hz, 1H).

PREPARATION EXAMPLE 3

Synthesis of 5-cyanopyridine-2-carboxylic acid

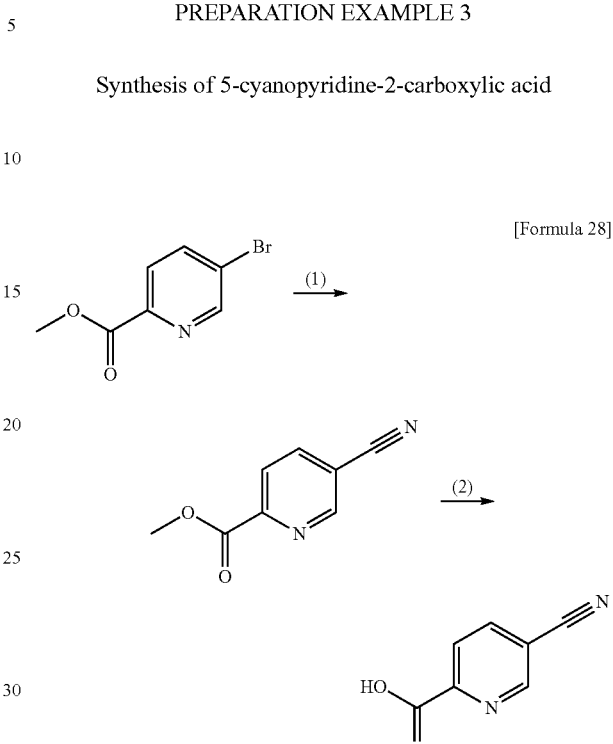

[Formula 28]

(1) Synthesis of methyl 5-cyanopyridine-2-carboxylate

A mixture of methyl 5-bromopyridine-2-carboxylate (2.8 g) and copper cyanide (3.6 g) in NMP (30 ml) was heated with stirring at 170° C. for 1.5 hours. Water was added to the reaction solution at room temperature, and the insoluble matter was removed by filtration. The filtrate was extracted with ethyl acetate. The extract was washed with brine and then dried over anhydrous magnesium sulfate. The drying agent was filtered off and the filtrate was concentrated under reduced pressure. The resulting crude product was purified by silica gel column chromatography to obtain the title compound (920 mg).

$^1$H-NMR (400 MHz, CDCl$_3$) δ (ppm): 4.06 (s, 3H), 8.16 (dd, J=2.0, 8.0 Hz, 1H), 8.27 (d, J=8.0 Hz, 1H), 9.01 (d, J=2.0 Hz, 1H).

(2) Synthesis of 5-cyanopyridine-2-carboxylic acid

A solution of the compound of Preparation Example 3-(1) (920 mg) and a 5 N sodium hydroxide solution (2.26 ml) in ethanol (30 ml) was stirred at room temperature for 10 minutes. 5 N hydrochloric acid (5.2 ml) was added to the reaction solution at room temperature, followed by extraction with ethyl acetate. The extract was dried over anhydrous magnesium sulfate. The drying agent was removed by filtration and the filtrate was concentrated under reduced pressure to obtain the title compound (800 mg).

$^1$H-NMR (400 MHz, DMSOd$_6$) δ (ppm): 8.18 (d, J=8.0 Hz, 1H), 8.51 (dd, J=2.0, 8.0 Hz, 1H), 9.12-9.18 (m, 1H).

PREPARATION EXAMPLE 4

Synthesis of 5-difluoromethoxypyrazine-2-carboxylic acid

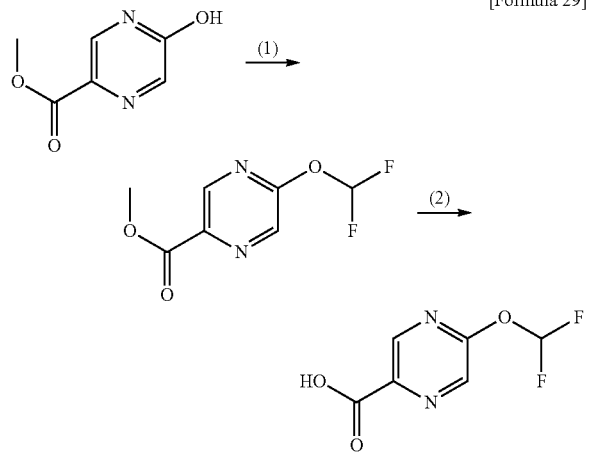

[Formula 29]

(1) Synthesis of methyl 5-difluoromethoxypyrazine-2-carbonxylate

Potassium carbonate (8.82 g) and sodium chlorodifluoroacetate (6.53 g) were added to a solution of methyl 5-hydroxypyrazine-2-carboxylate (3.3 g) in DMF (42.8 ml). The reaction solution was stirred at 100° C. for 30 minutes, and then saturated aqueous ammonium chloride was added, followed by extraction with ethyl acetate. The organic layer was washed with a saturated sodium bicarbonate solution and brine and then dried over magnesium sulfate. The drying agent was removed by filtration and then the solvent was evaporated under reduced pressure. The residue was purified by silica gel column chromatography to obtain the title compound (928 mg).

$^1$H-NMR (400 MHz, CDCl$_3$) δ (ppm): 4.04 (s, 3H), 7.49 (t, J=71.2 Hz, 1H), 8.47 (d, J=0.8 Hz, 1H), 8.92 (d, J=0.8 Hz, 1H).

(2) Synthesis of 5-difluoromethoxypyrazine-2-carboxylic acid

Water (1.54 ml) and a 5 N sodium hydroxide solution (492 ml) were added to a solution of the compound obtained in Preparation Example 4-(1) (250 mg) in THF (4.60 ml). The reaction solution was stirred at room temperature for five minutes and then a 2 N hydrochloric acid solution was added, followed by extraction with ethyl acetate. The organic layer was washed with brine and then dried over magnesium sulfate. The drying agent was removed by filtration and then the solvent was concentrated under reduced pressure to obtain the title compound (200 mg).

$^1$H-NMR (400 MHz, CDCl$_3$) δ (ppm): 7.51 (t, J=71.2 Hz, 1H), 8.39 (d, J=1.2 Hz, 1H), 9.04 (d, J=1.2 Hz, 1H).

PREPARATION EXAMPLE 5

Synthesis of tert-butyl (−)-[(4aR*,8aS*)-8a-(5-amino-2-trifluoromethoxyphenyl)-4,4a,5,6,8,8a-hexahydro-7-oxa-3-thia-1-azanaphthalen-2-yl]carbamate

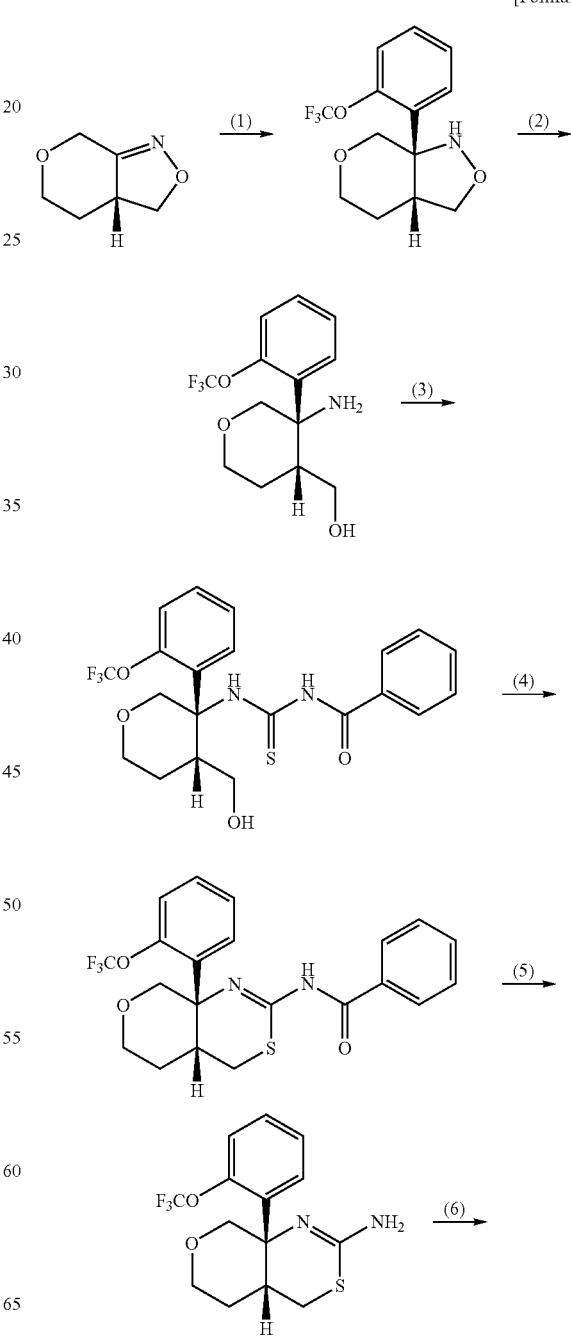

[Formula 30]

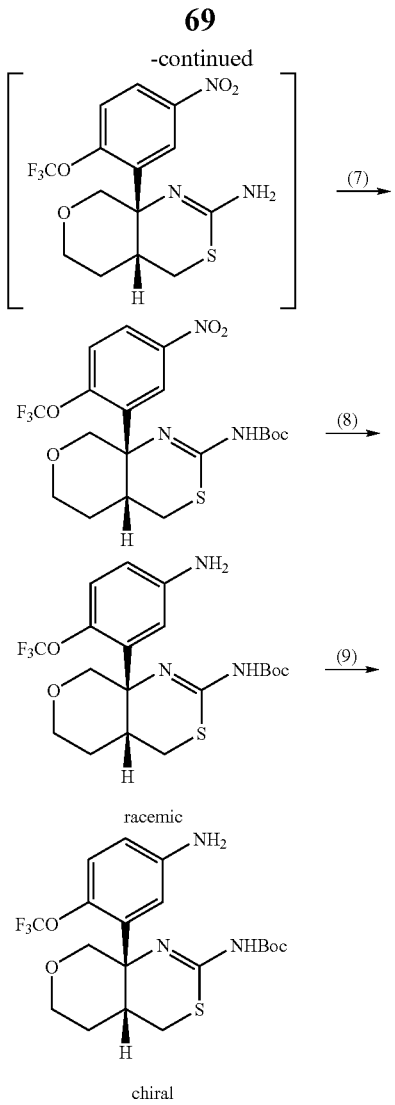

In Preparation Example 5, the compound obtained in Preparation Example 1-(2) was used as a starting material.

In Preparation Example 5-(1) and (2), synthesis was performed according to Preparation Example 1-(3) and (4).

(3) Synthesis of 1-benzoyl-3-[(3S*,4R*)-4-hydroxymethyl-3-(2-trifluoromethoxyphenyl)tetrahydropyran-3-yl]thiourea Benzoyl isothiocyanate (642 μl) was added to a solution of the compound obtained in the previous step (1.26 g) in dichloromethane (32.3 ml) at room temperature, and the mixture was stirred for two hours and 30 minutes. The reaction solution was concentrated under reduced pressure and the residue was purified by silica gel column chromatography to obtain the title compound (1.67 g).

$^1$H-NMR (400 MHz, CDCl$_3$) δ (ppm): 1.29-1.34 (m, 1H), 1.65-1.80 (m, 2H), 3.57-3.91 (m, 4H), 4.14-4.27 (m, 2H), 7.20-7.30 (m, 3H), 7.32-7.38 (m, 1H), 7.50-7.57 (m, 2H), 7.61-7.67 (m, 1H), 7.86-7.92 (m, 1H), 8.92 (brs, 1H).

(4) Synthesis of N-[(4aR*,8aS*)-8a-(2-trifluoromethoxyphenyl)-4,4a,5,6,8,8a-hexahydro-7-oxa-3-thia-1-azanaphthalen-2-yl]benzamide Concentrated hydrochloric acid (635 μl) was added to a solution of the compound obtained in the previous step (1.67 g) in methanol (25 ml), and the mixture was heated under reflux at 90° C. for two hours and 10 minutes. The reaction solution was returned to room temperature and concentrated under reduced pressure. A saturated sodium bicarbonate solution was added to the residue, followed by extraction with ethyl acetate. The organic layer was dried over anhydrous magnesium sulfate. The drying agent was filtered off and the filtrate was concentrated under reduced pressure to obtain the title compound (1.65 g).

$^1$H-NMR (400 MHz, CDCl$_3$) δ (ppm): 1.53-1.68 (m, 1H), 2.22-2.35 (m, 1H), 2.62-2.71 (m, 1H), 2.91-2.99 (m, 1H), 3.19-3.29 (m, 1H), 3.62-3.78 (m, 2H), 4.07-4.21 (m, 2H), 7.28-7.36 (m, 2H), 7.38-7.47 (m, 3H), 7.48-7.57 (m, 2H), 8.21-8.27 (m, 2H).

(5) Synthesis of (4aR*,8aS*)-8a-(2-trifluoromethoxyphenyl)-4,4a,5,6,8,8a-hexahydro-7-oxa-3-thia-1-azanaphthalen-2-ylamine DBU (1.28 ml) was added to a solution of the compound obtained in the previous step (1.65 g) in methanol (100 ml), and the mixture was heated under reflux at 80° C. for eight hours and 10 minutes. The reaction solution was returned to room temperature and concentrated under reduced pressure. The residue was purified by NH-silica gel column chromatography to obtain the title compound (870 mg).

$^1$H-NMR (400 MHz, CDCl$_3$) δ (ppm): 1.40-1.50 (m, 1H), 2.02-2.16 (m, 1H), 2.61-2.70 (m, 1H), 2.87-3.01 (m, 2H), 3.60-3.75 (m, 2H), 4.03-4.15 (m, 2H), 4.51 (brs, 2H), 7.21-7.34 (m, 3H), 7.48-7.52 (m, 1H).

In Preparation Example 5-(6), (7) and (8), synthesis was performed according to Preparation Example 1-(7) and (8).

(9) Synthesis of tert-butyl (−)-[(4aR*,8aS*)-8a-(5-amino-2-trifluoromethoxyphenyl)-4,4a,5,6,8,8a-hexahydro-7-oxa-3-thia-1-azanaphthalen-2-yl]carbamate The compound obtained in the previous step (12 mg) was purified by CHIRALPAK™ AD-H (mobile phase: hexane: ethanol=8:2, flow rate: 10 ml/min), and the fraction with a retention time of 15 to 20 minutes was collected to obtain the title compound. This operation was repeated to obtain the title compound (112 mg; >99% ee) from 240 mg of the racemate.

$^1$H-NMR (400 MHz, CDCl$_3$) δ (ppm): 1.53 (s, 9H), 1.54-1.60 (m, 1H), 2.13-2.27 (m, 1H), 2.51-2.60 (m, 1H), 2.90-2.96 (m, 1H), 3.03-3.12 (m, 1H), 3.58-3.67 (m, 2H), 3.80 (brs, 2H), 4.05-4.17 (m, 2H), 6.60 (dd, J=8.8, 2.8 Hz, 1H), 6.67 (d, J=2.8 Hz, 1H), 7.06-7.11 (m, 1H).

PREPARATION EXAMPLE 6

Synthesis of tert-butyl (−)-[(4aR*,6S*,8aS*)-8a-(5-amino-2-fluorophenyl)-6-methyl-4,4a,5,6,8,8a-hexahydro-7-oxa-3-thia-1-azanaphthalen-2-yl]carbamate

[Formula 31]

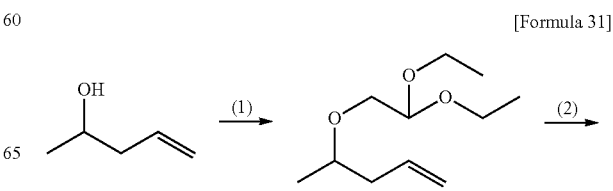

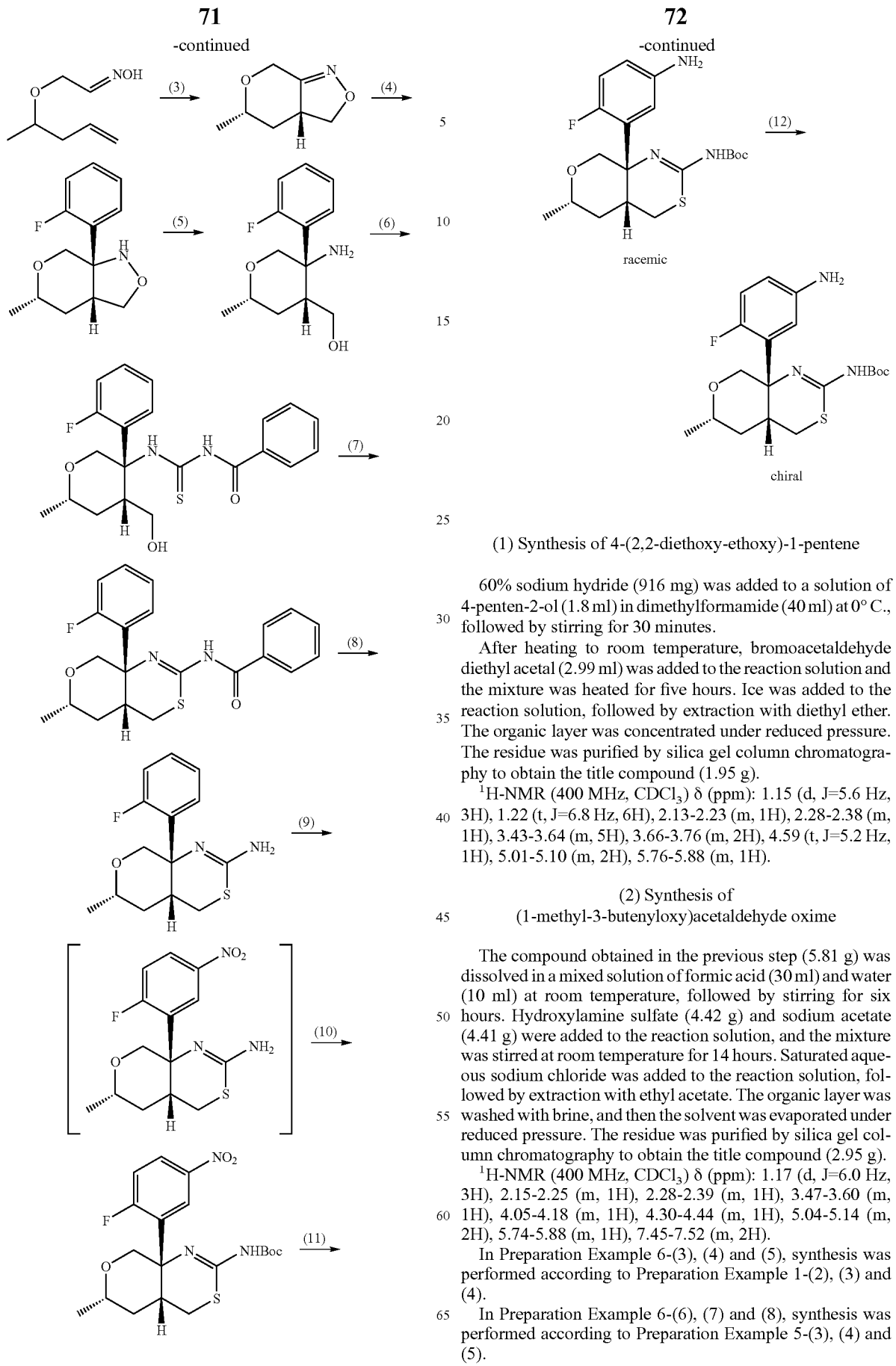

(1) Synthesis of 4-(2,2-diethoxy-ethoxy)-1-pentene

60% sodium hydride (916 mg) was added to a solution of 4-penten-2-ol (1.8 ml) in dimethylformamide (40 ml) at 0° C., followed by stirring for 30 minutes.

After heating to room temperature, bromoacetaldehyde diethyl acetal (2.99 ml) was added to the reaction solution and the mixture was heated for five hours. Ice was added to the reaction solution, followed by extraction with diethyl ether. The organic layer was concentrated under reduced pressure. The residue was purified by silica gel column chromatography to obtain the title compound (1.95 g).

$^1$H-NMR (400 MHz, CDCl$_3$) δ (ppm): 1.15 (d, J=5.6 Hz, 3H), 1.22 (t, J=6.8 Hz, 6H), 2.13-2.23 (m, 1H), 2.28-2.38 (m, 1H), 3.43-3.64 (m, 5H), 3.66-3.76 (m, 2H), 4.59 (t, J=5.2 Hz, 1H), 5.01-5.10 (m, 2H), 5.76-5.88 (m, 1H).

(2) Synthesis of (1-methyl-3-butenyloxy)acetaldehyde oxime

The compound obtained in the previous step (5.81 g) was dissolved in a mixed solution of formic acid (30 ml) and water (10 ml) at room temperature, followed by stirring for six hours. Hydroxylamine sulfate (4.42 g) and sodium acetate (4.41 g) were added to the reaction solution, and the mixture was stirred at room temperature for 14 hours. Saturated aqueous sodium chloride was added to the reaction solution, followed by extraction with ethyl acetate. The organic layer was washed with brine, and then the solvent was evaporated under reduced pressure. The residue was purified by silica gel column chromatography to obtain the title compound (2.95 g).

$^1$H-NMR (400 MHz, CDCl$_3$) δ (ppm): 1.17 (d, J=6.0 Hz, 3H), 2.15-2.25 (m, 1H), 2.28-2.39 (m, 1H), 3.47-3.60 (m, 1H), 4.05-4.18 (m, 1H), 4.30-4.44 (m, 1H), 5.04-5.14 (m, 2H), 5.74-5.88 (m, 1H), 7.45-7.52 (m, 2H).

In Preparation Example 6-(3), (4) and (5), synthesis was performed according to Preparation Example 1-(2), (3) and (4).

In Preparation Example 6-(6), (7) and (8), synthesis was performed according to Preparation Example 5-(3), (4) and (5).

In Preparation Example 6-(9), (10) and (11), synthesis was performed according to Preparation Example 1-(7) and (8).

(12) Synthesis of tert-butyl (−)-[(4aR*,6S*,8aS*)-8a-(5-amino-2-fluorophenyl)-6-methyl-4,4a,5,6,8,8a-hexahydro-7-oxa-3-thia-1-azanaphthalen-2-yl]carbamate The compound obtained in the previous step (27 mg) was purified by CHIRALPAK™ AD-H (mobile phase: hexane:ethanol=7:3, flow rate: 10 ml/min), and the fraction with a retention time of 16 to 19 minutes was collected to obtain the title compound. This operation was repeated to obtain the title compound (228 mg; >99% ee) from 540 mg of the racemate.

$^1$H-NMR (400 MHz, CDCl$_3$) δ (ppm): 1.28 (d, J=6.0 Hz, 3H), 1.53 (s, 9H), 1.55-1.61 (m, 1H), 1.80-1.93 (m, 1H), 2.47-2.55 (m, 1H), 2.93-3.01 (m, 1H), 3.02-3.11 (m, 1H), 3.59-3.82 (m, 4H), 4.11-4.18 (m, 1H), 6.54-6.62 (m, 2H), 6.81-6.89 (m, 1H).

PREPARATION EXAMPLE 7

Synthesis of tert-butyl (−)-[(4aR*,6R*,8aS*)-8a-(5-amino-2-fluorophenyl)-6-methoxymethyl-4,4a,5,6,8,8a-hexahydro-7-oxa-3-thia-1-azanaphthalen-2-yl]carbamate

[Formula 32]

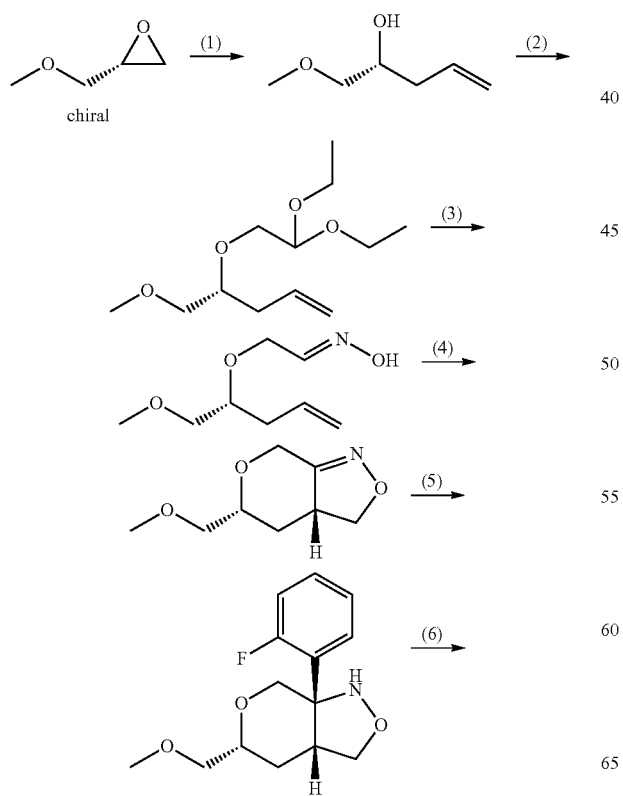

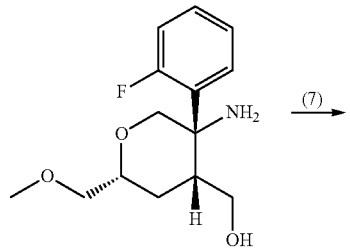

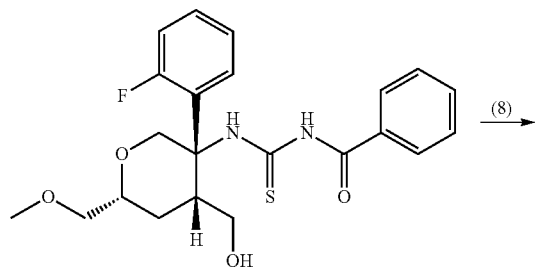

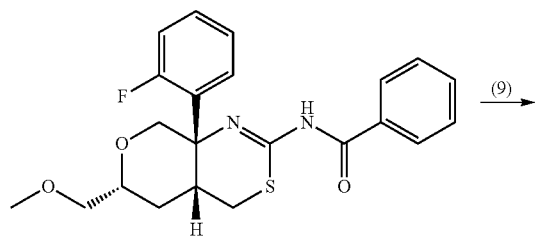

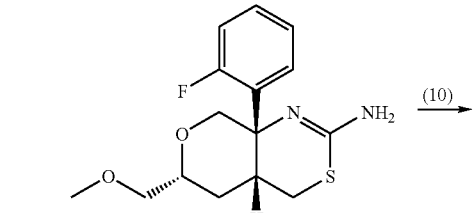

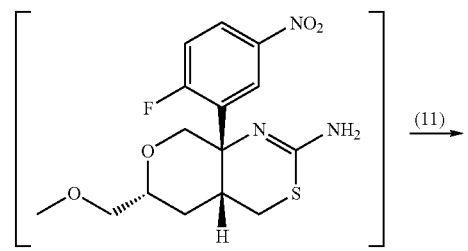

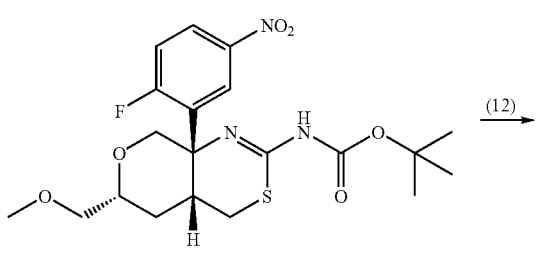

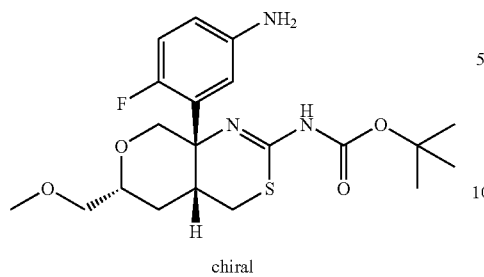

(1) Synthesis of (R)-1-methoxy-4-penten-2-ol

Copper iodide (630 mg) was suspended in tetrahydrofuran (200 ml), and a 1.38 M solution of vinylmagnesium chloride in tetrahydrofuran (32.3 ml) was added at −78° C., followed by stirring for 10 minutes. (R)-(−)Glycidyl methyl ether (2 ml) was added to the reaction solution at the same temperature, and the mixture was stirred at −78° C. for two hours and 25 minutes and at 0° C. for 25 minutes. A saturated ammonium chloride solution was added to the reaction solution. The mixture was sequentially extracted with a mixed solution of hexane and ethyl acetate (1:1), ethyl acetate and diethyl ether. The organic layer was dried over anhydrous magnesium sulfate. The drying agent was filtered off and the filtrate was concentrated under reduced pressure to obtain the title compound (2.60 g).

$^1$H-NMR (400 MHz, CDCl$_3$) δ (ppm): 2.21-2.30 (m, 3H), 3.29 (dd, J=9.6, 7.7 Hz, 1H), 3.39 (s, 3H), 3.43 (dd, J=9.6, 3.1 Hz, 1H), 3.81-3.90 (m, 1H), 5.09-5.18 (m, 2H), 5.78-5.91 (m, 1H).

In Preparation Example 7-(2) and (3), synthesis was performed according to Preparation Example 6-(1) and (2).

In Preparation Example 7-(4), (5) and (6), synthesis was performed according to Preparation Example 1-(2), (3) and (4).

In Preparation Example 7-(7), (8) and (9), synthesis was performed according to Preparation Example 5-(3), (4) and (5).

In Preparation Example 7-(10), (11) and (12), synthesis was performed according to Preparation Example 1-(7) and (8).

(12) Synthesis of tert-butyl (−)-[(4aR*,6R*,8aS*)-8a-(5-amino-2-fluorophenyl)-6-methoxymethyl-4,4a,5,6,8,8a-hexahydro-7-oxa-3-thia-1-azanaphthalen-2-yl]carbamate $^1$H-NMR (400 MHz, CDCl$_3$) δ (ppm): 1.48-1.57 (m, 1H), 1.53 (s, 9H), 1.82-1.96 (m, 1H), 2.49-2.56 (m, 1H), 2.96-3.03 (m, 1H), 3.04-3.13 (m, 1H), 3.37-3.43 (m, 1H), 3.41 (s, 3H), 3.50-3.58 (m, 1H), 3.65 (brs, 2H), 3.70-3.77 (m, 1H), 3.82-3.91 (m, 1H) 4.13-4.20 (m, 1H), 6.54-6.61 (m, 2H), 6.82-6.89 (m, 1H).

PREPARATION EXAMPLE 8

Synthesis of tert-butyl [(4aS,5S,8aS)-8a-(5-amino-2-fluorophenyl)-5-fluoro-4,4a,5,6,8,8a-hexahydro-7-oxa-3-thia-1-azanaphthalen-2-yl]carbamate

[Formula 33]

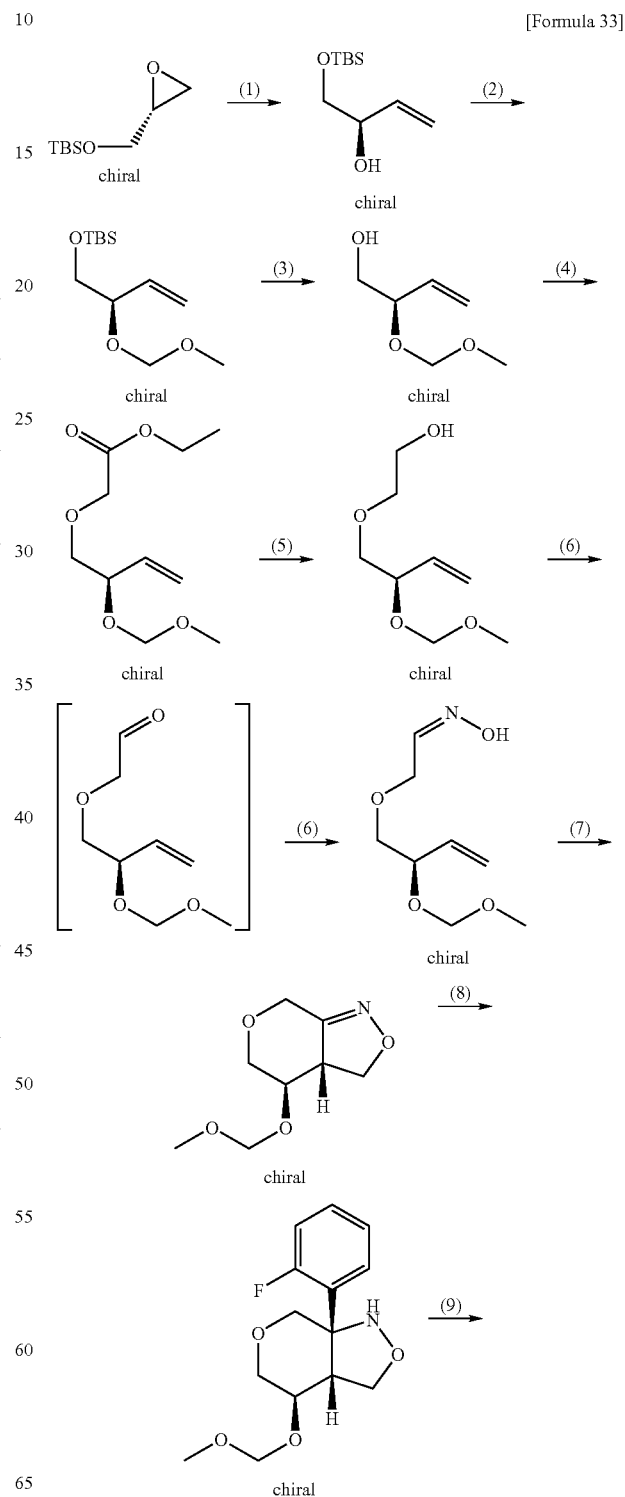

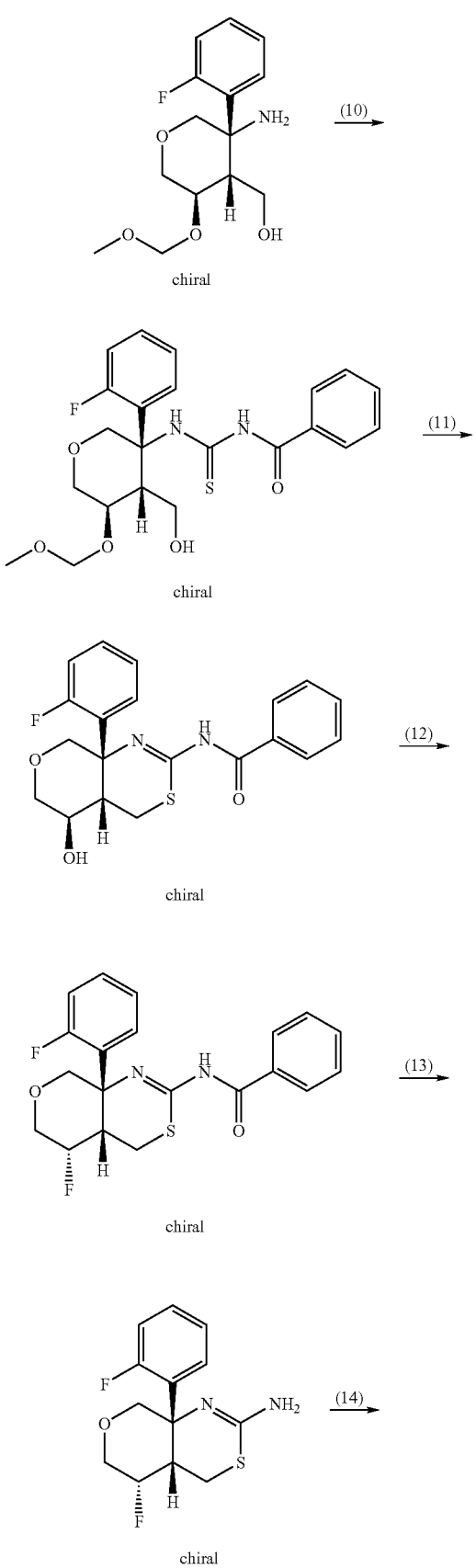

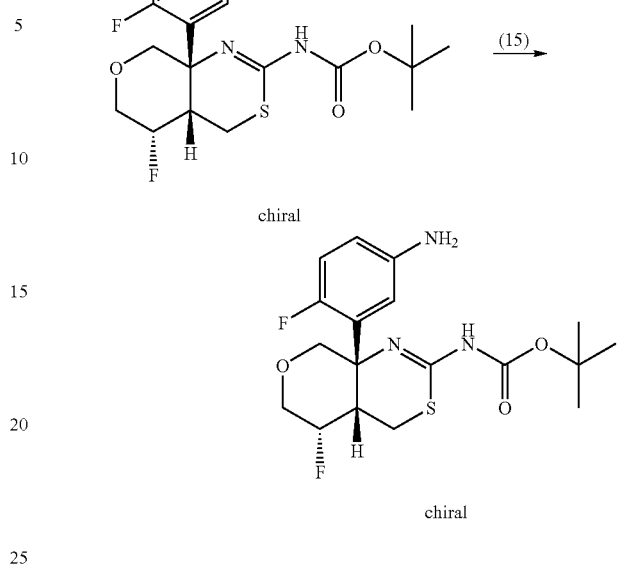

(1) Synthesis of (R)-1-(tert-butyldimethylsilany-loxy)-3-but en-2-ol n-Butyllithium (58.2 mL, 2.64 M solution in hexane) was added dropwise to a suspension of trimethylsulfonium iodide (32.4 g) in tetrahydrofuran (400 mL) in a nitrogen atmosphere at −20° C. The reaction solution was stirred at the same temperature for 30 minutes. tert-Butyldimethylsilyl (R)-(−)-glycidyl ether (10 g) was added dropwise to the reaction solution at the same temperature. The reaction solution was stirred for three hours with gradual heating to room temperature. Aqueous ammonium chloride and ethyl acetate were added to the reaction solution, and the organic layer was separated. The organic layer was washed with saturated aqueous sodium chloride twice. The organic layer was dried over anhydrous magnesium sulfate and concentrated under reduced pressure. The residue was purified by silica gel column chromatography to obtain the title compound (9.6 g).

$^1$H-NMR (400 MHz, CDCl$_3$) δ (ppm): 0.08 (s, 6H), 0.91 (s, 9H), 2.56 (d, J=3.6 Hz, 1H), 3.45 (dd, J=7.6, 10.0 Hz, 1H), 3.66 (dd, J=4.0, 10.0 Hz, 1H), 4.14-4.20 (m, 1H), 5.19 (ddd, J=1.6, 1.6, 10.8 Hz, 1H), 5.35 (ddd, J=1.6, 1.6, 17.6 Hz, 1H), 5.81 (ddd, J=6.0, 10.4, 17.6 Hz, 1H).

(2) Synthesis of tert-butyl-((R)-2-methoxymethoxy-3-butenyloxy)dimethylsilane

Chloromethyl methyl ether (9.03 mL) was added dropwise to a solution of the compound obtained in Preparation Example 8-(1) (9.6 g) and N,N-diisopropylethylamine (41.4 mL) in dichloromethane (200 mL) under ice-cooling. The reaction solution was heated to room temperature and stirred for 14 hours. Saturated aqueous sodium chloride was added to the reaction solution, and the organic layer was separated. The organic layer was dried over anhydrous magnesium sulfate and concentrated under reduced pressure. The residue was purified by silica gel column chromatography to obtain the title compound (11.3 g).

$^1$H-NMR (400 MHz, CDCl$_3$) δ (ppm): 0.07 (s, 6H), 0.89 (s, 9H), 3.39 (s, 3H), 3.60-3.70 (m, 2H), 4.09-4.14 (m, 1H), 4.64-4.72 (m, 2H), 5.27 (ddd, J=1.2, 2.0, 10.8 Hz, 1H), 5.30 (ddd, J=1.2, 2.0, 17.2 Hz, 1H), 5.74 (ddd, J=6.8, 10.4, 17.6 Hz, 1H).

(3) Synthesis of (R)-2-methoxymethoxy-3-buten-1-ol

Tetrabutylammonium fluoride (55 mL, 1 M solution in tetrahydrofuran) was added dropwise to a solution of the compound obtained in Preparation Example 8-(2) (11.3 g) in tetrahydrofuran (220 mL), and the mixture was stirred at room temperature for two hours. Saturated aqueous sodium chloride and ethyl acetate were added to the reaction solution, and the organic layer was separated. Ethyl acetate was added to the aqueous layer, and the organic layer was separated again. The combined organic layers were dried over anhydrous magnesium sulfate and concentrated under reduced pressure. The residue was purified by silica gel column chromatography to obtain the title compound (4.15 g).

$^1$H-NMR (400 MHz, CDCl$_3$) δ (ppm): 2.37-2.41 (m, 1H), 3.42 (s, 3H), 3.58-3.64 (m, 2H), 4.11-4.15 (m, 1H), 4.65-4.4.75 (m, 2H), 5.27-5.34 (m, 2H), 5.75 (ddd, J=6.4, 10.0, 17.2 Hz, 1H).

(4) Synthesis of ethyl ((R)-2-methoxymethoxy-3-butenyloxy)acetate

Sodium hydride (2.5 g) was added to a solution of the compound obtained in Preparation Example 8-(3) (4.15 g) in 1-methyl-2-pyrrolidinone (60 mL) under ice-cooling. The reaction solution was stirred at the same temperature for 30 minutes. Ethyl bromoacetate (10.4 mL) was added dropwise to the reaction solution. The reaction solution was heated to room temperature and stirred at the same temperature for five hours. Saturated aqueous ammonium chloride and ethyl acetate were added to the reaction solution, and the organic layer was separated. The organic layer was washed with aqueous sodium chloride and then dried over anhydrous magnesium sulfate. The organic layer was concentrated under reduced pressure. The residue was purified by silica gel column chromatography to obtain the title compound (4.77 g).

$^1$H-NMR (400 MHz, CDCl$_3$) δ (ppm): 1.24-1.31 (m, 3H), 3.39 (s, 3H), 3.59-3.69 (m, 2H), 4.10-4.22 (m, 4H), 4.23-4.32 (m, 1H), 4.64-4.74 (m, 2H), 5.28 (ddd, J=1.2, 1.2, 9.6 Hz, 1H), 5.35 (ddd, J=1.6, 1.6, 16.8 Hz, 1H), 5.78 (ddd, J=6.8, 10.4, 17.2 Hz, 1H).

(5) Synthesis of 2-((R)-2-methoxymethoxy-3-butenyloxy)ethanol

Lithium aluminum hydride (826 mg) was added to a solution of the compound obtained in Preparation Example 8-(4) (4.77 g) in tetrahydrofuran (100 mL) in a nitrogen atmosphere. The mixture was stirred at the same temperature for one hour. Methanol was added dropwise to the reaction solution, and then water was added dropwise. The insoluble matter in the reaction mixture was separated by filtration through celite and washed with ethyl acetate. Saturated aqueous sodium chloride was added to the filtrate, and the organic layer was separated. The organic layer was dried over anhydrous magnesium sulfate and concentrated under reduced pressure. The residue was purified by silica gel column chromatography to obtain the title compound (2.13 g).

$^1$H-NMR (400 MHz, CDCl$_3$) δ (ppm): 2.38 (t, J=6.0 Hz, 1H), 3.40 (s, 3H), 3.56-3.67 (m, 4H), 3.72-3.76 (m, 2H), 4.26 (q, J=6.0 Hz, 1H), 4.63-4.74 (m, 2H), 5.26-5.36 (m, 2H), 5.76 (ddd, J=6.8, 10.4, 15.6 Hz, 1H).

(6) Synthesis of ((R)-2-methoxymethoxy-3-butenyloxy)acetaldehyde oxime

A solution of dimethyl sulfoxide (605 μL) in dichloromethane (1 mL) was added dropwise to a solution of oxalyl chloride (633 μL) in dichloromethane (25 mL) in a nitrogen atmosphere at −78° C. The reaction solution was stirred at the same temperature for 10 minutes. A solution of the compound obtained in Preparation Example 8-(5) (1 g) in dichloromethane (4 mL) was added dropwise to the reaction solution at the same temperature. The reaction solution was stirred at the same temperature for 45 minutes. Triethylamine (3.81 mL) was added to the reaction solution, followed by heating to room temperature. The reaction solution was stirred at room temperature for one hour. Saturated aqueous ammonium chloride and ethyl acetate were added to the reaction solution, and the organic layer was separated. The organic layer was washed with saturated aqueous sodium chloride and dried over anhydrous magnesium sulfate. The organic layer was concentrated under reduced pressure, and ethanol (20 mL) and water (5 mL) were added to the residue. Sodium acetate (1.12 g) and hydroxylamine sulfate (1.12 g) were added to the reaction solution, and the mixture was stirred at room temperature for 13 hours. Ethyl acetate and saturated aqueous sodium chloride were added to the reaction solution, and the organic layer was separated. The organic layer was dried over anhydrous magnesium sulfate. The organic layer was concentrated under reduced pressure and the residue was purified by silica gel column chromatography to obtain the title compound (900 mg).

$^1$H-NMR (400 MHz, CDCl$_3$) δ (ppm): 3.39 (s, 1.5H), 3.40 (s, 1.5H), 3.54-3.58 (m, 2H), 4.14-4.16 (m, 1H), 4.22-4.29 (m, 1H), 4.40-4.41 (m, 1H), 4.62-4.74 (m, 2H), 5.26-5.37 (m, 2H), 5.71-5.81 (m, 1H), 6.93 (t, J=4.0 Hz, 0.5H), 7.51 (t, J=5.6 Hz, 0.5H).

(7) to (9) Synthesis of [(3S,4R,5R)-3-amino-3-(2-fluorophenyl)-5-methoxymethoxytetrahydropyran-4-yl]methanol The title compound (1 g) was obtained from the compound obtained in Preparation Example 8-(6) (900 mg) according to Preparation Example 1.

ESI-MS; m/z 286 [M$^+$+H].

$^1$H-NMR (400 MHz, CDCl$_3$) δ (ppm): 2.15-2.19 (m, 1H), 3.30-3.42 (m, 6H), 3.75 (dd, J=3.2, 12.0 Hz, 1H), 4.13-4.20 (m, 2H), 4.30 (dd, J=5.6, 10.8 Hz, 1H), 4.69-4.82 (m, 2H), 7.07 (ddd, J=1.6, 8.4, 12.8 Hz, 1H), 7.20-7.24 (m, 1H), 7.29-7.35 (m, 1H), 7.60-7.65 (m, 1H).

(10) Synthesis of 1-benzoyl-3-[(3S,4R,5R)-3-(2-fluorophenyl)-4-hydroxymethyl-5-methoxymethoxytetrahydropyran-3-yl]thiourea Benzoyl isocyanate (667 mg) was added to a solution of the compound obtained in Preparation Example 8-(9) (1 g) in dichloromethane (25 mL), and the mixture was stirred at room temperature for 15 hours. The reaction solution was concentrated under reduced pressure. The residue was purified by silica gel column chromatography to obtain the title compound (1.45 g).

ESI-MS; m/z 471 [M$^+$+Na].

¹H-NMR (400 MHz, CDCl₃) δ (ppm): 2.30-2.50 (brm, 1H), 3.0-3.2 (brm, 1H), 3.38-3.48 (m, 1H), 3.45 (s, 3H), 3.60-4.05 (m, 3H), 4.20-4.34 (m, 2H), 4.77 (s, 2H), 7.03-7.09 (m, 1H), 7.15-7.20 (m, 1H), 7.28-7.35 (m, 1H), 7.49-7.54 (m, 3H), 7.60-7.65 (m, 1H), 7.86-7.90 (m, 2H), 8.92 (s, 1H), 11.7 (s, 1H).

(11) Synthesis of N-[(4aS,5R,8aR)-8a-(2-fluorophenyl)-5-hydroxy-4,4a,5,6,8,8a-hexahydro-7-oxa-3-thia-1-azanaphthalen-2-yl]benzamide Concentrated hydrochloric acid (2 mL) was added to a solution of the compound obtained in Preparation Example 8-(10) (1.45 g) in methanol (20 mL), and the mixture was heated under reflux for one hour. The reaction solution was returned to room temperature and concentrated under reduced pressure. Ethyl acetate and aqueous sodium bicarbonate were added to the residue, and the organic layer was separated. The organic layer was washed with saturated aqueous sodium chloride and concentrated under reduced pressure. The residue was purified by silica gel column chromatography to obtain the title compound (895 mg).

ESI-MS; m/z 387 [M⁺+H].
¹H-NMR (400 MHz, CDCl₃) δ (ppm): 2.82 (dd, J=4.0, 12.8 Hz, 1H), 2.97-3.02 (m, 1H), 3.26-3.34 (m, 2H), 3.72 (d, J=12.0 Hz, 1H), 3.87 (dd, J=4.8, 6.8 Hz, 1H), 4.09-4.16 (m, 2H), 7.08-7.14 (m, 1H), 7.17-7.21 (m, 1H), 7.32-7.39 (m, 2H), 7.42-7.46 (m, 2H), 7.49-7.54 (m, 1H), 8.15-8.18 (m, 2H).

(12) Synthesis of N-[(4aS,5S,8aS)-5-fluoro-8a-(2-fluorophenyl)-4,4a,5,6,8,8a-hexahydro-7-oxa-3-thia-1-azanaphthalen-2-yl]benzamide

[Bis(2-methoxyethyl)amino]sulfur trifluoride (892 μL) was added dropwise to a solution of the compound obtained in Preparation Example 8-(11) (895 mg) in dichloromethane (25 mL) under ice-cooling. The reaction solution was stirred at the same temperature for two hours. Aqueous sodium bicarbonate and chloroform were added to the reaction solution, and the organic layer was separated. The organic layer was dried over anhydrous magnesium sulfate. The organic layer was concentrated under reduced pressure. The residue was purified by silica gel column chromatography to obtain the title compound (255 mg).

The recovered raw material (335 mg) was subjected to the same reaction as described above to obtain the title compound (120 mg).

ESI-MS; m/z 389 [M⁺+H].
¹H-NMR (400 MHz, CDCl₃) δ (ppm): 2.88 (dd, J=3.2, 13.2 Hz, 1H), 3.12-3.25 (m, 2H), 3.56-3.62 (m, 1H), 3.74-3.78 (m, 1H), 4.18 (d, J=12.0 Hz, 1H), 4.32 (dd, J=5.2, 10.8 Hz, 1H), 4.96-5.16 (m, 1H), 7.10-7.16 (m, 1H), 7.19-7.23 (m, 1H), 7.34-7.47 (m, 4H), 7.50-7.55 (m, 1H), 8.14-8.24 (m, 2H).

(13) Synthesis of (4aS,5S,8aS)-5-fluoro-8a-(2-fluorophenyl)-4,4a,5,6,8,8a-hexahydro-7-oxa-3-thia-1-azanaphthalen-2-ylamine 1,8-Diazabicyclo[5,4,0]-7-undecene (312 μL) was added to a solution of the compound obtained in Preparation Example 8-(12) (370 mg) in methanol (13 mL), and the mixture was heated under reflux for eight hours. The reaction solution was returned to room temperature and concentrated under reduced pressure. The residue was purified by NH-silica gel column chromatography to obtain the title compound (262 mg).

ESI-MS; m/z 285 [M⁺+H].
¹H-NMR (400 MHz, CDCl₃) δ (ppm): 2.81 (dd, J=3.6, 12.4 Hz, 1H), 2.95-3.02 (m, 1H), 3.11-3.15 (m, 1H), 3.49-3.56 (m, 1H), 3.69-3.84 (m, 1H), 4.08-4.12 (m, 1H), 4.25 (dd, J=5.6, 10.8 Hz, 1H), 4.50-4.65 (brm, 2H), 4.80-4.98 (m, 1H), 7.05 (ddd, J=1.2, 8.0, 12.8 Hz, 1H), 7.12-7.17 (m, 1H), 7.27-7.34 (m, 2H).

(14) to (15) Synthesis of tert-butyl [(4aS,5S,8aS)-8a-(5-amino-2-fluorophenyl)-5-fluoro-4,4a,5,6,8,8a-hexahydro-7-oxa-3-thia-1-azanaphthalen-2-yl]carbamate The title compound (195 mg) was obtained from the compound obtained in Preparation Example 8-(13) (262 mg) according to Preparation Example 1.

ESI-MS; m/z 400 [M⁺+H].
¹H-NMR (400 MHz, CDCl₃) δ (ppm): 1.52 (s, 9H), 2.82-2.87 (m, 1H), 3.02-3.10 (m, 2H), 3.53 (dd, J=4.0, 10.4 Hz, 1H), 3.64 (brs, 2H), 3.65-3.68 (m, 1H), 4.09 (dd, J=1.6, 11.6 Hz, 1H), 4.26 (dd, J=6.0, 10.8 Hz, 1H), 4.86-5.05 (m, 1H), 6.49 (dd, J=2.4, 6.8 Hz, 1H), 6.56-6.60 (m, 1H), 6.88 (dd, J=8.4, 12.0 Hz, 1H).

PREPARATION EXAMPLE 9

Synthesis of tert-butyl (-)-[(4aR*,5R*,8aS*)-8a-(5-amino-2-fluorophenyl)-5-methyloctahydro-7-oxa-3-thia-1-azanaphthalen-2-yl]carbamate and tert-butyl (-)-[(4aR*,5S*,8aS*)-8a-(5-amino-2-fluorophenyl)-5-methyloctahydro-7-oxa-3-thia-1-azanaphthalen-2-yl]carbamate

[Formula 34]

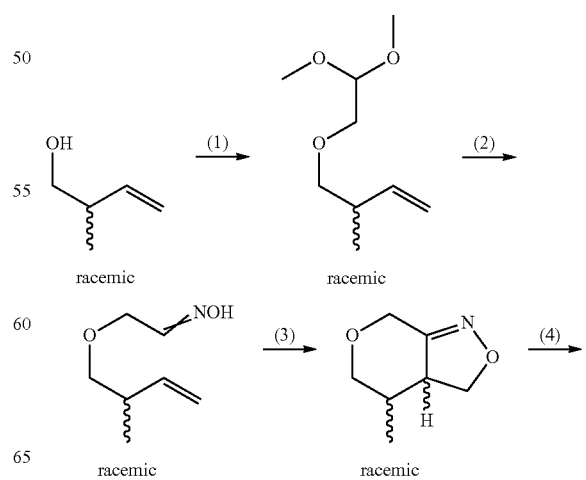

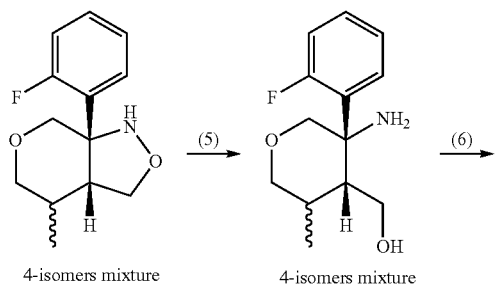
4-isomers mixture → 4-isomers mixture

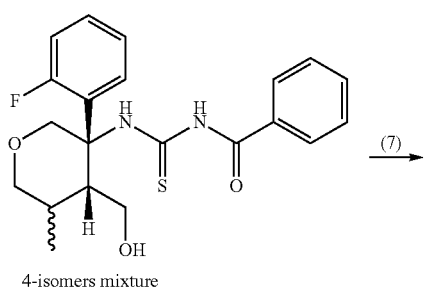
4-isomers mixture

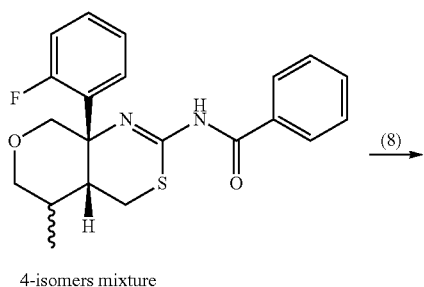
4-isomers mixture

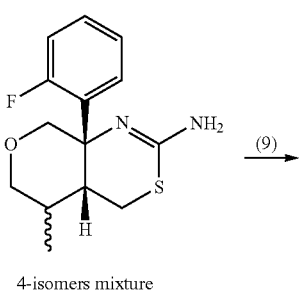
4-isomers mixture

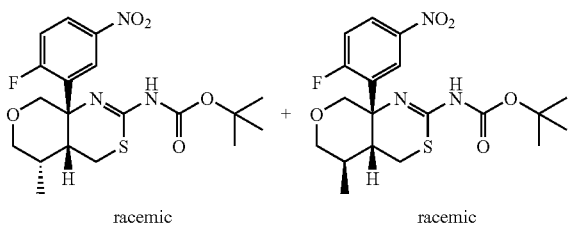
racemic + racemic

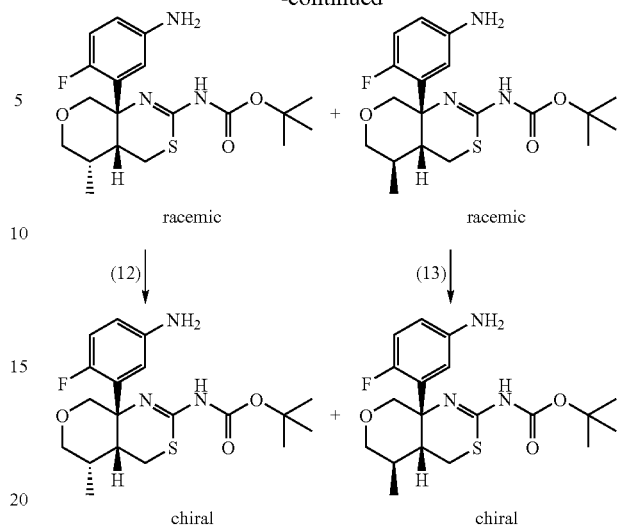
racemic + racemic
chiral + chiral (1) Synthesis of 4-(2,2-dimethoxyethoxy)-3-methyl-1-butene Sodium hydride (60 wt %, 928 mg) was added to a solution of 2-methyl-3-buten-1-ol (2 g) in DMF (30 mL) under ice-cooling, and the mixture was stirred at the same temperature for 30 minutes. Bromoacetaldehyde dimethyl acetal (5.45 mL) was added dropwise to the reaction solution at the same temperature. The reaction solution was stirred for 16 hours with gradual heating to room temperature. Ethyl acetate and aqueous sodium chloride were added to the reaction solution, and the organic layer was separated. The same operation was performed on the same scale. The combined organic layers were washed with saturated aqueous sodium chloride and dried over anhydrous magnesium sulfate. The organic layer was concentrated under reduced pressure and the residue was purified by silica gel column chromatography to obtain the title compound (4.92 g).

$^1$H-NMR (400 MHz, CDCl$_3$) δ (ppm): 1.02 (d, J=6.8 Hz, 3H), 2.45-2.52 (m, 1H), 3.32 (dd, J=7.2, 9.2 Hz, 1H), 3.36-3.40 (m, 2H), 3.40 (s, 6H), 3.49 (d, J=4.8 Hz, 1H), 4.51 (t, J=4.8 Hz, 1H), 4.99-5.09 (m, 2H), 5.77 (ddd, J=17.2, 10.8, 6.4 Hz, 1H).

(2) Synthesis of (2-methyl-3-butenyloxy)acetaldehyde oxime

A solution of the compound obtained in Preparation Example 9-(1) (4.92 g) in formic acid/water (20 mL/5 mL) was stirred at room temperature for 16 hours. Ethanol (30 mL), water (10 mL), sodium acetate (4.63 g) and hydroxylamine sulfate (4.63 g) were added to the reaction solution, and the mixture was stirred at room temperature for eight hours. Saturated aqueous sodium chloride and ethyl acetate were added to the reaction solution, and the organic layer was separated. The organic layer was washed again with saturated aqueous sodium chloride and then dried over anhydrous magnesium sulfate. The organic layer was concentrated under reduced pressure and the residue was purified by silica gel column chromatography to obtain the title compound (1.57 g).

$^1$H-NMR (400 MHz, CDCl$_3$) δ (ppm): 1.02 (d, J=7.2 Hz, 1.5H), 1,04 (d, J=6.4 Hz, 1.5H), 2.44-2.51 (m, 1H), 3.28-3.41 (m, 2H), 4.09 (d, J=6.4 Hz, 1H), 4.33 (d, J=3.6 Hz, 1H), 5.01-5.11 (m, 2H), 5.72-5.82 (m, 1H), 6.90 (t, J=3.6 Hz, 0.5H), 7.45 (brs, 1H), 7.49 (t, J=6.4 Hz, 0.5 Hz).

(3) to (7) Synthesis of (±)-N-[(4aR*,5S*,8aS*)-8a-(2-fluorophenyl)-5-methyl-4,4a,5,6,8,8a-hexahydro-7-oxa-3-thia-1-azanaphthalen-2-yl]benzamide and (±)-N-[(4aR*,5R*,8aS*)-8a-(2-fluorophenyl)-5-methyl-4,4a,5,6,8,8a-hexahydro-7-oxa-3-thia-1-azanaphthalen-2-yl]benzamide A mixture of the title compound (2.15 g) was obtained from the compound obtained in Preparation Example 9-(2) (1.57 g) according to Preparation Example 8.
ESI-MS; m/z 385 [M$^+$+H].

(8) to (9) Synthesis of (±)-N-[(4aR*,5S*,8aS*)-8a-(2-fluoro-5-nitrophenyl)-5-methyl-4,4a,5,6,8,8a-hexahydro-7-oxa-3-thia-1-azanaphthalen-2-yl]benzamide and (±)-N-[(4aR*,5R*,8aS*)-8a-(2-fluoro-5-nitrophenyl)-5-methyl-4,4a,5,6,8,8a-hexahydro-7-oxa-3-thia-1-azanaphthalen-2-yl]benzamide The title compound (±)-N-[(4aR*,5S*,8aS*)-8a-(2-fluoro-5-nitrophenyl)-5-methyl-4,4a,5,6,8,8a-hexahydro-7-oxa-3-thia-1-azanaphthalen-2-yl]benzamide (440 mg) and the title compound (±)-N-[(4aR*,5R*,8aS*)-8a-(2-fluoro-5-nitrophenyl)-5-methyl-4,4a,5,6,8,8a-hexahydro-7-oxa-3-thia-1-azanaphthalen-2-yl]benzamide (1.37 g) were obtained from the compound obtained in Preparation Example 9-(7) (2.15 g) according to Preparation Example 8.
ESI-MS; m/z 426 [M$^+$+H].

(10) Synthesis of tert-butyl (±)-[(4aR*,5S*,8aS*)-8a-(5-amino-2-fluorophenyl)-5-methyl-4,4a,5,6,8,8a-hexahydro-7-oxa-3-thia-1-azanaphthalen-2-yl]carbamate The title compound (225 mg) was obtained from (±)-N-[(4aR*,5S*,8aS*)-8a-(2-fluoro-5-nitrophenyl)-5-methyl-4,4a,5,6,8,8a-hexahydro-7-oxa-3-thia-1-azanaphthalen-2-yl]benzamide obtained in Preparation Example 9-(9) (440 mg) according to Preparation Example 8.
ESI-MS; m/z 396 [M$^+$+H].

(11) Synthesis of tert-butyl (±)-[(4aR*,5R*,8aS*)-8a-(5-amino-2-fluorophenyl)-5-methyl-4,4a,5,6,8,8a-hexahydro-7-oxa-3-thia-1-azanaphthalen-2-yl]carbamate The title compound (953 mg) was obtained from (±)-N-[(4aR*,5R*,8aS*)-8a-(2-fluoro-5-nitrophenyl)-5-methyl-4,4a,5,6,8, 8a-hexahydro-7-oxa-3-thia-1-azanaphthalen-2-yl]benzamide obtained in Preparation Example 9-(9) (1.37 g) according to Preparation Example 8.
ESI-MS; m/z 396 [M$^+$+H].

(12) Synthesis of tert-butyl (−)-[(4aR*,5S*,8aS*)-8a-(5-amino-2-fluorophenyl)-5-methyl-4,4a,5,6,8,8a-hexahydro-7-oxa-3-thia-1-azanaphthalen-2-yl]carbamate The compound obtained in Preparation Example 9-(10) was purified by CHIRALPAK™ AD-H (mobile phase: ethanol, flow rate: 10 ml/min), and the fraction with a retention time of 12.5 to 14.7 minutes was collected to obtain the title compound. The same operation was repeated to obtain the title compound (100 mg; >99% ee) from the raw material (225 mg).
$^1$H-NMR (400 MHz, CDCl$_3$) δ (ppm): 0.92 (d, J=6.8 Hz, 3H), 1.45 (s, 9H), 2.01-2.07 (m, 1H), 2.78-2.83 (m, 2H), 3.23-3.30 (m, 1H), 3.39-3.44 (m, 1H), 3.63-3.71 (m, 2H), 4.12 (d, J=12.8 Hz, 1H), 6.56-6.60 (m, 1H), 6.86 (dd, J=8.8, 11.6 Hz, 1H), 7.05-7.07 (m, 1H).
ESI-MS; m/z 396 [M$^+$+H].

(13) Synthesis of tert-butyl (−)-[(4aR*,5R*,8aS*)-8a-(5-amino-2-fluorophenyl)-5-methyl-4,4a,5,6,8,8a-hexahydro-7-oxa-3-thia-1-azanaphthalen-2-yl]carbamate The compound obtained in Preparation Example 9-(11) was purified by CHIRALCEL™ OJ-H (mobile phase: hexane:ethanol=1:1, flow rate: 10 ml/min), and the fraction with a retention time of 21.8 to 41.7 minutes was collected to obtain the title compound. The same operation was repeated to obtain the title compound (230 mg; >99% ee) from the raw material (500 mg).
$^1$H-NMR (400 MHz, CDCl$_3$) δ (ppm): 0.92 (d, J=6.4 Hz, 3H), 1.52 (s, 9H), 2.20-2.34 (m, 1H), 2.56-2.60 (m, 1H), 2.75-2.87 (m, 2H), 3.28 (t, J=11.6 Hz, 1H), 3.65 (brs, 2H), 3.67 (d, J=12.0 Hz, 1H), 3.96 (dd, J=4.8, 11.2 Hz, 1H), 4.11 (dd, J=1.6, 12.0 Hz, 1H), 6.54-6.60 (m, 2H), 6.82-6.88 (m, 1H).
ESI-MS; m/z 396 [M$^+$+H].

PREPARATION EXAMPLE 10

Synthesis of tert-butyl (−)-[(4aS*,5R*,8aS*)-8a-(5-amino-2-fluorophenyl)-5-methoxy-4,4a,5,6,8,8a-hexahydro-7-oxa-3-thia-1-azanaphthalen-2-yl]carbamate

[Formula 35]

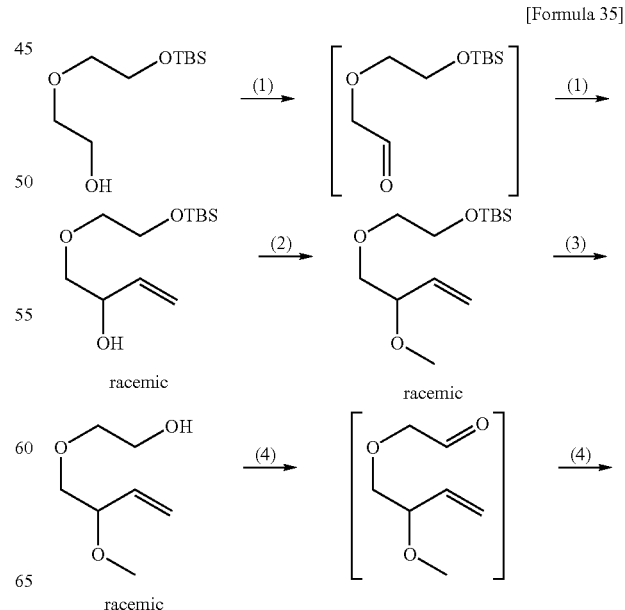

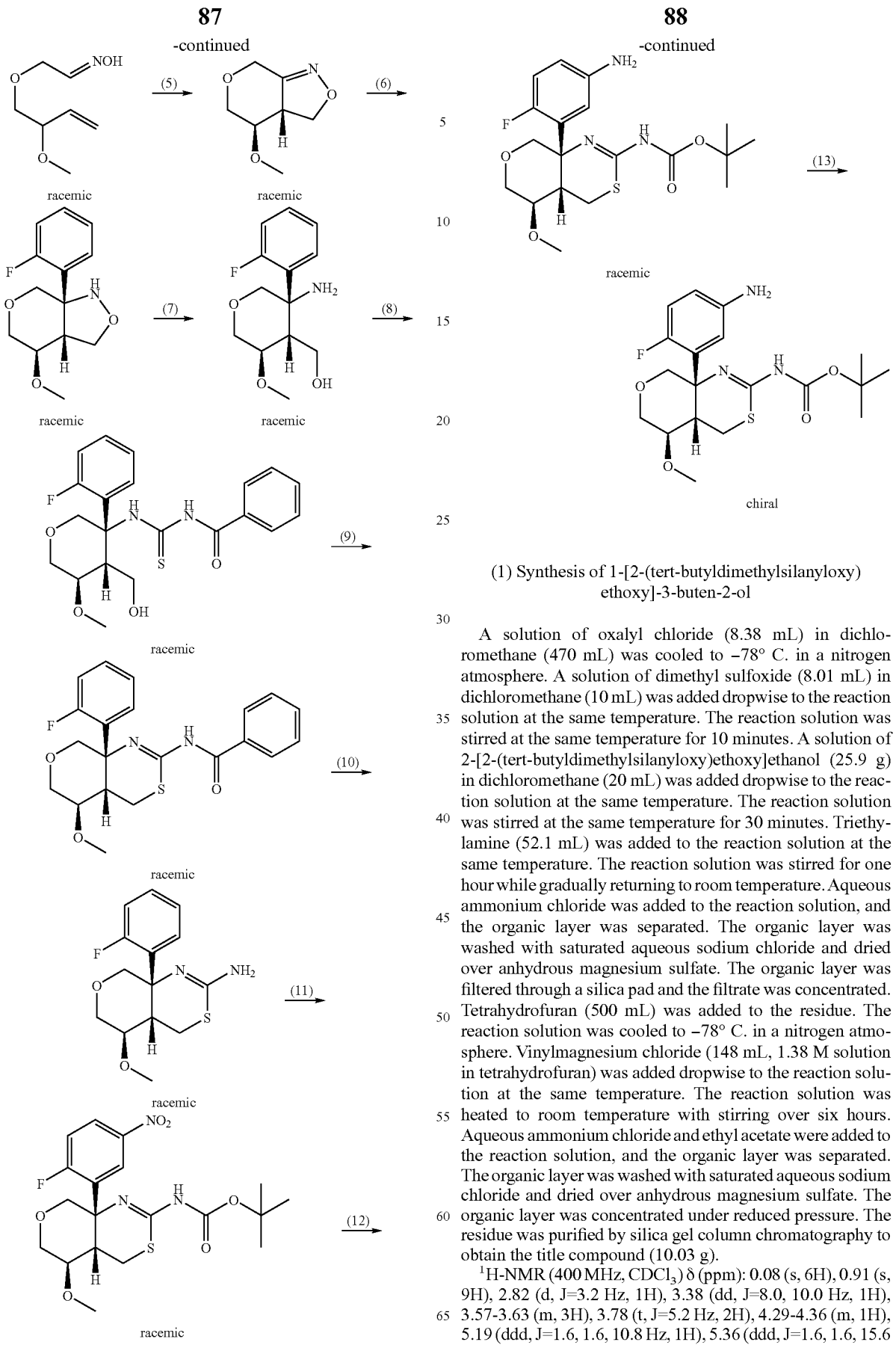

(1) Synthesis of 1-[2-(tert-butyldimethylsilanyloxy)ethoxy]-3-buten-2-ol

A solution of oxalyl chloride (8.38 mL) in dichloromethane (470 mL) was cooled to −78° C. in a nitrogen atmosphere. A solution of dimethyl sulfoxide (8.01 mL) in dichloromethane (10 mL) was added dropwise to the reaction solution at the same temperature. The reaction solution was stirred at the same temperature for 10 minutes. A solution of 2-[2-(tert-butyldimethylsilanyloxy)ethoxy]ethanol (25.9 g) in dichloromethane (20 mL) was added dropwise to the reaction solution at the same temperature. The reaction solution was stirred at the same temperature for 30 minutes. Triethylamine (52.1 mL) was added to the reaction solution at the same temperature. The reaction solution was stirred for one hour while gradually returning to room temperature. Aqueous ammonium chloride was added to the reaction solution, and the organic layer was separated. The organic layer was washed with saturated aqueous sodium chloride and dried over anhydrous magnesium sulfate. The organic layer was filtered through a silica pad and the filtrate was concentrated. Tetrahydrofuran (500 mL) was added to the residue. The reaction solution was cooled to −78° C. in a nitrogen atmosphere. Vinylmagnesium chloride (148 mL, 1.38 M solution in tetrahydrofuran) was added dropwise to the reaction solution at the same temperature. The reaction solution was heated to room temperature with stirring over six hours. Aqueous ammonium chloride and ethyl acetate were added to the reaction solution, and the organic layer was separated. The organic layer was washed with saturated aqueous sodium chloride and dried over anhydrous magnesium sulfate. The organic layer was concentrated under reduced pressure. The residue was purified by silica gel column chromatography to obtain the title compound (10.03 g).

$^1$H-NMR (400 MHz, CDCl$_3$) δ (ppm): 0.08 (s, 6H), 0.91 (s, 9H), 2.82 (d, J=3.2 Hz, 1H), 3.38 (dd, J=8.0, 10.0 Hz, 1H), 3.57-3.63 (m, 3H), 3.78 (t, J=5.2 Hz, 2H), 4.29-4.36 (m, 1H), 5.19 (ddd, J=1.6, 1.6, 10.8 Hz, 1H), 5.36 (ddd, J=1.6, 1.6, 15.6 Hz, 1H), 5.83 (ddd, J=5.2, 10.4, 15.6 Hz, 1H).

(2) Synthesis of tert-butyl-[2-(2-methoxy-3-butenyloxy)ethoxy]dimethylsilane Sodium hydride (357 mg, 60 wt %) was added to a solution of the compound obtained in Preparation Example 10-(1) (2 g) in DMF (20 mL) under ice-cooling, and the mixture was stirred at the same temperature for one hour. Methyl iodide (1.01 mL) was added to the reaction solution at the same temperature. The reaction solution was stirred at the same temperature for one hour. Aqueous ammonium chloride and ethyl acetate were added to the reaction solution, and the organic layer was separated. The organic layer was washed with saturated aqueous sodium chloride. The organic layer was dried over anhydrous magnesium sulfate. The organic layer was concentrated under reduced pressure. The residue was purified by silica gel column chromatography to obtain the title compound (1.30 g).

$^1$H-NMR (400 MHz, CDCl$_3$) δ (ppm): 0.06 (s, 6H), 0.89 (s, 9H), 3.34 (s, 3H), 3.49-3.76 (m, 4H), 3.76-3.81 (m, 3H), 5.25-5.33 (m, 2H), 5.72 (ddd, J=7.2, 10.4, 15.2 Hz, 1H).

(3) Synthesis of 2-(2-methoxy-3-butenyloxy)ethanol

Tetrabutylammonium fluoride (7.47 mL, 1 M solution in tetrahydrofuran) was added dropwise to a solution of the compound obtained in Preparation Example 10-(2) (1.3 g) in tetrahydrofuran (25 mL) under ice-cooling. The reaction solution was stirred at the same temperature for 10 minutes. The reaction solution was returned to room temperature and further stirred for five hours. Saturated aqueous sodium chloride and ethyl acetate were added to the reaction solution, and the organic layer was separated. Ethyl acetate was added to the aqueous layer, and the organic layer was separated. The organic layers were combined and dried over anhydrous magnesium sulfate. The organic layer was concentrated under reduced pressure. The residue was purified by silica gel column chromatography to obtain the title compound (500 mg).

$^1$H-NMR (400 MHz, CDCl$_3$) δ (ppm): 2.41 (s, 1H), 3.35 (s, 3H), 3.54-3.57 (m, 2H), 3.61-3.64 (m, 2H), 3.72-3.75 (m, 2H), 3.79-3.84 (m, 1H), 5.28-5.35 (m, 2H), 5.71 (ddd, J=7.6, 10.4, 15.6 Hz, 1H).

(4) Synthesis of (2-methoxy-3-butenyloxy)acetaldehyde oxime

The title compound (280 mg) was obtained from the compound obtained in Preparation Example 10-(3) (500 mg) according to Preparation Example 8.

$^1$H-NMR (400 MHz, CDCl$_3$) δ (ppm): 3.34 (s, 1.5H), 3.35 (s, 1.5H), 3.50-3.54 (m, 2H), 3.78-3.84 (m, 1H), 4.10-4.16 (m, 1H), 4.40 (d, J=4.0 Hz, 1H), 5.28-5.36 (m, 2H), 5.66-5.76 (m, 1H), 6.94 (t, J=3.2 Hz, 0.5H), 7.51 (t, J=5.2 Hz, 0.5H).

(5) to (12) Synthesis of tert-butyl (±)-[(4aS*,5R*,8aS*)-8a-(5-amino-2-fluorophenyl)-5-methoxy-4,4a,5,6,8,8a-hexahydro-7-oxa-3-thia-1-azanaphthalen-2-yl]carbamate The title compound (74 mg) was obtained from the compound obtained in Preparation Example 10-(4) (280 mg) according to Preparation Example 9.

ESI-MS; m/z 412 [M$^+$+H].

(13) Synthesis of tert-butyl (−)-[(4aS*,5R*,8aS*)-8a-(5-amino-2-fluorophenyl)-5-methoxy-4,4a,5,6,8,8a-hexahydro-7-oxa-3-thia-1-azanaphthalen-2-yl]carbamate The compound obtained in Preparation Example 10-(12) was purified by CHIRALCEL™ OJ-H (mobile phase: hexane:ethanol=1:1, flow rate: 10 ml/min), and the fraction with a retention time of 18.6 to 22.0 minutes was collected to obtain the title compound. The same operation was repeated to obtain the title compound (25 mg; >99% ee) from the raw material (70 mg).

$^1$H-NMR (400 MHz, CDCl$_3$) δ (ppm): 1.52 (s, 9H), 2.77 (dd, J=7.6, 12.8 Hz, 1H), 2.84-2.89 (m, 1H), 3.10 (dd, J=3.2, 12.8 Hz, 1H), 3.32 (dd, J=10.4, 10.4 Hz, 1H), 3.48 (s, 3H), 3.61-3.75 (m, 2H), 4.08 (dd, J=1.2, 12.0 Hz, 1H), 4.29 (dd, J=4.8, 10.8 Hz, 1H), 6.53 (dd, J=3.2, 6.4 Hz, 1H), 6.55-6.59 (m, 1H), 6.86 (dd, J=8.4, 12.0 Hz, 1H).

ESI-MS; m/z 412 [M$^+$+H].

PREPARATION EXAMPLE 11

Synthesis of tert-butyl (±)-[(2R*,4aR,8aS)-8a-(5-amino-2-fluorophenyl)-4-methyl-4,4a,5,6,8,8a-hexahydro-7-oxa-3-thia-1-azanaphthalen-2-yl]carbamate

[Formula 36]

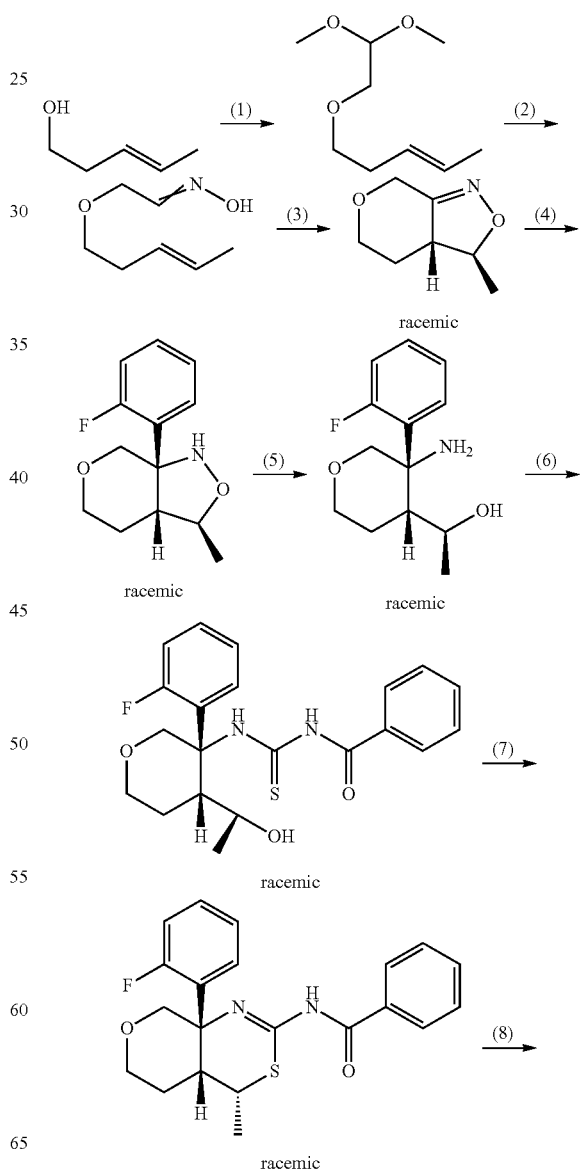

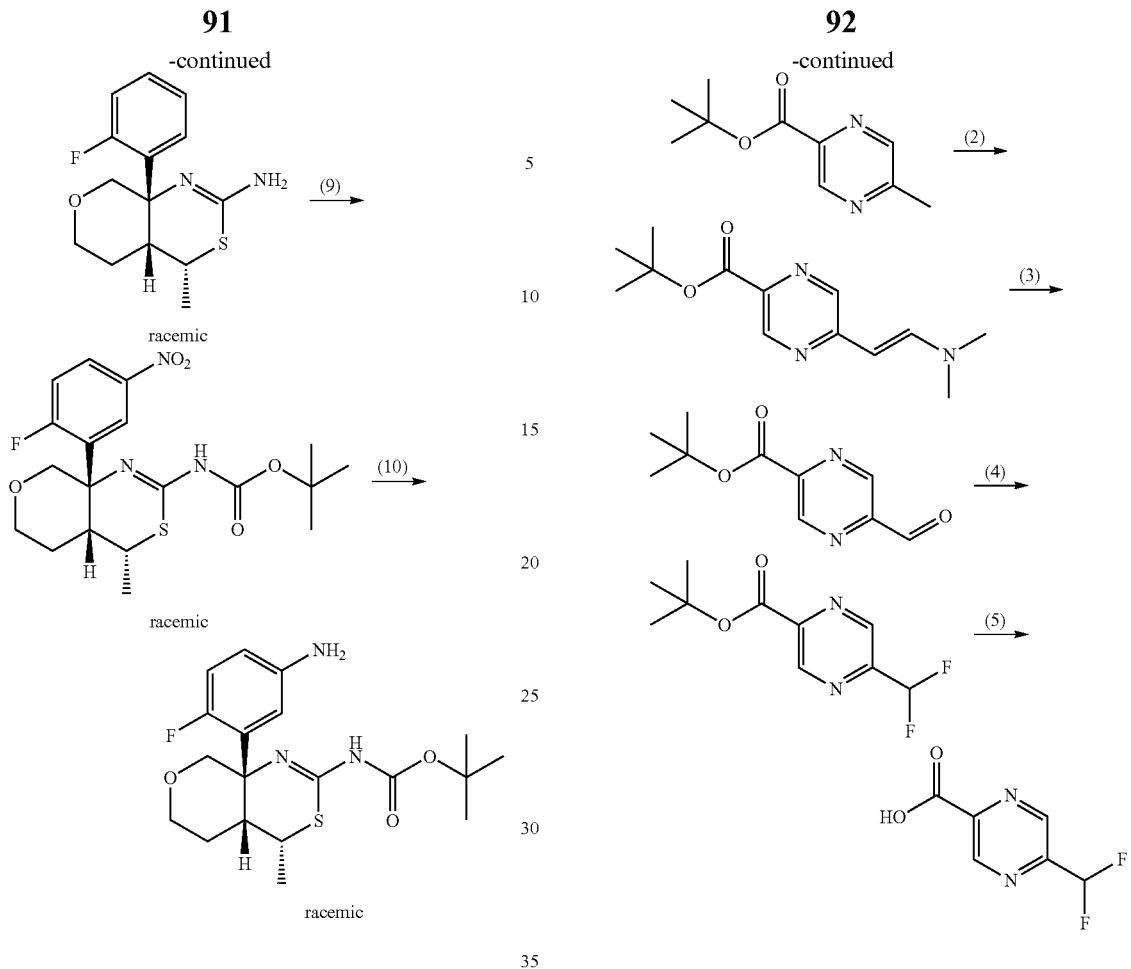

(1) to (10) Synthesis of tert-butyl (±)-[(2R*,4aR, 8aS)-8a-(5-amino-2-fluorophenyl)-4-methyl-4,4a,5, 6,8,8a-hexahydro-7-oxa-3-thia-1-azanaphthalen-2-yl]carbamate The title compound (384 mg) was obtained from trans-3-penten-1-ol (4.71 g) according to Preparation Example 9.

$^1$H-NMR (400 MHz, CDCl$_3$) δ (ppm): 1.18 (d, J=7.2 Hz, 3H), 1.53 (s, 9H), 1.85-1.96 (m, 1H), 2.80 (ddd, J=4.0, 4.0, 12.0 Hz, 1H), 3.22 (qd, J=7.2, 3.2 Hz, 1H), 3.61-3.70 (m, 3H), 4.05-4.17 (m, 2H), 6.54-6.58 (m, 2H), 6.83-6.88 (m, 1H).

ESI-MS; m/z 396 [M$^+$+H].

PREPARATION EXAMPLE 12

Synthesis of 5-difluoromethylpyrazine-2-carboxylic acid (1) Synthesis of t-butyl 5-methylpyrazine-2-carboxylate A boron trifluoride-diethyl ether complex (91.7 IL) was added dropwise to a suspension of 2-methylpyrazine-5-carboxylic acid (1 g) and tert-butyl 2,2,2-trichloroacetimidate (4.75 g) in tetrahydrofuran (20 mL) under ice-cooling. The reaction solution was heated to room temperature and stirred for two hours. A saturated sodium chloride solution and ethyl acetate were added to the reaction solution, and the organic layer was separated. The organic layer was dried over anhydrous magnesium sulfate, and the insoluble matter was separated by filtration. The filtrate was concentrated and purified by silica gel column chromatography to obtain the title compound (1.4 g).

$^1$H-NMR (CDCl$_3$) δ (ppm): 1.65 (s, 9H), 2.65 (s, 3H), 8.57 (d, J=1.2 Hz, 1H), 9.10 (d, J=1.6 Hz, 1H).

(2) Synthesis of t-butyl 5-((E)-2-dimethylaminovinyl)pyrazine-2-carboxylate

A mixture of t-butyl 5-methylpyrazine-2-carboxylate (1.35 g), N,N-dimethylformamide (25 mL) and N,N-dimethylformamide dimethylacetal (25 mL) was stirred at 130° C. for five hours. The reaction solution was cooled to room temperature and diluted with ethyl acetate. The mixture was washed with a saturated sodium chloride solution three times. The organic layer was dried over anhydrous magnesium sulfate, and the insoluble matter was separated by filtration. The filtrate was concentrated and the residue was purified by silica gel column chromatography to obtain the title compound (648 mg).

¹H-NMR (CDCl₃) δ (ppm): 1.63 (s, 9H), 3.00 (s, 6H), 5.16 (d, J=12.8 Hz, 1H), 7.72 (d, J=12.8 Hz, 1H), 8.16 (d, J=1.2 Hz, 1H), 8.81 (d, J=1.6 Hz, 1H).

(3) Synthesis of t-butyl 5-formylpyrazine-2-carboxylate

Sodium periodate (1.67 g) was added to a solution of t-butyl 5-((E)-2-dimethylamino-vinyl)pyrazine-2-carboxylate (645 mg) in 50% tetrahydrofuran-water (26 mL), and the mixture was stirred at room temperature for four hours. A saturated sodium bicarbonate solution and ethyl acetate were added to the reaction solution, and the organic layer was separated. The organic layer was washed with a saturated sodium chloride solution and dried over anhydrous magnesium sulfate. The insoluble matter was separated by filtration and the filtrate was concentrated. The residue was purified by silica gel column chromatography to obtain the title compound (249 mg).

¹H-NMR (CDCl₃) δ (ppm): 1.68 (s, 9H), 9.25 (d, J=1.2 Hz, 1H), 9.36 (d, J=1.6 Hz, 1H), 10.2 (s, 1H).

(4) Synthesis of t-butyl 5-difluoromethylpyrazine-2-carboxylate

[Bis(2-methoxyethyl)amino]sulfur trifluoride (662 μL) was added dropwise to a solution of t-butyl 5-formylpyrazine-2-carboxylate (249 mg) in dichloromethane (12 mL) in a nitrogen atmosphere under ice-cooling. The reaction solution was stirred for two hours while gradually returning to room temperature. A saturated sodium bicarbonate solution and ethyl acetate were added to the reaction solution, and the organic layer was separated. The organic layer was washed with a saturated sodium chloride solution and dried over anhydrous magnesium sulfate. The insoluble matter was separated by filtration and the filtrate was concentrated. The residue was purified by silica gel column chromatography to obtain the title compound (175 mg).

¹H-NMR (CDCl₃) δ (ppm): 1.67 (s, 9H), 6.75 (t, J=54.4 Hz, 1H), 9.02 (d, J=0.8 Hz, 1H), 9.25 (d, J=0.8 Hz, 1H).

(5) Synthesis of 5-difluoromethylpyrazine-2-carboxylic acid

Trifluoroacetic acid (1 mL) was added to a solution of t-butyl 5-difluoromethylpyrazine-2-carboxylate (175 mg) in dichloromethane (1 mL), and the mixture was stirred at room temperature for five hours. Ether and 5 N sodium hydroxide were added to the reaction solution. The aqueous layer was separated and made acidic with 5 N hydrochloric acid. Ethyl acetate was added to the aqueous layer, and the organic layer was separated. The organic layer was dried over anhydrous magnesium sulfate, and the insoluble matter was separated by filtration. The filtrate was concentrated to obtain the title compound (100 mg).

¹H-NMR (CDCl₃) δ (ppm): 6.80 (t, J=54.4 Hz, 1H), 9.02 (s, 1H), 9.47 (s, 1H).

PREPARATION EXAMPLE 13

Synthesis of tert-butyl [(4aR,6R,8aS)-8a-(5-amino-2-fluorophenyl)-6-hydroxymethyl-4,4a,5,6,8,8a-hexahydro-7-oxa-3-thia-1-azanaphthalen-2-yl]carbamate

[Formula 38]

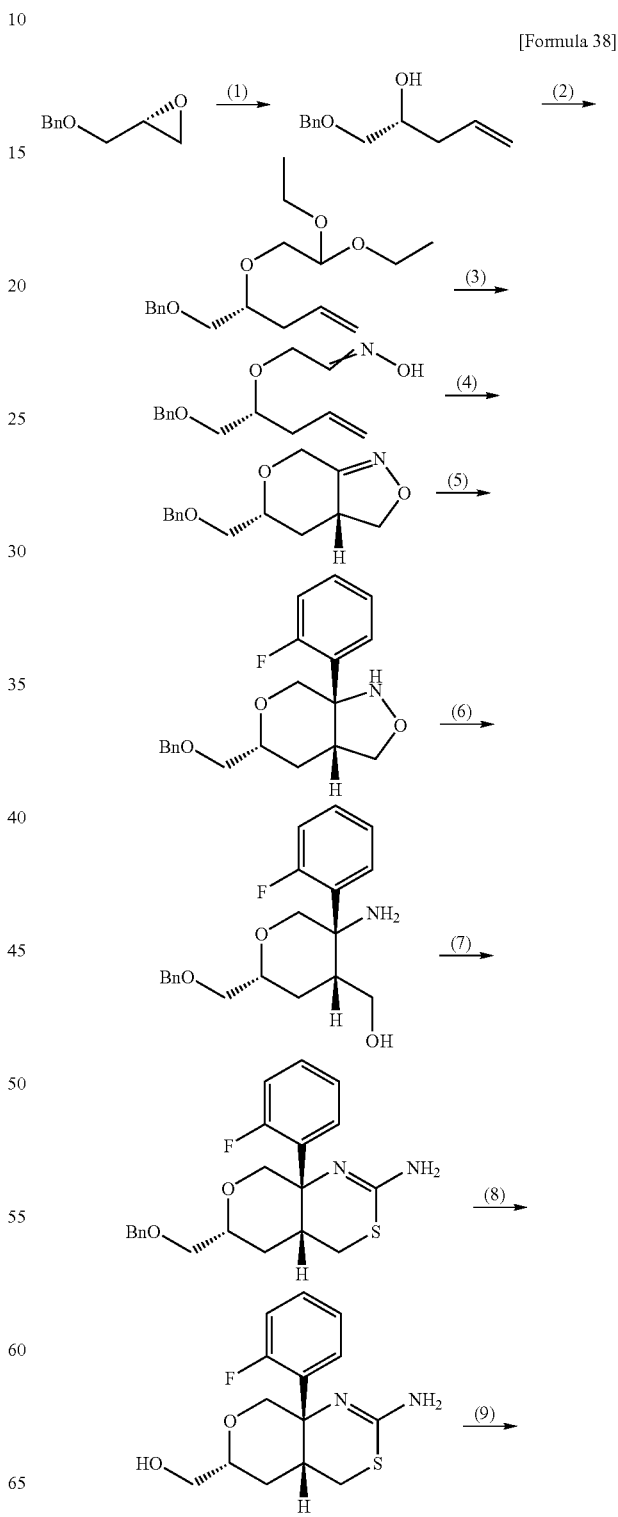

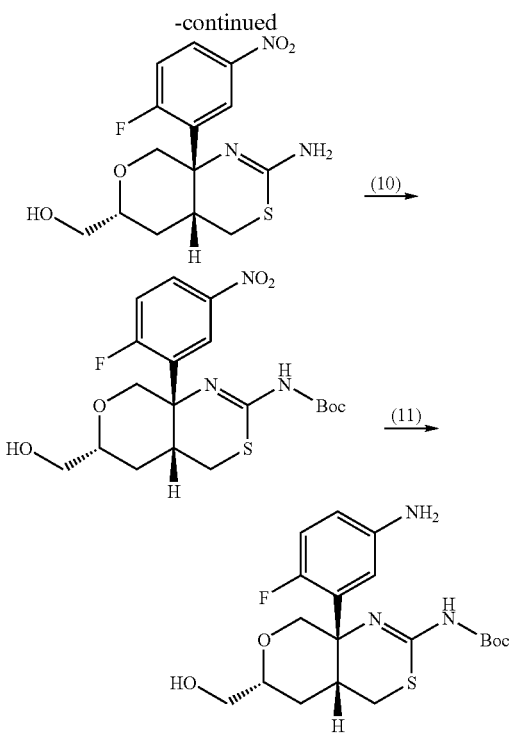

(1) Synthesis of (R)-1-benzyloxy-4-penten-2-ol

Ether (100 ml) and copper(I) iodide (580 mg) were added to a solution of (R)-benzyl glycidyl ether (10.0 g) in THF (100 ml). The mixture was cooled to −78° C., and vinylmagnesium chloride (1.38 M, 53.0 ml) was added dropwise. The mixture was stirred overnight with gradual heating to room temperature. Ice was added to the reaction solution, and an ammonium chloride solution was further added. The aqueous layer was extracted with ethyl acetate, and the organic layer was washed with an ammonium chloride solution. The insoluble matter was removed by filtration through celite, and the solvent was evaporated under reduced pressure to obtain the title compound (12.5 g).

$^1$H-NMR (400 MHz, CDCl$_3$) δ (ppm): 1.59 (d, J=2.0 Hz, 1H), 2.25-2.29 (m, 2H), 3.38 (dd, J=7.2, 9.2 Hz, 1H), 3.52 (dd, J=3.2, 9.2 Hz, 1H), 3.86-3.91 (m, 1H), 4.56 (s, 2H), 5.08-5.15 (m, 2H), 5.78-5.88 (m, 1H), 7.28-7.38 (m, 5H).

(2) Synthesis of [(R)-2-(2,2-diethoxyethoxy)-4-pentenyloxymethyl]benzene (R)-1-Benzyloxy-4-penten-2-ol (3.13 g) was dissolved in DMF (32 ml), and sodium hydride (60%, 0.91 g) was added in an ice bath. After stirring at the same temperature for 30 minutes, bromoacetaldehyde diethyl acetal (3.03 ml) was added. The mixture was heated to room temperature and stirred for two hours, and then heated to 50° C. and stirred for one hour. After cooling to room temperature, ice was added to the reaction solution. The reaction solution was extracted with ethyl acetate. The organic layer was washed with water and brine. The organic layer was dried over anhydrous magnesium sulfate, and the solvent was evaporated under reduced pressure. The residue was purified by silica gel column chromatography to obtain the title compound. The mixture containing the recovered raw material was reacted under the same conditions. The title compound was obtained by purification by the same method (total yield: 5.00 g).

$^1$H-NMR (400 MHz, CDCl$_3$) δ (ppm): 1.20 (t, J=7.2 Hz, 3H), 1.21 (t, J=7.2 Hz, 3H), 2.31-2.34 (m, 2H), 3.50 (dd, J=1.2, 5.2 Hz, 2H), 3.53-3.71 (m, 7H), 4.54 (s, 2H), 4.60 (t, J=5.2 Hz, 1H), 5.02-5.11 (m, 2H), 5.78-5.88 (m, 1H), 7.25-7.35 (m, 5H).

(3) Synthesis of ((R)-1-benzyloxymethyl-3-butenyloxy)acetaldehyde oxime

[(R)-2-(2,2-Diethoxyethoxy)-4-pentenyloxymethyl]benzene (20.0 g) was dissolved in formic acid (160 ml) and water (40 ml), and the mixture was stirred at room temperature for 30 minutes. Next, water (161 ml) and ethanol (400 ml) were added, and then hydroxylamine sulfate (6.38 g) and sodium acetate (8.82 g) were added, followed by stirring at room temperature overnight. Water was added to the reaction solution, and the insoluble matter was dissolved. Then, the excess of ethanol was evaporated under reduced pressure. The aqueous layer was extracted with ethyl acetate. The organic layer was washed with water and brine. The organic layer was dried over anhydrous magnesium sulfate, and the solvent was evaporated under reduced pressure. The residue was purified by silica gel column chromatography to obtain the title compound (13.7 g).

$^1$H-NMR (400 MHz, CDCl$_3$) δ (ppm): 2.30-2.35 (m, 2H), 3.47-3.62 (m, 3H), 4.17-4.27 (m, 1H), 4.46-4.47 (m, 1H), 4.55 (d, J=4.4 Hz, 2H), 5.04-5.11 (m, 2H), 5.74-5.85 (m, 1H), 6.94 (t, J=3.6 Hz, 0.35H), 7.28-7.37 (m, 5H), 7.50 (t, J=6.0 Hz, 0.65 Hz).

(4) Synthesis of (3aR,5R)-5-benzyloxymethyl-3,3a,4,5-tetrahydro-7H-pyrano[3,4-c]isoxazole ((R)-1-Benzyloxymethyl-3-butenyloxy)acetaldehyde oxime (13.7 g) was dissolved in dichloromethane (164 ml). A 5% sodium hypochlorite solution (164 ml) was added dropwise in an ice bath, and the mixture was stirred at the same temperature for two hours. The reaction solution was diluted with water, and the aqueous layer was extracted with dichloromethane. The organic layer was dried over anhydrous magnesium sulfate, and the solvent was evaporated under reduced pressure. The residue was purified by silica gel column chromatography to obtain the title compound (12.2 g).

$^1$H-NMR (400 MHz, CDCl$_3$) δ (ppm): 1.52-1.61 (m, 1H), 2.19 (ddd, J=0.8, 6.8, 14.4 Hz, 1H), 3.43-3.50 (m, 2H), 3.56 (dd, J=6.4, 10.0 Hz, 1H), 3.69-3.75 (m, 1H), 3.79 (dd, J=8.0, 12.0 Hz, 1H), 4.21 (dd, J=1.6 Hz, 13.6 Hz, 1H), 4.54-4.64 (m, 3H), 4.77 (d, J=13.2 Hz, 1H), 7.30-7.38 (m, 5H).

(5) Synthesis of (3aR,5R,7aS)-5-benzyloxymethyl-7a-(2-fluorophenyl)hexahydropyrano[3,4-c]isoxazole Toluene (100 ml) and THF (10 ml) were added to 2-bromofluorobenzene (3.11 g). The reaction solution was cooled to −78° C., and n-butyllithium (2.63 M, 6.15 ml) was added dropwise. After stirring at the same temperature for one hour, a mixed solution of (3aR,5R)-5-benzyloxymethyl-3,3a,4,5-tetrahydro-7H-pyrano[3,4-c]isoxazole (2.00 g) in toluene (20 ml) and THF (2 ml) and a boron trifluoride-diethyl ether complex (2.03 ml) were added dropwise at the same time. After stirring at the same temperature for two hours, an ammonium chloride solution was added to the reaction solution. The aqueous layer was extracted with ethyl acetate, and the organic layer was dried over anhydrous magnesium sulfate. The solvent was evaporated under reduced pressure and the residue was purified by silica gel column chromatography to obtain the title compound (2.29 g).

$^1$H-NMR (400 MHz, CDCl$_3$) δ (ppm): 1.51-1.60 (m, 1H), 1.81-1.88 (m, 1H), 3.10-3.18 (m, 1H), 3.49 (dd, J=4.0, 10.4 Hz, 1H), 3.54-3.58 (m, 2H), 3.70 (d, J=7.6 Hz, 1H), 3.88 (d, J=12.4 Hz, 2H), 4.19 (dd, J=2.0, 12.4 Hz, 1H), 4.57 (d, J=12.0, 1H), 4.63 (d, J=12.0, 1H), 6.30 (s, 1H), 7.03 (ddd, J=1.2, 8.0, 12.4 Hz, 1H), 7.16 (dt, J=1.2, 8.0 Hz, 1H), 7.23-7.37 (m, 6H), 7.93 (dt, J=1.6, 8.0 Hz, 1H).

(6) Synthesis of [(2R,4R,5S)-5-amino-2-benzyloxymethyl-5-(2-fluorophenyl)tetrahydropyran-4-yl]methanol Zinc powder (4.36 g) was added to a solution of (3aR,5R,7aS)-5-benzyloxymethyl-7a-(2-fluorophenyl)hexahydropyrano[3,4-c]isoxazole (2.29 g) in acetic acid (50 ml), and the mixture was stirred at room temperature overnight. The insoluble matter was removed by filtration through celite, and the solvent was evaporated under reduced pressure. Ice was added to the residue, followed by neutralization with a 5 N sodium hydroxide solution. The aqueous layer was extracted with dichloromethane, and the organic layer was dried over anhydrous magnesium sulfate. The solvent was evaporated under reduced pressure. The residue was purified by silica gel column chromatography to obtain the title compound (2.08 g).

$^1$H-NMR (400 MHz, CDCl$_3$) δ (ppm): 1.61-1.67 (m, 1H), 1.98-2.08 (m, 1H), 2.30-2.35 (m, 1H), 3.33 (dd, J=2.8, 11.2 Hz, 1H), 3.44 (d, J=11.2 Hz, 1H), 3.53-3.57 (m, 2H), 3.62 (dd, J=6.8, 10.4 Hz, 1H), 3.86-3.90 (m, 1H), 4.27 (dd, J=2.4, 11.2 Hz, 1H), 4.59 (d, J=12.0 Hz, 1H), 4.66 (d, J=12.0 Hz, 1H), 7.06 (ddd, J=1.6, 8.0 Hz, 13.2 Hz, 1H), 7.20 (dt, J=1.2, 7.6 Hz, 1H), 7.26-7.39 (m, 6H), 7.63 (dt, J=1.6, 7.6 Hz, 1H).

(7) Synthesis of (4aR,6R,8aS)-6-benzyloxymethyl-8a-(2-fluorophenyl)-4,4a,5,6,8,8a-hexahydro-7-oxa-3-thia-1-azanaphthalen-2-ylamine Benzoyl isothiocyanate (893 μl) was added dropwise to a solution of [(2R,4R,5S)-5-amino-2-benzyloxymethyl-5-(2-fluorophenyl)tetrahydropyran-4-yl]methanol (2.08 g) in dichloromethane (30 ml). The reaction solution was stirred at room temperature for three hours, and then the solvent was evaporated under reduced pressure. The residue was purified by silica gel column chromatography. Several drops of concentrated hydrochloric acid were added to a solution of the resulting intermediate in methanol (40 ml), and the mixture was heated under reflux for five hours. The reaction solution was returned to room temperature, and then the solvent was evaporated under reduced pressure. The residue was dissolved in methanol (40 ml) and DBU (2 ml) was added, followed by heating under reflux for five hours. The solvent was evaporated under reduced pressure and the residue was purified by NH-silica gel column chromatography to obtain the title compound (1.61 g).

$^1$H-NMR (400 MHz, CDCl$_3$) δ (ppm): 1.51 (ddd, J=2.4, 3.6, 13.2 Hz, 1H), 1.74-1.84 (m, 1H), 2.55-2.60 (m, 1H), 2.92-2.98 (m, 2H), 3.47 (dd, J=4.4, 9.6 Hz, 1H), 3.62 (dd, J=6.4, 10.0 Hz, 1H), 3.83 (d, J=10.8 Hz, 1H), 3.87-3.93 (m, 1H), 4.17 (dd, J=2.4, 11.2 Hz, 1H), 4.51 (brs, 2H), 4.56 (d, J=12.0 Hz, 1H), 4.63 (d, J=12.0 Hz, 1H), 7.02 (ddd, J=1.6, 8.0, 12.8 Hz, 1H), 7.12 (dt, J=1.6, 7.6 Hz, 1H), 7.22-7.37 (m, 7H).

(8) Synthesis of [(4aR,6R,8aS)-2-amino-8a-(2-fluorophenyl)-4,4a,5,6,8,8a-hexahydro-7-oxa-3-thia-1-azanaphthalen-6-yl]methanol Concentrated hydrochloric acid (25.2 ml) was added to (4aR,6R,8aS)-6-benzyloxymethyl-8a-(2-fluorophenyl)-4,4a,5,6,8,8a-hexahydro-7-oxa-3-thia-1-azanaphthalen-2-ylamine (1.26 g), and the mixture was heated under reflux for two hours. After cooling the reaction solution to room temperature, the reaction mixture was poured into ice. The mixture was neutralized with 5 N sodium hydroxide, and the aqueous layer was extracted with dichloromethane. The organic layer was dried over anhydrous magnesium sulfate. The solvent was evaporated under reduced pressure, and the residual solid was washed with a mixed solvent of heptane and ether to obtain the title compound (890 mg).

$^1$H-NMR (400 MHz, CDCl$_3$) δ (ppm): 1.40 (ddd, J=2.0, 6.0, 12.8 Hz, 1H), 1.81-1.90 (m, 1H), 2.59 (dd, J=4.4, 14.0 Hz, 1H), 2.95-2.99 (m, 2H), 3.61-3.69 (m, 2H), 3.69-3.81 (m, 1H), 3.83 (d, J=11.2 Hz, 1H), 4.17 (dd, J=2.0, 13.2 Hz, 1H), 7.03 (ddd, J=1.2, 8.4, 13.2 Hz, 1H), 7.13 (dt, J=1.6, 7.6 Hz, 1H), 7.24-7.29 (m, 1H), 7.35 (dt, J=1.6, 8.0 Hz, 1H).

(9) Synthesis of [(4aR,6R,8aS)-2-amino-8a-(2-fluoro-5-nitrophenyl)-4,4a,5,6,8,8a-hexahydro-7-oxa-3-thia-1-azanaphthalen-6-yl]methanol Concentrated sulfuric acid (2.5 ml) was added dropwise to a solution of [(4aR,6R,8aS)-2-amino-8a-(2-fluorophenyl)-4,4a,5,6,8,8a-hexahydro-7-oxa-3-thia-1-azanaphthalen-6-yl]methanol (700 mg) in TFA (5 ml) in an ice bath. Then, fuming nitric acid (specific gravity: 1.52, 103 μl) was added dropwise at the same temperature, followed by stirring for one hour. The reaction mixture was poured into ice and made basic with a 5 N sodium hydroxide solution, followed by stirring at room temperature for two hours. The aqueous layer was extracted with dichloromethane, and the organic layer was dried over anhydrous magnesium sulfate. The solvent was evaporated under reduced pressure to obtain the title compound (1.0 g).

$^1$H-NMR (400 MHz, CDCl$_3$) δ (ppm): 1.46 (ddd, J=2.4, 4.0, 13.2 Hz, 1H), 1.84-1.94 (m, 1H), 2.66 (dd, J=2.4, 12.4 Hz, 1H), 2.93 (dd, J=4.4, 12.4 Hz, 1H), 2.96-3.02 (m, 1H), 3.63-3.71 (m, 2H), 3.76-3.82 (m, 1H), 3.86 (d, J=11.2 Hz, 1H), 4.11 (dd, J=2.8, 10.4 Hz, 1H), 7.21 (dd, J=8.8, 10.8 Hz, 1H), 8.19 (ddd, J=3.2, 4.0, 8.8 Hz, 1H), 8.30 (dd, J=3.2, 6.8 Hz, 1H).

(10) Synthesis of tert-butyl [(4aR,6R,8aS)-8a-(2-fluoro-5-nitrophenyl)-6-hydroxymethyl-4,4a,5,6,8,8a-hexahydro-7-oxa-3-thia-1-azanaphthalen-2-yl]carbamate Triethylamine (1 ml) was added to a solution of [(4aR,6R,8aS)-2-amino-8a-(2-fluoro-5-nitrophenyl)-4,4a,5,6,8,8a-hexahydro-7-oxa-3-thia-1-azanaphthalen-6-yl]methanol (1.0 g) in THF (100 ml). Then, di-tert-butyl dicarbonate (1.28 g) was added and the mixture was stirred at room temperature overnight. The solvent was evaporated under reduced pressure and the residue was purified by NH-silica gel column chromatography to obtain the title compound (1.05 g).

$^1$H-NMR (400 MHz, CDCl$_3$) δ (ppm): 1.47-1.54 (m, 1H), 1.86-1.97 (m, 1H), 2.59 (dd, J=2.8, 12.8 Hz, 1H), 2.86 (dd, J=3.6, 12.8 Hz, 1H), 3.04-3.08 (m, 1H), 3.67 (d, J=6.0 Hz, 2H), 3.76-3.82 (m, 1H), 3.83 (d, J=11.6 Hz, 1H), 4.09 (dd, J=2.4, 11.2 Hz, 1H), 7.22-7.25 (m, 1H), 8.20-8.24 (m, 2H).

(11) Synthesis of tert-butyl [(4aR,6R,8aS)-8a-(5-amino-2-fluorophenyl)-6-hydroxymethyl-4,4a,5,6,8,8a-hexahydro-7-oxa-3-thia-1-azanaphthalen-2-yl]carbamate Iron powder (121 mg) and a saturated ammonium chloride solution (1 ml) were added to a solution of tert-butyl [(4aR,6R,8aS)-8a-(2-fluoro-5-nitrophenyl)-6-hydroxymethyl-4,4a,5,6,8,8a-hexahydro-7-oxa-3-thia-1-azanaphthalen-2-yl]carbamate (120 mg) in ethanol (20 ml). The reaction solution was heated under reflux for 40 minutes and then cooled to room temperature. The insoluble matter was filtered off through celite, and the filtrate was evaporated under reduced pressure. The residue was purified by NH-silica gel column chromatography to obtain the title compound (67 mg).

$^1$H-NMR (400 MHz, CDCl$_3$) δ (ppm): 1.47-1.54 (m, 1H), 1.53 (s, 9H), 1.86-1.96 (m, 1H), 2.53 (dd, 2.8, 12.8 Hz, 1H), 2.99 (dd, J=4.0, 12.4 Hz, 1H), 3.07-3.11 (m, 1H), 3.65-3.81 (m, 4H), 4.18 (dd, J=1.2, 12.0 Hz, 1H), 6.56-6.60 (m, 2H), 6.84-6.89 (m, 1H).

PREPARATION EXAMPLE 14

Synthesis of tert-butyl (+)-[(4aR*,6R*,8aS*)-8a-(5-amino-2-fluorophenyl)-6-trifluoromethyl-4,4a,5,6,8,8a-hexahydro-7-oxa-3-thia-1-azanaphthalen-2-yl]carbamate

[Formula 39]

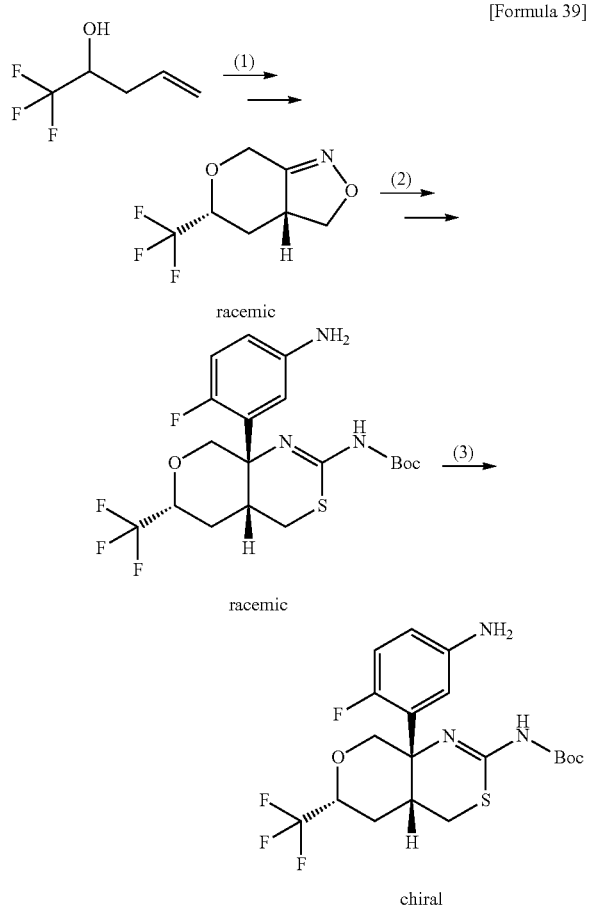

racemic chiral

(1) Synthesis of (±)-(3aR*,5R*)-5-trifluoromethyl-3,3a,4,5-tetrahydro-7H-pyrano[3,4-c]isoxazole The title compound (6.6 g) was obtained from 1,1,1-trifluoro-4-penten-2-ol (10.0 g) according to the method of Preparation Example 6.

$^1$H-NMR (400 MHz, CDCl$_3$) δ (ppm): 1.80 (dd, J=11.6, 24.4 Hz, 1H), 2.40 (ddd, J=2.0, 6.4, 12.8 Hz, 1H), 3.52 (ddd, J=6.4, 10.8, 22.0 Hz, 1H), 3.85-3.96 (m, 2H), 4.30 (dd, J=1.2, 13.6 Hz, 1H), 4.69 (dd, J=8.4, 10.4 Hz, 1H), 4.88 (d, J=13.2 Hz, 1H).

(2) Synthesis of tert-butyl (±)-[(4aR*,6R*,8aS*)-8a-(5-amino-2-fluorophenyl)-6-trifluoromethyl-4,4a,5,6,8,8a-hexahydro-7-oxa-3-thia-1-azanaphthalen-2-yl]carbamate The title compound (1.54 g) was obtained from (±)-(3aR*,5R*)-5-trifluoromethyl-3,3a,4,5-tetrahydro-7H-pyrano[3,4-c]isoxazole (2.00 g) according to the method of Preparation Example 6.

$^1$H-NMR (400 MHz, CDCl$_3$) δ (ppm): 1.53 (s, 9H), 1.74-1.79 (m, 1H), 2.50-2.20 (m, 1H), 2.57 (dd, J=2.8, 12.4 Hz, 1H), 2.99-3.07 (m, 2H), 3.66 (s, 2H), 3.85 (d, J=11.6 Hz, 1H), 4.03-4.06 (m, 1H), 4.17 (d, J=12.0 Hz, 1H), 6.53-6.60 (m, 2H), 6.86 (dd, J=8.8, 12.0 Hz, 1H).

(3) Synthesis of tert-butyl (+)-[(4aR*,6R*,8aS*)-8a-(5-amino-2-fluorophenyl)-6-trifluoromethyl-4,4a,5,6,8,8a-hexahydro-7-oxa-3-thia-1-azanaphthalen-2-yl]carbamate tert-Butyl (±)-[(4aR*,6R*,8aS*)-8a-(5-amino-2-fluorophenyl)-6-trifluoromethyl-4,4a,5,6,8,8a-hexahydro-7-oxa-3-thia-1-azanaphthalen-2-yl]carbamate (25 mg) was purified by CHIRALPAK™ AD-H (mobile phase: hexane:ethanol=81:19, flow rate: 10 ml/min). The fraction with a retention time of 17.7 to 22.6 minutes was collected to obtain the title compound. The same operation was repeated to obtain the title compound (580 mg; >99% ee) from the racemate (1.45 g).

$^1$H-NMR (400 MHz, CDCl$_3$) δ (ppm): 1.53 (s, 9H), 1.74-1.79 (m, 1H), 2.50-2.20 (m, 1H), 2.57 (dd, J=2.8, 12.4 Hz, 1H), 2.99-3.07 (m, 2H), 3.66 (s, 2H), 3.85 (d, J=11.6 Hz, 1H), 4.03-4.06 (m, 1H), 4.17 (d, J=12.0 Hz, 1H), 6.53-6.60 (m, 2H), 6.86 (dd, J=8.8, 12.0 Hz, 1H).

PREPARATION EXAMPLE 15

Synthesis of tert-butyl [(4aR,6R,8aS)-8a-(5-amino-2-fluorophenyl)-6-fluoromethyl-4,4a,5,6,8,8a-hexahydro-7-oxa-3-thia-1-azanaphthalen-2-yl]carbamate

[Formula 40]

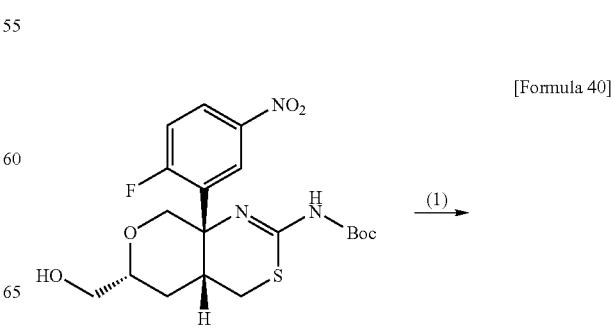

-continued

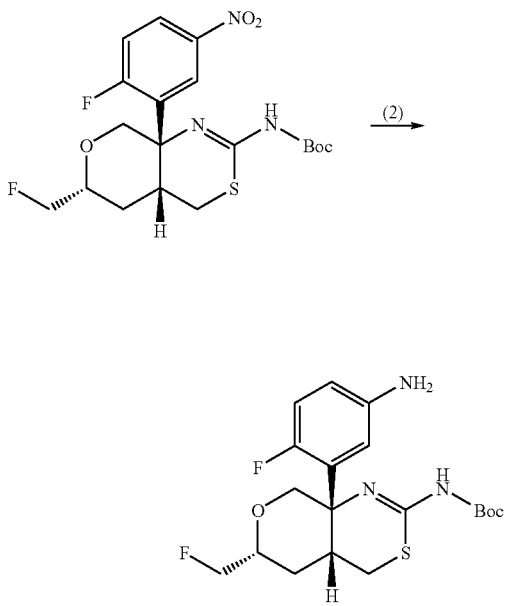

(1) Synthesis of tert-butyl [(4aR,6R,8aS)-8a-(5-nitro-2-fluorophenyl)-6-fluoromethyl-4,4a,5,6,8,8a-hexahydro-7-oxa-3-thia-1-azanaphthalen-2-yl]carbamate

[Bis(2-methoxyethyl)amino]sulfur trifluoride (285 µl) was added dropwise to a solution of tert-butyl [(4aR,6R,8aS)-8a-(5-nitro-2-fluorophenyl)-6-hydroxymethyl-4,4a,5,6,8,8a-hexahydro-7-oxa-3-thia-1-azanaphthalen-2-yl]carbamate obtained in Preparation Example 13 (575 mg) in dichloromethane (55 ml) at −78° C. The mixture was stirred overnight with gradual heating to room temperature. A sodium bicarbonate solution was added to the reaction solution, and the aqueous layer was extracted with chloroform. The organic layer was dried over anhydrous magnesium sulfate. The solvent was evaporated under reduced pressure and the residue was purified by NH-silica gel column chromatography to obtain the title compound (240 mg).

ESI-MS m/z 444 [M$^+$+H]

(2) Synthesis of tert-butyl [(4aR,6R,8aS)-8a-(5-amino-2-fluorophenyl)-6-fluoromethyl-4,4a,5,6,8,8a-hexahydro-7-oxa-3-thia-1-azanaphthalen-2-yl]carbamate The title compound (26 mg) was obtained from tert-butyl [(4aR,6R,8aS)-8a-(5-nitro-2-fluorophenyl)-6-fluoromethyl-4,4a,5,6,8,8a-hexahydro-7-oxa-3-thia-1-azanaphthalene-2-yl]carbamate (39 mg) according to Preparation Example 13.

ESI-MS m/z 414 [M$^+$+H]

PREPARATION EXAMPLE 16

Synthesis of (±)-N,N-di(tert-butyloxycarbonyl)-[(4aR*,6R*,8aS*)-8a-(5-bromo-2-fluorophenyl)-6-trifluoromethyl-4,4a,5,6,8,8a-hexahydro-7-oxa-3-thia-1-azanaphthalen-2-yl]amine

[Formula 41]

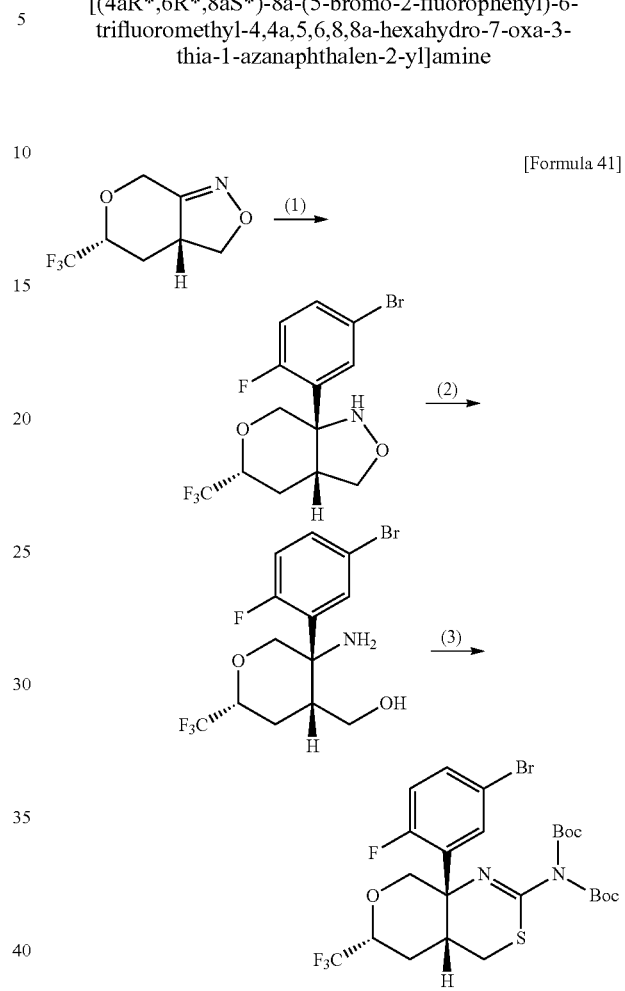

(1) Synthesis of (±)-(3aR*,5R*,7aS*)-7a-(5-bromo-2-fluorophenyl)-5-trifluoromethyl-hexahydropyrano[3,4-c]isoxazole The title compound (484 mg) was obtained from (±)-(3aR*,5R*)-5-trifluoromethyl-3,3a,4,5-tetrahydro-7H-pyrano[3,4-c]isoxazole obtained in Preparation Example 14 (300 mg) and 1,3-dibromo-4-fluorobenzene (855 mg) according to the method of Preparation Example 1-(3).

$^1$H-NMR (400 MHz, CDCl$_3$) δ (ppm): 1.74-1.83 (m, 1H), 2.04-2.10 (m, 1H), 3.12-3.18 (m, 1H), 3.64 (dd, J=5.2, 8.0 Hz, 1H), 3.79 (d, J=7.6 Hz, 1H), 3.94-4.05 (m, 2H), 4.15 (dd, J=2.0, 8.0 Hz, 1H), 6.22 (s, 1H), 6.96 (dd, J=8.4, 11.6 Hz, 1H), 7.43 (ddd, J=2.8, 4.4, 8.4 Hz, 1H), 8.09 (dd, J=2.4, 6.8 Hz, 1H).

(2) Synthesis of (±)-[(2R*,4R*,5S*)-5-amino-5-(5-bromo-2-fluorophenyl)-2-trifluoromethyl-tetrahydropyran-4-yl]methanol The title compound (390 mg) was obtained from (±)-(3aR*,5R*,7aS*)-7a-(5-bromo-2-fluorophenyl)-5-trifluoromethylhexahydropyrano[3,4-c]isoxazole (484 mg) according to Preparation Example 1-(4).

¹H-NMR (400 MHz, CDCl₃) δ (ppm): 1.86-1.92 (m, 1H), 2.19-2.30 (m, 1H), 2.37-2.42 (m, 1H), 3.41 (dd, J=3.2, 11.6 Hz, 1H), 3.51 (d, J=12.4 Hz, 1H), 3.43 (dd, J=3.2, 12.0 Hz, 1H), 4.00-4.05 (m, 1H), 4.23 (dd, J=2.0, 11.2 Hz, 1H), 6.97 (dd, J=8.4, 12.0 Hz, 1H), 7.45 (ddd, J=2.4, 4.4, 8.8 Hz, 1H), 7.84 (dd, J=2.4, 6.8 Hz, 1H).

(3) Synthesis of (±)-N,N-di(tert-butyloxycarbonyl)-[(4aR*,6R*,8aS*)-8a-(5-bromo-2-fluorophenyl)-6-trifluoromethyl-4,4a,5,6,8,8a-hexahydro-7-oxa-3-thia-1-azanaphthalen-2-yl]amine Benzoyl isothiocyanate (156 μl) was added to a solution of (±)-[(2R*,4R*,5S*)-5-amino-5-(5-bromo-2-fluorophenyl)-2-trifluoromethyltetrahydropyran-4-yl]methanol (390 mg) in dichloromethane (10 ml), and the mixture was stirred at room temperature overnight. The solvent was evaporated under reduced pressure and the residue was purified by silica gel chromatography. The resulting intermediate was dissolved in methanol (50 ml). Concentrated hydrochloric acid (1.0 ml) was added and the mixture was heated under reflux for five hours. When the reaction was completed, the reaction solution was returned to room temperature, and the solvent was evaporated under reduced pressure. Methanol (50 ml) and DBU (500 μl) were added to the residue, followed by heating under reflux for four hours. When the reaction was completed, the reaction solution was returned to room temperature, and the solvent was evaporated under reduced pressure. The residue was purified by NH-silica gel column chromatography. The resulting intermediate was dissolved in THF (10 ml). Di-tert-butyl dicarbonate (458 mg) and DMAP (385 mg) were added and the mixture was stirred at room temperature overnight. The solvent was evaporated under reduced pressure and the residue was purified by silica gel column chromatography to obtain the title compound (138 mg).

¹H-NMR (400 MHz, CDCl₃) δ (ppm): 1.55 (s, 18H), 1.71-1.75 (m, 1H), 2.29 (ddd, J=3.2, 12.0, 24.8 Hz, 1H), 2.73 (dd, J=2.8, 12.8 Hz, 1H), 3.04-3.13 (m, 2H), 4.00-4.13 (m, 3H), 6.94 (dd, J=8.8, 12.4 Hz, 1H), 7.41 (ddd, J=2.4, 4.4, 8.8 Hz, 1H), 7.82 (dd, J=2.8, 7.2 Hz, 1H).

PREPARATION EXAMPLE 17

Synthesis of N,N-di(tert-butyloxycarbonyl)-[(4aR,6R,8aS)-8a-(5-bromo-2-fluorophenyl)-6-fluoromethyl-4,4a,5,6,8,8a-hexahydro-7-oxa-3-thia-1-azanaphthalen-2-yl]amine

[Formula 42]

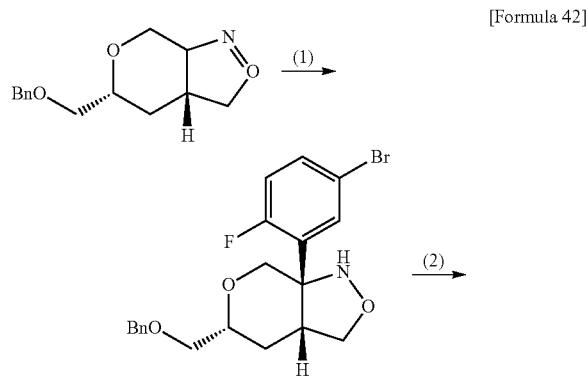

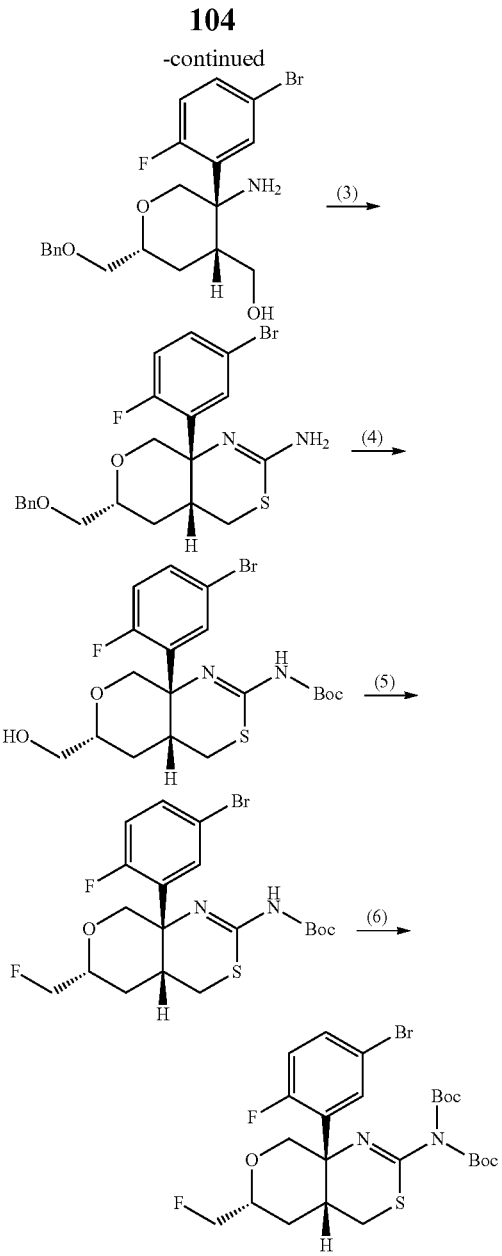

(1) Synthesis of (3aR,5R,7aS)-5-benzyloxymethyl-7a-(5-bromo-2-fluorophenyl)hexahydropyrano[3,4-c]isoxazole THF (10 ml) was added to a solution of 1,3-dibromo-4-fluorobenzene (4.31 g) in toluene (100 ml).

The mixture was cooled to −78° C. and n-butyllithium (2.63 M, 6.15 ml) was added dropwise. After stirring at the same temperature for one hour, a solution of (3aR,5R)-5-benzyloxymethyl-3,3a,4,5-tetrahydro-7H-pyrano[3,4-c]isoxazole obtained in Preparation Example 13-(4) (2.00 g) in toluene-THF (10:1) (20 ml) and a boron trifluoride-diethyl ether complex (2.03 ml) were added dropwise at the same time. After stirring at the same temperature for two hours, a saturated ammonium chloride solution was added to terminate the reaction. The aqueous layer was extracted with ethyl acetate, and the organic layer was dried over anhydrous magnesium sulfate. The solvent was evaporated under reduced pressure and the residue was purified by silica gel column chromatography to obtain the title compound (2.74 g).

¹H-NMR (400 MHz, CDCl₃) δ (ppm): 1.47-1.57 (m, 1H), 1.85 (ddd, J=1.6, 6.8, 14.0 Hz, 1H), 3.07-3.12 (m, 1H), 3.47-3.59 (m, 3H), 3.72 (d, J=7.6 Hz, 1H), 3.82-3.88 (m, 2H), 4.11 (dd, J=2.0, 13.2 Hz, 1H), 4.56 (d, J=12.0 Hz, 1H), 4.63 (d, J=12.0 Hz, 1H), 6.26 (s, 1H), 6.92 (dd, J=8.4, 10.0 Hz, 1H), 7.30-7.41 (m, 6H), 8.09 (dd, J=2.4, 6.8 Hz, 1H).

(2) Synthesis of [(2R,4R,5S)-5-amino-2-benzyloxymethyl-5-(5-bromo-2-fluorophenyl)tetrahydropyran-4-yl]methanol Zinc powder (4.24 g) was added to a solution of (3aR,5R,7aS)-5-benzyloxymethyl-7a-(5-bromo-2-fluorophenyl)hexahydropyrano[3,4-c]isoxazole (2.74 g) in acetic acid (40 ml). After stirring at room temperature overnight, the insoluble matter was removed by filtration through celite. The solvent was evaporated under reduced pressure and ice was added to the residue, followed by neutralization with a 5 N sodium hydroxide solution. The aqueous layer was extracted with dichloromethane, and the organic layer was dried over anhydrous magnesium sulfate. The solvent was evaporated under reduced pressure and the residue was purified by silica gel column chromatography to obtain the title compound (2.22 g).

¹H-NMR (400 MHz, CDCl₃) δ (ppm): 1.63-1.67 (m, 1H), 1.95-2.05 (m, 1H), 2.31-2.34 (m, 1H), 3.35 (dd, J=3.2, 11.6 Hz, 1H), 3.48 (d, J=11.2 Hz, 1H), 3.53-3.64 (m, 3H), 3.83-3.87 (m, 1H), 4.21 (dd, J=2.0, 11.2 Hz, 1H), 4.57-4.67 (m, 2H), 6.95 (dd, J=9.2, 12.0 Hz, 1H), 7.24-7.37 (m, 5H), 7.41 (ddd, J=2.8, 4.4, 9.2 Hz, 1H), 7.80 (dd, J=2.4, 6.8 Hz, 1H).

(3) Synthesis of (4aR,6R,8aS)-6-benzyloxymethyl-8a-(5-bromo-2-fluorophenyl)-4,4a,5,6,8,8a-hexahydro-7-oxa-3-thia-1-aza-naphthalen-2-ylamine

[(2R,4R,5S)-5-Amino-2-benzyloxymethyl-5-(5-bromo-2-fluorophenyl)tetrahydropyran-4-yl]methanol (2.22 g) was dissolved in dichloromethane (30 ml), and benzoyl isothiocyanate (776 µl) was added. The mixture was stirred at room temperature for five hours, and then the solvent was evaporated under reduced pressure. The residue was purified by silica gel column chromatography to obtain an intermediate. The resulting intermediate was dissolved in methanol (50 ml), and concentrated hydrochloric acid (2 ml) was added. The mixture was heated under reflux for six hours and then cooled to room temperature. The solvent was evaporated under reduced pressure. Methanol (30 ml) and DBU (2 ml) were added to the residue, followed by heating under reflux for three hours. The reaction solution was cooled to room temperature, and the solvent was evaporated under reduced pressure. The residue was purified by NH-silica gel column chromatography to obtain the title compound (2.30 g).

¹H-NMR (400 MHz, CDCl₃) δ (ppm): 1.50-1.54 (m, 1H), 1.74-1.77 (m, 1H), 2.58-2.60 (m, 1H), 2.90-2.99 (m, 2H), 3.46 (dd, J=4.4, 10.0 Hz, 1H), 3.62 (dd, J=6.4, 10.0 Hz, 1H), 3.80 (d, J=10.8 Hz, 1H), 3.85-3.90 (m, 1H), 4.08-4.11 (m, 1H), 4.54-4.64 (m, 2H), 6.91 (dd, J=8.4, 12.0 Hz, 1H), 7.27-7.38 (m, 6H), 7.45 (dd, J=2.4, 6.8 Hz, 1H).

(4) Synthesis of tert-butyl [(4aR,6R,8aS)-8a-(5-bromo-2-fluorophenyl)-6-hydroxymethyl-4,4a,5,6,8,8a-hexahydro-7-oxa-3-thia-1-azanaphthalen-2-yl]carbamate Concentrated hydrochloric acid (20 ml) was added to (4aR,6R,8aS)-6-benzyloxymethyl-8a-(5-bromo-2-fluorophenyl)-4,4a,5,6,8,8a-hexahydro-7-oxa-3-thia-1-azanaphthalen-2-ylamine (2.20 g), and the mixture was heated under reflux for two hours. The reaction solution was returned to room temperature, and ice was added to the reaction mixture. The mixture was neutralized with 5 N sodium hydroxide, and the generated solid was collected by a glass filter. The solid was dried under reduced pressure and then dissolved in THF (138 ml). Triethylamine (5.0 ml) and di-tert-butyl dicarbonate (2.06 g) were added and the mixture was stirred at room temperature for six hours. The solvent was evaporated under reduced pressure and the residue was purified by silica gel column chromatography to obtain the title compound (1.24 g).

¹H-NMR (400 MHz, CDCl₃) δ (ppm): 1.53 (s, 9H), 1.56-1.59 (m, 1H), 1.85-1.94 (m, 1H), 2.55 (dd, J=2.8, 12.8 Hz, 1H), 2.93 (dd, J=4.0, 13.2 Hz, 1H), 3.00-3.10 (m, 1H), 3.65-3.66 (m, 2H), 3.77-3.80 (m, 2H), 4.09-4.13 (m, 1H), 6.97 (dd, J=8.4, 12.0 Hz, 1H), 7.38-7.45 (m, 2H).

(5) Synthesis of tert-butyl [(4aR,6R,8aS)-8a-(5-bromo-2-fluorophenyl)-6-fluoromethyl-4,4a,5,6,8,8a-hexahydro-7-oxa-3-thia-1-azanaphthalen-2-yl]carbamate

[Bis(2-methoxyethyl)amino]sulfur trifluoride (155 µl) was added dropwise to a solution of tert-butyl [(4aR,6R,8aS)-8a-(5-bromo-2-fluorophenyl)-6-hydroxymethyl-4,4a,5,6,8,8a-hexahydro-7-oxa-3-thia-1-azanaphthalen-2-yl]carbamate (200 mg) in dichloromethane (5.0 ml) at −78° C. The mixture was stirred overnight with gradual heating to room temperature. A sodium bicarbonate solution was added to the reaction mixture to terminate the reaction. The aqueous layer was extracted with ethyl acetate, and the organic layer was dried over anhydrous magnesium sulfate. The solvent was evaporated under reduced pressure and the residue was purified by silica gel column chromatography to obtain the title compound (145 mg).

¹H-NMR (400 MHz, CDCl₃) δ (ppm): 1.53 (s, 9H), 1.57-1.60 (m, 1H), 1.87-1.96 (m, 1H), 2.56 (dd, J=3.2, 12.8 Hz, 1H), 2.94 (dd, J=4.0, 12.8 Hz, 1H), 3.04-3.07 (m, 1H), 3.79 (d, J=11.6 Hz, 1H), 3.92-3.97 (m, 1H), 4.10-4.13 (m, 1H), 4.34-4.54 (m, 2H), 6.97 (dd, J=8.4, 11.6 Hz, 1H), 7.37-7.44 (m, 2H).

(6) Synthesis of N,N-di(tert-butyloxycarbonyl)-[(4aR,6R,8aS)-8a-(5-bromo-2-fluorophenyl)-6-fluoromethyl-4,4a,5,6,8,8a-hexahydro-7-oxa-3-thia-1-azanaphthalen-2-yl]amine Di-tert-butyl dicarbonate (185 mg) and DMAP (69.1 mg) were added to a solution of tert-butyl [(4aR,6R,8aS)-8a-(5-bromo-2-fluorophenyl)-6-fluoromethyl-4,4a,5,6,8,8a-hexahydro-7-oxa-3-thia-1-azanaphthalen-2-yl]carbamate (135 mg) in THF (30 ml). The mixture was stirred at room temperature for two hours, and then the solvent was evaporated under reduced pressure. The residue was purified by silica gel column chromatography to obtain the title compound (121 mg).

¹H-NMR (400 MHz, CDCl₃) δ (ppm): 1.55-1.56 (m, 19H), 1.95-2.05 (m, 1H), 2.69 (dd, J=2.8, 12.8 Hz, 1H), 3.05-3.12 (m, 2H), 3.92-4.00 (m, 1H), 4.01 (d, J=10.8 Hz, 1H), 4.09 (dd, J=2.4, 11.6 Hz, 1H), 4.30-4.58 (m, 2H), 6.93 (dd, J=8.4, 12.0 Hz, 1H), 7.39 (ddd, J=2.4, 4.4, 8.8 Hz, 1H), 7.80 (dd, J=2.8, 7.6 Hz, 1H).

PREPARATION EXAMPLE 18

Synthesis of (±)-N-benzoyl-N-(tert-butyloxycarbonyl)-[(4aR*,8aS*)-8a-(5-bromo-2-fluorophenyl)-4,4a,5,6,8,8a-hexahydro-7-oxa-3-thia-1-azanaphthalen-2-yl]amine

[Formula 43]

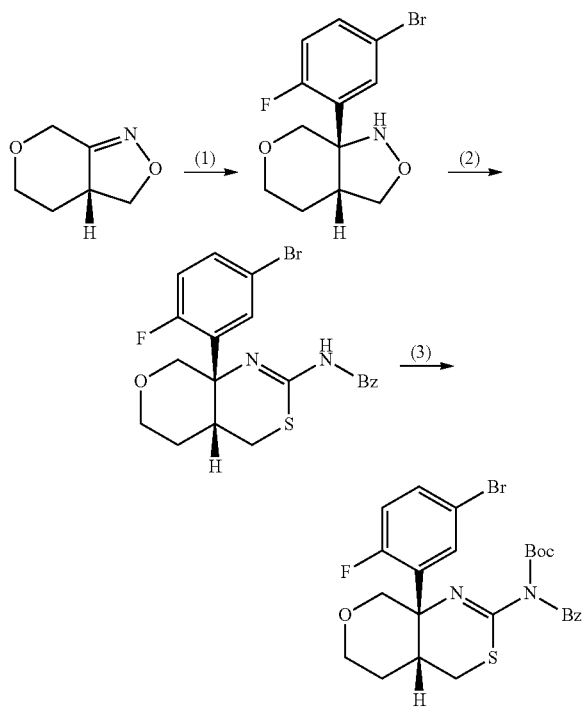

(1) Synthesis of (±)-(3aR*,7aS*)-7a-(5-bromo-2-fluorophenyl)-hexahydropyrano[3,4-c]isoxazole 1,3-Dibromo-4-fluorobenzene (837 mg) was dissolved in a toluene-THF (10:1) mixture (15 ml). The mixture was cooled to −78° C. and n-butyllithium (2.64 M, 1.19 ml) was added dropwise. After stirring at the same temperature for one hour, a solution of (±)-3,3a,4,5-tetrahydro-7H-pyrano[3,4-c]isoxazole obtained in Preparation Example 1-(2) (200 mg) in toluene-THF (10:1) (5.0 ml) and a boron trifluoride-diethyl ether complex (394 μl) were added dropwise at the same time. After stirring at the same temperature for three hours, the reaction was terminated with an ammonium chloride solution. The aqueous layer was extracted with ethyl acetate, and the organic layer was washed with water and brine. The organic layer was dried over anhydrous magnesium sulfate, and the solvent was evaporated under reduced pressure. The residue was purified by silica gel column chromatography to obtain the title compound (365 mg).

$^1$H-NMR (400 MHz, CDCl$_3$) δ (ppm): 1.76-1.91 (m, 2H), 3.03-3.08 (m, 1H), 3.61-3.77 (m, 4H), 4.00-4.06 (m, 2H), 6.28 (s, 1H), 6.93 (dd, J=8.8, 11.6 Hz, 1H), 7.37-7.41 (m, 1H), 8.09 (dd, J=2.4, 6.8 Hz, 1H).

(2) Synthesis of (±)-N-[(4aR*,8aS*)-8a-(5-bromo-2-fluorophenyl)-4,4a,5,6,8,8a-hexahydro-7-oxa-3-thia-1-azanaphthalen-2-yl]benzamide Zinc powder (759 mg) was added to a solution of (±)-(3aR*,7aS*)-7a-(5-bromo-2-fluorophenyl)hexahydropyrano[3,4-c]isoxazole (350 mg) in acetic acid (6.73 ml). After stirring at room temperature overnight, the insoluble matter was removed by filtration through celite. The solvent was evaporated under reduced pressure, and the resulting residue was neutralized with 5 N sodium hydroxide in an ice bath. The aqueous layer was extracted with ethyl acetate, and the organic layer was washed with brine. The organic layer was dried over anhydrous magnesium sulfate, and the solvent was evaporated under reduced pressure. The residue was purified by silica gel column chromatography to obtain an intermediate (300 mg). Benzoyl isothiocyanate (133 μl) was added to a solution of the resulting intermediate in dichloromethane (10 ml), and the mixture was stirred at room temperature overnight. The solvent was evaporated under reduced pressure. Methanol (10 ml) and concentrated hydrochloric acid (several drops) were added to the resulting residue, and the mixture was heated under reflux for two hours. The reaction solution was returned to room temperature, and the solvent was evaporated under reduced pressure. The resulting residue was neutralized with a sodium bicarbonate solution, and the aqueous layer was extracted with ethyl acetate. The organic layer was washed with brine and dried over anhydrous magnesium sulfate. The solvent was evaporated under reduced pressure and the residue was purified by NH-silica gel column chromatography to obtain the title compound (211 mg).

ESI-MS m/z 449 [M$^+$+H]

(3) Synthesis of (±)-N-benzoyl-N-(tert-butyloxycarbonyl)-[(4aR*,8aS*)-8a-(5-bromo-2-fluorophenyl)-4,4a,5,6,8,8a-hexahydro-7-oxa-3-thia-1-azanaphthalen-2-yl]amine DMAP (86.1 mg) and di-tert-butyl dicarbonate (123 mg) were added to a solution of (±)-N-[(4aR*,8aS*)-8a-(5-bromo-2-fluorophenyl)-4,4a,5,6,8,8a-hexahydro-7-oxa-3-thia-1-azanaphthalen-2-yl]benzamide (211 mg) in THF (10 ml). The mixture was stirred at room temperature overnight, and then the solvent was evaporated under reduced pressure. The residue was purified by silica gel column chromatography to obtain the title compound (229 mg).

$^1$H-NMR (400 MHz, CDCl$_3$) δ (ppm): 1.34 (s, 9H), 1.37-1.49 (m, 1H), 2.18-2.27 (m, 1H), 2.70 (dd, J=2.8, 12.8 Hz, 1H), 2.93-2.98 (m, 1H), 3.08 (dd, J=3.6, 12.8 Hz, 1H), 3.62-3.67 (m, 1H), 3.66 (d, J=10.8 Hz, 1H), 4.06-4.08 (m, 2H), 6.94 (dd, J=8.4, 12.0 Hz, 1H), 7.38-7.47 (m, 3H), 7.52-7.56 (m, 1H), 7.75-7.78 (m, 2H), 7.93 (dd, J=2.4, 6.8 Hz, 1H).

PREPARATION EXAMPLE 19

Synthesis of (+)-N,N-di(tert-butyloxycarbonyl)-[(4aR*,8aS*)-8a-(4-aminothiophen-2-yl)-4,4a,5,6,8,8a-hexahydro-7-oxa-3-thia-1-azanaphthalen-2-yl]amine

[Formula 44]

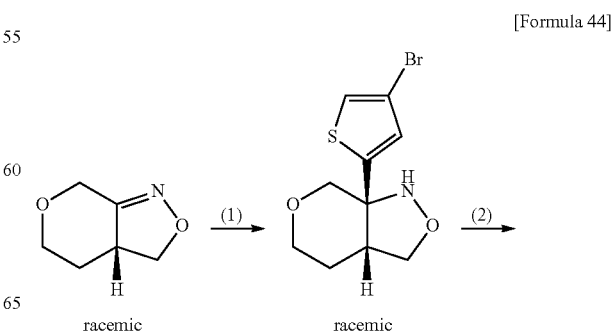

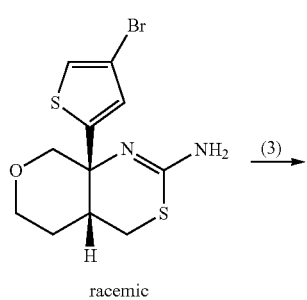
racemic

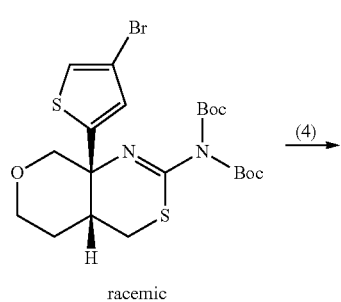
racemic

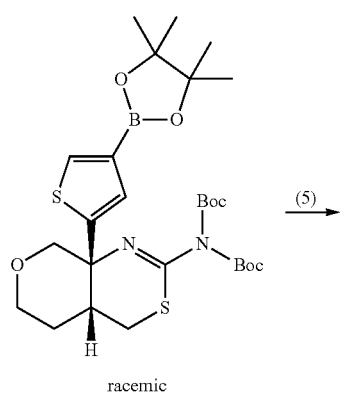
racemic

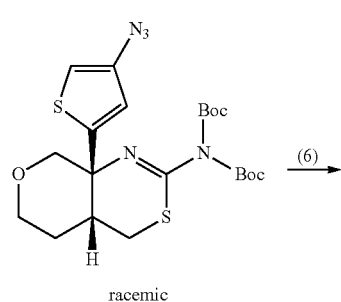
racemic

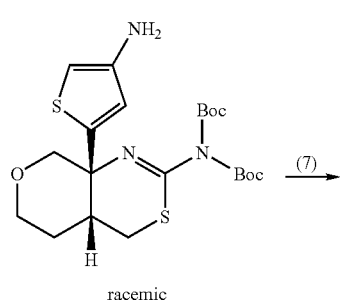
racemic

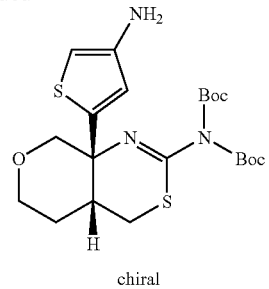
chiral (1) Synthesis of (±)-(3aR*,7aS*)-7a-(4-bromothiophen-2-yl)-hexahydropyrano[3,4-c]isoxazole n-Butyllithium (2.63 M, 2.99 ml) was added dropwise to a solution of 2,4-dibromothiophene (2.00 g) in toluene-THF (10:1) (22 ml) at −78° C. After stirring at the same temperature for one hour, a solution of (±)-3,3a,4,5-tetrahydro-7H-pyrano[3,4-c]isoxazole obtained in Preparation Example 1-(2) (500 mg) in toluene-THF (10:1) (10 ml) and a boron trifluoride-diethyl ether complex (990 µl) were added dropwise at the same time. After stirring at the same temperature for two hours, an ammonium chloride solution was added to terminate the reaction. The aqueous layer was extracted with ethyl acetate, and the organic layer was dried over anhydrous magnesium sulfate. The solvent was evaporated under reduced pressure and the residue was purified by silica gel column chromatography to obtain the title compound (700 mg).
$^1$H-NMR (400 MHz, CDCl$_3$) δ (ppm): 1.74-1.92 (m, 2H), 2.82-2.87 (m, 1H), 3.58-4.03 (m, 6H), 6.96 (d, J=1.6 H, 1H), 7.16 (d, J=1.6 Hz, 1H).

(2) Synthesis of (±)-(4aR*,8aS*)-8a-(4-bromothiophen-2-yl)-4,4a,5,6,8,8a-hexahydro-7-oxa-3-thia-1-azanaphthalen-2-ylamine Zinc powder (1.58 g) was added to a solution of (±)-(3aR*,7aS*)-7a-(4-bromothiophen-2-yl)hexahydropyrano[3,4-c]isoxazole (700 mg) in acetic acid (20 ml). After stirring at room temperature overnight, the insoluble matter was removed by filtration through celite. The solvent was evaporated under reduced pressure, and the residue was neutralized with ice and 5 N sodium hydroxide. The aqueous layer was extracted with ethyl acetate, and the organic layer was washed with brine. The organic layer was dried over anhydrous magnesium sulfate, and the solvent was evaporated under reduced pressure. The residue was purified by silica gel column chromatography. The resulting intermediate was dissolved in dichloromethane (20 ml), and benzoyl isothiocyanate (324 µl) was added. The mixture was stirred at room temperature overnight, and then the solvent was evaporated under reduced pressure. The residue was purified by silica gel column chromatography. The resulting intermediate was dissolved in methanol (20 ml), and concentrated hydrochloric acid (several drops) was added. The mixture was heated under reflux for six hours and then cooled to room temperature. The solvent was evaporated under reduced pressure. The residue was dissolved in methanol (20 ml) and DBU (1.00 ml) was added, followed by heating under reflux for eight hours. The solvent was evaporated under reduced pressure and the residue was purified by NH-silica gel column chromatography to obtain the title compound (770 mg).

¹H-NMR (400 MHz, CDCl₃) δ (ppm): 1.45-1.48 (m, 1H), 2.14 (ddd, J=4.8, 12.4, 26.0 Hz, 1H), 2.24-2.30 (m, 1H), 2.62 (dd, J=3.2, 12.4 Hz, 1H), 3.26 (dd, J=3.6, 12.4 Hz, 1H), 3.54 (d, J=11.6 Hz, 1H), 3.57-3.64 (m, 1H), 3.91 (d, J=11.2 Hz, 1H), 4.08-4.12 (m, 1H), 6.76 (d, J=1.2 Hz, 1H), 7.12 (d, J=1.2 Hz, 1H).

(3) Synthesis of (±)-N,N-di(tert-butyloxycarbonyl)-[(4aR*,8aS*)-8a-(4-bromothiophen-2-yl)-4,4a,5,6,8,8a-hexahydro-7-oxa-3-thia-1-azanaphthalen-2-yl]amine DMAP (847 mg) and di-tert-butyl dicarbonate (1.51 g) were added to a solution of (±)-(4aR*,8aS*)-8a-(4-bromothiophen-2-yl)-4,4a,5,6,8,8a-hexahydro-7-oxa-3-thia-1-azanaphthalen-2-ylamine (770 mg) in THF (10 ml). The mixture was stirred at room temperature for three hours, and then the solvent was evaporated under reduced pressure. The residue was purified by silica gel column chromatography to obtain the title compound (1.07 g).

¹H-NMR (400 MHz, CDCl₃) δ (ppm): 1.50-1.51 (m, 1H), 1.53 (s, 18H), 2.24 (ddd, J=4.4, 12.4, 25.2 Hz, 1H), 2.33-2.38 (m, 1H), 2.68 (dd, J=3.2, 12.8 Hz, 1H), 3.33 (dd, J=3.6, 13.2 Hz, 1H), 3.56-3.63 (m, 2H), 4.04 (dd, J=4.4, 11.6 Hz, 1H), 4.11 (d, J=11.6 Hz, 1H), 6.54 (d, J=1.6 Hz, 1H), 7.16 (d, J=1.6 Hz, 1H).

(4) Synthesis of (±)-N,N-di(tert-butyloxycarbonyl)-[(4aR*,8aR*)-8a-[4-(4,4,5,5-tetramethyl-[1,3,2]dioxaborolan-2-yl)-thiophen-2-yl]-4,4a,5,6,8,8a-hexahydro-7-oxa-3-thia-1-azanaphthalen-2-yl]amine Bis(pinacolato)diboron (2.15 g), potassium acetate (663 mg) and a 1,1'-bis(diphenylphosphino)ferrocene palladium-dichloromethane complex (138 mg) were added to a solution of (±)-N,N-di(tert-butyloxycarbonyl)-[(4aR*,8aS*)-8a-(4-bromothiophen-2-yl)-4,4a,5,6,8,8a-hexahydro-7-oxa-3-thia-1-azanaphthalen-2-yl]amine (900 mg) in DMF (46.9 ml). After replacement with nitrogen, the mixture was stirred at 80° C. for six hours. The reaction solution was returned to room temperature and diluted with ethyl acetate. The organic layer was washed with water and dried over anhydrous magnesium sulfate. The solvent was evaporated under reduced pressure and the residue was purified by silica gel column chromatography to obtain the title compound (790 mg).

ESI-MS m/z 581 [M¹+H]

(5) Synthesis of (±)-N,N-di(tert-butyloxycarbonyl)-[(4aR*,8aR*)-8a-(4-azidothiophen-2-yl)-4,4a,5,6,8,8a-hexahydro-7-oxa-3-thia-1-azanaphthalen-2-yl]amine Sodium azide (177 mg) and copper (II) acetate (99.2 mg) were added to a solution of (±)-N,N-di(tert-butyloxycarbonyl)-[(4aR*,8aR*)-8a-[4-(4,4,5,5-tetramethyl-[1,3,2]dioxaborolan-2-yl)-thiophen-2-yl]-4,4a,5,6,8,8a-hexahydro-7-oxa-3-thia-1-azanaphthalen-2-yl]amine (790 mg) in methanol (88 ml). The mixture was stirred at room temperature overnight, and then the excess of methanol was evaporated under reduced pressure. An ammonium chloride solution was added to the residue, and the aqueous layer was with ethyl acetate. The organic layer was dried over anhydrous magnesium sulfate, and the solvent was evaporated under reduced pressure. The residue was purified by NH-silica gel column chromatography to obtain the title compound (503 mg).

ESI-MS m/z 518 [M⁺+H]

(6) Synthesis of (±)-N,N-di(tert-butyloxycarbonyl)-[(4aR*,8aS*)-8a-(4-aminothiophen-2-yl)-4,4a,5,6,8,8a-hexahydro-7-oxa-3-thia-1-azanaphthalen-2-yl]amine Zinc powder (133 mg) and ammonium formate (320 mg) were added to a solution of (±)-N,N-di(tert-butyloxycarbonyl)-[(4aR*,8aR*)-8a-(4-azidothiophen-2-yl)-4,4a,5,6,8,8a-hexahydro-7-oxa-3-thia-1-azanaphthalen-2-yl]amine (503 mg) in methanol (76.2 ml). The mixture was stirred at room temperature overnight, and then the solvent was evaporated under reduced pressure at room temperature or lower. Water was added to the residue, and the aqueous layer was extracted with ethyl acetate. The organic layer was dried over anhydrous magnesium sulfate, and the solvent was evaporated under reduced pressure. The residue was purified by silica gel column chromatography to obtain the title compound (325 mg).

ESI-MS m/z 518 [M⁺+Na]

(7) Synthesis of (+)-N,N-di(tert-butyloxycarbonyl)-[(4aR*,8aS*)-8a-(4-aminothiophen-2-yl)-4,4a,5,6,8,8a-hexahydro-7-oxa-3-thia-1-azanaphthalen-2-yl]amine (±)-N,N-Di(tert-butyloxycarbonyl)-[(4aR*,8aS*)-8a-(4-aminothiophen-2-yl)-4,4a,5,6,8,8a-hexahydro-7-oxa-3-thia-1-azanaphthalen-2-yl]amine (32.5 mg) was purified by CHIRALCEL™ OJ-H (mobile phase: hexane:ethanol=8:2, flow rate: 10 ml/min), and the fraction with a retention time of 14.9 to 23.5 minutes was collected to obtain the title compound. The same operation was repeated to obtain the title compound (112 mg) from the raw material (325 mg).

¹H-NMR (400 MHz, CDCl₃) δ (ppm): 1.46-1.48 (m, 1H), 1.53 (s, 18H), 2.16-2.33 (m, 2H), 2.64 (dd, J=2.8, 12.8 Hz, 1H), 3.39 (dd, J=3.6, 12.8 Hz, 1H), 3.55-3.62 (m, 1H), 3.65 (d, J=11.2 Hz, 1H), 4.03 (dd, J=4.8, 11.6 Hz, 1H), 4.13 (d, J=2.8 Hz, 1H), 6.07 (d, J=2.0 Hz, 1H), 6.67 (d, J=2.0 Hz, 1H).

PREPARATION EXAMPLE 20

Synthesis of N,N-di-(tert-butyloxycarbonyl)-[(4aR,6R,8aS)-8a-(5-bromo-2-fluorophenyl)-6-benzyloxymethyl-4,4a,5,6,8,8a-hexahydro-7-oxa-3-thia-1-azanaphthalen-2-yl]amine

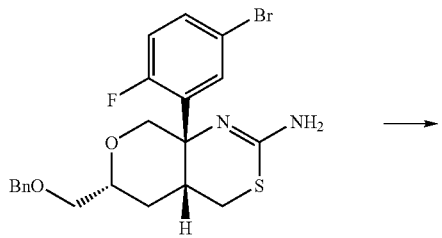

[Formula 45]

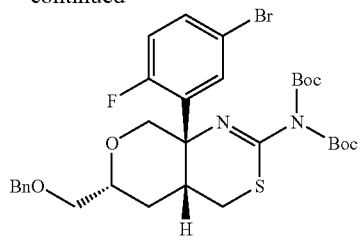

Di-tert-butyl dicarbonate (113 mg) and DMAP (63.0 mg) were added to a solution of (4aR,6R,8aS)-6-benzyloxymethyl-8a-(5-bromo-2-fluorophenyl)-4,4a,5,6,8,8a-hexahydro-7-oxa-3-thia-1-azanaphthalen-2-ylamine obtained by the method of Preparation Example 17-(3) (80.0 mg) in THF (5.0 ml). The mixture was stirred at room temperature overnight, and then the solvent was evaporated under reduced pressure. The residue was purified by silica gel column chromatography to obtain the title compound (95.0 mg).

¹H-NMR (400 MHz, CDCl₃) δ (ppm): 1.54-1.56 (m, 19H), 1.88-1.98 (m, 1H), 2.65-2.67 (m, 1H), 2.99-3.10 (m, 2H), 3.44 (dd, J=4.4, 9.6 Hz, 1H), 3.62 (dd, J=10.0, 16.8 Hz, 1H), 3.85-3.90 (m, 1H), 3.99-4.10 (m, 2H), 4.52-4.64 (m, 2H), 6.92 (dd, J=8.4, 12.0 Hz, 1H), 7.28-7.39 (m, 6H), 7.79 (dd, J=2.4, 7.2 Hz, 1H).

PREPARATION EXAMPLE 21

Synthesis of tert-butyl (±)-[(4aR*,8aS*)-8a-(6-amino-2,2-difluorobenzo[1,3]dioxol-4-yl)-4,4a,5,6,8,8a-hexahydro-7-oxa-3-thia-1-azanaphthalen-2-yl] carbamate

[Formula 46]

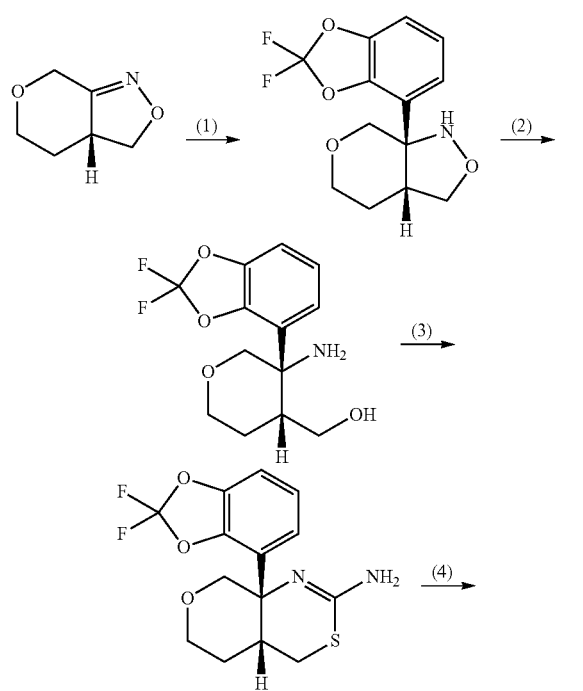

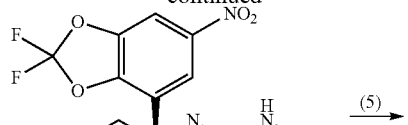

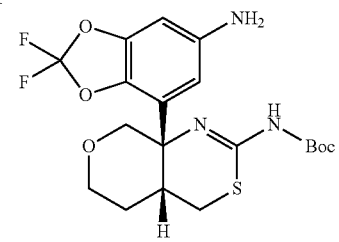

(1) Synthesis of (±)-(3aR*,7aS*)-7a-(2,2-difluorobenzo[1,3]dioxol-4-yl)hexahydropyrano[3,4-c]isoxazole THF (2.0 ml) was added to a solution of 4-bromo-2,2-difluoro-1,3-benzodioxol (1.96 g) in toluene (20 ml). The mixture was cooled to −78° C., and a solution of (±)-3,3a,4,5-tetrahydro-7H-pyrano[3,4-c]isoxazole obtained in Preparation Example 1-(2) (500 mg) in toluene-THF (10:1) (10 ml) and a boron trifluoride-diethyl ether complex (990 µl) were added dropwise at the same time. After stirring at the same temperature for two hours, an ammonium chloride solution was added to terminate the reaction. The aqueous layer was extracted with ethyl acetate, and the organic layer was dried over anhydrous magnesium sulfate. The solvent was evaporated under reduced pressure and the residue was purified by silica gel column chromatography to obtain the title compound (873 mg).

¹H-NMR (400 MHz, CDCl₃) δ (ppm): 1.75-1.92 (m, 2H), 3.04-3.09 (m, 1H), 3.63-3.85 (m, 4H), 3.99 (d, J=12.8 Hz, 1H), 4.03-4.06 (m, 1H), 6.30 (s, 1H), 7.01 (dd, J=1.2, 8.4 Hz, 1H), 7.10 (t, J=8.4 Hz, 1H), 7.60 (dd, J=1.2, 8.0 Hz, 1H).

(2) Synthesis of (±)-[(3S*,4R*)-3-amino-3-(2,2-difluoro-benzo[1,3]dioxol-4-yl)-tetrahydropyran-4-yl]methanol Zinc powder (2.01 g) was added to a solution of (±)-(3aR*,7aS*)-7a-(2,2-difluoro-benzo[1,3]dioxol-4-yl)-hexahydro-pyrano[3,4-c]isoxazole (875 mg) in acetic acid (30 ml), and the mixture was stirred at room temperature overnight. The insoluble matter was removed by filtration through celite, and the solvent was evaporated under reduced pressure. Ice was added to the residue, followed by neutralization with a 5 N sodium hydroxide solution. The aqueous layer was extracted with dichloromethane, and the organic layer was dried over anhydrous magnesium sulfate. The solvent was evaporated under reduced pressure and the residue was purified by silica gel column chromatography to obtain the title compound (661 mg).

¹H-NMR (400 MHz, CDCl₃) δ (ppm): 1.62-1.66 (m, 1H), 2.14-2.20 (m, 1H), 2.22-2.31 (m, 1H), 3.38 (dd, J=2.4, 11.2 Hz, 2H), 3.56-3.68 (m, 2H), 4.04 (d, J=11.6 Hz, 1H), 4.17 (dd, J=4.4, 11.2 Hz, 1H), 7.05 (dd, J=1.2, 8.0 Hz, 1H), 7.14 (t, J=8.0 Hz, 1H), 7.32 (dd, J=1.2, 8.0 Hz, 1H).

(3) Synthesis of (±)-(4aR*,8aS*)-8a-(2,2-difluorobenzo[1,3]dioxol-4-yl)-4,4a,5,6,8,8a-hexahydro-7-oxa-3-thia-1-azanaphthalen-2-ylamine Benzoyl isothiocyanate (372 μl) was added to a solution of (±)-[(3S*,4R*)-3-amino-3-(2,2-difluorobenzo[1,3]dioxol-4-yl)tetrahydropyran-4-yl]methanol (661 mg) in dichloromethane (9.53 ml). The mixture was stirred at room temperature for three hours, and then the solvent was evaporated under reduced pressure. The residue was purified by silica gel column chromatography. The resulting intermediate was dissolved in methanol (20 ml). Concentrated hydrochloric acid (five drops) was added and the mixture was heated under reflux for five hours. The reaction solution was cooled to room temperature, and the solvent was evaporated under reduced pressure. The residue was dissolved in methanol (20 ml) and DBU (700 μl) was added, followed by heating under reflux for five hours. The reaction solution was cooled to room temperature, and the solvent was evaporated under reduced pressure. The residue was purified by NH-silica gel column chromatography to obtain the title compound (350 mg). $^1$H-NMR (400 MHz, CDCl$_3$) δ (ppm): 1.43-1.48 (m, 1H), 2.08-2.19 (m, 1H), 2.64 (dd, J=2.8, 12.4 Hz, 1H), 2.74-2.80 (m, 1H), 2.98 (dd, J=4.4, 12.4 Hz, 1H), 3.69 (ddd, J=2.4, 11.6, 12.8 Hz, 1H), 3.79 (d, 11.2 Hz, 1H), 3.93 (d, J=10.8 Hz, 1H), 4.10 (dd, J=5.2, 11.2 Hz, 1H) 6.99 (dd, J=2.0, 7.2 Hz, 1H), 7.03-7.09 (m, 2H).

(4) Synthesis of tert-butyl (±)-[(4aR*,8aS*)-8a-(2,2-difluoro-6-nitrobenzo[1,3]dioxol-4-yl)-4,4a,5,6,8,8a-hexahydro-7-oxa-3-thia-1-azanaphthalen-2-yl]carbamate Fuming nitric acid (7.60 μl) was added to a solution (±)-(4aR*,8aS*)-8a-(2,2-difluorobenzo[1,3]dioxol-4-yl)-4,4a,5,6,8,8a-hexahydro-7-oxa-3-thia-1-azanaphthalen-2-ylamine (50.0 mg) in TFA (1.0 ml) in an ice bath. Then, concentrated sulfuric acid (0.5 ml) was added dropwise. After stirring at the same temperature for one hour, the reaction mixture was poured into ice to terminate the reaction. The mixture was neutralized with 5 N hydroxide. The aqueous layer was extracted with dichloromethane, and the organic layer was dried over anhydrous magnesium sulfate. The solvent was evaporated under reduced pressure to obtain an intermediate. The resulting intermediate was dissolved in THF (10 ml). Di-tert-butyl dicarbonate (66.8 mg) and triethylamine (64.5 μl) were added and the mixture was stirred at room temperature for one hour. Further, di-tert-butyl dicarbonate (130 mg) and triethylamine (1.00 ml) were added and the mixture was stirred at room temperature overnight. The solvent was evaporated under reduced pressure and the residue was purified by silica gel column chromatography to obtain the title compound (62.0 mg).
$^1$-NMR (400 MHz, CDCl$_3$) δ (ppm): 1.51 (s, 9H), 1.55-1.59 (m, 1H), 2.15-2.25 (m, 1H), 2.63-2.66 (m, 1H), 2.87-2.89 (m, 2H), 3.65-3.71 (m, 1H), 3.76-3.84 (m, 2H), 4.10-4.15 (m, 1H), 7.93 (d, J=2.0 Hz, 1H), 8.05 (d, J=2.0 Hz, 1H).
ESI-MS m/z 496 [M$^+$+Na]

(5) Synthesis of tert-butyl (±)-[(4aR*,8aS*)-8a-(6-amino-2,2-difluorobenzo[1,3]dioxol-4-yl)-4,4a,5,6,8,8a-hexahydro-7-oxa-3-thia-1-azanaphthalen-2-yl]carbamate Iron powder (7.09 mg) and a saturated ammonium chloride solution (1.0 ml) were added to a solution of tert-butyl (±)-[(4aR*,8aS*)-8a-(2,2-difluoro-6-nitrobenzo[1,3]dioxol-4-yl)-4,4a,5,6,8,8a-hexahydro-7-oxa-3-thia-1-azanaphthalen-2-yl]carbamate (60.0 mg) in ethanol (20 ml), and the mixture was heated under reflux for 30 minutes. The reaction solution was returned to room temperature and the insoluble matter was removed by filtration through celite. The solvent was evaporated under reduced pressure and the residue was purified by silica gel column chromatography to obtain the title compound (50.0 mg).
ESI-MS m/z 444 [M$^+$+H]

PREPARATION EXAMPLE 22

Synthesis of 5-(2-methoxyethoxy)pyrazine-2-carboxylic acid

[Formula 47]

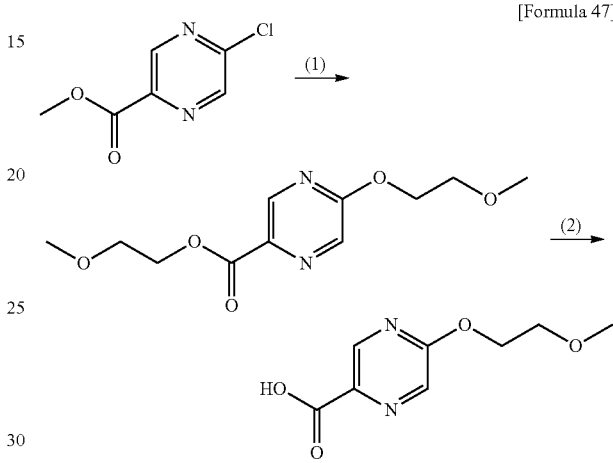

(1) Synthesis of 2-methoxyethyl 5-(2-methoxyethoxy)-pyrazine-2-carboxylate

60% sodium hydride (27.8 mg) was added to a solution of 2-methoxyethanol (50.2 μl) in DMF (1 ml) under ice-cooling, followed by stirring for 10 minutes. A solution of methyl 5-chloropyrazine-2-carboxylate (100 mg) in DMF (1 ml) was added to the reaction solution at the same temperature, followed by stirring for one hour and 50 minutes. Acetic acid (50.0 μl) and water were added to the reaction solution, followed by extraction with ethyl acetate. The organic layer was concentrated under reduced pressure and the residue was purified by silica gel column chromatography to obtain the title compound (19.7 mg).
$^1$H-NMR (400 MHz, CDCl$_3$) δ (ppm): 3.24 (s, 3H), 3.45 (s, 3H), 3.73-3.81 (m, 4H), 4.53-4.61 (m, 4H), 8.34-8.38 (m, 1H), 8.86-8.90 (m, 1H).

(2) Synthesis of 5-(2-methoxyethoxy)pyrazine-2-carboxylic acid

Potassium trimethylsilanolate (14.8 mg) was added to a solution of the compound obtained in the previous step (19.7 mg) in tetrahydrofuran (1 ml), and the mixture was stirred at room temperature for one hour. The reaction solution was concentrated under reduced pressure. Water and ethyl acetate were added to the residue, and the aqueous layer was separated. 5 M hydrochloric acid was added to the aqueous layer, followed by extraction with chloroform. The organic layer was concentrated under reduced pressure to obtain the title compound (13.2 mg).
$^1$H-NMR (400 MHz, CDCl$_3$) δ (ppm): 3.45 (s, 3H), 3.77-3.82 (m, 2H), 4.60-4.64 (m, 2H), 8.24 (d, J=1.4 Hz, 1H), 8.96 (d, J=1.4 Hz, 1H).

EXAMPLE 1

Synthesis of N-[3-((4aR*,8aS*)-2-amino-4,4a,5,6,8,8a-hexahydro-7-oxa-3-thia-1-azanaphthalen-8a-yl)-4-fluorophenyl]-5-cyanopyridine-2-carboxamide

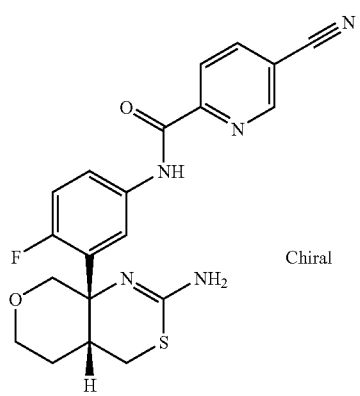

[Formula 48]

Chiral

Oxalyl chloride (140 μl) was added to a suspension of 5-cyanopyridine-2-carboxylic acid (50 mg) in dichloromethane (2 ml) under ice-cooling. Tetrahydrofuran (4 ml) was further added at the same temperature, and the solid was completely dissolved. After confirming completion of foaming, the solvent was evaporated under reduced pressure. Tetrahydrofuran (5 ml) was added to the residue to obtain an acid chloride solution. The acid chloride solution prepared above (788 μl) was added to a solution of tert-butyl (−)-[(4aR*,8aS*)-8a-(5-amino-2-fluorophenyl)-4,4a,5,6,8,8a-hexahydro-7-oxa-3-thia-1-azanaphthalen-2-yl]carbamate (14.5 mg) in tetrahydrofuran (5 ml) under ice-cooling. After adding pyridine (500 μl) at the same temperature, the mixture was heated to room temperature and stirred for two hours. After completion of the reaction, a sodium bicarbonate solution was added to the reaction solution. The aqueous layer was extracted with ethyl acetate, and the organic layer was dried over anhydrous magnesium sulfate. The solvent was evaporated under reduced pressure to obtain an amide compound. The resulting amide compound was dissolved in dichloromethane (4 ml), and trifluoroacetic acid (1 ml) was added. The mixture was stirred at room temperature for three hours, and then ice was added. The aqueous layer was neutralized with a sodium bicarbonate solution, followed by extraction with ethyl acetate. The organic layer was dried over anhydrous magnesium sulfate, and the solvent was evaporated under reduced pressure. The residue was purified by NH-silica gel column chromatography to obtain the title compound (8.0 mg).

$^1$H-NMR (400 MHz, CDCl$_3$) δ (ppm): 1.45 (ddd, J=2.0, 4.0, 13.6 Hz, 1H), 2.14 (m, 1H), 2.65 (dd, J=2.8, 12.4 Hz, 1H), 2.94 (ddd, J=4.0, 7.2, 11.6 Hz, 1H), 3.02 (dd, J=4.0, 12.0 Hz, 1H), 3.69 (m, 1H), 3.77 (d, J=10.8 Hz, 1H), 4.06 (dd, J=2.0, 10.8 Hz, 1H), 4.10 (m, 1H), 7.09 (dd, J=8.8, 11.6 Hz, 1H), 7.39 (dd, J=2.8, 6.8 Hz, 1H), 8.01 (ddd, J=2.8, 4.4, 9.2 Hz, 1H), 8.20 (dd, J=1.6, 8.0 Hz, 1H), 8.42 (dd, J=0.8, 8.0 Hz, 1H), 8.89 (dd, J=0.8, 2.0 Hz, 1H), 9.82 (s, 1H).

EXAMPLE 2

Synthesis of N-[3-((8aR*)-2-amino-4,4a,5,6,8,8a-hexahydro-7-oxa-3-thia-1-azanaphthalen-8a-yl)-4-fluorophenyl]-5-fluoromethoxypyrazine-2-carboxamide

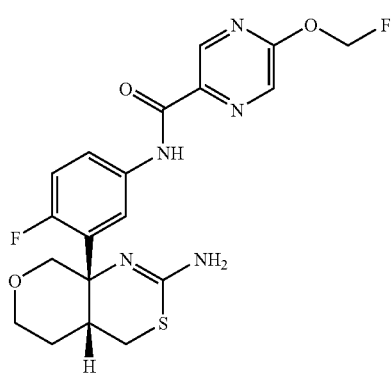

[Formula 49]

The compound obtained in Preparation Example 2 (19.0 mg), N,N-diisopropylethylamine (41.1 μL) and PyBOP (102 mg) were added to a solution of the compound obtained in Preparation Example 1 (30.0 mg) in dichloromethane (857 μL). The reaction solution was stirred at room temperature for 16 hours and 30 minutes. Then, the reaction mixture was purified by silica gel column chromatography to obtain an amide compound. The resulting amide compound was dissolved in dichloromethane (643 μL), and trifluoroacetic acid (214 μL) was added. The reaction solution was allowed to stand at room temperature for one hour, and then the solvent was evaporated under reduced pressure. A saturated sodium bicarbonate solution was added to the residue, followed by extraction with ethyl acetate. The organic layer was concentrated under reduced pressure. The residue was purified by NH-silica gel column chromatography to obtain the title compound (15.4 mg).

$^1$H-NMR (400 MHz, CDCl$_3$) δ (ppm): 1.41-1.48 (m, 1H), 2.08-2.20 (m, 1H), 2.64 (dd, J=12.2, 3.5 Hz, 1H), 2.89-2.98 (m, 1H), 3.02 (dd, J=12.2, 5.0 Hz, 1H), 3.64-3.74 (m, 1H), 3.74-3.80 (m, 1H), 4.03-4.13 (m, 2H), 6.08-6.10 (m, 1H), 6.21-6.23 (m, 1H), 7.08 (dd, J=12.0, 8.8 Hz, 1H), 7.33 (dd, J=6.8, 2.8 Hz, 1H), 7.99-8.04 (m, 1H), 8.29 (d, J=1.2 Hz, 1H), 9.08 (d, J=1.2 Hz, 1H), 9.47 (brs, 1H).

EXAMPLE 3

Synthesis of N-[3-((4aR*,8aS*)-2-amino-4,4a,5,6,8,8a-hexahydro-7-oxa-3-thia-1-azanaphthalen-8a-yl)-4-fluorophenyl]-5-difluoromethoxypyrazine-2-carboxamide

[Formula 50]

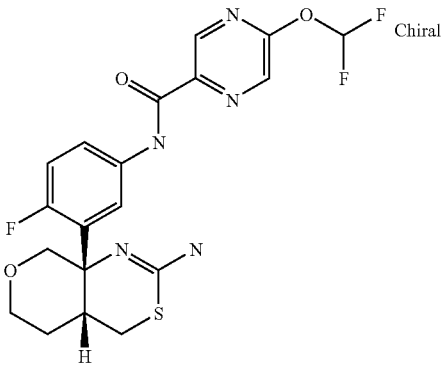

Chiral

The title compound (14.0 mg) was obtained from the compound obtained in Preparation Example 1 (18.0 mg) and 5-difluoromethoxypyrazine-2-carboxylic acid (24.9 mg) according to the method of Example 2.

1-NMR (400 MHz, CDCl₃)) δ (ppm): 1.46-1.49 (m, 1H), 2.08-2.16 (m, 2H), 2.65-2.68 (m, 1H), 2.98-3.04 (m, 2H), 3.66-3.72 (m, 1H), 3.81-3.84 (m, 1H), 4.04-4.07 (m, 1H), 7.06-7.12 (m, 1H), 7.36-7.39 (m, 1H), 7.51 (t, J=71.6 Hz, 1H), 8.02-8.04 (m, 1H), 8.34 (s, 1H), 9.06 (s, 1H), 9.50 (s, 1H)

EXAMPLES 4 to 5

The compounds of Examples 4 to 5 were synthesized below according to Example 2 using the compound of Preparation Example 5-(9) and the corresponding carboxylic acids, as shown in the following Table 1.

TABLE 1

| Example 4 | Chemical structure | Compound name: 4)N-[3-((4aR*,8aS*)-2-amino-4,4a,5,6,8,8a-hexahydro-7-oxa-3-thia-1-azanaphthalen-8a-yl)-4-trifluoromethoxyphenyl]-5-cyanopyridine-2-carboxamide ESI-MS m/z 478 [M⁺ + H] |
|---|---|---|
| Example 5 | Chemical structure | Compound name: 5)N-[3-((8aS*)-2-amino-4,4a,5,6,8,8a-hexahydro-7-oxa-3-thia-1-azanaphthalen-8a-yl)-4-trifluoromethoxyphenyl]-5-chloropyridine-2-carboxamide ESI-MS m/z 487 [M⁺ + H] |

EXAMPLES 6 to 10

The compounds of Examples 6 to 10 were synthesized below according to Example 2 using the compound of Preparation Example 6-(12) and the corresponding carboxylic acids, as shown in the following Table 2.

TABLE 2

| Example 6 | Chemical structure | Compound name: 6)N-[3-((4aR*,6S*,8aS*)-2-amino-6-methyl-4,4a,5,6,8,8a-hexhydro-7-oxa-3-thia-1-azanaphthalen-8a-yl)-4-fluorophenyl]-5-chloropyridine-2-carboxamide ESI-MS m/z 435 [M⁺ + H] |
|---|---|---|

TABLE 2-continued

| Example 7 | Chemical structure 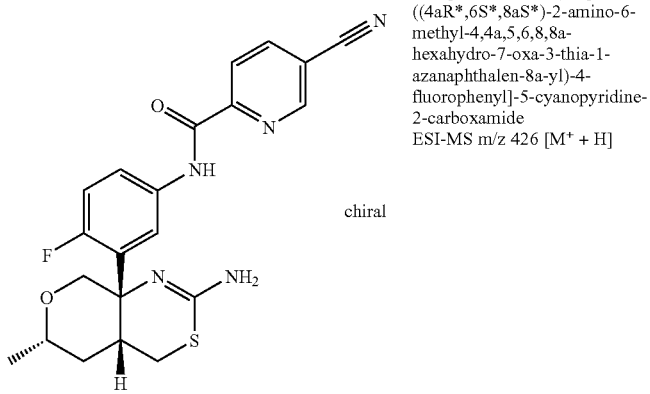 chiral | Compound name: 7)N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-cyanopyridine-2-carboxamide<br>ESI-MS m/z 426 [M+ + H] |
|---|---|---|
| Example 8 | Chemical structure 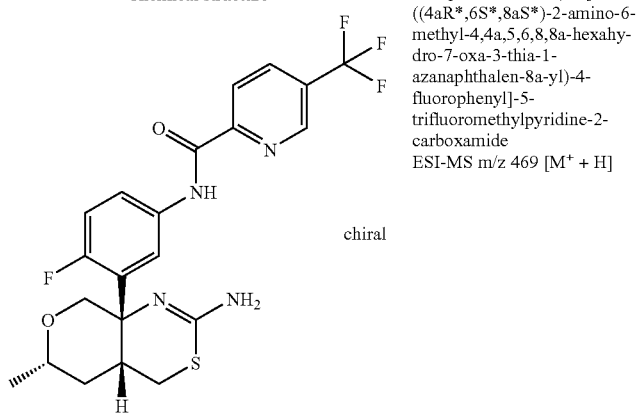 chiral | Compound name: 8)N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-trifluoromethylpyridine-2-carboxamide<br>ESI-MS m/z 469 [M+ + H] |
| Example 9 | Chemical structure 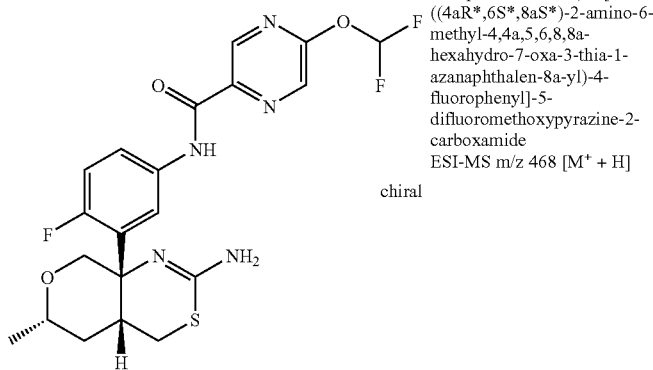 chiral | Compound name: 9)N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-difluoromethoxypyrazine-2-carboxamide<br>ESI-MS m/z 468 [M+ + H] |
| Example 10 | Chemical structure 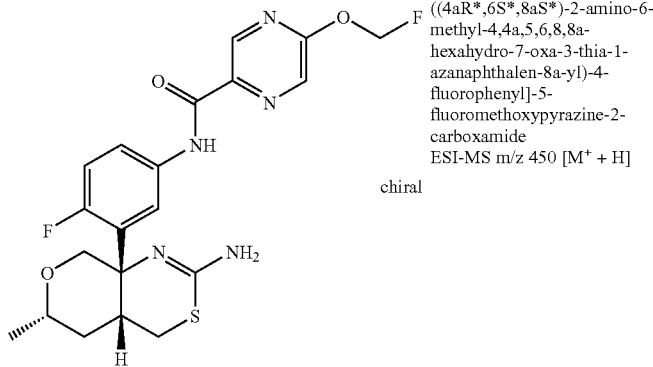 chiral | Compound name: 10 N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-fluoromethoxypyrazine-2-carboxamide<br>ESI-MS m/z 450 [M+ + H] |

EXAMPLES 11 to 15

The compounds of Examples 11 to 15 were synthesized below according to Example 2 using the compound of Preparation Example 7-(12) and the corresponding carboxylic acids, as shown in the following Table 3.

TABLE 3

| Example 11 | Chemical structure 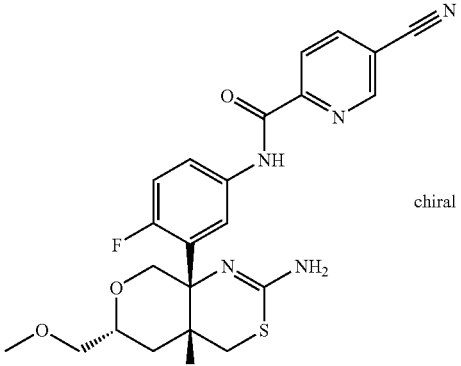 | Compound name: N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-cyanopyridine-2-carboxamide<br>$^1$H-NMR (400 MHz, CDCl$_3$) δ (ppm): 1.45-1.53 (m, 1H), 1.80-1.93 (m, 1H), 2.58-2.67 (m, 1H), 2.94-3.07 (m, 2H), 3.43 (s, 3H), 3.43-3.57 (m, 2H), 3.81-3.92 (m, 2H), 4.14-4.21 (m, 1H), 7.02-7.11 (m, 1H), 7.35-7.41 (m, 1H), 7.97-8.06 (m, 1H), 8.16-8.23 (m, 1H), 8.37-8.44 (m, 1H), 8.86-8.91 (m, 1H), 9.80 (brs, 1H).<br>ESI-MS m/z 456 [M$^+$ + H] |
| --- | --- | --- |
| Example 12 | Chemical structure 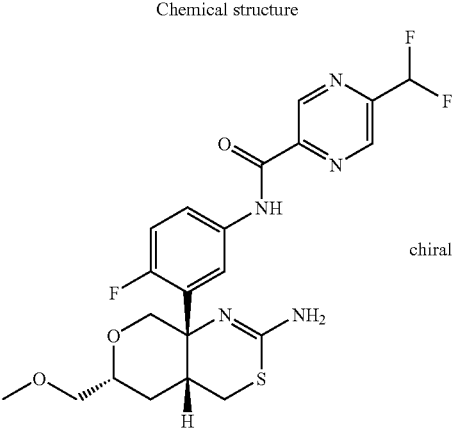 | Compound name: 12)N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-difluoromethylpyrazine-2-carboxamide<br>$^1$H-NMR (400 MHz, CDCl$_3$) δ (ppm): 1.45-1.54 (m, 1H), 1.79-1.92 (m, 1H), 2.58-2.67 (m, 1H), 2.94-3.07 (m, 2H), 3.42 (s, 3H), 3.43-3.48 (m, 1H), 3.50-3.57 (m, 1H), 3.82-3.92 (m, 2H), 4.13-4.20 (m, 1H), 6.79 (t, J = 54.6 Hz, 1H), 7.02-7.10 (m, 1H), 7.35-7.41 (m, 1H), 7.96-8.04 (m, 1H), 8.88-8.93 (m, 1H), 9.47-9.52 (m, 1H), 9.60 (brs, 1H).<br>ESI-MS m/z 482 [M$^+$ + H] |
| Example 13 | Chemical structure 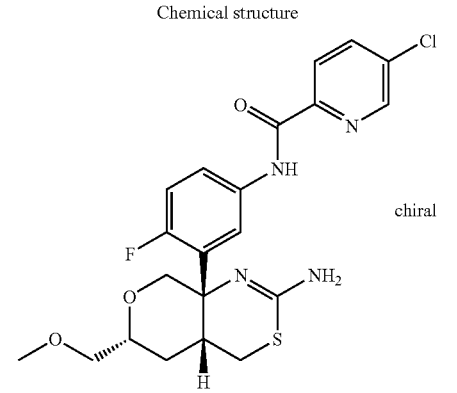 | Compound name: 13) N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-chloropyridine-2-carboxamide<br>ESI-MS m/z 465 [M$^+$ + H] |

TABLE 3-continued

| Example 14 | Chemical structure | |
|---|---|---|
| | 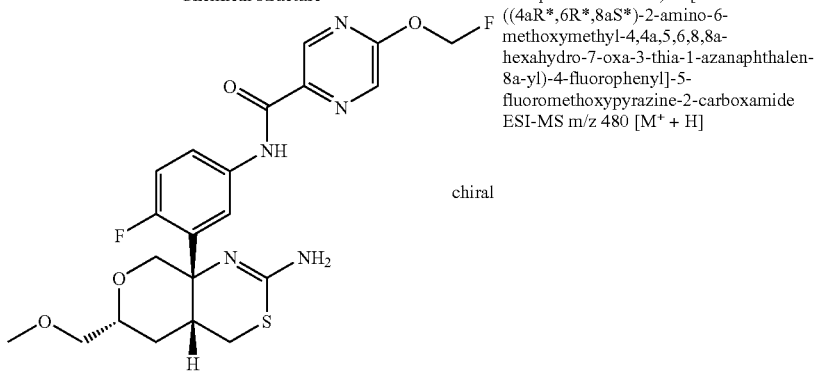 chiral | Compound name: 14) N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-fluoromethoxypyrazine-2-carboxamide ESI-MS m/z 480 [M+ + H] |
| Example 15 | 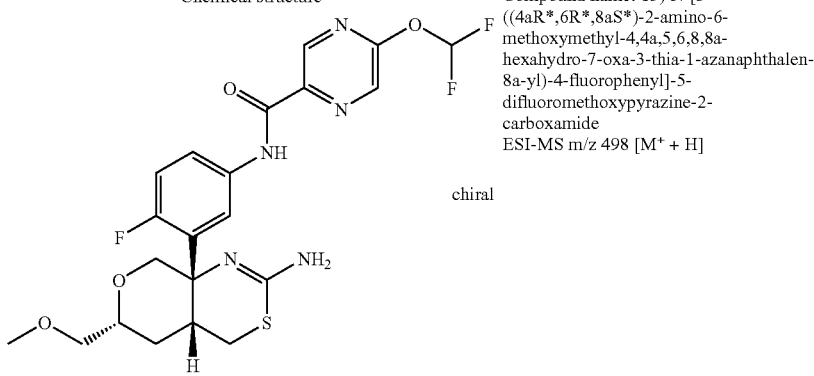 chiral | Compound name: 15) N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-difluoromethoxypyrazine-2-carboxamide ESI-MS m/z 498 [M+ + H] |

EXAMPLES 16 to 30

The compounds of Examples 16 to 30 were synthesized according to Example 2 using the corresponding carboxylic acids and the corresponding aniline intermediates in Preparation Examples, as shown in the following Table 4.

TABLE 4

| Example 16 | 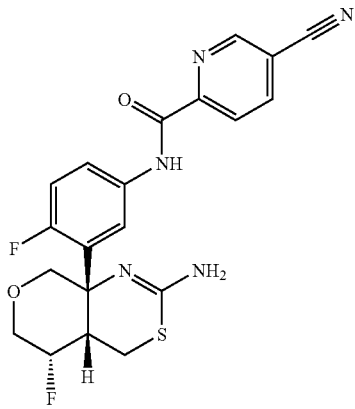 | Compound name: 16 N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-cyanopyridine-2-carboxamide<br>$^{1}$H-NMR (400 MHz, CDCl$_3$) δ (ppm): 2.87 (dd, J = 4.0, 12.4 Hz, 1H), 2.99-3.07 (m, 1H), 3.17 (dd, J = 2.8, 12.8 Hz, 1H), 3.53 (ddd, J = 4.8, 10.4, 10.4 Hz, 1H), 3.74 (dd, J = 2.4, 11.2 Hz, 1H), 4.08 (dd, J = 2.0, 11.2 Hz, 1H), 4.26 (dd, J = 5.6, 10.4 Hz, 1H), 4.18-5.01 (m, 1H), 7.11 (dd, J = 8.8, 11.6 Hz, 1H), 7.42 (dd, J = 2.8, 6.8 Hz, 1H), 7.97 (ddd, J = 2.8, 4.0, 8.4 Hz, 1H), 8.20 (dd, J = 2.4, 8.0 Hz, 1H), 8.41 (dd, J = 0.8, 8.0 Hz, 1H), 8.88 (dd, J = 0.8, 2.0 Hz, 1H), 9.81 (s, 1H). ESI-MS m/z 430 [M+ + H] |

TABLE 4-continued

| Example 17 | 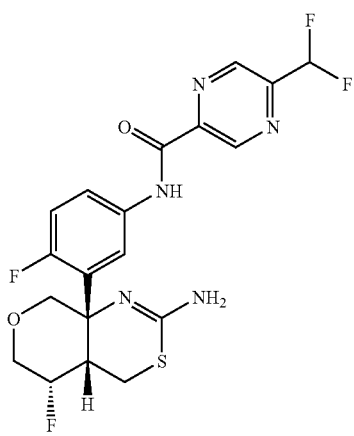 | Compound name: 17) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-difluoromethylpyrazine-2-carboxamide<br>$^1$H-NMR (400 MHz, CDCl$_3$) δ (ppm): 2.87 (dd, J = 4.0, 12.8 Hz, 1H), 2.99-3.07 (m, 1H), 3.17 (dd, J = 3.2, 12.8 Hz, 1H), 3.50-3.57 (m, 1H) 3.74 (dd, J = 2.4, 10.8 Hz, 1H), 4.08 (dd, J = 2.0, 10.8 Hz, 1H), 4.27 (dd, J = 5.6, 10.4 Hz, 1H), 4.80-5.00 (m, 1H), 6.80 (t, J = 54.4 Hz, 1H), 7.13 (dd, J = 8.8, 11.6 Hz, 1H), 7.43 (dd, J = 2.4, 6.4 Hz, 1H), 7.95-7.99 (m, 1H), 8.93 (s, 1H), 9.52 (s, 1H), 9.62 (s, 1H).<br>ESI-MS m/z 456 [M$^+$ + H] |
| --- | --- | --- |
| Example 18 | 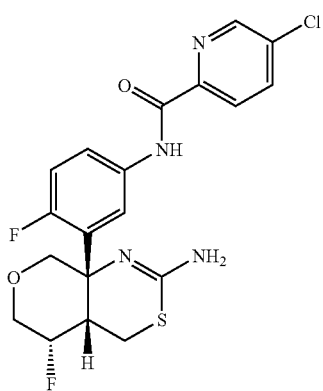 | Compound name: 18) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-chloropyridine-2-carboxamide<br>ESI-MS m/z 439 [M$^+$ + H] |
| Example 19 | 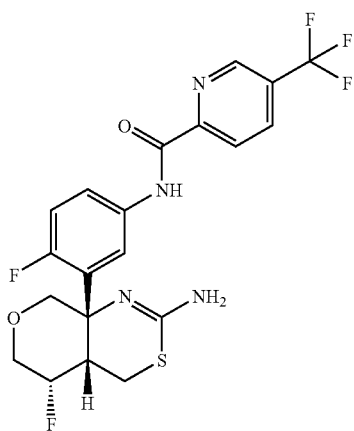 | Compound name: 19) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-trifluoromethylpyridine-2-carboxamide<br>ESI-MS m/z 473 [M$^+$ + H] |
| Example 20 | 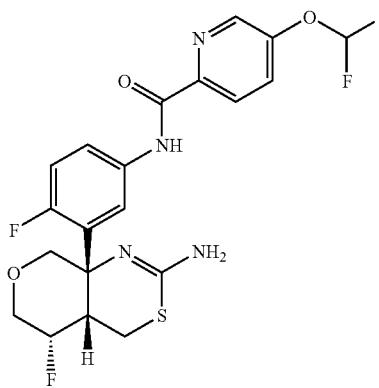 | Compound name: 20) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-difluoromethoxypyridine-2-carboxamide<br>ESI-MS m/z 471 [M$^+$ + H] |

TABLE 4-continued

| Example 21 | 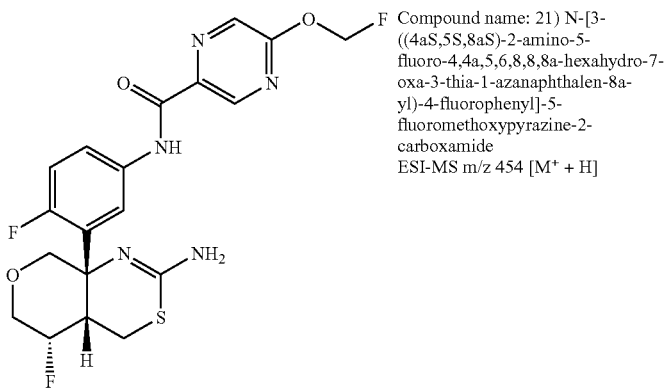 | Compound name: 21) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-fluoromethoxypyrazine-2-carboxamide<br>ESI-MS m/z 454 [M$^+$ + H] |
| --- | --- | --- |
| Example 22 | 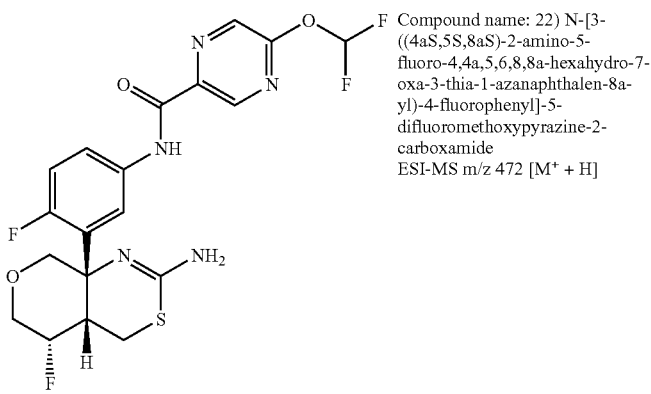 | Compound name: 22) N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-difluoromethoxypyrazine-2-carboxamide<br>ESI-MS m/z 472 [M$^+$ + H] |
| Example 23 | 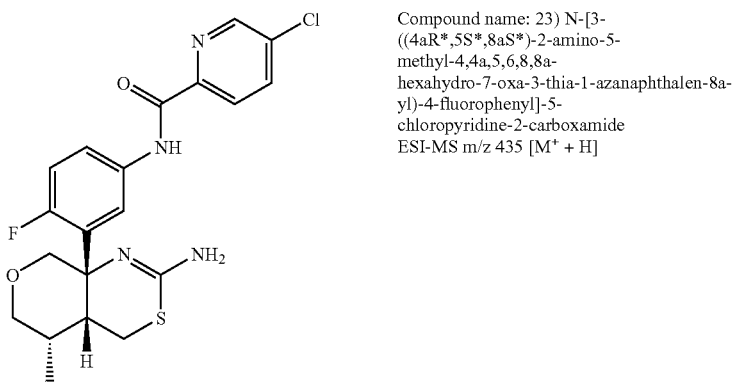 | Compound name: 23) N-[3-((4aR*,5S*,8aS*)-2-amino-5-methyl-4,4a,5,6,8,8a-hexahydro-7-oxa-3-thia-1-azanaphthalen-8a-yl)-4-fluorophenyl]-5-chloropyridine-2-carboxamide<br>ESI-MS m/z 435 [M$^+$ + H] |
| Example 24 | 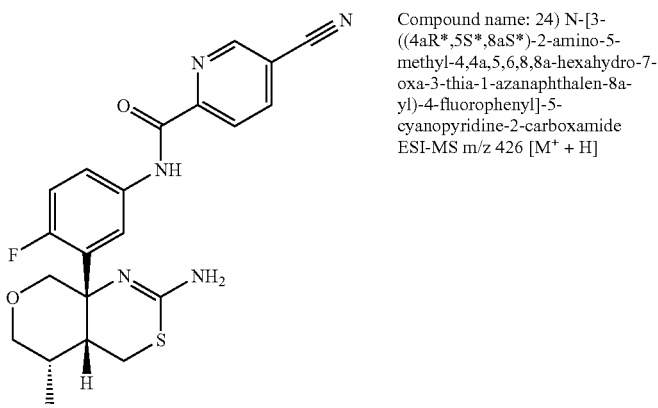 | Compound name: 24) N-[3-((4aR*,5S*,8aS*)-2-amino-5-methyl-4,4a,5,6,8,8a-hexahydro-7-oxa-3-thia-1-azanaphthalen-8a-yl)-4-fluorophenyl]-5-cyanopyridine-2-carboxamide<br>ESI-MS m/z 426 [M$^+$ + H] |

TABLE 4-continued

| Example 25 | 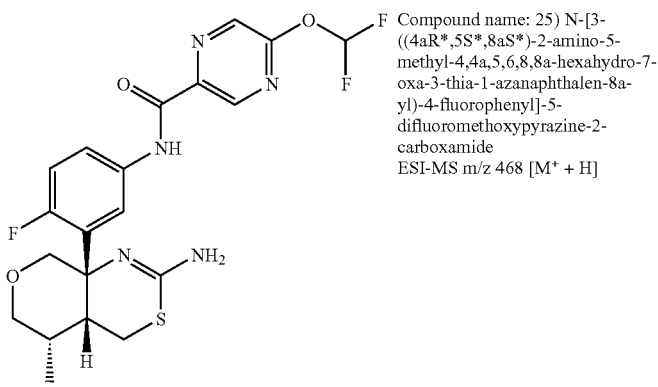 | Compound name: 25) N-[3-((4aR*,5S*,8aS*)-2-amino-5-methyl-4,4a,5,6,8,8a-hexahydro-7-oxa-3-thia-1-azanaphthalen-8a-yl)-4-fluorophenyl]-5-difluoromethoxypyrazine-2-carboxamide<br>ESI-MS m/z 468 [M⁺ + H] |
|---|---|---|
| Example 26 | 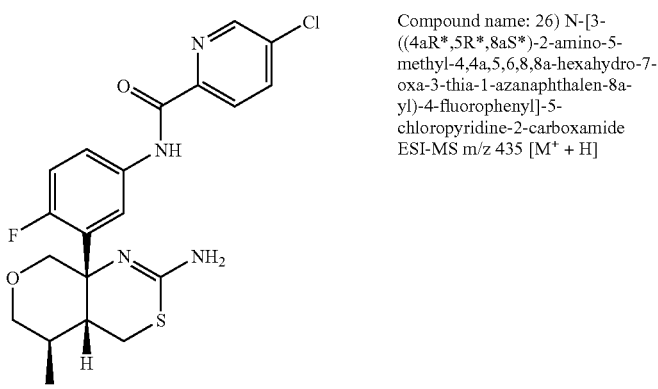 | Compound name: 26) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-chloropyridine-2-carboxamide<br>ESI-MS m/z 435 [M⁺ + H] |
| Example 27 | 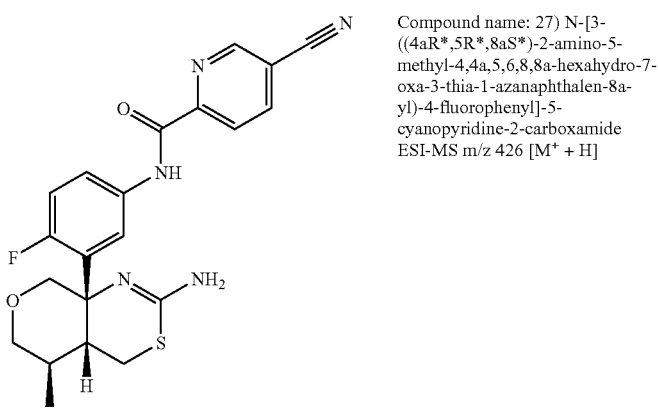 | Compound name: 27) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-cyanopyridine-2-carboxamide<br>ESI-MS m/z 426 [M⁺ + H] |
| Example 28 | 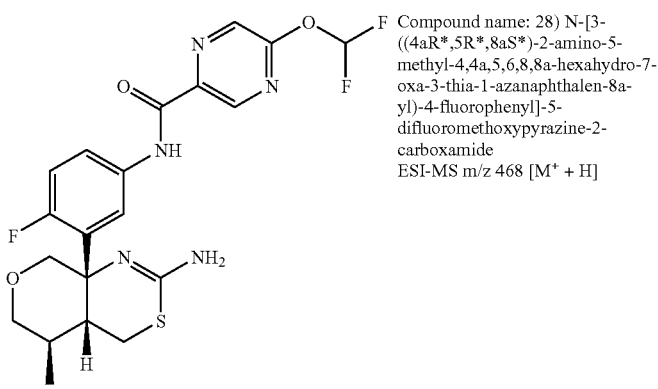 | Compound name: 28) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-difluoromethoxypyrazine-2-carboxamide<br>ESI-MS m/z 468 [M⁺ + H] |

TABLE 4-continued

Example 29

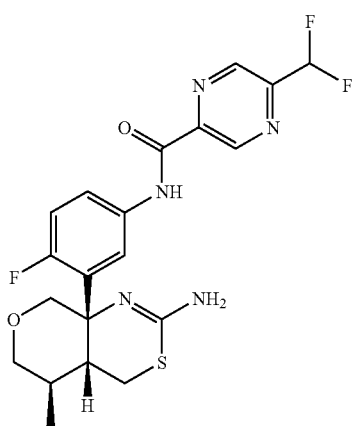

Compound name: 29) N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-difluoromethylpyrazine-2-carboxamide
ESI-MS m/z 452 [M$^+$ + H]

Example 30

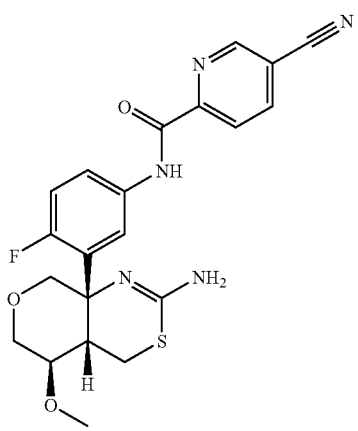

Compound name: 30) N-[3-((4aS*,5R*,8aS*)-2-amino-5-methoxy-4,4a,5,6,8,8a-hexahydro-7-oxa-3-thia-1-azanaphthalen-8a-yl)-4-fluorophenyl]-5-cyanopyridine-2-carboxamide
ESI-MS m/z 442 [M$^+$ + H]

EXAMPLE 31

Synthesis of N-[3-((2R*,4aR*,8aS*)-2-amino-4-methyl-4,4a,5,6,8,8a-hexahydro-7-oxa-3-thia-1-aza-naphthalen-8a-yl)-4-fluorophenyl]-5-cyanopyridine-2-carboxamide

[Formula 51]

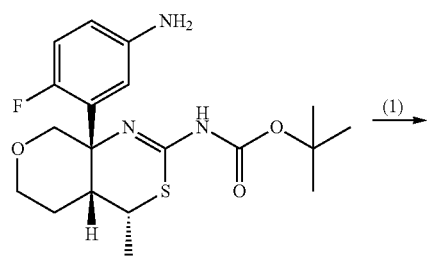

-continued

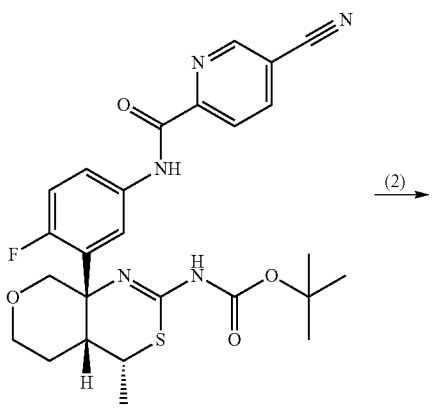

-continued

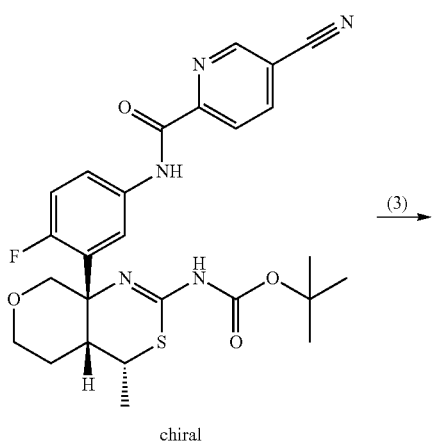

chiral (1) Synthesis of tert-butyl (±)-((2R*,4aR*,8aS*)-8a-{5-[(5-cyanopyridine-2-carbonyl)-amino]-2-fluorophenyl}-4-methyl-4,4a,5,6,8, 8a-hexahydro-7-oxa-3-thia-1-azanaphthalen-2-yl)-carbamate PyBOP (357 mg) was added to a solution of the compound obtained in Preparation Example 11-(10) (100 mg), the compound obtained in Preparation Example 3-(2) (56 mg) and N,N-diisopropylethylamine (143 μL) in dichloromethane (5 mL), and the mixture was stirred at room temperature for five hours. The reaction solution was directly charged to a silica gel and purified by silica gel column chromatography to obtain the title compound (100 mg).

ESI-MS; m/z 526 [M$^+$+H].

(2) Synthesis of tert-butyl (+)-((2R*,4aR*,8aS*)-8a-{5-[(5-cyanopyridine-2-carbonyl)-amino]-2-fluorophenyl}-4-methyl-4,4a,5,6,8, 8a-hexahydro-7-oxa-3-thia-1-azanaphthalen-2-yl)-carbamate The compound obtained in Example 31-(1) was purified by CHIRALPAK™ IB (mobile phase: hexane:ethanol=7:3, flow rate: 10 ml/min), and the fraction with a retention time of 23.4 to 26.7 minutes was collected to obtain the title compound.

The same operation was repeated to obtain the title compound (20 mg; >99% ee) from the raw material (100 mg).

ESI-MS; m/z 526 [M$^+$+H].

(3) Synthesis of N-[3-((2R*,4aR*,8aS*)-2-amino-4-methyl-4,4a,5,6,8,8a-hexahydro-7-oxa-3-thia-1-azanaphthalen-8a-yl)-4-fluorophenyl]-5-cyanopyridine-2-carboxamide TFA (1 mL) was added to a solution of the compound obtained in Example 31-(2) (20 mg) in chloroform (2 mL), and the mixture was stirred at room temperature for five hours. The reaction solution was neutralized with saturated aqueous sodium bicarbonate. Chloroform was added to the mixture, and the organic layer was separated. The organic layer was dried over anhydrous magnesium sulfate. The organic layer was concentrated under reduced pressure to obtain the title compound (14 mg).

ESI-MS; m/z 426 [M$^+$+H].

EXAMPLE 32

Synthesis of N-[3-((2R*,4aR*,8aS*)-2-amino-4-methyl-4,4a,5,6,8,8a-hexahydro-7-oxa-3-thia-1-azanaphthalen-8a-yl)-4-fluorophenyl]-5-difluoromethylpyrazine-2-carboxamide

[Formula 52]

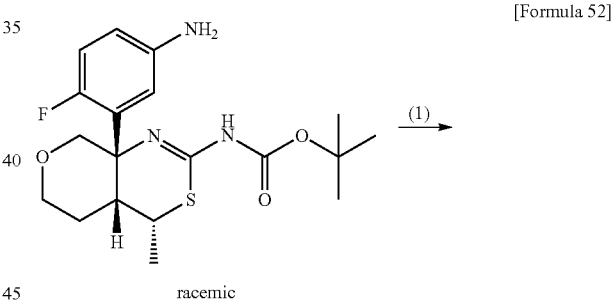

racemic

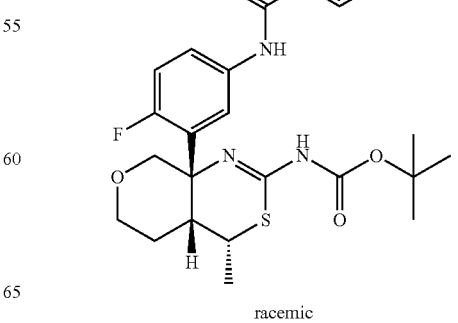

racemic

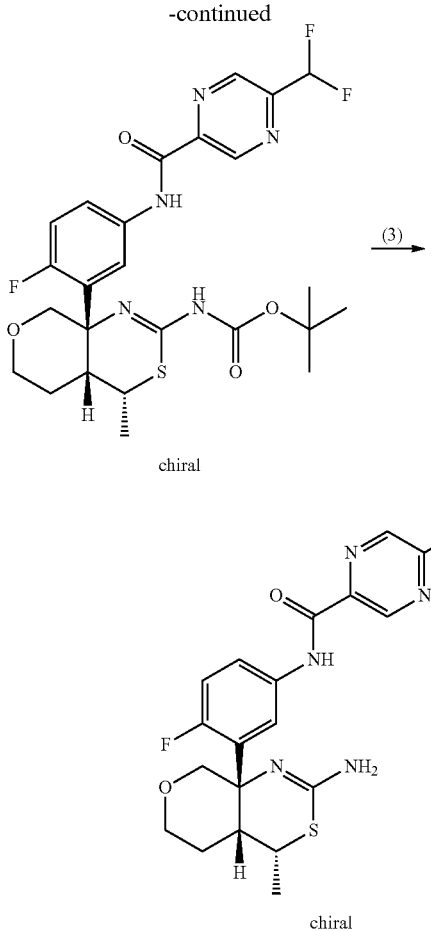

chiral (1) Synthesis of tert-butyl (±)-((2R*,4aR*,8aS*)-8a-{5-[(5-difluoromethylpyrazine-2-carbonyl)-amino]-2-fluoro-phenyl}-4-methyl-4,4a,5,6,8,8a-hexahydro-7-oxa-3-thia-1-aza-naphthalen-2-yl)-carbamate The title compound (132 mg) was obtained from the compound obtained in Preparation Example 11-(10) (100 mg) and the compound obtained in Preparation Example 12-(5) (56 mg) according to Example 31-(1).

ESI-MS; m/z 552 [M$^+$+H].

(2) Synthesis of tert-butyl (+)-((2R*,4aR*,8aS*)-8a-{5-[(5-difluoromethylpyrazine-2-carbonyl)-amino]-2-fluoro-phenyl}-4-methyl-4,4a,5,6,8,8a-hexahydro-7-oxa-3-thia-1-azanaphthalen-2-yl)-carbamate The compound obtained in Example 32-(1) was purified by CHIRALPAK™ IA (mobile phase: ethanol, flow rate: 10 ml/min), and the fraction with a retention time of 10.8 to 13.5 minutes was collected to obtain the title compound. The same operation was repeated to obtain the title compound (52 mg; >99% ee) from the raw material (130 mg).

ESI-MS; m/z 552 [M$^+$+H].

(3) Synthesis of N-[3-((2R*,4aR*,8aS*)-2-amino-4-methyl-4,4a,5,6,8,8a-hexahydro-7-oxa-3-thia-1-azanaphthalen-8a-yl)-4-fluorophenyl]-5-cyanopyridine-2-carboxamide TFA (1 mL) was added to a solution of the compound obtained in Example 32-(2) (52 mg) in chloroform (3 mL), and the mixture was stirred at room temperature for four hours. The reaction solution was neutralized with saturated aqueous sodium bicarbonate. Chloroform was added to the mixture, and the organic layer was separated. The organic layer was dried over anhydrous magnesium sulfate. The organic layer was concentrated under reduced pressure. The residue was purified by NH-silica gel column chromatography to obtain the title compound (42 mg).

ESI-MS; m/z 452 [M$^+$+H].

EXAMPLES 33 to 34

The compounds of Examples 33 to 34 were synthesized according to Example 2 using the corresponding carboxylic acids and the corresponding aniline intermediates in Preparation Examples, as shown in the following Table 5.

TABLE 5

| Example 33 | Chemical structure | Compound name: N-[3-((4aR,6R,8aS)-2-amino-6-hydroxymethyl-4,4a,5,6,8,8a-hexahydro-7-oxa-3-thia-1-azanaphthalen-8a-yl)-4-fluorophenyl]-5-chloropyridine-2-carboxamide ESI-MS m/z 451 [M$^+$ + H] |
|---|---|---|

TABLE 5-continued

| Example | Chemical structure | |
|---|---|---|
| 34 | structure | Compound name: N-[3-((4aR,6R,8aS)-2-amino-6-hydroxymethyl-4,4a,5,6,8,8a-hexahydro-7-oxa-3-thia-1-azanaphthalen-8a-yl)-4-fluorophenyl]-5-cyanopyridine-2-carboxamide<br>ESI-MS m/z 442 [M$^+$ + H] |

EXAMPLES 35 to 43

The compounds of Examples 35 to 43 were synthesized according to Example 2 using the corresponding carboxylic acids and the corresponding aniline intermediates in Preparation Examples, as shown in the following Table 6.

TABLE 6

| Example | Chemical structure | |
|---|---|---|
| 35 | structure | Compound name: N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-cyanopyridine-2-carboxamide<br>$^1$H-NMR (400 MHz, CDCl$_3$) δ (ppm): 1.69-1.73 (m, 1H), 2.12 (ddd, J = 2.4, 12.4, 24.8 Hz, 1H), 2.67 (dd, J = 2.4, 12.4 Hz, 1H), 2.99-3.07 (m, 2H), 3.95 (d, J = 11.2 Hz, 1H), 4.05-4.09 (m, 1H), 4.18 (d, J = 2.0, 11.2 Hz, 1H), 7.09 (dd, J = 8.8, 11.6 Hz, 1H), 7.40 (dd, J = 2.8, 6.4 Hz, 1H), 8.00-8.05 (m, 1H), 8.21 (dd, J = 2.0, 8.0 Hz, 1H), 8.42 (d, J = 8.0 Hz, 1H), 8.90 (s, 1H), 9.81 (s, 1H). |
| 36 | structure | Compound name: N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-difluoromethoxypyrazine-2-carboxamide<br>$^1$H-NMR (400 MHz, CDCl$_3$) δ (ppm): 1.69-1.73 (m, 1H), 2.13 (ddd, J = 2.4, 12.0, 24.8 Hz, 1H), 2.67 (dd, J = 2.4, 12.0 Hz, 1H), 2.98-3.07 (m, 2H), 3.98 (d, J = 10.8 Hz, 1H), 4.04-4.11 (m, 1H), 4.17 (dd, J = 2.0, 12.8 Hz, 1H), 7.02 (dd, J = 8.4, 11.6 Hz, 1H), 7.38 (dd, J = 2.8, 6.8 Hz, 1H), 7.51 (t, J = 71.2 Hz, 1H), 7.91-7.95 (m, 1H), 8.27 (d, J = 1.2 Hz, 1H), 9.01 (d, J-1.2 Hz, 1H), 9.37 (s, 1H). |

TABLE 6-continued

| Example 37 | Chemical structure | 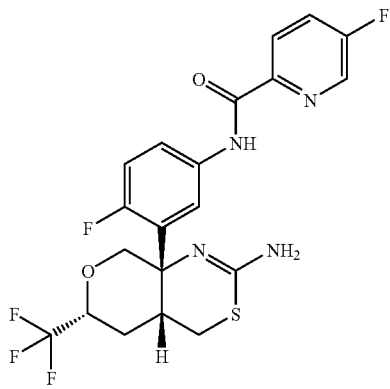 | Compound name: N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-fluoropyridine-2-carboxamide<br>ESI-MS m/z 473 [M+ + H] |

| Example 38 | Chemical structure | 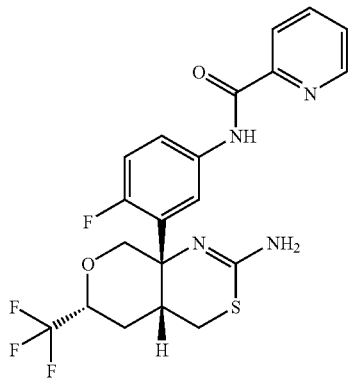 | Compound name: N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-pyridine-2-carboxamide<br>ESI-MS m/z 455 [M+ + H] |

| Example 39 | Chemical structure | 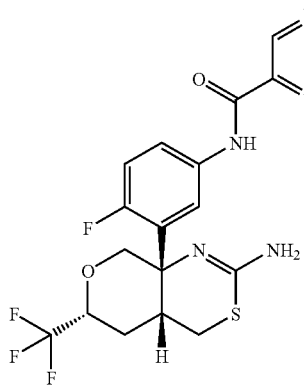 | Compound name: N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-fluoromethoxypyrazine-2-carboxamide<br>ESI-MS m/z 504 [M+ + H] |

TABLE 6-continued

| Example 40 | Chemical structure | 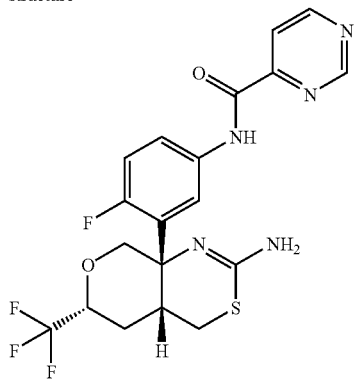 | Compound name: N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-pyrimidine-4-carboxamide<br>ESI-MS m/z 456 [M+ + H] |
|---|---|---|---|
| Example 41 | Chemical structure | 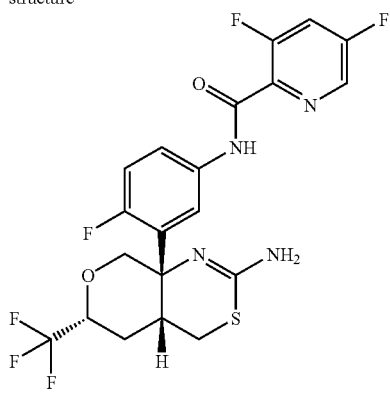 | Compound name: N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-3,5-difluoropyridine-2-carboxamide<br>ESI-MS m/z 491 [M+ + H] |
| Example 42 | Chemical structure | 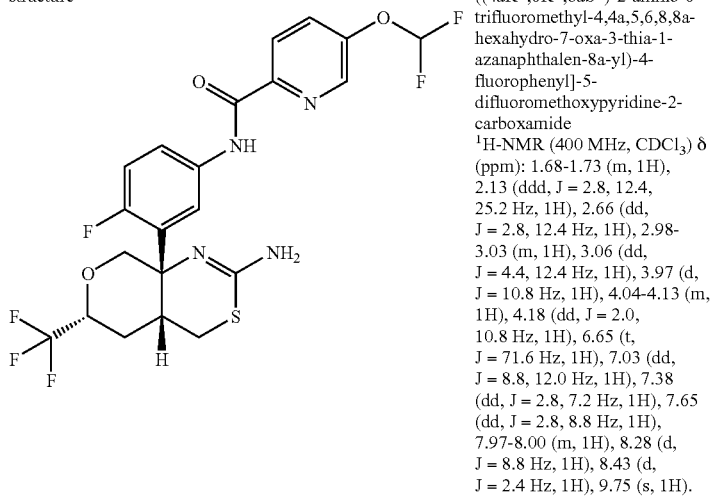 | Compound name: N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-difluoromethoxypyridine-2-carboxamide<br>$^1$H-NMR (400 MHz, CDCl$_3$) δ (ppm): 1.68-1.73 (m, 1H), 2.13 (ddd, J = 2.8, 12.4, 25.2 Hz, 1H), 2.66 (dd, J = 2.8, 12.4 Hz, 1H), 2.98-3.03 (m, 1H), 3.06 (dd, J = 4.4, 12.4 Hz, 1H), 3.97 (d, J = 10.8 Hz, 1H), 4.04-4.13 (m, 1H), 4.18 (dd, J = 2.0, 10.8 Hz, 1H), 6.65 (t, J = 71.6 Hz, 1H), 7.03 (dd, J = 8.8, 12.0 Hz, 1H), 7.38 (dd, J = 2.8, 7.2 Hz, 1H), 7.65 (dd, J = 2.8, 8.8 Hz, 1H), 7.97-8.00 (m, 1H), 8.28 (d, J = 8.8 Hz, 1H), 8.43 (d, J = 2.4 Hz, 1H), 9.75 (s, 1H). |

TABLE 6-continued

| Example 43 | Chemical structure | Compound name: N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-difluoromethylpyrazine-2-carboxamide<br>$^1$H-NMR (400 MHz, CDCl$_3$) δ (ppm): 1.69-1.74 (m, 1H), 2.12 (ddd, J = 2.4, 12.0, 24.8 Hz, 1H), 2.68 (dd, J = 2.8, 12.4 Hz, 1H), 2.99-3.08 (m, 2H), 3.95 (d, J = 11.2 Hz, 1H), 4.05-4.11 (m, 1H), 3.18 (dd, J = 2.0, 10.8 Hz, 1H), 6.80 (t, J = 54.4 Hz, 1H), 7.09 (dd, J = 8.8, 12.0 Hz, 1H), 7.41 (dd, J = 2.8, 7.2 Hz, 1H), 7.97-8.01 (m, 1H), 8.91 (d, J = 0.8 Hz, 1H), 9.51 (t, J = 0.8 Hz, 1H), 9.60 (s, 1H). |
|---|---|---|

EXAMPLES 44 to 48

The compounds of Examples 44 to 48 were synthesized according to Example 2 using the corresponding carboxylic acids and the corresponding aniline intermediates in Preparation Examples, as shown in the following Table 7.

TABLE 7

| Example 44 | Chemical structure | Compound name: N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-cyanopyridine-2-carboxamide<br>ESI-MS m/z 444 [M$^+$ + H] |
|---|---|---|
| Example 45 | Chemical structure | Compound name: N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-chloropyridine-2-carboxamide<br>ESI-MS m/z 453 [M$^+$ + H] |

TABLE 7-continued

| Example 46 | Chemical structure | Compound name: N-[3-((4aR,6R,8aS)-2-amino-6-fluoromethyl-4,4a,5,6,8,8a-tetrahydro-7-oxa-3-thia-1-azanaphthalen-8a-yl)-4-fluorophenyl]-5-trifluoromethylpyridine-2-carboxamide<br>ESI-MS m/z 487 [M⁺ + H] |
|---|---|---|
| Example 47 | Chemical structure | Compound name: N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-fluoromethoxypyrazine-2-carboxamide<br>¹H-NMR (400 MHz, CDCl₃) δ (ppm): 1.49-1.54 (m, 1H), 1.83-1.92 (m, 1H), 2.63 (dd, J = 2.4, 12.4 Hz, 1H), 3.00-3.07 (m, 2H), 3.90 (d, J = 11.2 Hz, 1H), 3.93-4.00 (m, 1H), 4.16 (dd, J = 1.6, 11.2 Hz, 1H), 4.35-4.58 (m, 2H), 6.09 (dd, J = 2.0, 3.6 Hz, 1H), 6.21 (dd, J = 2.0, 4.0 Hz, 1H), 7.06 (dd, J = 8.8, 12.0 Hz, 1H), 7.35 (dd, J = 2.4, 6.4 Hz, 1H), 7.97-8.01 (m, 1H), 8.27 (d, J = 0.8 Hz, 1H), 9.06 (t, J = 0.8 Hz, 1H), 9.45 (s, 1H). |
| Example 48 | Chemical structure | Compound name: N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-difluoromethylpyrazine-2-carboxamide<br>¹H-NMR (400 MHz, CDCl₃) δ (ppm): 1.49-1.54 (m, 1H), 1.83-1.92 (m, 1H), 2.65 (dd, J = 2.8, 12.4 Hz, 1H), 3.00-3.07 (m, 2H), 3.89 (d, J = 10.8 Hz, 1H), 3.93-4.00 (m, 1H), 4.17 (dd, J = 2.0, 10.8 Hz, 1H), 3.45-4.59 (m, 2H), 6.76 (t, J = 54.8 Hz, 1H), 7.08 (dd, J = 8.8, 12.0 Hz, 1H), 7.40 (dd, J = 2.8, 6.4 Hz, 1H), 7.97-8.01 (m, 1H), 8.91 (d, J = 1.2 Hz, 1H), 9.51 (d, J = 1.2 Hz, 1H), 9.60 (s, 1H). |

EXAMPLES 49 to 58

The compounds of Examples 49 to 58 were synthesized according to Example 2 using the corresponding carboxylic acids and the corresponding aniline intermediates in Preparation Examples, as shown in the following Table 8.

TABLE 8

| Example 49 | Chemical structure | Compound name: N-[3-((4aR*,8aS*)-2-amino-4,4a,5,6,8,8a-hexahydro-7-oxa-3-thia-1-azanaphthalen-8a-yl)-4-fluorophenyl]-5-chloropyridine-2-carboxamide<br>$^1$H-NMR (400 MHz, CDCl$_3$) δ (ppm): 1.45 (dd, J = 2.0, 13.6 Hz, 1H), 2.10-2.20 (m, 1H), 2.63 (dd, J = 2.8, 12.4 Hz, 1H), 2.92-2.96 (m, 1H), 3.02 (dd, J = 4.4, 12.8 Hz, 1H), 3.66-3.72 (m, 1H), 3.80 (d, J = 10.8 Hz, 1H), 4.04-4.15 (m, 2H), 7.05 (dd, J = 8.8, 11.6 Hz, 1H), 7.37 (dd, J = 2.8, 6.8 Hz, 1H), 7.87 (dd, J = 2.0, 8.4 Hz, 1H), 7.97-8.01 (m, 1H), 8.21 (d, J = 8.4 Hz, 1H), 8.53 (d, J = 2.0 Hz, 1H), 9.77 (s, 1H). |
|---|---|---|
| Example 50 | Chemical structure | Compound name: N-[3-((4aR*,8aS*)-2-amino-4,4a,5,6,8,8a-hexahydro-7-oxa-3-thia-1-azanaphthalen-8a-yl)-4-fluorophenyl]-5-bromopyridine-2-carboxamide<br>$^1$H-NMR (400 MHz, CDCl$_3$) δ (ppm): 1.45 (d, J = 12.8 Hz, 1H), 2.10-2.19 (m, 1H), 2.65 (dd, J = 2.4, 12.4 Hz, 1H), 2.93-2.97 (m, 1H), 3.03 (dd, J = 4.0, 12.0 Hz, 1H), 3.69 (t, J = 12.0 Hz, 1H), 3.79 (d, J = 10.8 Hz, 1H), 4.05-4.14 (m, 2H), 7.07 (dd, J = 8.8, 12.0 Hz, 1H), 7.36-7.39 (m, 1H), 7.98-8.05 (m, 2H). 8.16 (d, J = 8.0 Hz, 1H), 8.66 (s, 1H), 9.79 (s, 1H) |
| Example 51 | Chemical structure | Compound name: N-[3-((4aR*,8aS*)-2-amino-4,4a,5,6,8,8a-hexahydro-7-oxa-3-thia-1-azanaphthalen-8a-yl)-4-fluorophenyl]-3,5-difluoropyridine-2-carboxamide<br>$^1$H-NMR (400 MHz, CDCl$_3$) δ (ppm): 1.45 (dt, J = 2.0, 13.6 Hz, 1H). 2.05-2.19 (m, 1H). 2.64 (dd, J = 3.2, 12.4 Hz, 1H), 2.91-2.97 (m, 1H), 3.02 (dd, J = 4.0, 12.0 Hz, 1H), 3.65-3.72 (m, 1H), 3.78 (d, J = 10.8 Hz, 1H), 4.03-4.15 (m, 2H), 7.06 (dd, J = 8.8, 12.0 Hz, 1H), 7.24-7.27 (m, 1H), 7.36-7.41 (m, 1H), 8.05-8.09 (m, 1H), 8.33 (d, J = 2.0 Hz, 1H), 9.56 (s, 1H). |
| Example 52 | Chemical structure | Compound name: N-[3-((4aR*,8aS*)-2-amino-4,4a,5,6,8,8a-hexahydro-7-oxa-3-thia-1-azanaphthalen-8a-yl)-4-fluorophenyl]-3,5-dichloropyridine-2-carboxamide<br>$^1$H-NMR (400 MHz, CDCl$_3$) δ (ppm): 1.43-1.47 (m, 1H), 2.08-2.19 (m, 1H), 2.64 (dd, J = 3.2, 12.4 Hz, 1H), 2.92-2.97 (m, 1H), 3.01 (dd, J = 4.4, 12.4 Hz, 1H), 3.65-3.71 (m, 1H), 3.76 (d, J = 11.2 Hz, 1H), 4.03-4.11 (m, 2H), 7.07 (dd, J = 9.2, 12.0 Hz, 1H), 7.19 (dd, J = 2.8, 6.8 Hz, 1H), 7.90 (d, J = 2.0 Hz, 1H), 8.11-8.15 (m, 1H), 8.46 (d, J = 2.0 Hz, 1H), 9.68 (s, 1H). |

TABLE 8-continued

| Example 53 | Chemical structure | |
|---|---|---|

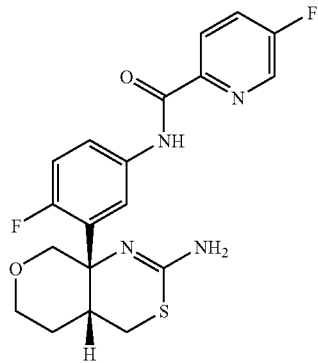

Compound name: N-[3-((4aR*,8aS*)-2-amino-4,4a,5,6,8,8a-hexahydro-7-oxa-3-thia-1-azanaphthalen-8a-yl)-4-fluorophenyl]-5-fluoropyridine-2-carboxamide
$^1$H-NMR (400 MHz, CDCl$_3$) δ (ppm): 1.43-1.47 (m, 1H), 2.09-2.20 (m, 1H), 1.43-1.47 (m, 1H), 2.09-2.20 (m, 1H), 2.63 (dd, J = 2.8, 12.0 Hz, 1H), 2.91-2.97 (m, 1H), 3.02 (dd, J = 4.0, 12.0 Hz, 1H), 3.65-3.72 (m, 1H), 3.79 (d, J = 10.8 Hz, 1H), 4.04-4.12 (m, 2H), 7.06 (dd, J = 8.8, 11.6 Hz, 1H), 7.35 (dd, J = 2.4, 6.4 Hz, 1H), 7.59 (dt, J = 2.4, 8.4 Hz, 1H), 7.99-8.03 (m, 1H), 8.31 (dd, J = 4.4, 8.4 Hz, 1H), 8.44 (d, J = 2.8 Hz, 1H), 9.76 (s, 1H).

| Example 54 | Chemical structure | |
|---|---|---|

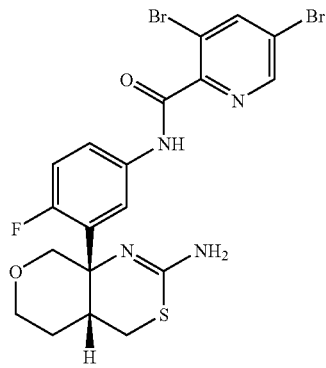

Compound name: N-[3-((4aR*,8aS*)-2-amino-4,4a,5,6,8,8a-hexahydro-7-oxa-3-thia-1-azanaphthalen-8a-yl)-4-fluorophenyl]-3,5-dibromopyridine-2-carboxamide
ESI-MS m/z 545 [M$^+$ + H]

| Example 55 | Chemical structure | |
|---|---|---|

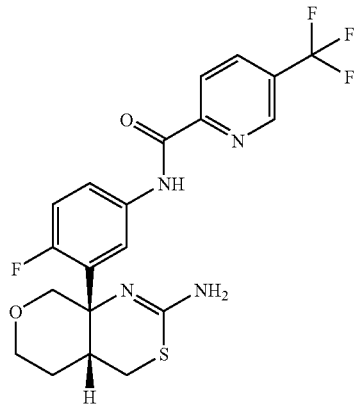

Compound name: N-[3-((4aR*,8aS*)-2-amino-4,4a,5,6,8,8a-hexahydro-7-oxa-3-thia-1-azanaphthalen-8a-yl)-4-fluorophenyl]-5-trifluoromethylpyridine-2-carboxamide
$^1$H-NMR (400 MHz, CDCl$_3$) δ (ppm):. 1.43-1.47 (m, 1H) , 2.10-2.19 (m, 1H), 2.65 (dd, J = 3.2, 12.4 Hz, 1H), 2.92-2.97 (m, 1H), 3.03 (dd, J = 4.0, 12.0 Hz, 1H), 3.66-3.72 (m, 1H), 3.79 (d, J = 11.2 Hz, 1H), 4.05-4.12 (m, 2H), 7.08 (dd, J = 8.8, 12.0 Hz, 1H), 7.39 (dd, J = 2.8, 6.4 Hz, 1H), 8.00-8.04 (m, 1H), 8.16 (dd, J = 1.6, 8.4 Hz, 1H), 8.42 (d, J = 8.0 Hz, 1H), 8.88 (t, J = 0.8 Hz, 1H), 9.89 (s, 1H).

TABLE 8-continued

| Example 56 | Chemical structure | Compound name: N-[3-((4aR*,8aS*)-2-amino-4,4a,5,6,8,8a-hexahydro-7-oxa-3-thia-1-azanaphthalen-8a-yl)-4-fluorophenyl]-5-difluoromethylpyridine-2-carboxamide<br>$^1$H-NMR (400 MHz, CDCl$_3$) δ (ppm): 1.43-1.47 (m, 1H), 2.09-2.21 (m, 1H). 2.64 (dd, J = 2.8, 12.0 Hz, 1H), 2.92-2.98 (m, 1H), 3.02 (dd, J = 8.0, 12.4 Hz, 1H), 3.66-3.72 (m, 1H), 3.81 (d, J = 10.8 Hz, 1H), 4.05-4.15 (m, 2H), 6.81 (t, J = 55.6 Hz, 1H), 7.05 (dd, J = 9.2, 12.0 Hz, 1H), 8.40 (dd, J = 2.8, 6.8 Hz, 1H), 7.98-8.06 (m, 2H), 8.36 (d, J = 8.4 Hz, 1H), 8.73 (s, 1H), 9.90 (s, 1H). |
|---|---|---|
| | 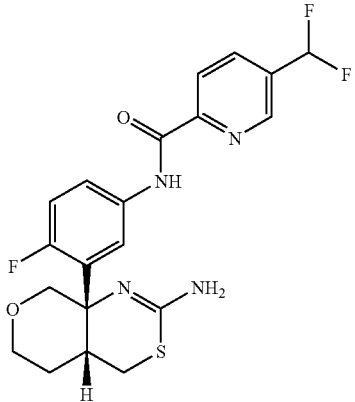 | |
| Example 57 | Chemical structure | Compound name: N-[3-((4aR*,8aS*)-2-amino-4,4a,5,6,8,8a-hexahydro-7-oxa-3-thia-1-azanaphthalen-8a-yl)-4-fluorophenyl]-5-difluoromethylpyrazine-2-carboxamide<br>$^1$H-NMR (400 MHz, CDCl$_3$) δ (ppm): 1.44-1.48 (m, 1H), 2.10-2.19 (m, 1H), 2.65 (dd, J = 2.8, 12.0 Hz, 1H), 2.93-3.04 (m, 2H), 3.66-3.72 (m, 1H), 3.80 (d, J = 11.2 Hz, 1H), 4.04-4.15 (m, 2H), 6.79 (t, J = 54.4 Hz. 1H). 7.08 (dd, J = 8.8, 12.0 Hz, 1H), 7.40 (dd, J = 2.8, 6.4 Hz, 1H), 7.97-8.01 (m, 1H), 8.90 (d, J = 0.8 Hz, 1H), 9.50 (s, 1H), 9.60 (s, 1H). |
| | 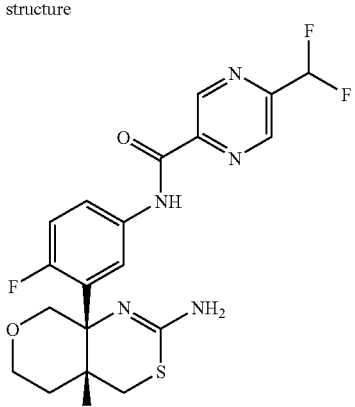 | |
| Example 58 | Chemical structure | Compound name: N-[3-((4aR*,8aS*)-2-amino-4,4a,5,6,8,8a-hexahydro-7-oxa-3-thia-1-azanaphthalen-8a-yl)-4-fluorophenyl]-5-difluoromethoxypyridine-2-carboxamide<br>$^1$H-NMR (400 MHz, CDCl$_3$) δ (ppm): 1.43-1.47 (m, 1H), 2.05-2.20 (m, 1H), 2.63 (dd, J = 2.8, 12.0 Hz, 1H), 2.91-2.97 (m, 1H), 3.03 (dd, J = 4.0, 12.4 Hz, 1H), 3.65-3.72 (m, 1H), 8.79 (d, J = 11.2 Hz, 1H), 4.04-4.13 (m, 2H), 6.65 (t, J = 72.0 Hz, 1H), 7.07 (dd, J = 8.8, 12.0 Hz, 1H). 7.36 (dd, J = 3.2, 7.2 Hz, 1H), 7.66 (dd, J = 3.2, 8.8 Hz, 1H), 8.00-8.04 (m, 1H), 8.31 (d, J = 9.2 Hz, 1H), 8.46 (d, J = 2.4 Hz, 1H), 9.80 (s, 1H). |
| | 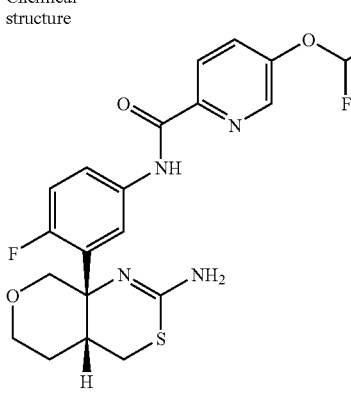 | |

EXAMPLE 59

Synthesis of (±)-(4aR*,6R*,8aS*)-8a-[2-fluoro-5-(2-fluoropyridin-3-yl)phenyl]-6-trifluoromethyl-4,4a,5,6,8,8a-hexahydro-7-oxa-3-thia-1-azanaphthalen-2-ylamine

[Formula 53]

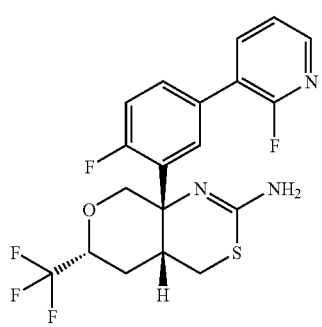

2-Fluoropyridine-3-boronic acid (63.9 mg), tetrakis(triphenylphosphine)palladium (26.2 mg) and a 1 N sodium carbonate solution (453 μl) were added to a solution of (±)-N,N-di(tert-butyloxycarbonyl)-[(4aR*,6R*,8aS*)-8a-(5-bromo-2-fluorophenyl)-6-trifluoromethyl-4,4a,5,6,8,8a-hexahydro-7-oxa-3-thia-1-azanaphthalen-2-yl]amine (138 mg) in DMF (9.9 ml), and the mixture was stirred in a nitrogen atmosphere at 85° C. for seven hours. The reaction solution was cooled to room temperature and then diluted with ethyl acetate. The organic layer was washed with water and brine. The organic layer was dried over anhydrous magnesium sulfate, and the solvent was evaporated under reduced pressure. Dichloromethane (4.0 ml) and TFA (1.0 ml) were added to the residue, and the mixture was stirred at room temperature for four hours. When the reaction was completed, the reaction solution was diluted with dichloromethane and ice was added, followed by neutralization with a sodium bicarbonate solution. The aqueous layer was extracted with chloroform, and the organic layer was dried over anhydrous magnesium sulfate. The solvent was evaporated under reduced pressure and the residue was purified by NH-silica gel column chromatography. The resulting white solid was washed with diethyl ether to obtain the title compound (14.0 mg).

$^1$H-NMR (400 MHz, CDCl$_3$) δ (ppm): 1.68-1.72 (m, 1H), 2.12 (ddd, J=2.8, 12.0, 24.8 Hz, 1H), 2.68 (dd, J=2.4, 12.4 Hz, 1H), 2.99-3.08 (m, 2H), 3.96 (d, J=11.6 Hz, 1H), 4.06-4.11 (m, 1H), 4.20 (dd, J=2.0, 11.2 Hz, 1H), 7.15 (dd, J=8.8, 12.4 Hz, 1H), 7.25-7.30 (m, 1H), 7.50-7.54 (m, 2H), 7.83 (ddd, J=1.6, 7.2, 9.2 Hz, 1H), 8.19-8.21 (m, 1H).

EXAMPLE 60

Synthesis of (4aR,6R,8aS)-8a-[2-fluoro-5-(2-fluoropyridin-3-yl)phenyl]-6-fluoromethyl-4,4a,5,6,8,8a-hexahydro-7-oxa-3-thia-1-azanaphthalen-2-ylamine

[Formula 54]

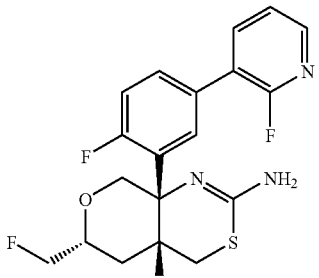

2-Fluoropyridine-3-boronic acid (51.1 mg), tetrakis(triphenylphosphine)palladium (19.1 mg) and a 1 N sodium carbonate solution (363 μl) were added to a solution of N,N-di(tert-butyloxycarbonyl)-[(4aR,6R,8aS)-8a-(5-bromo-2-fluorophenyl)-6-fluoromethyl-4,4a,5,6,8,8a-hexahydro-7-oxa-3-thia-1-azanaphthalen-2-yl]amine (95 mg) in DMF (6.79 ml). After replacement with nitrogen, the mixture was stirred at 85° C. for two hours. After cooling to room temperature, the mixture was diluted with water. The aqueous layer was extracted with ethyl acetate, and the organic layer was washed with water. The organic layer was dried over anhydrous magnesium sulfate, and the solvent was evaporated under reduced pressure. The residue was purified by silica gel column chromatography. The resulting intermediate was dissolved in dichloromethane (4.0 ml). TFA (1.0 ml) was added and the mixture was stirred at room temperature for three hours. Ice was added to the reaction mixture, followed by neutralization with a sodium bicarbonate solution. The aqueous layer was extracted with chloroform, and the organic layer was dried over anhydrous magnesium sulfate. The solvent was evaporated under reduced pressure and the residue was purified by silica gel column chromatography to obtain the title compound (59.0 mg).

$^1$-NMR (400 MHz, CDCl) δ (ppm): 1.48-1.53 (m, 1H), 1.82-1.92 (m, 1H), 2.63-2.66 (m, 1H), 2.98-3.07 (m, 2H), 3.89 (d, J=10.8 Hz, 1H), 3.93-4.01 (m, 1H), 4.17-4.20 (m, 1H), 4.35-4.58 (m, 2H), 7.14 (dd, J=8.0, 12.0 Hz, 1H), 7.25-7.22 (m, 1H), 7.48-7.55 (m, 2H), 7.78-7.83 (m, 1H), 8.16-8.18 (m, 1H).

EXAMPLE 61

Synthesis of (±)-(4aR*,8aS*)-8a-[2-fluoro-5-(2-fluoropyridin-3-yl)phenyl]-4,4a,5,6,8,8a-hexahydro-7-oxa-3-thia-1-azanaphthalen-2-ylamine

[Formula 55]

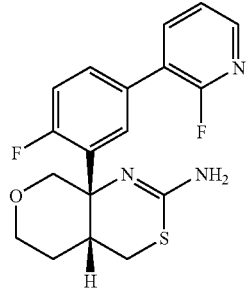

2-Fluoropyridine-3-boronic acid (25.6 mg), tetrakis(triphenylphosphine)palladium (10.5 mg) and a 1 N sodium carbonate solution (182 μl) were added to a solution of (±)-N-benzoyl-N-(tert-butyloxycarbonyl)-[(4aR*,8aS*)-8a-(5-bromo-2-fluorophenyl)-4,4a,5,6,8,8a-hexahydro-7-oxa-3-thia-1-azanaphthalen-2-yl]amine (50 mg) in DMF (5.0 ml). After replacement with nitrogen, the mixture was stirred at 90° C. for six hours. The reaction solution was cooled to room temperature and diluted with water. The aqueous layer was extracted with ethyl acetate. The organic layer was washed with water and brine and dried over anhydrous magnesium sulfate. The solvent was evaporated under reduced pressure and the residue was purified by NH-silica gel column chromatography to obtain the title compound (12.7 mg).

$^1$-NMR (400 MHz, CDCl$_3$) δ (ppm): 1.43-1.47 (m, 1H), 2.08-2.20 (m, 1H), 2.66 (dd, J=2.8, 12.0 Hz, 1H), 2.90-2.96 (m, 1H), 3.01 (dd, J=4.0, 12.4 Hz, 1H), 3.69 (dt, J=2.8, 12.4 Hz, 1H), 3.79 (d, J=11.2 Hz, 1H), 4.07-4.13 (m, 2H), 4.60 (brs, 2H), 7.14 (dd, J=8.4, 12.0 Hz, 1H), 7.25-7.28 (m, 1H), 7.48-7.55 (m, 2H), 7.81-7.86 (m, 1H), 8.18-8.20 (m, 1H).

EXAMPLES 62 to 63

The compounds of Examples 62 to 63 were synthesized according to Example 61 using the corresponding boron acids, as shown in the following Table 9.

TABLE 9

| Example | Chemical structure | |
|---|---|---|
| 62 | 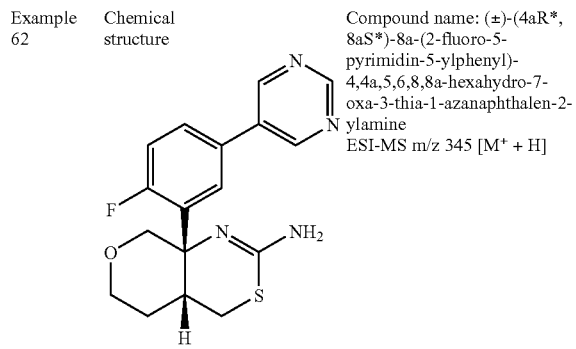 | Compound name: (±)-(4aR*,8aS*)-8a-(2-fluoro-5-pyrimidin-5-ylphenyl)-4,4a,5,6,8,8a-hexahydro-7-oxa-3-thia-1-azanaphthalen-2-ylamine<br>ESI-MS m/z 345 [M$^+$ + H] |
| 63 | 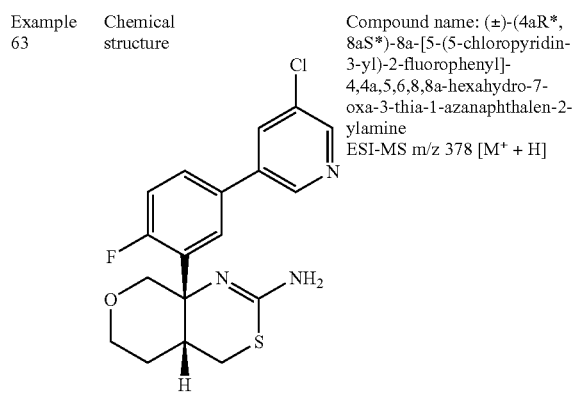 | Compound name: (±)-(4aR*,8aS*)-8a-[5-(5-chloropyridin-3-yl)-2-fluorophenyl]-4,4a,5,6,8,8a-hexahydro-7-oxa-3-thia-1-azanaphthalen-2-ylamine<br>ESI-MS m/z 378 [M$^+$ + H] |

EXAMPLE 64

Synthesis of N-[5-((4aR*,8aS*)-2-amino-4,4a,5,6,8,8a-hexahydro-7-oxa-3-thia-1-azanaphthalen-8a-yl)thiophen-3-yl]-5-cyanopyridine-2-carboxamide

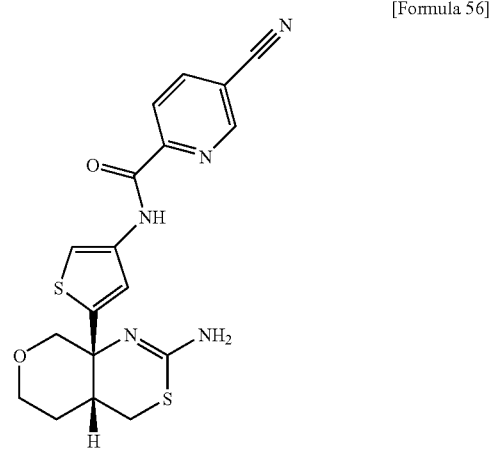

[Formula 56]

5-Cyanopyridine-2-carboxylic acid (19.0 mg), diisopropylethylamine (50.7 μl) and PyBOP (83.5 mg) were sequentially added to a solution of (+)-N,N-di(tert-butyloxycarbonyl)-[(4aR*,8aS*)-8a-(4-aminothiophen-2-yl)-4,4a,5,6,8,8a-hexahydro-7-oxa-3-thia-1-azanaphthalen-2-yl]amine (50 mg) in dichloromethane (5.0 ml) in an ice bath. The mixture was returned to room temperature and stirred overnight. The solvent was evaporated under reduced pressure and the residue was purified by NH-silica gel column chromatography. The resulting intermediate was dissolved in dichloromethane (4.0 ml) and TFA (1.0 ml) was added. After stirring at room temperature for four hours, ice was added to terminate the reaction. The mixture was neutralized with a sodium bicarbonate solution, and the aqueous layer was neutralized with ethyl acetate. The organic layer was dried over anhydrous magnesium sulfate, and the solvent was evaporated under reduced pressure. The residue was purified by NH-silica gel column chromatography to obtain the title compound (33.9 mg).

ESI-MS m/z 400 [M$^+$+H]

EXAMPLE 65

Synthesis of (±)-(4aR*,8aR*)-8a-[4-(2-fluoropyridin-3-yl)-thiophen-2-yl]-4,4a,5,6,8,8a-hexahydro-7-oxa-3-thia-1-azanaphthalen-2-ylamine

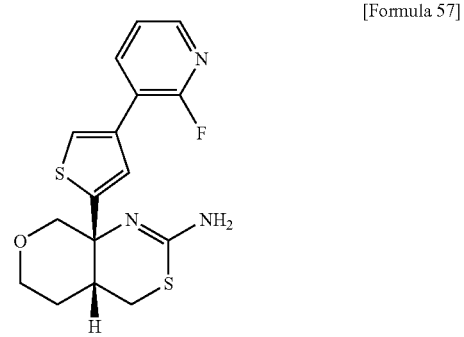

[Formula 57]

2-Fluoropyridine-3-boronic acid (26.9 mg), tetrakis(triphenylphosphine)palladium (11.0 mg) and a 1 N sodium carbonate solution (191 µl) were sequentially added to a solution of (±)-N,N-di-(tert-butyloxycarbonyl)-[(4aR*,8aS*)-8a-(4-bromothiophen-2-yl)-4,4a,5,6,8,8a-hexahydro-7-oxa-3-thia-1-azanaphthalen-2-yl]amine obtained in Preparation Example 19-(3) (51.0 mg) in DMF (2.0 ml). After replacement with nitrogen, the mixture was stirred at 80° C. for five hours. The reaction solution was returned to room temperature and diluted with water. The aqueous layer was extracted with ethyl acetate, and the organic layer was washed with water. The organic layer was dried over anhydrous magnesium sulfate, and the solvent was evaporated under reduced pressure. The residue was purified by silica gel column chromatography to obtain an intermediate. The resulting intermediate was dissolved in dichloromethane (5.0 ml). TFA (2.0 ml) was added and the mixture was stirred at room temperature for three hours. Ice was added to the mixture, followed by neutralization with a sodium bicarbonate solution. The aqueous layer was extracted with ethyl acetate, and the organic layer was dried over anhydrous magnesium sulfate. The solvent was evaporated under reduced pressure and the residue was purified by NH-silica gel column chromatography to obtain the title compound (22.0 mg).

ESI-MS m/z 350 [M++H]

EXAMPLE 66

Synthesis of (4aR,6R,8aS)-8a-[2-fluoro-5-(2-fluoropyridin-3-yl)phenyl]-6-benzyloxymethyl-4,4a,5,6,8,8a-hexahydro-7-oxa-3-thia-1-azanaphthalen-2-ylamine

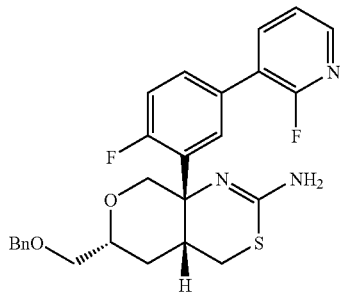

[Formula 58]

2-Fluoropyridine-3-boronic acid (44.0 mg), tetrakis(triphenylphosphine)palladium (18.0 mg) and a 1 N sodium carbonate solution (312 µl) were added to a solution of N,N-di-(tert-butyloxycarbonyl)-[(4aR,6R,8aS)-8a-(5-bromo-2-fluorophenyl)-6-benzyloxymethyl-4,4a,5,6,8,8a-hexahydro-7-oxa-3-thia-1-azanaphthalen-2-yl]amine (95 mg) in DMF (6.79 ml). After replacement with nitrogen, the mixture was stirred at 85° C. for seven hours. After cooling to room temperature, the mixture was diluted with water. The aqueous layer was extracted with ethyl acetate, and the organic layer was washed with water. The organic layer was dried over anhydrous magnesium sulfate, and the solvent was evaporated under reduced pressure. The residue was purified by silica gel column chromatography. The resulting intermediate was dissolved in dichloromethane (4.0 ml). TFA (1.0 ml) was added and the mixture was stirred at room temperature for three hours. Ice was added to the reaction mixture, followed by neutralization with a sodium bicarbonate solution. The aqueous layer was extracted with chloroform, and the organic layer was dried over anhydrous magnesium sulfate. The solvent was evaporated under reduced pressure and the residue was purified by silica gel column chromatography to obtain the title compound (23.0 mg).

ESI-MS m/z 482 [M++H]

EXAMPLE 67

Synthesis of (±)-N-[7-((4aR*,8aS*)-2-amino-4,4a,5,6,8,8a-hexahydro-7-oxa-3-thia-1-azanaphthalen-8a-yl)-2,2-difluorobenzo[1,3]dioxol-5-yl]-5-cyanopyridine-2-carboxamide

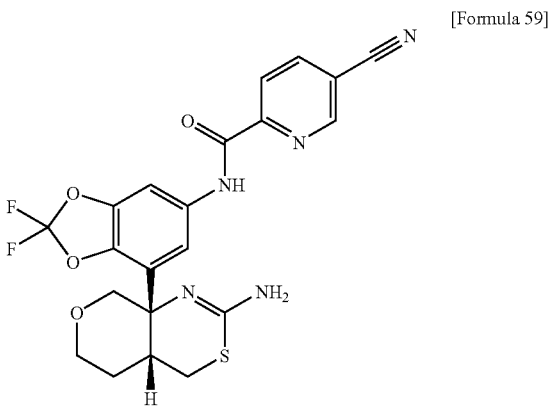

[Formula 59]

5-Cyanopyridine-2-carboxylic acid (4.0 mg), diisopropylethylamine (11.5 µl) and PyBOP (17.6 mg) were added to a solution of tert-butyl (±)-[(4aR*,8aS*)-8a-(6-amino-2,2-difluorobenzo[1,3]dioxol-4-yl)-4,4a,5,6,8,8a-hexahydro-7-oxa-3-thia-1-azanaphthalen-2-yl]carbamate (10 mg) in dichloromethane (2.0 ml) in an ice bath. The mixture was heated to room temperature and stirred for four hours. The solvent was evaporated under reduced pressure and the residue was purified by NH-pTLC to obtain an intermediate. The resulting intermediate was dissolved in dichloromethane (3.0 ml) and TFA (1.0 ml) was added. After stirring at room temperature for four hours, the reaction solution was diluted with water and neutralized with a sodium bicarbonate solution. The aqueous layer was extracted with dichloromethane, and the organic layer was dried over anhydrous magnesium sulfate. The solvent was evaporated under reduced pressure and the residue was purified by NH-pTLC to obtain the title compound.

$^1$H-NMR (400 MHz, CDCl$_3$) δ (ppm): 1.51-1.53 (m, 1H), 2.15 (ddd, J=5.2, 13.2, 26.0 Hz, 1H), 2.71 (dd, J=2.8, 12.4 Hz, 1H), 2.86-2.90 (m, 1H), 3.07 (dd, J=4.4, 12.4 Hz, 1H), 3.68-3.73 (m, 1H), 3.85-3.91 (m, 2H), 4.11-4.15 (m, 1H), 7.03 (d, J=2.0 Hz, 1H), 8.07 (d, J=2.0 Hz, 1H), 8.21 (dd, J=2.0, 8.0 Hz, 1H), 8.41 (dd, J=0.8, 8.0 Hz, 1H), 8.92 (dd, J=0.8, 2.0 Hz, 1H), 9.94 (brs, 1H).

EXAMPLES 68 to 73

The compounds of Examples 68 to 73 were synthesized according to Example 2 using the corresponding carboxylic acids and the corresponding aniline intermediates in Preparation Examples, as shown in the following Table 10.

TABLE 10

| Example 68 | Chemical structure | Compound name: N-[3-((4aR*,8aS*)-2-amino-4,4a,5,6,8,8a-hexahydro-7-oxa-3-thia-1-azanaphthalen-8a-yl)-4-fluorophenyl]-5-(2-methoxyethoxy)-pyrazine-2-carboxamide<br>¹H-NMR (400 MHz, CDCl₃) δ (ppm): 1.40-1.50 (m, 1H), 2.01-2.21 (m, 1H), 2.59-2.68 (m, 1H), 2.88-2.98 (m, 1H), 2.98-3.06 (m, 1H), 3.46 (s, 3H), 3.63-3.73 (m, 1H), 3.73-3.84 (m, 3H), 4.01-4.12 (m, 2H), 4.55-4.65 (m, 2H), 7.02-7.11 (m, 1H), 7.29-7.35 (m, 1H), 7.98-8.06 (m, 1H), 8.19-8.24 (m, 1H), 8.96-9.01 (m, 1H), 9.46 (brs, 1H).<br>ESI-MS m/z 462 [M⁺ + H] |
|---|---|---|
| Example 69 | Chemical structure | Compound name: N-[3-((4aR*,8aS*)-2-amino-4,4a,5,6,8,8a-hexahydro-7-oxa-3-thia-1-azanaphthalen-8a-yl)-4-fluorophenyl]-2-methylthiazole-4-carboxamide<br>¹H-NMR (400 MHz, CDCl₃) δ (ppm): 1.39-1.50 (m, 1H), 2.06-2.21 (m, 1H), 2.59-2.67 (m, 1H), 2.76 (s, 3H), 2.89-2.97 (m, 1H), 2.98-3.07 (m, 1H), 3.62-3.73 (m, 1H), 3.73-3.81 (m, 1H), 4.01-4.13 (m, 2H), 7.02-7.10 (m, 1H), 7.28-7.34 (m, 1H), 7.93-7.99 (m, 1H), 8.04 (s, 1H), 9.17 (brs, 1H).<br>ESI-MS m/z 407 [M⁺ + H] |
| Example 70 | Chemical structure | Compound name: N-[3-((4aR*,5R*,8aS*)<br>Compound name: N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-2,5-dimethylfuran-3-carboxamide<br>¹H-NMR (400 MHz, CDCl₃) δ (ppm): 0.94 (d, J = 6.8 Hz, 3H), 2.21-2.27 (m, 1H), 2.28 (s, 3H), 2.58 (s, 3H), 2.61-2.68 (m, 1H), 2.93-2.96 (m, 2H), 3.25-3.36 (m, 1H), 3.85-3.92 (m, 1H), 3.95-4.07 (m, 2H), 6.21 (brs, 1H), 7.03-7.11 (m, 2H), 7.58-7.63 (m, 1H).<br>ESI-MS m/z 418 [M⁺ + H] |
| Example 71 | Chemical structure | Compound name: N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-4-methyl-[1,2,3]thiadiazole-5-carboxamide<br>¹H-NMR (400 MHz, CDCl₃) δ (ppm): 0.91 (d, J = 6.4 Hz, 3H), 2.07-2.20 (m, 1H), 2.44-2.52 (m, 1H), 2.78-2.86 (m, 1H), 2.86-2.93 (m, 1H), 2.96 (s, 3H), 3.22-3.31 (m, 1H), 3.66-3.74 (m, 1H), 3.84-3.91 (m, 1H), 4.02-4.08 (m, 2H), 7.05-7.12 (m, 1H), 7.14-7.19 (m, 1H), 7.91 (brs, 1H).<br>ESI-MS m/z 422 [M⁺ + H] |

TABLE 10-continued

| Example | Chemical structure | |
|---|---|---|
| 72 | 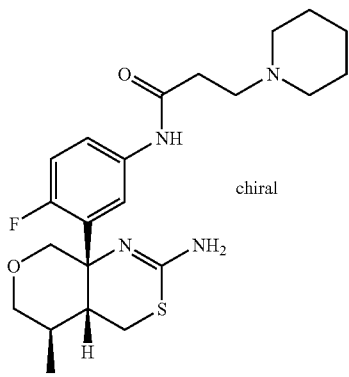 | Compound name: N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-3-piperidin-1-ylpropionamide<br>$^1$H-NMR (400 MHz, CDCl$_3$) δ (ppm): 0.92 (d, J = 6.8 Hz, 3H), 1.56-1.86 (m, 6H) 2.10-2.23 (m, 1H) , 2.42-2.73 (m, 9H), 2.84-2.96 (m, 2H), 3.24-3.36 (m, 1H), 3.83-4.01 (m, 2H), 4.06-4.13 (m, 1H), 6.96-7.12 (m, 2H), 7.90-8.01 (m, 1H), 11.5 (brs, 1H).<br>ESI-MS m/z 435 [M$^+$ + H] |
| 73 | 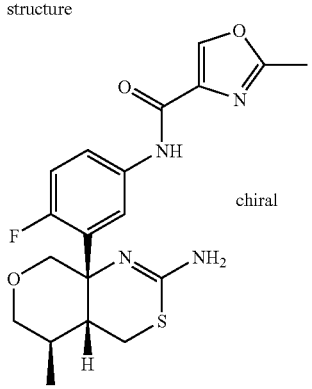 | Compound name: N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-2-methyloxazol-4-carboxamide<br>$^1$H-NMR (400 MHz, CDCl$_3$) δ (ppm): 0.91 (d, J = 6.8 Hz, 3H), 2.11-2.27 (m, 1H), 2.42-2.50 (m, 1H), 2.50-2.57 (m, 3H), 2.80-2.94 (m, 2H), 3.23-3.34 (m, 1H), 3.72-3.81 (m, 1H), 3.89-3.97 (m, 1H), 4.05-4.12 (m, 1H), 6.99-7.08 (m, 1H), 7.25-7.32 (m, 1H), 7.89-7.96 (m 1H), 8.14-8.19 (m, 1H), 8.65 (brs, 1H).<br>ESI-MS m/z 405 [M$^+$ + H] |

EXAMPLE 74

Synthesis of (4aR,6R,8aS)-8a-[2-fluoro-5-(2H-pyrazol-3-yl)phenyl]-6-methoxymethyl-4,4a,5,6,8,8a-hexahydro-7-oxa-3-thia-1-azanaphthalen-2-yl]amine

[Formula 60]

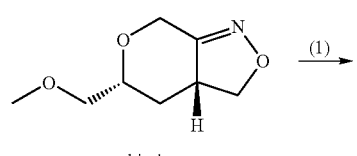

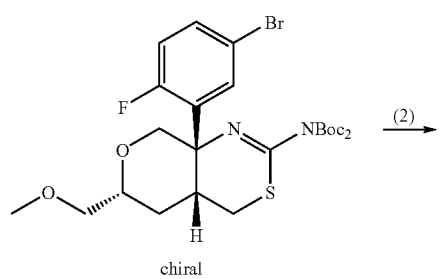

-continued

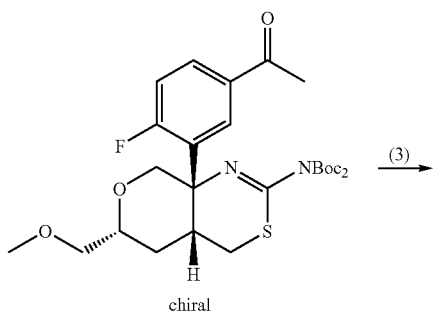

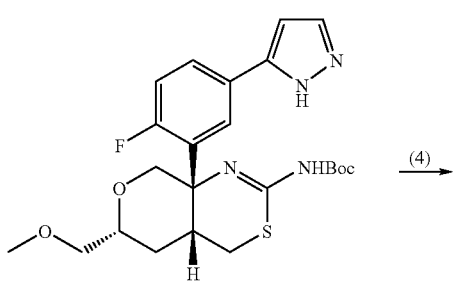

-continued

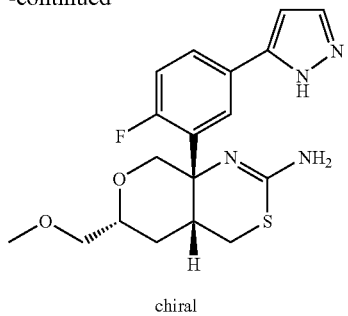

chiral (1) Synthesis of di-tert-butyl [(4aR,6R,8aS)-8a-(5-bromo-2-fluorophenyl)-6-methoxymethyl-4,4a,5,6,8,8a-hexahydropyrano[3,4-d][1,3]thiazin-2-yl]imidodicarbonate The title compound was synthesized from the compound obtained in Preparation Example 7-(4) according to Preparation Example 16 (1)-(3).

ESI-MS; m/z 611 [M$^+$+Na].

(2) Synthesis of di-tert-butyl [(4aR,6R,8aS)-8a-(5-acetyl-2-fluorophenyl)-6-methoxymethyl-4,4a,5,6,8,8a-hexahydropyrano[3,4-d][1,3]thiazin-2-yl]imidodicarbonate The compound obtained in Example 74-(1) (2.73 g) was dissolved in 1,4-dioxane (40 mL). 1-Ethoxyvinyltri-n-butyltin (2.42 mL), cesium fluoride (1.55 g) and bis(tri-t-butylphosphine)palladium (118 mg) were sequentially added to the solution, and the mixture was stirred in a nitrogen atmosphere at 100° C. After 1.5 hours, the reaction solution was left to cool. The reaction mixture was filtered through celite and washed with ethyl acetate. The filtrate was concentrated under reduced pressure. Ethyl acetate and 1 N KHSO4 were added to the residue, and the organic layer was separated. The organic layer was sequentially washed with 1 N KHSO4, a saturated sodium bicarbonate solution and brine. The organic layer was dried over anhydrous magnesium sulfate. The drying agent was removed by filtration and the filtrate was concentrated under reduced pressure. The residue was subjected to silica gel chromatography to obtain di-tert-butyl {(4aR,6R,8aS)-8a-[5-(1-ethoxyvinyl)-2-fluorophenyl]-6-methoxymethyl-4,4a,5,6,8,8a-hexahydropyrano[3,4-d][1,3]thiazin-2-yl}imidodicarbonate (1.91 g). 1.5 g of 1.91 g of the resulting compound was dissolved in THF (10 mL). Then, 2 N hydrochloric acid (3.5 mL) was added and the mixture was stirred at room temperature. After one hour, ethyl acetate was added to the reaction solution, and the mixture was sequentially washed with a saturated sodium bicarbonate solution and brine. The organic layer was dried over anhydrous magnesium sulfate. The drying agent was removed by filtration and the filtrate was concentrated under reduced pressure. The residue was subjected to silica gel chromatography to obtain the title compound (1.2 g).

ESI-MS; m/z 575 [M$^+$+Na].

(3) Synthesis of t-butyl {(4aR,6R,8aS)-8a-[2-fluoro-5-(2H-pyrazol-3-yl)phenyl]-6-methoxymethyl-4,4a,5,6,8,8a-hexahydro-7-oxa-3-thia-1-azanaphthalen-2-yl}carbamate The compound obtained in Example 74-(2) (207 mg) was dissolved in N,N-dimethylformamide dimethyl acetal (2.3 mL), and then the solution was stirred in a nitrogen atmosphere at 110° C. After about 14 hours, the reaction solution was left to cool and then concentrated under reduced pressure. Ethanol (3 mL) was added to the residue and then hydrazine hydrate (78 µL) was added, followed by stirring at room temperature. After about three days, the reaction solution was concentrated under reduced pressure. Ethyl acetate and a saturated sodium bicarbonate solution were added to the residue, and the organic layer was separated. The organic layer was dried over anhydrous magnesium sulfate. The drying agent was removed by filtration and the filtrate was concentrated under reduced pressure. The residue was subjected to silica gel chromatography to obtain the title compound (38 mg).

ESI-MS; m/z 477 [M$^l$+1].

(4) Synthesis of (4aR,6R,8aS)-8a-[2-fluoro-5-(2H-pyrazol-3-yl)phenyl]-6-methoxymethyl-4,4a,5,6,8,8a-hexahydro-7-oxa-3-thia-1-azanaphthalen-2-yl]amine The compound obtained in Example 74-(3) (38 mg) was dissolved in dichloromethane (2 mL), and then trifluoroacetic acid (0.4 mL) was added, followed by stirring at room temperature. After three hours, the reaction solution was concentrated under reduced pressure. Chloroform and a saturated sodium bicarbonate solution were added to the residue, and the organic layer was separated. The organic layer was dried over anhydrous magnesium sulfate. The drying agent was removed by filtration and the filtrate was concentrated under reduced pressure. The residue was subjected to column chromatography to obtain the title compound (18 mg).

ESI-MS; m/z 377 [M$^+$+1].

EXAMPLE 75

Synthesis of (4aR,6R,8aS)-8a-[2-fluoro-5-(2H-pyrazol-3-yl)phenyl]-6-methoxymethyl-4,4a,5,6,8,8a-hexahydro-7-oxa-3-thia-1-azanaphthalen-2-yl]amine

[Formula 61]

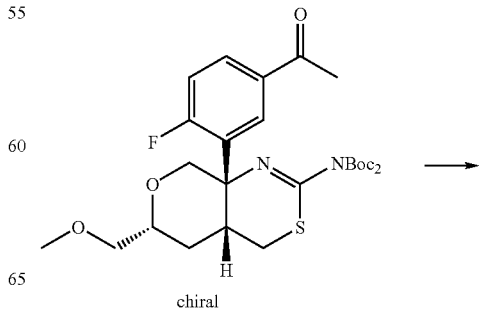

chiral

-continued

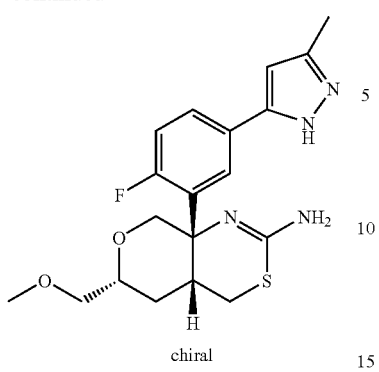

The title compound was synthesized according to Example 74 using N,N-dimethylacetamide dimethyl acetal in place of N,N-dimethylformamide dimethyl acetal.

ESI-MS; m/z 391 [M⁺+1].

EXAMPLE 76

Synthesis of (4aR,6R,8aS)-8a-[2-fluoro-5-(2-fluoro-pyridin-3-yl)phenyl]-6-methoxymethyl-4,4a,5,6,8,8a-hexahydro-7-oxa-3-thia-1-azanaphthalen-2-yl]amine

[Formula 62]

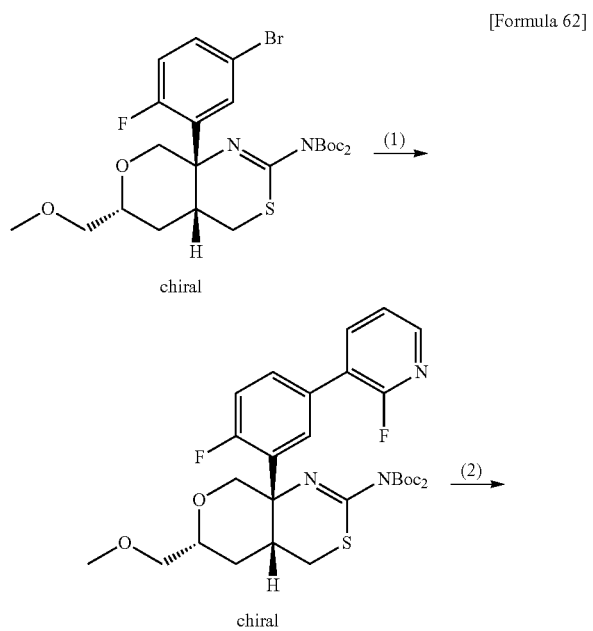

(1) Synthesis of di-tert-butyl [(4aR,6R,8aS)-8a-[2-fluoro-5-(2-fluoropyridin-3-yl)phenyl]-6-methoxym-ethyl-4,4a,5,6,8,8a-hexahydropyrano[3,4-d][1,3]thiazine-2-yl]imidodicarbonate The compound obtained in Example 74-(1) (1.33 g) was dissolved in THF (28 mL). 2-Fluoropyridine-3-boronic acid (955 mg), potassium fluoride (558 mg), Pd2DBA3 (200 mg) and Pd(t-Bu3P)2 (220 mg) were added to the solution, and the mixture was stirred in a nitrogen atmosphere at room temperature overnight. The reaction solution was diluted with ethyl acetate and filtered through NH silica gel. The filtrate was further washed with a mixture of ethyl acetate:heptane=4:1. The filtrate was concentrated under reduced pressure to obtain a residue. The residue was subjected to silica gel chromatography to obtain the title compound (547 mg).

ESI-MS; m/z 628 [M⁺+Na].

(2) Synthesis of (4aR,6R,8aS)-8a-[2-fluoro-5-(2-fluoropyridin-3-yl)phenyl]-6-methoxymethyl-4,4a,5,6,8,8a-hexahydro-7-oxa-3-thia-1-azanaphthalen-2-yl]amine The compound obtained in Example 76-(1) (67 mg) was dissolved in dichloromethane (2 mL), and then TFA (0.5 mL) was added. After two hours, the reaction solution was concentrated under reduced pressure. Chloroform, a 1 N sodium hydroxide solution and a saturated sodium bicarbonate solution were added to the residue, and the organic layer was separated. The organic layer was dried over anhydrous magnesium sulfate. The drying agent was removed by filtration and the filtrate was concentrated. The residue was subjected to silica gel chromatography to obtain the title compound (30 mg).

ESI-MS; m/z 406 [Mⁱ+1].

EXAMPLE 77

Synthesis of (4aR,6R,8aS)-8a-[2-fluoro-5-(3-fluoropyridin-4-yl)phenyl]-6-methoxymethyl-4,4a,5,6,8,8a-hexahydro-7-oxa-3-thia-1-azanaphthalen-2-yl]amine

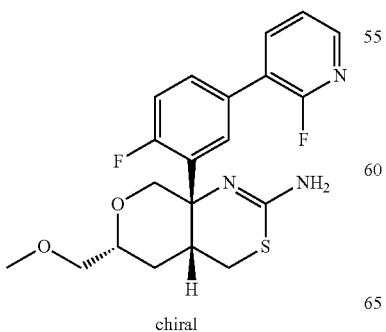

[Formula 63]

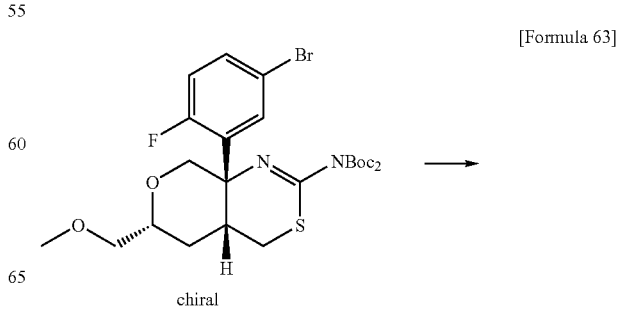

169
-continued

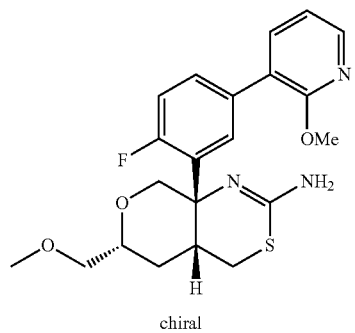

chiral

The title compound was synthesized according to Example 76.

ESI-MS; m/z 406 [M⁺+1].

EXAMPLE 78

Synthesis of (4aR,6R,8aS)-8a-[2-fluoro-5-(2-methoxypyridin-3-yl)phenyl]-6-methoxymethyl-4,4a,5,6,8,8a-hexahydro-7-oxa-3-thia-1-azanaphthalen-2-yl]amine

[Formula 64]

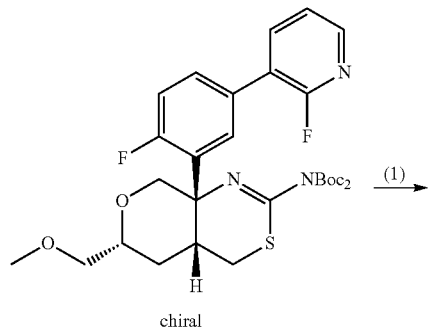

chiral

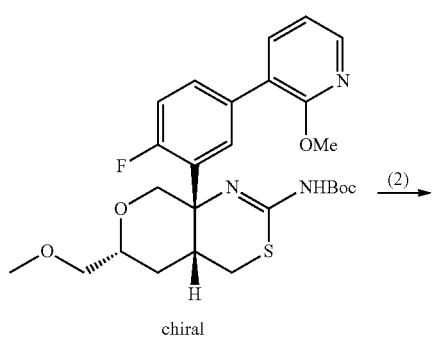

chiral

170
-continued

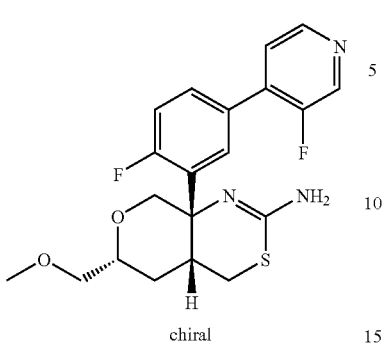

chiral (1) Synthesis of t-butyl {(4aR,6R,8aS)-8a-[2-fluoro-5-(2-methoxypyridin-3-yl)phenyl]-6-methoxymethyl-4,4a,5,6,8,8a-hexahydro-7-oxa-3-thia-1-azanaphthalen-2-yl}carbamate Methanol (1 mL) and a 28% sodium methoxide-methanol solution (1 mL) were added to the compound synthesized in Example 76-(1) (164 mg), followed by stirring at 50° C. After three hours and 30 minutes, the reaction solution was left to cool. Ethyl acetate and a saturated ammonium chloride solution were added to the reaction solution, and the organic layer was separated. The organic layer was washed with brine. The organic layer was dried over anhydrous magnesium sulfate. The drying agent was removed by filtration and the filtrate was concentrated under reduced pressure. The residue was subjected to silica gel chromatography to obtain the title compound (114 mg).

ESI-MS; m/z 540 [M⁺+Na].

(2) Synthesis of {(4aR,6R,8aS)-8a-[2-fluoro-5-(2-methoxypyridin-3-yl)phenyl]-6-methoxymethyl-4,4a,5,6,8,8a-hexahydro-7-oxa-3-thia-1-azanaphthalen-2-yl}amine The compound obtained in Example 78-(1) (114 mg) was dissolved in dichloromethane (3 mL), and then TFA (1 mL) was added, followed by stirring at room temperature. After three hours, the reaction solution was concentrated under reduced pressure. Chloroform and a saturated sodium bicarbonate solution were added to the residue, and the organic layer was separated. The organic layer was dried over anhydrous magnesium sulfate. The drying agent was removed by filtration and the filtrate was concentrated under reduced pressure. The residue was subjected to column chromatography to obtain the title compound (61 mg).

ESI-MS; m/z 418 [M⁺+1].

EXAMPLE 79

Synthesis of (4aR,6R,8aS)-8a-[2-fluoro-5-pyridazin-3-ylphenyl]-6-methoxymethyl-4,4a,5,6,8,8a-hexahydro-7-oxa-3-thia-1-azanaphthalen-2-yl]amine

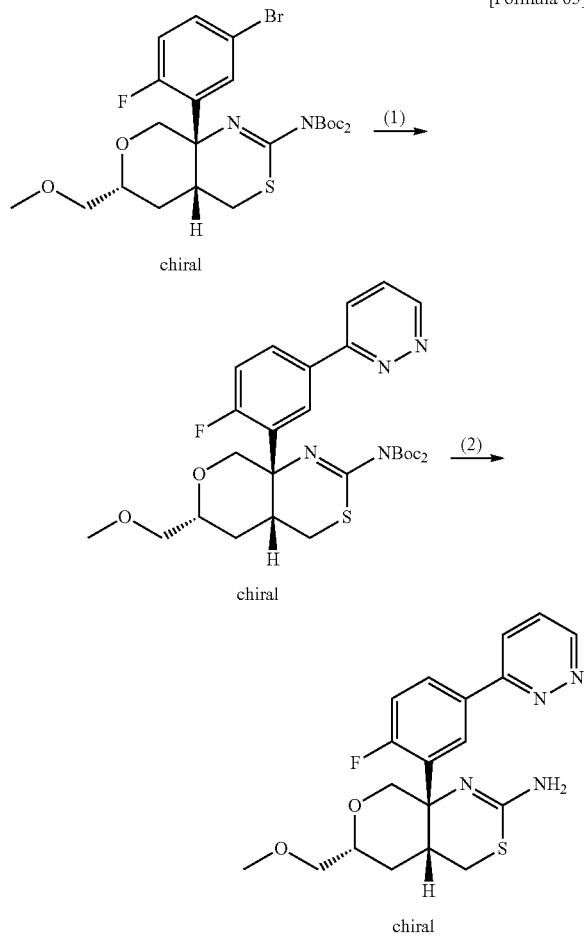

[Formula 65]

(1) Synthesis of di-tert-butyl [(4aR,6R,8aS)-8a-(2-fluoro-5-pyridazin-3-ylphenyl)-6-methoxymethyl-4,4a,5,6,8,8a-hexahydropyrano[3,4-d][1,3]thiazin-2-yl]imidodicarbonate The compound synthesized in Example 76-(1) (229 mg) was dissolved in 1,4-dioxane (4 mL). 3-(Tributylstannyl)pyridazine (215 mg), cesium fluoride (130 mg) and bis(tri-t-butylphosphine)palladium (10 mg) were sequentially added to the solution, and the mixture was stirred in a nitrogen atmosphere at 100° C. After two hours, the reaction solution was left to cool. The reaction mixture was filtered through celite and washed with ethyl acetate. The filtrate was concentrated under reduced pressure. The residue was subjected to silica gel chromatography to obtain the title compound (116 mg).

ESI-MS; m/z 611 [M$^+$+Na].

(2) Synthesis of (4aR,6R,8aS)-8a-[2-fluoro-5-pyridazin-3-ylphenyl]-6-methoxymethyl-4,4a,5,6,8,8a-hexahydro-7-oxa-3-thia-1-azanaphthalen-2-yl]amine The compound obtained in Example 79-(1) (116 mg) was dissolved in dichloromethane (3 mL), and then TFA (1 mL) was added, followed by stirring at room temperature. After three hours, the reaction solution was concentrated under reduced pressure. Chloroform and a saturated sodium bicarbonate solution were added to the residue, and the organic layer was separated. The organic layer was dried over anhydrous magnesium sulfate. The drying agent was removed by filtration and the filtrate was concentrated under reduced pressure. The residue was subjected to column chromatography to obtain the title compound (48 mg).

ESI-MS; m/z 389 [M$^+$+1].

EXAMPLE 80

The following compound as shown in the following Table 11 was synthesized according to Example 2 using the corresponding carboxylic acids.

TABLE 11

| Example 80 | | Compound name: N-[3-((4aR*,6R*,8aS*)-2-amino-6-trifluoromethyl-4,4a,5,6,8,8a-hexahydro-7-oxa-3-thia-1-aza-naphthalen-8a-yl)-4-fluorophenyl]-5-difluoromethylpyridine-2-carboxamide ESI-MS m/z 505 ]M$^+$ + H] |
|---|---|---|

EXAMPLE 81

Synthesis of N-[3-((4aR*,8aS*)-2-amino-4,4a,5,6,8,8a-hexahydro-7-oxa-3-thia-1-azanaphthalen-8a-yl)-4-fluorophenyl]-5-ethoxypyrazine-2-carboxamide

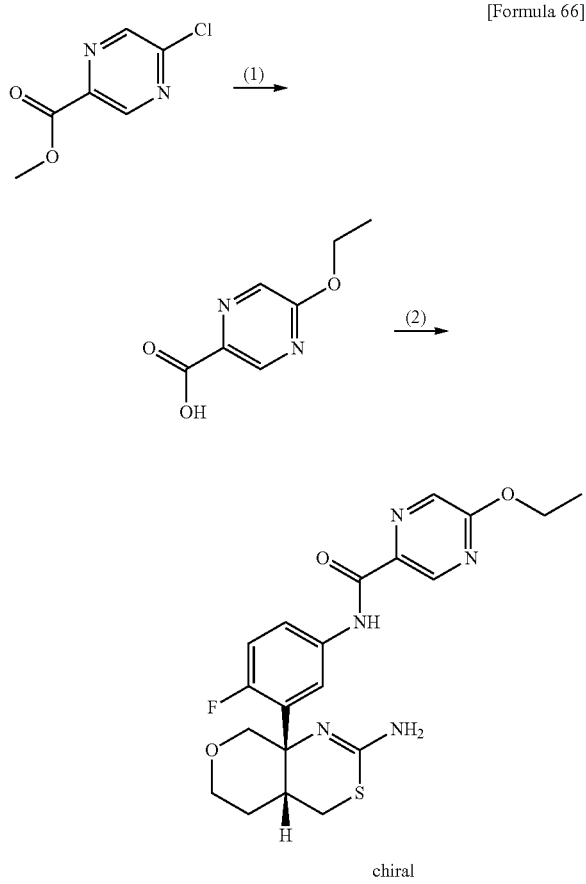

[Formula 66]

chiral

(1) Synthesis of 5-ethoxypyrazine-2-carboxylic acid

A 5 N sodium hydroxide solution (2 mL) was added to a solution of methyl 5-chloropyrazine-2-carboxylate (150 mg) in ethanol (4 mL), and the mixture was stirred at room temperature for five hours. Ethyl acetate and water were added to the reaction solution, and the aqueous layer was separated. The aqueous layer was made acidic with concentrated hydrochloric acid. Brine and ethyl acetate were added to the mixture, and the organic layer was separated. The organic layer was dried over anhydrous magnesium sulfate. The organic layer was concentrated to obtain the title compound (135 mg).

$^1$H-NMR (400 MHz, CDCl$_3$) δ (ppm): 1.46 (t, J=7.2 Hz, 3H), 4.51 (q, J=7.2 Hz, 2H), 8.17 (s, 1H), 8.96 (s, 1H).

(2) Synthesis of N-[3-((4aR*,8aS*)-2-amino-4,4a,5,6,8,8a-hexahydro-7-oxa-3-thia-1-azanaphthalen-8a-yl)-4-fluorophenyl]-5-ethoxypyrazine-2-carboxamide The title compound (30 mg) was obtained from the compound obtained in Preparation Example 1-(9) (30 mg) and the compound obtained in Example 81-(1) (16.9 mg) according to Example (2).

ESI-MS; m/z 432 [M$^+$+H]

$^1$H-NMR (400 MHz, CDCl$_3$) δ (ppm): 1.40-1.46 (m, 1H), 1.45 (t, J=7.2 Hz, 3H), 2.07-2.18 (m, 1H), 2.64 (dd, J=2.8, 8.0 Hz, 1H), 2.94 (ddd, J=4.0, 7.6, 11.6 Hz, 1H), 3.02 (dd, J=4.0, 12.0 Hz, 1H), 3.65-3.71 (m, 1H), 3.78 (d, J=10.8 Hz, 1H), 4.04-4.11 (m, 2H), 4.49 (q, J=7.2 Hz, 2H), 7.06 (dd, J=8.8, 12.0 Hz, 1H), 7.32 (dd, J=2.8, 7.2 Hz, 1H), 7.99-8.03 (m, 1H), 8.11 (s, 1H), 8.98 (s, 1H), 9.47 (s, 1H).

EXAMPLES 82 to 87

The compounds of Examples 82 to 87 were synthesized according to Example 3 using the corresponding carboxylic acids, as shown in the following Table 12.

TABLE 12

| Example | Chemical structure | |
|---|---|---|
| 82 | (structure shown) | Compound name: N-[3-((8S*,8aR*)-2-amino-4,4a,5,6,8,8a-hexahydro-7-oxa-3-thia-1-azanaphthalen-8a-yl)-4-fluorophenyl]-5-methoxypyrazine-2-carboxamide<br>$^1$H-NMR (400 MHz, CDCl$_3$): δ (ppm): 1.44-1.47 (m, 1H), 2.08-2.18 (m, 1H), 2.64 (dd, J = 2.4, 12.0 Hz, 1H), 2.89-2.98 (m, 1H), 3.03 (dd, J = 4.0, 12.0 Hz, 1H), 3.65-3.72 (m, 1H), 3.79 (d, J = 10.8 Hz, 1H), 4.02-4.12 (m, 5H), 7.07 (dd, J = 8.8, 12.0 Hz, 1H), 7.32 (dd, J = 2.8, 6.8 Hz, 1H), 8.02 (ddd, J = 2.8, 4.0, 8.8 Hz, 1H), 8.15 (d, J = 1.2 Hz, 1H), 9.01 (d, J = 1.6 Hz, 1H), 9.48 (bs, 1H)<br>ESI-MS m/z 418 [M$^+$ + H] |

| Example 83 | Chemical structure | 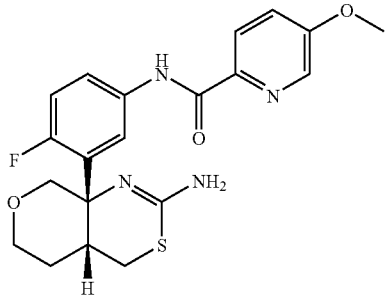 | Compound name: N-[3-((8S*,8aR*)-2-amino-4,4a,5,6,8,8a-hexahydro-7-oxa-3-thia-1-azanaphthalen-8a-yl)-4-fluorophenyl]-5-methoxypyridine-2-carboxamide<br>$^1$H-NMR (400 MHz, CDCl$_3$): 1.42-1.47 (m, 1H), 2.08-2.20 (m, 1H), 2.63 (dd, J = 2.8, 12.4 Hz, 1H), 2.91-2.97 (m, 1H), 3.03 (dd, J = 4.0, 12.4 Hz, 1H), 3.65-3.72 (m, 1H), 3.78 (d, J = 10.8 Hz, 1H), 3.94 (s, 3H), 4.05-4.11 (m, 2H), 7.06 (dd, J = 8.8, 12.0 Hz, 1H) 7.33 (dd, J = 2.8, 8.8 Hz, 2H), 8.04 (ddd, J = 2.8, 4.0, 8.8 Hz, 1H), 8.23 (d, J = 8.8 Hz, 1H), 8.27 (d, J = 2.8 Hz, 1H) 9.80 (bs, 1H)<br>ESI-MS m/z 417 [M$^+$ + H] |
|---|---|---|---|
| Example 84 | Chemical structure | 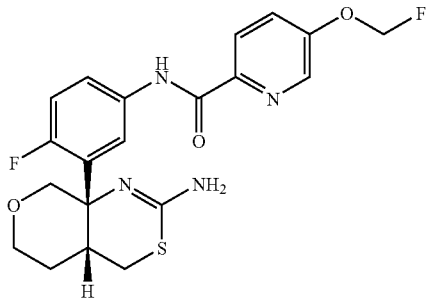 | Compound name: N-[3-((8S*,8aR*)-2-amino-4,4a,5,6,8,8a-hexahydro-7-oxa-3-thia-1-azanaphthalen-8a-yl)-4-fluorophenyl]-5-fluoromethoxypyridine-2-carboxamide<br>$^1$H-NMR (400 MHz, CDCl$_3$): 1.44-1.48 (m, 1H), 2.09-2.19 (m, 1H), 2.65 (dd, J = 3.2, 12.4 Hz, 1H), 2.95-2.99 (m, 1H), 3.04 (dd, J = 4.0, 12.0 Hz, 1H), 3.65-3.72 (m, 1H), 3.80 (d, J = 11.2 Hz, 1H), 4.04-4.13 (m, 2H), 5.81 (d, J = 50.0 Hz, 2H), 7.08 (dd, J = 8.8, 12.0 Hz, 1H) 7.35 (dd, J = 2.8, 6.8 Hz, 1H), 7.57 (ddd, J = 0.8, 2.8, 8.4 Hz, 1H), 8.05 (ddd, J = 2.8, 4.4, 8.8 Hz, 1H), 8.28 (dd, J = 0.4, 8.4 Hz, 1H), 8.42 (d, J = 2.8 Hz, 1H), 9.82 (bs, 1H)<br>ESI-MS m/z 435 [M$^+$ + H] |
| Example 85 | Chemical structure | 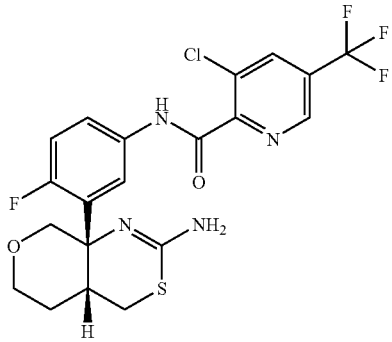 | Compound name: N-[3-((8S*,8aR*)-2-amino-4,4a,5,6,8,8a-hexahydro-7-oxa-3-thia-1-azanaphthalen-8a-yl)-4-fluorophenyl]-3-chloro-5-trifluoromethylpyridine-2-carboxamide<br>$^1$H-NMR (400 MHz, CDCl$_3$): 1.45-1.48 (m, 1H), 2.07-2.18 (m, 1H), 2.66 (dd, J = 2.8, 12.4 Hz, 1H), 2.95-3.05 (m, 2H), 3.65-3.72 (m, 1H), 3.78 (d, J = 11.2 Hz, 1H), 4.03-4.12 (m, 2H), 7.07-7.12 (m, 1H), 7.21 (dd, J = 2.4, 6.8 Hz, 1H), 8.13-8.18 (m, 2H), 8.79 (dd, J = 0.8, 4.0 Hz, 1H), 9.75 (bs, 1H)<br>ESI-MS m/z 489 [M$^+$+ H] |

TABLE 12-continued

| Example | Chemical structure | |
|---|---|---|
| Example 86 | 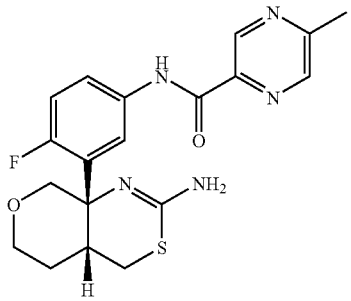 | Compound name: N-[3-((8S*,8aR*)-2-amino-4,4a,5,6,8,8a-hexahydro-7-oxa-3-thia-1-azanaphthalen-8a-yl)-4-fluorophenyl]-5-methylpyridine-2-carboxamide<br>$^1$H-NMR (400 MHz, CDCl$_3$): 1.44-1.47 (m, 1H), 2.12-2.15 (m, 1H), 2.65 (dd, J = 2.8, 12.4 Hz, 1H), 2.70 (s, 3H), 2.93-2.97 (m, 1H), 3.03 (dd, J = 4.0, 12.4 Hz, 1H), 3.66-3.72 (m, 1H), 3.78 (d, J = 11.2 Hz, 1H), 4.05-4.12 (m, 2H), 7.08 (dd, J = 8.8, 12.0 Hz, 1H) 7.36 (dd, J = 2.8, 6.8 Hz, 1H), 8.01-8.05 (m, 1H) 8.44 (s, 1H), 9.36 (d, J = 0.8 Hz, 1H), 9.61 (bs, 1H)<br>ESI-MS m/z 402 [M$^+$ + H] |
| Example 87 | 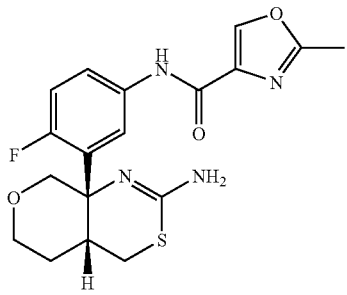 | Compound name: N-[3-((8S*,8aR*)-2-amino-4,4a,5,6,8,8a-hexahydro-7-oxa-3-thia-1-azanaphthalen-8a-yl)-4-fluorophenyl]-2-methyloxazole-4-carboxamide<br>$^1$H-NMR (400 MHz, CDCl$_3$): 1.45-1.48 (m, 1H), 2.11-2.14 (m, 1H), 2.53 (s, 3H), 2.63-2.67 (m, 1H), 2.95-3.05 (m, 2H), 3.65-3.71 (m, 1H), 3.81 (d, J = 11.6 Hz, 1H), 4.03-4.06 (m, 1H), 4.08-4.12 (m, 1H), 7.03-7.09 (m, 1H), 7.30-7.32 (m, 1H), 7.93-7.97 (m, 1H), 8.17 (s, 1H), 8.71 (bs, 1H)<br>ESI-MS m/z 391 [M$^+$ + H] |

EXAMPLE 88

The compound of Example 88 was synthesized according to Example 2 using the corresponding carboxylic acid and the corresponding aniline intermediate in Preparation Examples, as shown in the following Table 13.

TABLE 13

| Example | Chemical structure | |
|---|---|---|
| Example 88 | 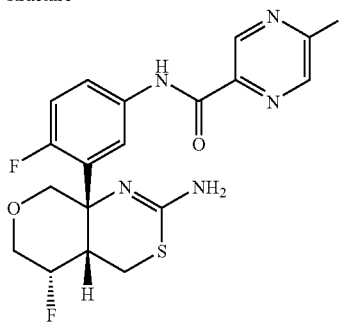 | Compound name: N-[3-((8S,8aS)-2-amino-5-fluoro-4,4a,5,6,8,8a-hexahydro-7-oxa-3-thia-1-azanaphthalen-8a-yl)-4-fluorophenyl]-5-methoxypyrazine-2-carboxamide<br>$^1$H-NMR (400 MHz, CDCl$_3$): 2.87-2.91 (m, 1H), 3.01-3.06 (m, 1H), 3.16 (dd, J = 2.8, 12.4 Hz, 1H), 3.53 (dt, J = 4.8, 10.4 Hz, 1H), 3.75 (dd, J = 2.0, 10.8 Hz, 1H), 4.07-4.10 (m, 4H), 4.26 (dd, J = 1.6, 10.8 Hz, 1H), 4.84-4.98 (m, 1H), 7.10 (dd, J = 8.8, 12.0 Hz, 1H), 7.36 (dd, J = 2.4, 6.8 Hz, 1H), 7.97-8.01 (m, 1H), 8.15 (d, J = 1.2 Hz, 1H), 9.01 (d, J = 1.2 Hz, 1H), 9.48 (bs, 1H)<br>ESI-MS m/z 436 [M$^+$ + H] |

TEST EXAMPLE 1

Quantification of Aβ Peptide in Culture of Neurons from Rat Fetus Brain (1) Rat Primary Neuronal Culture Primary neuronal cultures were prepared from the cerebral cortex of embryonic day 18 Wistar rats (Charles River Japan, Yokohama, Japan). Specifically, the embryos were aseptically removed from pregnant rats under ether anesthesia. The brain was isolated from the embryo and immersed in an ice-cold L-15 medium (such as Invitrogen Corp. Cat #11415-064, Carlsbad, Calif., USA, or SIGMA L1518). The cerebral cortex was collected from the isolated brain under a stereoscopic microscope. The cerebral cortex fragments collected were enzymatically treated in an enzyme solution containing 0.25% trypsin (Invitrogen Corp. Cat #15050-065, Carlsbad, Calif., USA) and 0.01% DNase (Sigma D5025, St. Louis, Mo., USA) at 37° C. for 30 minutes to disperse the cells. Here, the enzymatic reaction was stopped by adding inactivated horse serum to the solution. The enzymatically treated solution was centrifuged at 1,500 rpm for five minutes to remove the supernatant. 5 to 10 ml of a medium was added to the resulting cell mass. Neurobasal medium (Invitrogen Corp. Cat #21103-049, Carlsbad, Calif., USA) supplemented with 2% B27 supplement (Invitrogen Corp. Cat #17504-044, Carlsbad, Calif., USA), 25 μM 2-mercaptoethanol (2-ME, WAKO Cat #139-06861, Osaka, Japan), 0.5 mM L-glutamine (Invitrogen Corp. Cat #25030-081, Carlsbad, Calif., USA), and Antibiotics-Antimycotics (Invitrogen Corp. Cat #15240-062, Carlsbad, Calif., USA) was used as the medium (Neurobasal/B27/2-ME). However, the above Neurobasal medium not supplemented with 2-ME (Neurobasal/B27) was used for the assay. The cells were redispersed by mild pipetting of the cell mass to which the medium was added. The cell dispersion was filtered through a 40-μm nylon mesh (Cell Strainer, Cat #35-2340, Becton Dickinson Labware, Franklin Lakes, N.J., USA) to remove the remaining cell mass, and thus a neuronal cell suspension was obtained. The neuronal cell suspension was diluted with the medium and then plated in a volume of 100 μl/well at an initial cell density of $5 \times 10^5$ cells/cm$^2$ in a 96-well polystyrene culture plate pre-coated with poly-L or D-lysine (Falcon Cat #35-3075, Becton Dickinson Labware, Franklin Lakes, N.J., USA coated with poly-L-lysine using the method shown below, or BIOCOAT™ cell environments Poly-D-lysine cell ware 96-well plate, Cat #35-6461, Becton Dickinson Labware, Franklin Lakes, N.J., USA). Poly-L-lysine coating was carried out as follows. 100 μg/ml of a poly-L-lysine (SIGMA P2636, St. Louis, Mo., USA) solution was aseptically prepared with a 0.15 M borate buffer (pH 8.5). 100 μg/well of the solution was added to the 96-well polystyrene culture plate and incubated at room temperature for one or more hours or at 4° C. overnight or longer. Thereafter, the coated 96-well polystyrene culture plate was washed with sterile water four or more times, and then dried or rinsed with, for example, sterile PBS or medium, and used for cell plating. The plated cells were cultured in the culture plate at 37° C. in 5% $CO_2$-95% air for one day. Then, the total amount of the medium was replaced with a fresh Neurobasal/B27/2-ME medium, and then the cells were cultured for further three days.

(2) Addition of Compound

The drug was added to the culture plate on Day 4 of culture as follows. The total amount of the medium was removed from the wells, and 180 μl/well of Neurobasal medium not containing 2-ME and containing 2% B-27 (Neurobasal/B27) was added thereto. A solution of the test compound in dimethyl sulfoxide (hereinafter abbreviated as DMSO) was diluted with Neurobasal/B27 to a concentration 10-fold higher than the final concentration. 20 μl/well of the dilution was added to and sufficiently mixed with the medium. The final DMSO concentration was 1% or less. Only DMSO was added to the control group.

(3) Sampling

The cells were cultured for three days after addition of the compound, and the total amount of the medium was collected. The resulting medium was used as an ELISA sample. The sample was not diluted for ELISA measurement of Aβx-42 and diluted to 5-fold with a diluent supplied with an ELISA kit for ELISA measurement of Aβx-40.

(4) Evaluation of Cell Survival

Cell survival was evaluated by an MTT assay according to the following procedure. After collecting the medium, 100 μl/well of a pre-warmed medium was added to the wells. Further, 8 μl/well of a solution of 8 mg/ml of MTT (SIGMA M2128, St. Louis, Mo., USA) in D-PBS(−) (Dulbecco's phosphate buffered Saline, SIGMA D8537, St. Louis, Mo., USA) was added to the wells. The 96-well polystyrene culture plate was incubated in an incubator at 37° C. in 5% $CO_2$-95% air for 20 minutes. 100 μl/well of an MTT lysis buffer was added thereto, and MTT formazan crystals were sufficiently dissolved in the buffer in the incubator at 37° C. in 5% $CO_2$-95% air. Then, the absorbance at 550 nm in each well was measured. The MTT lysis buffer was prepared as follows. 100 g of SDS (sodium dodecyl sulfate (sodium lauryl sulfate), WAKO 191-07145, Osaka, Japan) was dissolved in a mixed solution of 250 mL of N,N-dimethylformamide (WAKO 045-02916, Osaka, Japan) with 250 mL of distilled water. 350 μl each of concentrated hydrochloric acid and acetic acid were further added to the solution to allow the solution to have a final pH of about 4.7.

Upon measurement, wells having no cells plated and containing only the medium and MTT solution were set as background (bkg). The measured values were respectively applied to the following formula including subtracting bkg values from them. Thus, the proportion against the control group (group not treated with the drug, CTRL) (% of CTRL) was calculated to compare and evaluate cell survival activities.

% of CTRL=($A550\_sample−A550\_bkg$)/
($A550\_CTRL−A550\_bkg$)×100

(A550_sample: absorbance at 550 nm of sample well, A550_bkg: absorbance at 550 nm of background well, A550_CTRL: absorbance at 550 nm of control group well)

(5) Aβ ELISA

Human/Rat β Amyloid (42) ELISA Kit Wako (#290-62601) and Human/Rat β Amyloid (40) ELISA Kit Wako (#294-62501) from Wako Pure Chemical Industries, Ltd. were used for Aβ ELISA. Aβ ELISA was carried out according to the protocols recommended by the manufacturers (methods described in the attached documents). However, the Aβ calibration curve was created using beta-amyloid peptide 1-42, rat and beta-amyloid peptide 1-40, rat (Calbiochem, #171596 [Aβ$_{42}$]. #171593 [Aβ$_{40}$]). The results are shown in Table 14 in term of IC50 value (μM) to decrease the Aβ42 concentration in the medium.

TABLE 14

| Test compound | Aβ42 production reducing effect IC50 (μM) |
|---|---|
| 1 | 0.0017 |
| 2 | 0.002 |
| 3 | 0.001 |

TABLE 14-continued

| Test compound | Aβ42 production reducing effect IC50 (μM) |
|---|---|
| 4 | 0.011 |
| 5 | 0.058 |
| 6 | 0.0012 |
| 7 | 0.0007 |
| 8 | 0.0016 |
| 9 | 0.0006 |
| 10 | 0.001 |
| 11 | 0.0007 |
| 12 | 0.0011 |
| 13 | 0.001 |
| 14 | 0.0008 |
| 15 | 0.0004 |
| 16 | 0.0011 |
| 17 | 0.004 |
| 18 | 0.007 |
| 19 | 0.002 |
| 20 | 0.009 |
| 21 | 0.01 |
| 22 | 0.004 |
| 23 | 0.012 |
| 24 | 0.009 |
| 25 | 0.014 |
| 26 | 0.003 |
| 27 | 0.008 |
| 28 | 0.0014 |
| 29 | 0.003 |
| 30 | 0.006 |
| 31 | 0.0019 |
| 32 | 0.003 |
| 33 | 0.0011 |
| 34 | 0.002 |
| 35 | 0.0021 |
| 36 | 0.0005 |
| 37 | 0.002 |
| 38 | 0.003 |
| 39 | 0.001 |
| 40 | 0.002 |
| 41 | 0.002 |
| 42 | 0.0009 |
| 43 | 0.0017 |
| 44 | 0.0007 |
| 45 | 0.002 |
| 46 | 0.001 |
| 47 | 0.004 |
| 48 | 0.002 |
| 49 | 0.002 |
| 50 | 0.002 |
| 51 | 0.006 |
| 52 | 0.002 |
| 53 | 0.0056 |
| 54 | 0.002 |
| 55 | 0.0014 |
| 56 | 0.003 |
| 57 | 0.002 |
| 58 | 0.004 |
| 59 | 0.087 |
| 60 | 0.032 |
| 61 | 0.319 |
| 64 | 0.014 |
| 65 | 0.37 |
| 66 | 0.263 |

As is clear from the results of Table 14, the compound of the present invention was proved to have an Aβ42 production reducing effect.

The compound of the general formula (I) or pharmaceutically acceptable salt thereof, or solvate thereof according to the present invention has an Aβ42 production reducing effect. Thus, the present invention can particularly provide a therapeutic or prophylactic agent for a neurodegenerative disease caused by Aβ such as Alzheimer-type dementia or Down's syndrome.

The invention claimed is:

1. A compound represented by the formula (I):

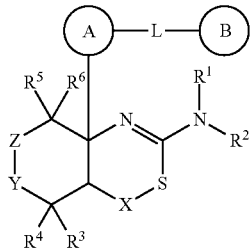

(I)

or a pharmaceutically acceptable salt thereof, wherein
Ring A is a $C_{6-14}$ aryl group which may have 1 to 3 substituents selected from Substituent Group α or a 5- to 6-membered heteroaryl group which may have 1 to 3 substituents selected from Substituent Group α,
L is a single bond or —$NR^L CO$— (wherein $R^L$ is a hydrogen atom or a $C_{1-6}$ alkyl group which may have 1 to 3 substituents selected from Substituent Group α),
Ring B is a $C_{6-14}$ aryl group which may have 1 to 3 substituents selected from Substituent Group α or a 5- to 10-membered heterocyclic group which may have 1 to 3 substituents selected from Substituent Group α,
X is a methylene group which may have 1 to 2 substituents selected from Substituent Group α,
Y is a methylene group which may have 1 to 2 substituents selected from Substituent Group α,
Z is an oxygen atom,
$R^1$ and $R^2$ are hydrogen atoms, and
$R^3$, $R^4$, $R^5$ and $R^6$ are independently a hydrogen atom, a halogen atom, a hydroxy group, a $C_{1-6}$ alkyl group which may have 1 to 3 substituents selected from Substituent Group α, or
$R^4$ and $R^6$ together may form a ring represented by the formula (II):

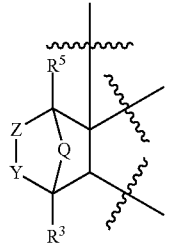

(II)

wherein Y, Z, $R^5$ and $R^3$ are the same as defined above and Q is an oxygen atom, a methylene group or an ethylene group
Substituent Group α is a hydrogen atom, a halogen atom, a hydroxy group, a nitro group, a $C_{1-6}$ alkylthio group, a $C_{6-14}$ aryl group, a $C_{6-14}$ aryloxycarbonyl group, a $C_{6-14}$ arylcarbonyl group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group may be substituted with 1 to 2 $C_{1-6}$ alkyl groups), a $C_{2-6}$ alkenyl group which may have 1 to 2 substituents selected from Substituent Group β, a $C_{2-6}$ alkynyl group which may have 1 to 2 substituents selected from Substituent Group β, a carbamoyl group which may be substituted with 1 to 2 $C_{1-6}$ alkyl groups, a $C_{1-6}$ alkoxy group which may have 1 to 3 substituents selected from Substituent Group β, a $C_{1-6}$ alkyl group which may have 1 to 3 substituents selected from Substituent Group β and a 5- to 10-membered heterocyclic group which may have 1 to 3 substituents selected from Substituent Group β, Substituent Group β is a halogen atom, a cyano group, a hydroxy group and a $C_{1-6}$ alkoxy group (wherein the alkoxy group may be substituted with a phenyl group which may be substituted with 1 to 3 substituents selected from a hydrogen atom, a halogen atom, a hydroxy group and a nitro group).

2. The compound or pharmaceutically acceptable salt thereof, according to claim 1, wherein L is —$NR^LCO$— (wherein $R^L$ is a hydrogen atom or a $C_{1-6}$ alkyl group which may have 1 to 3 substituents selected from Substituent Group α).

3. The compound or pharmaceutically acceptable salt thereof, according to claim 1, wherein the substituents selected from Substituent Group α is a hydrogen atom, a halogen atom, a $C_{1-6}$ alkoxy group which may have 1 to 3 substituents selected from Substituent Group β or a $C_{1-6}$ alkyl group which may have 1 to 3 substituents selected from Substituent Group β.

4. A compound selected from the following compounds:
N-[3-((4aR*,8aS*)-2-amino-4,4a,5,6,8,8a-hexahydro-7-oxa-3-thia-1-azanaphthalen-8a-yl)-4-fluorophenyl]-5-cyanopyridine-2-carboxamide,
N-[3-((8aR*)-2-amino-4,4a,5,6,8,8a-hexahydro-7-oxa-3-thia-1-azanaphthalen-8a-yl)-4-fluorophenyl]-5-fluoromethoxypyrazine-2-carboxamide,
N-[3-((4aR*,8aS*)-2-amino-4,4a,5,6,8,8a-hexahydro-7-oxa-3-thia-1-azanaphthalen-8a-yl)-4-fluorophenyl]-5-difluoromethoxypyrazine-2-carboxamide,
N-[3-((4aS*,8aS*)-2-amino-4,4a,5,6,8,8a-hexahydro-7-oxa-3thia-1-azanaphthalen-8a-yl)-4-trifluoromethoxyphenyl]-5-cyanopyridine-2-carboxamide,
N-[3-((8aS*)-2-amino-4,4a,5,6,8,8a-hexahydro-7-oxa-3-thia-1-azanaphthalen-8a-yl)-4-trifluoromethoxyphenyl]-5-chloropyridine-2-carboxamide,
N-[3-((4aR*,6S*, 8aS*)-2-amino-6-4,4a,5,6,8,8a-hexahydro-7-oxa-3-thia-1-azanaphthalen-8a-yl)-4-fluorophenyl]-5-chloropyridine-2-carboxamide,
N-[3-((4aR*,6S*, 8aS*)-2-amino-6-4,4a,5,6,8,8a-hexahydro-7-oxa-3-thia-1-azanaphthalen-8a-yl)-4-fluorophenyl]-5-cyanopyridine-2- carboxamide,
N-[3-((4aR*,6S*, 8aS*)-2-amino-6-4,4a,5,6,8,8a-hexahydro-7-oxa-3-thia-1-azanaphthalen-8a-yl)-4-fluorophenyl]-5-trifluoromethylpyridine-2-carboxamide,
N-[3-((4aR*,6S*, 8aS*)-2-amino-6-methyl-4,4a,5,6,8,8a-hexahydro-7-oxa-3-thia-1-azanaphthalen-8a-yl)-4-fluorophenyl]-5-difluoromethoxypyrazine-2-carboxamide,
N-[3-((4aR*,6S*, 8aS*)-2-amino-6-methyl-4,4a,5,6,8,8a-hexahydro-7-oxa-3-thia-1-azanaphthalen-8a-yl)-4-fluorophenyl]-5-fluoromethoxypyrazine-2-carboxamide,
N-[3-((4aR*,6R*,8aS*)-2-amino-6-methoxymethyl-4,4a, 5,6,8,8a-hexahydro-7-oxa-3thia-1-azanaphthalen-8a-yl)-4-fluorophenyl]-5- cyanopyridine-2-carboxamide,
N-[3-((4aR*,6R*,8aS*)-2-amino-6-methoxymethyl-4,4a, 5,6,8,8a-hexahydro-7-oxa-3-thia-1-azanaphthalen-8a-yl)-4-fluorophenyl]-5-difluormethylpyrazine-2-carboxamide,
N-[3-((4aR*,6R*,8aS*)-2-amino-6-methoxymethyl-4,4a, 5,6,8,8a-hexahydro-7-oxa-3thia-1-azanaphthalen-8a-yl)-4-fluorophenyl]-5-chloropyridine-2-carboxamide,
N-[3-((4aR*,6R*,8aS*)-2-amino-6-methoxymethyl-4,4a, 5,6,8,8a-hexahydro-7-oxa-3thia-1-azanaphthalen-8a-yl)-4-fluorophenyl]-5-fluoromethoxypyrazine-2-carboxamide,
N-[3-((4aR*,6R*,8aS*)-2-amino-6-methoxymethyl-4,4a, 5,6,8,8a-hexahydro-7-oxa-3-thia-1-azanaphthalen-8a-yl)-4-fluorophenyl]-5-difluoromethoxypyrazine-2-carboxamide,
N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-cyanopyridine-2-carboxamide,
N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-difluoromethylpyrazine-2-carboxamide,
N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-chloropyridine-2-carboxamide,
N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-trifluoromethylpyridine-2-carboxamide,
N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-difluoromethoxypyridine-2-carboxamide,
N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-fluoromethoxypyrazine-2-carboxamide,
N-[3-((4aS,5S,8aS)-2-amino-5-fluoro-4,4a,5,6,8,8a-hexahydro-7-oxa-3-thia-1-azanaphthalen-8a-yl)-4-fluorophenyl]-5-difluoromethoxypyrazine-2-carboxamide,
N-[3-((4aS*,5S,8aS*)-2-amino-5-methyl-4,4a,5,6,8,8a-hexahydro-7-oxa-3-thia-1-azanaphthalen-8a-yl)-4-fluorophenyl]-5-chloropyridine-2-carboxamide,
N-[3-((4aR*,5S*,8aS*)-2-amino-5-methyl-4,4a,5,6,8,8a-hexahydro-7-oxa-3-thia-1-azanaphthalen-8a-yl)-4-fluorophenyl]-5-cyanopyridine-2-carboxamide,
N-[3-((4aR*,5S*,8aS*)-2-amino-5-methyl-4,4a,5,6,8,8a-hexahydro-7-oxa-3-thia-1-azanaphthalen-8a-yl)-4-fluorophenyl]-5-difluoromethoxypyrazine-2-carboxamide,
N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-chloropyridine-2-carboxamide,
N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-cyanopyridine-2-carboxamide,
N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-difluormethoxypyrazine-2-carboxamide,
N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-difluormethylpyrazine-2-carboxamide,
N-[3-((4aS*,5R*,8aS*)-2-amino-5-methoxy-4,4a,5,6,8, 8a-hexahydro-7-oxa-3-thia-1-azanaphthalen-8a-yl)-4-fluorophenyl]-5-cyanopyridine-2-carboxamide,
N-[3-((2R*,4aR*,8aS*)-2-amino-4-methyl-4,4a,5,6,8,8a-hexahydro-7-oxa-3-thia-1-azanaphthalen-8a-yl)-4-fluorophenyl]-5-cyanopyridine-2-carboxamide, N-[3-((2R*,4aR*,8aS*)-2-amino-4-methyl-4,4a,5,6,8,8a-hexahydro-7-oxa-3-thia-1-azanaphthalen-8a-yl)-4-fluorophenyl]-5-difluoromethylpyrazine-2-carboxamide, N-[3-((4aR,6R,8aS)-2-amino-6-hydroxymethyl-4,4a,5,6,8,8a-hexahydro-7-oxa-3-thia-1-azanaphthalen-8a-yl)-4-fluorophenyl]-5-chloropyridine-2-carboxamide, N-[3-((4aR,6R,8aS)-2-amino-6-hydroxymethyl-4,4a,5,6,8,8a-hexahydro-7-oxa-3-thia-1-azanaphthalen-8a-yl)-4-fluorophenyl]-5-cyanopyridine-2-carboxamide, N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-cyanopyridine-2-carboxamide, N-[3-((4aR*,6R*,8aS*)-2-amino-6-trifluoromenthyl-4,4a,5,6,8,8a-hexahydro-7-oxa-3-thia-1-azanaphthalen-8a-yl)-4-fluorophenyl]-5-difluormethoxypyrazine-2-carboxamide, N-[3-((4aR*,6R*,8aS*)-2-amino-6-trifluoromenthyl-4,4a,5,6,8,8a-hexahydro-7-oxa-3-thia-1-azanaphthalen-8a-yl)-4-fluorophenyl]-5-fluoropyridine-2-carboxamide, N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-pyridine-2-carboxamide, N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-fluoromethoxypyrazine-2-carboxamide, N-[3-((4aR*,6R*,8aS*)-2-amino-6-trifluoromenthyl-4,4a,5,6,8,8a-hexahydro-7-oxa-3-thia-1-azanaphthalen-8a-yl)-4-fluorophenyl]pyrimidine-4-carboxamide, N-[3-((4aR*,6R*,8aS*)-2-amino-6-trifluoromenthyl-4,4a,5,6,8,8a-hexahydro-7-oxa-3-thia-1-azanaphthalen-8a-yl)-4-fluorophenyl]-3,5-difluoropyridine-2-carboxamide, N-[3-((4aR*,6R*,8aS*)-2-amino-6-trifluoromenthyl-4,4a,5,6,8,8a-hexahydro-7-oxa-3-thia-1-azanaphthalen-8a-yl)-4-fluorophenyl]-5-difluoromethoxypyridine-2-carboxamide, N-[3-((4aR*,6R*,8aS*)-2-amino-6-trifluoromenthyl-4,4a,5,6,8,8a-hexahydro-7oxa-3-thia-1-azanaphthalen-8a-yl)-4-fluorophenyl]-5-difluoromethylypyrazine-2-carboxamide, N-[3-((4aR,6R,8aS)-2-amino-6-fluoromenthyl-4,4a,5,6,8,8a-hexahydro-7-oxa-3-thia-1-azanaphthalen-8a-yl)-4-fluorophenyl]-5-cyanopyridine-2-carboxamide, N-[3-((4aR,6R,8aS)-2-amino-6-fluoromenthyl-4,4a,5,6,8,8a-hexahydro-7-oxa-3-thia-1-azanaphthalen-8a-yl)-4-fluorophenyl]-5-chloropyridine-2-carboxamide, N-[3-((4aR,6R,8aS)-2-amino-6-fluoromenthyl-4,4a,5,6,8,8a-hexahydro-7-oxa-3-thia-1-azanaphthalen-8a-yl)-4-fluorophenyl]-5-trifluormethylpyridine-2-carboxamide, N-[3-((4aR,6R,8aS)-2-amino-6-fluoromenthyl-4,4a,5,6,8,8a-hexahydro-7-oxa-3-thia-1-azanaphthalen-8a-yl)-4-fluorophenyl]-5-fluoromethoxypyrazine-2-carboxamide, N-[3-((4aR,6R,8aS)-2-amino-6-fluoromenthyl-4,4a,5,6,8,8a-hexahydro-7-oxa-3-thia-1-azanaphthalen-8a-yl)-4-fluorophenyl]-5-difluoromethylpyrazine-2-carboxamide, N-[3-((4aR*,8aS*)-2-amino-4,4a,5,6,8,8a-hexahydro-7-oxa-3-thia-1-azanaphthalen-8a-yl)-4-fluorophenyl]-5-chloropyridine-2-carboxamide, N-[3-((4aR*,8aS*)-2-amino-4,4a,5,6,8,8a-hexahydro-7-oxa-3-thia-1-azanaphthalen-8a-yl)-4-fluorophenyl]-5-bromopyridine-2-carboxamide, N-[3-((4aR*,8aS*)-2-amino-4,4a,5,6,8,8a-hexahydro-7-oxa-3-thia-1-azanaphthalen-8a-yl)-4-fluorophenyl]-3,5-difluoropyridine-2-carboxamide, N-[3-((4aR*,8aS*)-2-amino-4,4a,5,6,8,8a-hexahydro-7-oxa-3-thia-1-azanaphthalen-8a-yl)-4-fluorophenyl]-3,5-dichloropyridine-2-carboxamide, N-[3-((4aR*,8aS*)-2-amino-4,4a,5,6,8,8a-hexahydro-7-oxa-3-thia-1-azanaphthalen-8a-yl)-4-fluorophenyl]-5-fluoropyridine-2-carboxamide, N-[3-((4aR*,8aS*)-2-amino-4,4a,5,6,8,8a-hexahydro-7-oxa-3-thia-1-azanaphthalen-8a-yl)-4-fluorophenyl]-3,5-dibromopyridine-2-carboxamide, N-[3-((4aR*,8aS*)-2-amino-4,4a,5,6,8,8a-hexahydro-7-oxa-3-thia-1-azanaphthalen-8a-yl)-4-fluorophenyl]-5-trifluoromethylpyridine-2-carboxamide, N-[3-((4aR*,8aS*)-2-amino-4,4a,5,6,8,8a-hexahydro-7-oxa-3-thia-1-azanaphthalen-8a-yl)-4-fluorophenyl]-5-difluoromethylpyridine-2-carboxamide, N-[3-((4aR*,8aS*)-2-amino-4,4a,5,6,8,8a-hexahydro-7-oxa-3-thia-1-azanaphthalen-8a-yl)-4-fluorophenyl]-5-difluoromethylpyrazine-2-carboxamide, N-[3-((4aR*,8aS*)-2-amino-4,4a,5,6,8,8a-hexahydro-7-oxa-3-thia-1-azanaphthalen-8a-yl)-4-fluorophenyl]-5-difluoromethoxypyridine-2-carboxamide, 59)(±)-(4aR*,6R*,8aS*)-8a-[2-fluoro-5-(2-fluoropyridin-3-yl)phenyl]-6-trifluoromethyl-4,4a,5,6,8,8a-hexahydro-7-oxa-3-thia-1azanaphthalen-2-ylamine, 60)(4aR,6R,8aS)-8a-[2-fluoro-5-(2-fluoropyridin-3-yl)phenyl]-6-fluoromethyl-4,4a,5,6,8,8a-hexahydro-7-oxa-3-thia-1azanaphthalen-2-ylamine, 61)(±)-(4aR*,8aS*)-8a-[2-fluoro-5-(2-fluoropyridin-3-yl)phenyl]-4,4a,5,6,8,8a-hexahydro-7-oxa-3-thia-1-azanaphthalen-2-ylamine, 62)(±)-(4aR*,8aS*)-8a-(2-fluoro-5-pyrimidin-5-ylphenyl)-4,4a,5,6,8,8a-hexahydro-7-oxa-3-thia-1-azanaphthalen-2-ylamine, 63)(±)-(4aR*,8aS*)-8a-[5-(5-chloropyridin-3-yl)-2-fluorophenyl]-4,4a,5,6,8,8a-hexahydro-7-oxa-3-thia-1-azanaphthalen-2-ylamine, N-[5-((4aR*,8aS*)-2-amino-4,4a,5,6,8,8a-hexahydro-7-oxa-3-thia-1-azanaphthalen-8a-yl)thiophen-3-yl]-5-cyanopyridine-2-carboxamide, 65)(±)-(4aR*,8aR*)-8a-[4-(2-fluoropyridin-3-yl)-thiophen-2-yl]-4,4a,5,6,8,8a-hexahydro-7-oxa-3-thia-1-azanaphthalen-2-ylamine, 66)(4aR,6R,8aS)-8a-[2-fluoro-5-(2-fluoropyridin-3-yl)phenyl]-6-benzyloxymethyl-4,4a,5,6,8,8a-hexahydro-7-oxa-3-thia-1-azanaphthalen-2-ylamine, (±)-N-[7-((4aR*,8aS*)-2-amino-4,4a,5,6,8,8a-hexahydro-7-oxa-3-thia-1-azanaphthalen-8a-yl)-2,2-difluorobenzo[1,3]dioxol-5-yl]-5-cyanopyridine-2-carboxamide, N-[3-((4aR*,8aS*)-2-amino-4,4a,5,6,8,8a-hexahydro-7-oxa-3-thia-1-azanaphthalen-8a-yl)-4-fluorophenyl]-5-(2-methoxyethoxy)-pyrazine-2-carboxamide, N-[3-((4aR*,8aS*)-2-amino-4,4a,5,6,8,8a-hexahydro-7-oxa-3-thia-1-azanaphthalen-8a-yl)-4-fluorophenyl]-2-methylthiazole-4-carboxamide, N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-2,5-dimethylfuran-3-carboxamide, N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-4-methyl-[1,2,3]thiadiazole-5-carboxamide, or N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-2-methyloxazole-4-carboxamide, or a pharmaceutically acceptable salt thereof, or a solvate thereof.

5. A pharmaceutical composition comprising the compound or pharmaceutically acceptable salt thereof, or solvate thereof according to claim 1 as an active ingredient.

6. A method of inhibiting production of amyloid-β protein, comprising administering an effective amount of the pharmaceutical compostion according to claim 5 to a subject in need thereof.

7. A method of inhibiting beta-site amyloid-β precursor protein cleaving enzyme 1 (BACE1), comprising administering an effective amount of the pharmaceutical compostion according to claim 5 to subject in need thereof.

8. A method of treating a neurodegenerative disease, comprising administering an effective amount of the pharmaceutical composition according to claim 5 to subject in need thereof.

9. The method according to claim 8, wherein the neurodegenerative disease is Alzheimer-type dementia or Down's syndrome.

* * * * *

UNITED STATES PATENT AND TRADEMARK OFFICE
CERTIFICATE OF CORRECTION

PATENT NO. : 8,198,269 B2
APPLICATION NO. : 12/568151
DATED : June 12, 2012
INVENTOR(S) : Takafumi Motoki et al.

It is certified that error appears in the above-identified patent and that said Letters Patent is hereby corrected as shown below:

In the Claims

Claim 1, Column 182
Lines 35-38, replace "$R^3$, $R^4$, $R^5$ and $R^6$ are independently a hydrogen atom, a halogen atom, a hydroxy group, a $C_{1-6}$ alkyl group which may have 1 to 3 substituents selected from Substituent Group α" with --$R^3$, $R^4$, $R^5$ and $R^6$ are independently a hydrogen atom, a halogen atom, a hydroxy group, a $C_{1-6}$ alkyl group which may have 1 to 3 substituents selected from Substituent Group α or a $C_{1-6}$ alkoxy group which may have 1 to 3 substituents selected from Substituent Group α, or--.

Claim 2, Column 183
Line 16, after "thereof" delete ",".

Claim 3, Column 183
Line 21, after "thereof" delete ",".

Claim 4, Column 183
Lines 43-45, replace "N-[3-((4aR*,6S*, 8aS*)-2-amino-6-4,4a,5,6,8,8a-hexahydro-7-oxa-3-thia-1-azanaphthalen-8a-yl)-4-fluorophenyl]-5-chloropyridine-2-carboxamide," with --N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-chloropyridine-2-carboxamide,--.

Claim 4, Column 183
Lines 46-48, replace "N-[3-((4aR*,6S*, 8aS*)-2-amino-6-4,4a,5,6,8,8a-hexahydro-7-oxa-3-thia-1-azanaphthalen-8a-yl)-4-fluorophenyl]-5-cyanopyridine-2-carboxamide," with --N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-cyanopyridine-2-carboxamide,--.

Signed and Sealed this
Eleventh Day of March, 2014

Michelle K. Lee
*Deputy Director of the United States Patent and Trademark Office*

CERTIFICATE OF CORRECTION (continued)
U.S. Pat. No. 8,198,269 B2

Claim 4, Column 183
Lines 49-52, replace "N-[3-((4aR*,6S*, 8aS*)-2-amino-6-4,4a,5,6,8,8a-hexahydro-7-oxa-3-thia-1-azanaphthalen-8a-yl)-4-fluorophenyl]-5-trifluoromethylpyridine-2-carboxamide," with --N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-trifluoromethylpyridine-2-carboxamide--.

Claim 4, Column 183
Lines 53-56, replace "N-[3-((4aR*,6S*, 8aS*)-2-amino-6-4,4a,5,6,8,8a-hexahydro-7-oxa-3-thia-1-azanaphthalen-8a-yl)-4-fluorophenyl]-5-difluoromethoxypyrazine-2-carboxamide," with --N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-difluoromethoxypyrazine-2-carboxamide,--.

Claim 4, Column 183
Lines 57-60, replace "N-[3-((4aR*,6S*, 8aS*)-2-amino-6-methyl-4,4a,5,6,8,8a-hexahydro-7-oxa-3-thia-1-azanaphthalen-8a-yl)-4-fluorophenyl]-5-fluoromethoxypyrazine-2-carboxamide," with --N-[3-((4aR*,6S*,8aS*)-2-amino-6-methyl-4,4a,5,6,8,8a-hexahydro-7-oxa-3-thia-1-azanaphthalen-8a-yl)-4-fluorophenyl]-5-fluoromethoxypyrazine-2-carboxamide,--.

Claim 4, Column 183
Lines 61-63, replace "N-[3-((4aR*,6R*,8aS*)-2-amino-6-methoxymethyl-4,4a,5,6,8,8a-hexahydro-7-oxa-3thia-1-azanaphthalen-8a-yl)-4-fluorophenyl]-5-cyanopyridine-2-carboxamide," with --N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-cyanopyridine-2-carboxamide,--.

Claim 4, Column 183
Lines 64-67, replace "N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-difluormethylpyrazine-2-carboxamide," with --N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-difluoromethylpyrazine-2-carboxamide,--.

Claim 4, Column 184
Lines 1-3, replace "N-[3-((4aR*,6R*,8aS*)-2-amino-6-methoxymethyl-4,4a,5,6,8,8a-hexahydro-7-oxa-3thia-1-azanaphthalen-8a-yl)-4-fluorophenyl]-5-chloropyridine-2-carboxamide," with --N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-chloropyridine-2-carboxamide,--.

Claim 4, Column 184
Lines 4-7, replace "N-[3-((4aR*,6R*,8aS*)-2-amino-6-methoxymethyl-4,4a,5,6,8,8a-hexahydro-7-oxa-3thia-1-azanaphthalen-8a-yl)-4-fluorophenyl]-5-fluoromethoxypyrazine-2-carboxamide," with --N-[3-((4aR*,6R*,8aS*)-2-amino-6-methoxymethyl-4,4a,5,6,8,8a-hexahydro-7-oxa-3-thia-1-azanaphthalen-8a-yl)-4-fluorophenyl]-5-fluoromethoxypyrazine-2-carboxamide,--.

Claim 4, Column 184
Lines 38-40, replace "N-[3-((4aS*,5S*,8aS*)-2-amino-5-methyl-4,4a,5,6,8,8a-hexahydro-7-oxa-3-thia-1-azanaphthalen-8a-yl)-4-fluorophenyl]-5-chloropyridine-2-carboxamide," with --N-[3-((4aR*,5S*,8aS*)-2-amino-5-methyl-4,4a,5,6,8,8a-hexahydro-7-oxa-3-thia-1-azanaphthalen-8a-yl)-4-fluorophenyl]-5-chloropyridine-2-carboxamide,--.

Claim 4, Column 184
Lines 54-57, replace "N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-difluormethoxypyrazine-2-carboxamide," with --N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-difluoromethoxypyrazine-2-carboxamide,--.

Claim 4, Column 184
Lines 58-60, replace "N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-difluormethylpyrazine-2-carboxamide," with --N-[3-((4aR*,5R*,8aS*)-2-amino-5-methyl-4,4a,5,6,8,8a-hexahydro-7-oxa-3-thia-1-azanaphthalen-8a-yl)-4-fluorophenyl]-5-difluoromethylpyrazine-2-carboxamide,--.

Claim 4, Column 185
Lines 14-17, replace "N-[3-((4aR*,6R*,8aS*)-2-amino-6-trifluoromenthyl-4,4a,5,6,8,8a-hexahydro-7-oxa-3-thia-1-azanaphthalen-8a-yl)-4-fluorophenyl]-5-difluormethoxypyrazine-2-carboxamide," with --N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-difluoromethoxypyrazine-2-carboxamide,--.

Claim 4, Column 185
Lines 18-21, replace "N-[3-((4aR*,6R*,8aS*)-2-amino-6-trifluoromenthyl-4,4a,5,6,8,8a-hexahydro-7-oxa-3-thia-1-azanaphthalen-8a-yl)-4-fluorophenyl]-5-fluoropyridine-2-carboxamide," with --N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-fluoropyridine-2-carboxamide,--.

Claim 4, Column 185
Lines 22-24, replace "N-[3-((4aR*,6R*,8aS*)-2-amino-6-trifluoromenthyl-4,4a,5,6,8,8a-hexahydro-7-oxa-3-thia-1 -azanaphthalen-8a-yl)-4-fluorophenyl]-pyridine-2-carboxamide," with --N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-pyridine-2-carboxamide,--.

Claim 4, Column 185
Lines 25-28, replace "N-[3-((4aR*,6R*,8aS*)-2-amino-6-trifluoromenthyl-4,4a,5,6,8,8a-hexahydro-7-oxa-3-thia-1-azanaphthalen-8a-yl)-4-fluorophenyl]-5-fluoromethoxypyrazine-2-carboxamide," with --N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-fluoromethoxypyrazine-2-carboxamide,--.

CERTIFICATE OF CORRECTION (continued)
U.S. Pat. No. 8,198,269 B2

Claim 4, Column 185
Lines 29-31, replace "N-[3-((4aR*,6R*,8aS*)-2-amino-6-trifluoromenthyl-4,4a,5,6,8,8a-hexahydro-7-oxa-3-thia-1-azanaphthalen-8a-yl)-4-fluorophenyl]pyrimidine-4-carboxamide,"
with --N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-pyrimidine-4-carboxamide,--.

Claim 4, Column 185
Lines 32-35, replace "N-[3-((4aR*,6R*,8aS*)-2-amino-6-trifluoromenthyl-4,4a,5,6,8,8a-hexahydro-7-oxa-3-thia-1-azanaphthalen-8a-yl)-4-fluorophenyl]-3,5-difluoropyridine-2-carboxamide," with --N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-3,5-difluoropyridine-2-carboxamide,--.

Claim 4, Column 185
Lines 36-39, replace "N-[3-((4aR*,6R*,8aS*)-2-amino-6-trifluoromenthyl-4,4a,5,6,8,8a-hexahydro-7-oxa-3-thia-1-azanaphthalen-8a-yl)-4-fluorophenyl]-5-difluoromethoxypyridine-2-carboxamide," with --N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-difluoromethoxypyridine-2-carboxamide,--.

Claim 4, Column 185
Lines 40-43, replace "N-[3-((4aR*,6R*,8aS*)-2-amino-6-trifluoromenthyl-4,4a,5,6,8,8a-hexahydro-7-oxa-3-thia-1-azanaphthalen-8a-yl)-4-fluorophenyl]-5-difluoromethylypyrazine-2-carboxamide," with --N-[3-((4aR*,6R*,8aS*)-2-amino-6-trifluoromethyl-4,4a,5,6,8,8a-hexahydro-7-oxa-3-thia-1-azanaphthalen-8a-yl)-4-fluorophenyl]-5-difluoromethylpyrazine-2-carboxamide,--.

Claim 4, Column 185
Lines 44-46, replace "N-[3-((4aR,6R,8aS)-2-amino-6-fluoromenthyl-4,4a,5,6,8,8a-hexahydro-7-oxa-3-thia-1-azanaphthalen-8a-yl)-4-fluorophenyl]-5-cyanopyridine-2-carboxamide," with --N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-cyanopyridine-2-carboxamide,--.

Claim 4, Column 185
Lines 47-49, replace "N-[3-((4aR,6R,8aS)-2-amino-6-fluoromenthyl-4,4a,5,6,8,8a-hexahydro-7-oxa-3-thia-1-azanaphthalen-8a-yl)-4-fluorophenyl]-5-chloropyridine-2-carboxamide," with --N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-chloropyridine-2-carboxamide,--.

Claim 4, Column 185
Lines 50-53, replace "N-[3-((4aR,6R,8aS)-2-amino-6-fluoromenthyl-4,4a,5,6,8,8a-hexahydro-7-oxa-3-thia-1-azanaphthalen-8a-yl)-4-fluorophenyl]-5-trifluormethylpyridine-2-carboxamide," with --N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-trifluoromethylpyridine-2-carboxamide,--.

Claim 4, Column 185
Lines 54-57, replace "N-[3-((4aR,6R,8aS)-2-amino-6-fluoromenthyl-4,4a,5,6,8,8a-hexahydro-7-oxa-3-thia-1-azanaphthalen-8a-yl)-4-fluorophenyl]-5-fluoromethoxypyrazine-2-carboxamide," with --N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-fluoromethoxypyrazine-2-carboxamide,--.

Claim 4, Column 185
Lines 58-61, replace "N-[3-((4aR,6R,8aS)-2-amino-6-fluoromenthyl-4,4a,5,6,8,8a-hexahydro-7-oxa-3-thia-1-azanaphthalen-8a-yl)-4-fluorophenyl]-5-difluoromethylpyrazine-2-carboxamide," with --N-[3-((4aR,6R,8aS)-2-amino-6-fluoromethyl-4,4a,5,6,8,8a-hexahydro-7-oxa-3-thia-1-azanaphthalen-8a-yl)-4-fluorophenyl]-5-difluoromethylpyrazine-2-carboxamide,--.

Claim 4, Column 186
Lines 26-28, replace "59) (±)-(4aR*,6R*,8aS*)-8a-[2-fluoro-5-(2-fluoropyridin-3-yl)phenyl]-6-trifluoromethyl-4,4a,5,6,8,8a-hexahydro-7-oxa-3-thia-1azanaphthalen-2-ylamine," with --59) (±)-(4aR*,6R*,8aS*)-8a-[2-fluoro-5-(2-fluoropyridin-3-yl)phenyl]-6-trifluoromethyl-4,4a,5,6,8,8a-hexahydro-7-oxa-3-thia-1-azanaphthalen-2-ylamine,--.

Claim 4, Column 186
Lines 29-31, replace "60) (4aR,6R,8aS)-8a-[2-fluoro-5-(2-fluoropyridin-3-yl)phenyl]-6-fluoromethyl-4,4a,5,6,8,8a-hexahydro-7-oxa-3-thia-1azanaphthalen-2-ylamine," with --60) (4aR,6R,8aS)-8a-[2-fluoro-5-(2-fluoropyridin-3-yl)phenyl]-6-fluoromethyl-4,4a,5,6,8,8a-hexahydro-7-oxa-3-thia-1-azanaphthalcn-2-ylamine,--.

Claim 4, Column 187
Lines 4-5, replace "or a pharmaceutically acceptable salt thereof, or a solvate thereof" with --or a pharmaceutically acceptable salt thereof--.

Claim 5, Column 187
Line 7, replace "or pharmaceutically acceptable salt thereof, or solvate thereof" with --or pharmaceutically acceptable salt thereof--.

Claim 6, Column 187
Line 12, replace "compostion" with --composition--.

Claim 8, Column 188
Lines 3-4, replace "compostion according to claim 5 to subject" with --composition according to claim 5 to a subject--.

Claim 8, Column 188
Line 7, after "claim 5 to" insert --a--.